US007736884B2

(12) United States Patent
Gunnarsson et al.

(10) Patent No.: US 7,736,884 B2
(45) Date of Patent: Jun. 15, 2010

(54) **METABOLICALLY ENGINEERED *SACCHAROMYCES* CELLS FOR THE PRODUCTION OF POLYUNSATURATED FATTY ACIDS**

(75) Inventors: Nina Katarina Gunnarsson, Copenhagen N (DK); Jochen Forster, Copenhagen V (DK); Jens Bredal Nielsen, Charlottenlund (DK)

(73) Assignee: Fluxome Sciences A/S, Lyngby (DK)

( * ) Notice: Subject to any disclaimer, the term of this patent is extended or adjusted under 35 U.S.C. 154(b) by 523 days.

(21) Appl. No.: 11/146,428

(22) Filed: Jun. 6, 2005

(65) Prior Publication Data

US 2006/0051847 A1 Mar. 9, 2006

Related U.S. Application Data

(60) Provisional application No. 60/577,245, filed on Jun. 4, 2004.

(51) Int. Cl.
*C12N 1/19* (2006.01)
*C12P 1/19* (2006.01)
*A23K 1/16* (2006.01)
*A23L 1/30* (2006.01)
*A61K 8/33* (2006.01)
*C12N 15/81* (2006.01)
*C12N 9/02* (2006.01)
*A23D 7/00* (2006.01)

(52) U.S. Cl. .................... 435/254.1; 435/134; 435/189; 435/320.1; 426/53; 426/585; 426/601; 426/648; 424/401

(58) Field of Classification Search ....................... None
See application file for complete search history.

(56) References Cited

U.S. PATENT DOCUMENTS 4,582,788 A 4/1986 Erlich (Continued)

FOREIGN PATENT DOCUMENTS

EP 0 050 424 4/1982

(Continued)

OTHER PUBLICATIONS

McDonough, V. M., et al., 1992, "Specificity of unsaturated fatty acid-regulated expression of the *Saccharomyces cerevisiae* OLE1 gene", The Journal of Biological Chemistry, 267(9): 5931-5936.*

(Continued)

*Primary Examiner*—Nashaat T Nashed
*Assistant Examiner*—William W Moore
(74) *Attorney, Agent, or Firm*—Frommer Lawrence & Haug LLP; Thomas J. Kowalski; Deborah L. Lu

(57) ABSTRACT

The present invention relates to the construction and engineering of cells, more particularly microorganisms for producing PUFAs with four or more double bonds from non-fatty acid substrates through heterologous expression of an oxygen requiring pathway.

The invention especially involves improvement of the PUFA content in the host organism through fermentation optimization, e.g. decreasing the temperature and/or designing an optimal medium, or through improving the flux towards fatty acids by metabolic engineering, e.g. through over-expression of fatty acid synthases, over-expression of other enzymes involved in biosynthesis of the precursors for PUFAs, or codon optimization of the heterologous genes, or expression of heterologous enzymes involved in the biosynthesis of the precursor for PUFAs.

18 Claims, 24 Drawing Sheets

U.S. PATENT DOCUMENTS

| | | | | |
|---|---|---|---|---|
| 4,683,194 | A | 7/1987 | Saiki et al. | |
| 4,683,202 | A | 7/1987 | Mullis | |
| 5,057,419 | A * | 10/1991 | Martin et al. | 435/134 |
| 5,777,201 | A * | 7/1998 | Poutre et al. | 800/281 |
| 5,869,304 | A * | 2/1999 | Dickson et al. | 800/281 |
| 5,972,664 | A | 10/1999 | Knutzon et al. | |
| 6,025,172 | A | 2/2000 | Dani et al. | |
| 6,051,755 | A * | 4/2000 | Zou et al. | 800/281 |
| 6,136,574 | A | 10/2000 | Knutzon et al. | |
| 6,194,167 | B1 | 2/2001 | Browse et al. | |
| 6,225,528 | B1 * | 5/2001 | Chin et al. | 800/279 |
| 6,355,861 | B1 | 3/2002 | Thomas | |
| 6,372,965 | B1 | 4/2002 | Lightner et al. | |
| 6,403,349 | B1 | 6/2002 | Mukerji et al. | |
| 6,428,990 | B1 * | 8/2002 | Mukerji et al. | 435/134 |
| 6,432,684 | B1 | 8/2002 | Mukerji et al. | |
| 6,441,278 | B1 | 8/2002 | DeBonte et al. | |
| 6,485,947 | B1 * | 11/2002 | Rajgarhia et al. | 435/139 |
| 6,492,108 | B1 | 12/2002 | Hillman et al. | |
| 6,686,186 | B2 | 2/2004 | Shanklin et al. | |
| 6,825,335 | B1 * | 11/2004 | Martin et al. | 536/23.74 |
| 6,913,916 | B1 * | 7/2005 | Mukerji et al. | 435/183 |
| 7,067,285 | B2 * | 6/2006 | Mukerji et al. | 435/71.1 |
| 7,109,010 | B2 * | 9/2006 | Rajgarhia et al. | 435/190 |
| 7,125,672 | B2 * | 10/2006 | Picataggio et al. | 435/6 |
| 7,193,134 | B2 * | 3/2007 | Qiu et al. | 800/281 |
| 7,198,937 | B2 * | 4/2007 | Xue et al. | 435/254.2 |
| 7,208,297 | B2 * | 4/2007 | Mukerji et al. | 435/134 |
| 7,214,491 | B2 * | 5/2007 | Yadav et al. | 435/6 |
| 7,238,482 | B2 * | 7/2007 | Picataggio et al. | 435/6 |
| 7,259,255 | B2 * | 8/2007 | Picataggio et al. | 536/24.1 |
| 7,267,976 | B2 * | 9/2007 | Yadav et al. | 435/254.2 |
| 7,273,746 | B2 * | 9/2007 | Yadav et al. | 435/254.2 |
| 7,465,564 | B2 * | 12/2008 | Zhu et al. | 435/134 |
| 7,504,259 | B2 * | 3/2009 | Yadav et al. | 435/471 |
| 7,537,920 | B2 * | 5/2009 | Renz et al. | 435/194 |
| 2002/0045232 | A1 * | 4/2002 | Qiu | 435/190 |
| 2002/0108147 | A1 | 8/2002 | Thomas | |
| 2002/0138874 | A1 | 9/2002 | Mukerji et al. | |
| 2002/0151019 | A1 | 10/2002 | Shanklin | |
| 2002/0170090 | A1 | 11/2002 | Browse et al. | |
| 2003/0004299 | A1 * | 1/2003 | Srienc et al. | 528/272 |
| 2003/0066104 | A1 | 4/2003 | Lightner et al. | |
| 2003/0074694 | A1 | 4/2003 | Lightner et al. | |
| 2003/0159173 | A1 * | 8/2003 | Wolter et al. | 800/281 |
| 2003/0172398 | A1 | 9/2003 | Browse | |
| 2003/0177508 | A1 | 9/2003 | Mukerji et al. | |
| 2003/0180802 | A1 | 9/2003 | Kloek et al. | |
| 2004/0049805 | A1 * | 3/2004 | Lerchl et al. | 800/281 |
| 2005/0227339 | A1 * | 10/2005 | Camps Diez et al. | 435/134 |
| 2006/0078973 | A1 * | 4/2006 | Renz et al. | 435/134 |
| 2006/0110806 | A1 * | 5/2006 | Damude et al. | 435/134 |
| 2006/0115881 | A1 * | 6/2006 | Damude et al. | 435/134 |
| 2006/0168687 | A1 * | 7/2006 | Renz et al. | 800/281 |
| 2006/0246556 | A1 * | 11/2006 | Napier et al. | 435/128 |

FOREIGN PATENT DOCUMENTS

| | | |
|---|---|---|
| EP | 0 084 796 | 8/1983 |
| EP | 0 201 184 | 12/1986 |
| EP | 0 258 017 | 3/1988 |
| WO | WO 94/11516 | 5/1994 |
| WO | WO 98/46763 | 10/1998 |
| WO | WO 98/46764 | 10/1998 |
| WO | WO 98/46765 | 10/1998 |
| WO | WO 99/27111 | 6/1999 |
| WO | WO 99/33958 | 7/1999 |
| WO | WO 00/34439 | 6/2000 |
| WO | WO 00/40705 | 7/2000 |
| WO | WO 00/55330 | 9/2000 |
| WO | WO 01/02591 | 1/2001 |
| WO | WO 01/04636 | 1/2001 |
| WO | WO 01/14538 | 3/2001 |
| WO | WO 01/20001 | 3/2001 |
| WO | WO 01/44485 | 6/2001 |
| WO | WO 01/59128 | 8/2001 |
| WO | WO 01/75069 | 10/2001 |
| WO | WO 01/79499 | 10/2001 |
| WO | WO 01/85968 | 11/2001 |
| WO | WO 02/08401 | 1/2002 |
| WO | WO 02/26946 | 4/2002 |
| WO | WO 02/34940 | 5/2002 |
| WO | WO 02/44320 | 6/2002 |
| WO | WO 02/072028 | 9/2002 |
| WO | WO 02/077213 | 10/2002 |
| WO | WO 02/081668 | 10/2002 |
| WO | WO 02/081702 | 10/2002 |
| WO | WO 02/090493 | 11/2002 |
| WO | WO 03/012092 | 2/2003 |
| WO | WO 03/064638 | 8/2003 |
| WO | WO 03/072784 | 9/2003 |
| WO | WO 03/102138 | 12/2003 |
| WO | WO 2004/005442 | 1/2004 |

OTHER PUBLICATIONS

Huang, Y.-S., et al., 1999, "Cloning of delta12- and delta6-desaturases from *Mortierella alpina* and recombinant production of gamma-linoleic acid in *Saccharomyces cerevisiae*", Lipids, 34(7): 649-659.*

Wattts, J. L., et al., 2000, "A palmitoyl-CoA-specific delta9 fatty acid desaturase from *Caenorhabditis elegans*", Biochemical and Biophysical Research Communications, 272(1): 263-269.*

Chuang, L.-T., et al., 2001, "Effect of conjugated linoleic acid on fungal delta6-desaturase activity in a transformed yeast system", Lipids, 36(2): 139-143.*

Kelder, B., et al., 2001, "Expression of fungal desaturase genes in cultured mammalian cells", Molecular and Cellular Biochemistry, 219(1): 7-11.*

Kajiwara, S., et al., 2002, "Molecular cloning and characterization of the delta9 fatty acid desaturase gene and its promoter from *Saccharomyces kluyveri*", FEMS Yeast Research, 2(3): 333-339.*

Domergue, F., et al., Apr. 2003, "New insight into *Phaeodactylum tricornatum* fatty acid metabolism. Cloning and functional characterization of plastidial and microsomal delta12-fatty acid desaturases", Plant Physiology, 131: 1648-1660.*

Stephen F. Altschul et al., "Basic Local Alignment Search Tool", J. Mol. Biol. (1990), vol. 215, pp. 403-410.

Stephen F. Altschul, et al. "Gapped BLAST and PSI-BLAST: a new generation of protein database search programs", Nucleic Acids Research, 1997, vol. 25, No. 17, pp. 3389-3402.

Frederic Beaudoin, et al., "Heterologous reconstitution in yeast of the polyunsaturated fatty acid biosynthetic pathway", PNAS, Jun. 6, 2000, vol. 97, No. 12, pp. 6421-6426.

Frederic Domergue, et al. "Acyl Carriers Used as Substrates by the Desaturases and Elongases Involved in Very Long-chain Polyunsaturated Fatty Acids Biosynthesis Reconstituted in Yeast", The Journal of Biological Chemistry, vol. 278, No. 37, Sep. 12, 2003, pp. 35115-35126.

Naz Erdeniz, et al. "Cloning-Free PCR-Based Allele Replacement Methods", Genome Research, vol. 7, pp. 1174-1183.

Silvana Gargano, et al. "A Temperature-Sensitive Strain of *Histoplasma capsulatum* Has an Altered $\Delta^9$—Fatty Acid Desaturase Gene", Lipids, vol. 30, No. 10, (1995), pp. 899-906.

Nicola Hastings, et al., "A vertebrate fatty acid desaturase with Δ5 and Δ6 acitivities", PNAS, Dec. 4, 2001, vol. 98, No. 25, pp. 14304-14309.

Patent Abstracts of Japan; Publication No. 2001095588; Publication Date Apr. 10, 2001.

Masataka Kajikawa et al., Isolation and characterization of $\Delta^6$-desaturase, an ELO-like enzyme and $\Delta^{5}$-desaturase from the liverwort *Marchantia polymorpha* and production of arachidonic and eicosapentaenoic acids in the methylotrophic yeast *Pichia pastoris*, Plant Molecular Biology, 2004, vol. 54, pp. 335-352.

Samuel Karlin et al., "Methods for assessing the statistical significance of molecular sequence features by using general scoring schemes", Poc. Natl. Acad. Sci. USA,, Mar. 1990, vol. 87, pp. 2264-2268.

Samuel Karlin et al., "Applications and statistics for multiple high-scoring segments in molecular sequences", Proc. Natl. Acad. Sci. USA, Jun. 1993, vol. 90, pp. 5873-5877.

Christoph Kirsch et al., "Rapid transient, and highly localized induction of plastidial ω-3 fatty acid desaturase mRNA at fungal infection sites in *Petroselinum crispum*", Proc. Natl. Acad. Sci. USA, Mar. 1997, vol. 94, pp. 2079-2084.

Kobkul Laoteng, et al., "$\Delta^6$-Desaturase of *Mucor rouzii* with High Similarity to Plant $\Delta^6$-Desaturase and Its Heterologous Expression in *Saccharomyces cerevisiae*", Biochemical and Biophysical Research Communications, 2000, vol. 279, pp. 17-22.

Weitian Liu, et al., "Cloning and functional expression of a cDNA encoding a metabolic acyl-CoA Δ9 -desaturase of the cabbage looper moth, *Trichoplusia ni*", Insect Biochemistry and Molecular Biology, 1999, vol. 29, pp. 435-443.

Patricia A. E. P. Meesters et al., "Isolation and Characterization of a Δ-9 Fatty Acid Desaturase Gene from the Oleaginous Yeast *Cryptococcus curvatus* CBS 570", Yeast, 1996, vol. 12, pp. 723-730.

Astrid Meyer et al., "Biosynthesis of Docosahexaenoic Acid in *Euglena gracilis*: Biochemical and Molecular Evidence for the Involvement of a Δ4-Fatty Acyl Group Desaturase", Biochemistry 2003, vol. 42, pp. 9779-9788.

H.T.T. Nguyen, et al., "Engineering of *Saccharomyces cerevisiae* for the production of L-glycerol 3-phosphate", Metabolic Engineering, 2004, vol. 6, pp. 155-163.

Torben L. Nissen, et al., "Optimization of Ethanol Production in *Saccharomyces cerevisiae* by Metabolic Engineering of the Ammonium Assimilation", Metabolic Engineering, 2000, vol. 2, pp. 69-77.

Chan-Seok Oh, et al., "*ELO2*and *ELO3*, Homologues of the *Saccharomyces cerevisiae ELO1* Gene, Function in Fatty Acid Elongation and Are Required for Sphingolipid Formation", The Journal of Biological Chemistry, Jul. 11, 1997, vol. 272, No. 28, pp. 17376-17384.

Takahiro Oura et al., "*Saccharomyces kluyveri* FAD3 encodes an ω3 fatty acid desaturase", Microbiology, 2004, vol. 150, pp. 1983-1990.

Supapon Passorn, et al., "Heterologous Expression of *Mucor rouxii* $\Delta^{12}$-Desaturase Gene in *Saccharomyces cerevisiae*", Biochemical and Biophysical Research Communications, 1999, vol. 263, pp. 47-51.

Suzette L. Pereira, et al., "Identification of two novel microalgal enzymes involved in the conversion of the ω3-fatty acid, eicosapentaenoic acid, into docosahexaenoic acid", Biochem. J., 2004, vol. 384, pp. 357-366.

Eiji Sakuradani, et al., "A novel fungal ω3-desaturase with wide substrate specificity from arachidonic acid-producing *Mortierella alpina* 1S-4", Appl. Microbiol Biotechnol, 2005, vol. 66, pp. 648-654.

Baoxiu Qi, et al., "Production of very long chain polyunsaturated omega-3 and omega-6 fatty acids in plants", Nature Biotechnology, Jun. 2004, vol. 22, No. 6, pp. 739-745.

C. Ratledge, "Regulation of lipid accumulation in oleaginous microorganisms", Biochemical Society, 2002, pp. 1047-1050.

Line Sandager et al., "Storage Lipid Synthesis Is Non-essential in Yeast", The Journal of Biological Chemistry, Feb. 22, 2002, vol. 277, No. 8, pp. 6478-6482.

Olga Sayanova, et al., "Expression of a borage desaturase cDNA containing an N-terminal cytochrome $b_5$ domain results in the accumulation of high levels of $\Delta^6$-desaturated fatty acids in transgenic tobacco", Proc. Natl. Acad. Sci. USA, Apr. 1997, vol. 94, pp. 4211-4216.

L. Sijtsma et al., "Biotechnological production and applications of the ω-3 polyunsaturated fatty acid docosahexaenoic acid", Appl. Microbiol Biotechnol, 2004, vol. 64, pp. 146-153.

David A. Toke, et al., "Isolation and Characterization of a Gene Affecting Fatty Acid Elongation in *Saccharomyces cerevisiae*", The Journal of Biological Chemistry, Aug. 2, 1996, vol. 271, No. 31, pp. 18413-18422.

Petr Tvrdik, et al., "Role of a New Mammalian Gene Family in the Biosynthesis of Very Long Chain Fatty Acids and Sphingolipids", The Journal of Cell Biology, May 1, 2000, vol. 149, No. 3, pp. 707-717.

James G. Wallis, et al., "The $\Delta^8$-Desaturase of *Euglena gracilis*: An Alternate Pathway for Synthesis of 20-Carbon Polyunsaturated Fatty Acids[1]", Archives of Biochemistry and Biophysics, May 15, 1999, vol. 365, No. 2, pp. 307-316.

Kyoko Watanabe, et al., "Yeast Δ12 Fatty Acid Desaturase: Gene Cloning, Expression, and Function", Biosci, Biotechnol. Biochem., 2004, vol. 68, No. 3, pp. 721-727.

Heather M. Whitney, et al., "Functional characterisation of two cytochrome *b*5-fusion desaturases from *Anemone leveillei*: the unexpected identification of a fatty acid $\Delta^6$-desaturase", Planta, 2003, vol. 217, pp. 983-992.

Richard A. Wilson, et al., "Characterization of the *Aspergillus parasiticus* $\Delta^{12}$-desaturase gene: a role for lipid metabolism in the *Aspergillus*-seed interaction", Microbiology, 2004, vol. 150, pp. 2881-2888.

Prasert Wongwathanarat, et al., Two fatty acid Δ9-desaturase genes, *ole 1* and *ole 2*, from *Mortierella alpina* complement the yeast *ole 1* mutation, Microbiology, 1999, vol. 145, pp. 2939-2946.

Narendra S. Yadav, et al., "Cloning of Higher Plant ω-3 Fatty Acid Desaturases[1]", Plant Physiol., 1993, vol. 103, pp. 467-476.

M. Zhu, et al., "An inexpensive medium for production of arachidonic acid by *Mortierella alpina*", J Ind. Microbiol Biotechnol, 2003, vol. 30, pp. 75-79.

Abbadi et al: "Transgenic oilseeds as sustainable source of nutritionally relevant C20 and C22 polyunsaturated fatty acids?" European Journal of Lipid Science and Technology, Wiley VCH Verlag, Weinheim, DE, vol. 103, No. 2, Feb. 2001, pp. 106-113, XP002228744.

* cited by examiner

METABOLICALLY ENGINEERED *SACCHAROMYCES* CELLS FOR THE PRODUCTION OF POLYUNSATURATED FATTY ACIDS

CROSS-REFERENCE TO RELATED APPLICATIONS AND INCORPORATION BY REFERENCE

This application claims priority from U.S. Provisional Application Ser. No. 60/577,245, filed on Jun. 4, 2004.

Each of these applications, patents, and each document cited in this text, and each of the documents cited in each of these applications, patents, and documents ("application cited documents"), and each document referenced or cited in the application cited documents, either in the text or during the prosecution of the applications and patents thereof, as well as all arguments in support of patentability advanced during prosecution thereof, are hereby incorporated herein by reference.

FIELD OF THE INVENTION

This invention relates generally to the production of fatty acids and particularly to the production of polyunsaturated fatty acids (PUFAs) in various cells, more specifically, to the expression of heterologous pathways in microorganisms for the production of fatty acids and particularly polyunsaturated fatty acids.

BACKGROUND OF THE INVENTION

PUFAs are polyunsaturated fatty acids with a long hydrocarbon chain composed of 18 or more carbon atoms having two or more double bonds and a terminal carboxylate group.

The properties of polyunsaturated fatty acids are highly influenced by the position of the double bond, and one differentiates omega-3 PUFAs, which have the first double bond at the third position counting from the methyl end of the carbon chain, and omega-6 PUFAs, which have the first double bond at the sixth position counting from the methyl end of the carbon chain. Eicosapentaenoic acid belongs to the former group, particularly eicosapentaenoic acid with double bonds in position 5, 8, 11, 14 and 17 (EPA) and docosahexaenoic acid, particularly docosahexaenoic acid with double bonds in position 4, 7, 10, 13, 16, 19 (DHA), while, for example, arachidonic acid (ARA) belongs to the latter group.

PUFAs are essential for humans, and it has been proven that they have many beneficial effects on human health, including proper development of brain and visual functions and prevention of disease, such as cardiovascular disease and cancer.

The omega-6 PUFA arachidonic acid plays an important role in the structure and function of biological membranes, and is a precursor of the biologically active prostaglandins and leukotrienes. Arachidonic acid is necessary for the neurological and neurophysiological development of both term and preterm infants, and many expert organizations, including the Food and Agriculture Organization of the United Nations (FAO) and the World Health Organization (WHO) recommend that infant formula should be supplemented with arachidonic acid.

The omega-3 PUFA EPA and DHA, as well, possess a number of physiological functions in humans. They are part of the human tissue, and in the rod outer segment in the retina, DHA represents more than 60% of the total fatty acids. DHA is regarded to be essential for proper visual function and neurological development of infants. Preterm and young infants are unable to synthesize sufficient amounts of DHA and receive the remaining by breast milk. DHA also reduces or eliminates the risk factor involved in various diseases like cardiovascular diseases and exerts positive effects on hypertension, arthritis, arteriosclerosis and thrombosis.

Various publications, patents and patent application focus on the production of PUFA from fatty acid substrates. Recently, the pathway from linoleic acid to arachidonic acid was reconstituted in *S. cerevisiae* (Domergue et al., 2003, Beaudoin et al., 2000) and synthesis of polyunsaturated fatty acids was established by supplying the precursor metabolite, linoleic acid, to the medium.

Other groups have established parts of the PUFA pathway in reconstitution experiments. For example, U.S. Pat. No. 6,432,684 describes the sequence of a delta-5 desaturase from human, which, when expressed in yeast, produces arachidonic acid, when dihomo-gamma-linolenic acid is supplied.

U.S. 2002/0170090 describes an omega-3 desaturase from *Caenorhabditis elegans* and its expression in various organisms including bacteria, cyanobacteria, phytoplanton, algae, fungi, plants and animals, and the production of a lipid from an organism that expresses the omega-3 desaturase. The enzyme catalyzes the conversion of omega-6 fatty acids with 18, 20 and 22 carbon atoms to the corresponding omega-3 fatty acids. Yeast cells, expressing the omega-3 desaturase from *C. elegans*, converted exogenously supplied linoleic acid and omega-6 docosatetraenoic acid into alpha-linolenic acid and omega-3 docosapentaenoic acid, respectively.

PCT/US98/07422 describes the isolation of a delta-5 desaturase from *Mortierella alpina* and expression of said enzyme in microbial cells, particularly in *Saccharomyces cerevisiae*, and reports production of arachidonic acid when dihomo-gamma-linolenic acid is supplied in the growth medium. WO 99/27111 describes a delta-6 desaturase from *C. elegans* and its expression in yeast, which led to production of gamma-linolenic acid from exogenously, supplied oleic acid. In WO99/33958, the expression of a delta-5 desaturase (originally obtained from *C. elegans*) in microorganisms, such as algae, bacteria and fungi, and particularly, its expression in yeast is disclosed. WO 02/44320 describes a number of different human elongases, many of which have been tested for functionality in yeast using a number of different fatty acids as externally supplied substrates.

A method for the production of arachidonic acid in transgenic organisms (WO 03/012092) has been applied. Here, the inventors describe the expression of a delta-5 desaturase, which leads to the production of arachidonic acid in yeast; however, it requires dihomo-gamma linolenic acid as an external substrate.

The inventors of PCT/US98/07421 test the expression of various desaturases including delta-12 desaturase, delta-6 desaturase and delta-5 desaturase and reconstitute the function of these enzymes by adding fatty acid substrates to the growth medium and analysing their conversion.

In all the above-mentioned publications, patents and patent applications, processes have been described, where it is necessary to supply fatty acids as external substrates in the medium in order to produce PUFAs.

In the following a few publications are described, which report production of PUFAs with up to 3 double bonds from non-fatty acid substrates. In U.S. Pat. No. 6,355,861 it is shown that the expression of delta-12 and delta-6 desaturase from *Cynecosystis* in *Cynecococcus* leads both to the production of linoleic acid and gamma-linolenic acid, fatty acids with two double bonds and three double bounds, respectively. Furthermore, expression of a delta-6 desaturase from prime rose in a bacterial, fungal or plant cell is disclosed, including expression of said delta-6 desaturase in various plants for the production of gamma-linolenic acid.

U.S. Pat. No. 6,136,574 describe the production of gamma-linoleic acid in yeast from endogenously available oleic acid. PCT/US98/07126 describes the expression of a delta-6 desaturase and a delta-12 desaturase and reports, for example that expression of these genes in a host cell leads to the production of gamma-linoleic acid.

No prior art reference discloses successful heterologous PUFA production with four or more double bonds in microorganisms from carbon sources other than fatty acids, despite the fact that a high number of different genes involved in PUFA biosynthesis have been identified. This clearly demonstrates that it is a difficult task to produce PUFAs with four or more double bonds at sufficient or detectable titers in microorganisms that usually do not produce PUFA. Although the inventors of U.S. 2003/0177508 describe sequences of four genes that are involved in PUFA elongation and show the function of all these genes, the inventors can only speculate in an example (example III) that expression of delta-12 desaturase, delta-6 desaturase, delta-5 desaturase, and a *Mortierella alpina* elongase cDNA in yeast could result in the production of arachidonic acid without the need of exogenous supply of fatty acids.

As an intermediate summary of the above paragraphs, it can be concluded that, except for the speculations specified in U.S. 2003/0177508, there have until now been no reports on expressing a heterologous pathway for the production and PUFA from non-fatty acid substrates in microorganisms. Until now, reports concerning heterologous PUFA production from non-fatty acid substrates in microscopic hosts, such as yeast, have been limited to PUFAs with less than four double bonds, namely three or less double bonds, such as linoleic acid and gamma-linolenic acid.

If the strategy suggested in U.S. 2003/0177508 is followed, one will expect a low content of arachidonic acid in bakers yeast, as this organism has a low content (approximately 10% of cell dry weight) of fatty acids. Furthermore, the fatty acids in bakers yeast primarily consists of fatty acids with 16 carbon atoms, and the most dominant mono-unsaturated fatty acid is palmitoleic acid, which can not serve as a precursor for synthesis of arachidonic acid. The result of simply expressing the mentioned four genes in *S. cerevisiae*, where expression of these four genes, results in an arachidonic acid content of 0.8% of the fatty acids, or corresponding to less than 0.08% of the yeast dry weight.

The production of polyunsaturated omega-3 and omega-6 fatty acids with four and five double bonds, but not six double bonds, has recently been reported in plants. Qi and co-workers were able to produce the omega-3 fatty acid EPA and the omega-6 fatty acid arachidonic acid in the plant *Arabidopsis thaliana* (Qi et al. 2004).

Qi and co-workers show for the first time that arachidonic acid and EPA can be produced via a heterologous pathway in an organism, such as a plant, using a non-fatty acid substrate. The authors succeed by simultaneously expressing genes coding for delta-9 elongase, delta-8 desaturase and delta-5 desaturase, an approach that makes use of the endogenous delta-12 desaturase and endogenous omega-3 desaturase activities of *A. thaliana* for production of arachidonic acid and EPA. In many organisms, including microorganisms, such as many yeasts and filamentous fungi, it would be necessary to express at least 4 or at least 5 heterologous genes in order to produce PUFA with at least four or at least five double bonds. Until now the expression of more than 3 heterologous genes at the same time for the production of PUFAs has never been applied. Moreover, the production of polyunsaturated fatty acids from non-fatty acid substrates has not yet been shown in non-plant cells.

In WO 2004/057001 the inventors describe that the technology works in both plants and microorganims. However, the inventors have yet only confirmed the described technology in plants. PCT/US2004/014541 describes the production of PUFAs, such as arachidonic acid and EPA using oleaginous yeast. The inventors define oleaginous yeast as yeast that can accumulate at least 25% of its cell dry weight as oil. The invention uses oleaginous yeast such as *Yarrowia, Candida, Rhodotorula, Rhodosporidium, Cryptococcus, Trichosporon* and *Lipomyces* as host cell. It does not provide or claim information about other organisms or non-oleaginous yeast such as *Saccharomyces cerevisiae*. The inventors exemplify their technology by heterologous expression of three additional enzymes in *Yarrowia lipolytica* using delta-6 desaturase, delta-5 desaturase and delta-17 desaturase. The latter is equivalent to omega-3 desaturases. This approach makes use of the endogenous delta-12 desaturase.

In WO2005/01236 the inventors show that it is possible to produce PUFAs in yeast by supplying a fatty acid together with a non-fatty acid substrate. The inventors express delta-4 desaturase, elongases and/or delta-5 desaturase in *Saccharomyces cerevisiae*. By providing EPA or stearidonic acid together with galactose, *Saccharomyces cerevisiae* produces DHA.

PUFAs are increasingly supplied in food, for example in infant formula, and also in pharmaceutical formulations. A general source of PUFAs is fish oil. However, the fatty acid content of fish oil may vary during the fishing season and in some cases the fish oil may be contaminated because of environmental pollution. Besides this, fish oil has an obnoxious smell, which precludes its use as a food supplement.

Hence, proper and expensive purification steps are necessary for some application of PUFAs. The need for PUFAs produced by well-defined methods and in large quantities will increase dramatically during the next 5-10 years, and it is estimated that PUFAs will be used in many different products as a supplement. In order to meet the increasing demand for high quality PUFAs focus has moved towards reproducible production methods and this includes production methods using non-fatty acids substrates. The latter allows a more defined production of unsaturated fatty acids.

The present invention addresses this demand, and presents an efficient new, cost effective and alternative method for the high-level production of mono unsaturated fatty acids and particular PUFAs.

Citation or identification of any document in this application is not an admission that such document is available as prior art to the present invention.

SUMMARY OF THE INVENTION

In one aspect, the present invention relates to the construction and engineering of non-plants more particularly microorganisms for producing PUFAs with four or more double bonds from non-fatty acid substrates through heterologous expression of an oxygen requiring pathway.

In another aspect, the present invention refers to the construction and engineering of non-plants more particularly microorganisms for producing PUFAs with four or more double bonds using a non-fatty acid substrate or substrates as one or several exclusive carbon sources through heterologous expression of an oxygen requiring pathway.

In particular, the present invention describes a method for producing polyunsaturated fatty acids with four or more double bonds comprising heterologous expression of an oxygen-requiring pathway in a *Saccharomyces cerevisiae* grown on a non-fatty acid substrate.

Furthermore, the present invention relates to the construction and engineering of microorganisms for heterologous production of mono unsaturated fatty acid and particular PUFAs, including oleic acid, linoleic acid, alpha-linolenic, gamma-linoleic acid, dihomo-gamma-linolenic acid, arachidonic acid, 5,8,11,14,17-eicosapentaenoic acid (EPA), docosatetraenoic acid, stearidonic acid, eicosadienoic acid, eicosatrienoic acid, eicosatetraenoic acid, 7,10,13,16,19-docosapentaenoic acid and 4,7,10,13,16,19-docosahexaenoic acid (DHA).

The invention especially involves a genetically transformed microorganism containing a heterologous pathway from stearic acid to mono unsaturated fatty acids and PUFAs, i.e. oleic acid, arachidonic acid, DHA or EPA through expression of the following heterologous enzymes delta-9 desaturase, delta-12 desaturase, delta-9 elongase, delta-8 desaturase, omega-3 desaturase, delta-6 desaturase, delta-6 elongase, delta-5 desaturase, delta-5 elongase, delta-4 desaturase or subsets hereof (FIG. 1 and FIG. 2).

Furthermore, the present invention relates to improvement of the PUFA content in the host organism through optimization of fermentation conditions, e.g. decreasing the temperature and/or designing an optimal medium, or through improving the flux towards fatty acids by metabolic engineering, e.g. through overexpression of fatty acid synthases, over-expression of other enzymes involved in biosynthesis of the precursors for PUFAs, or codon optimization of the heterologous genes, or expression of heterologous enzymes involved in the biosynthesis of the precursor for PUFAs, i.e. oleic acid.

The invention also relates to a composition comprising at least 2% polyunsaturated fatty acids produced from a microorganism that expresses a heterologous pathway leading to PUFAs.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, wherein.

Plasmid map over pESC-LEU Ssc2 and

Plasmid map over pESC-LEU-Ssc2-SK33.

Figure 21:
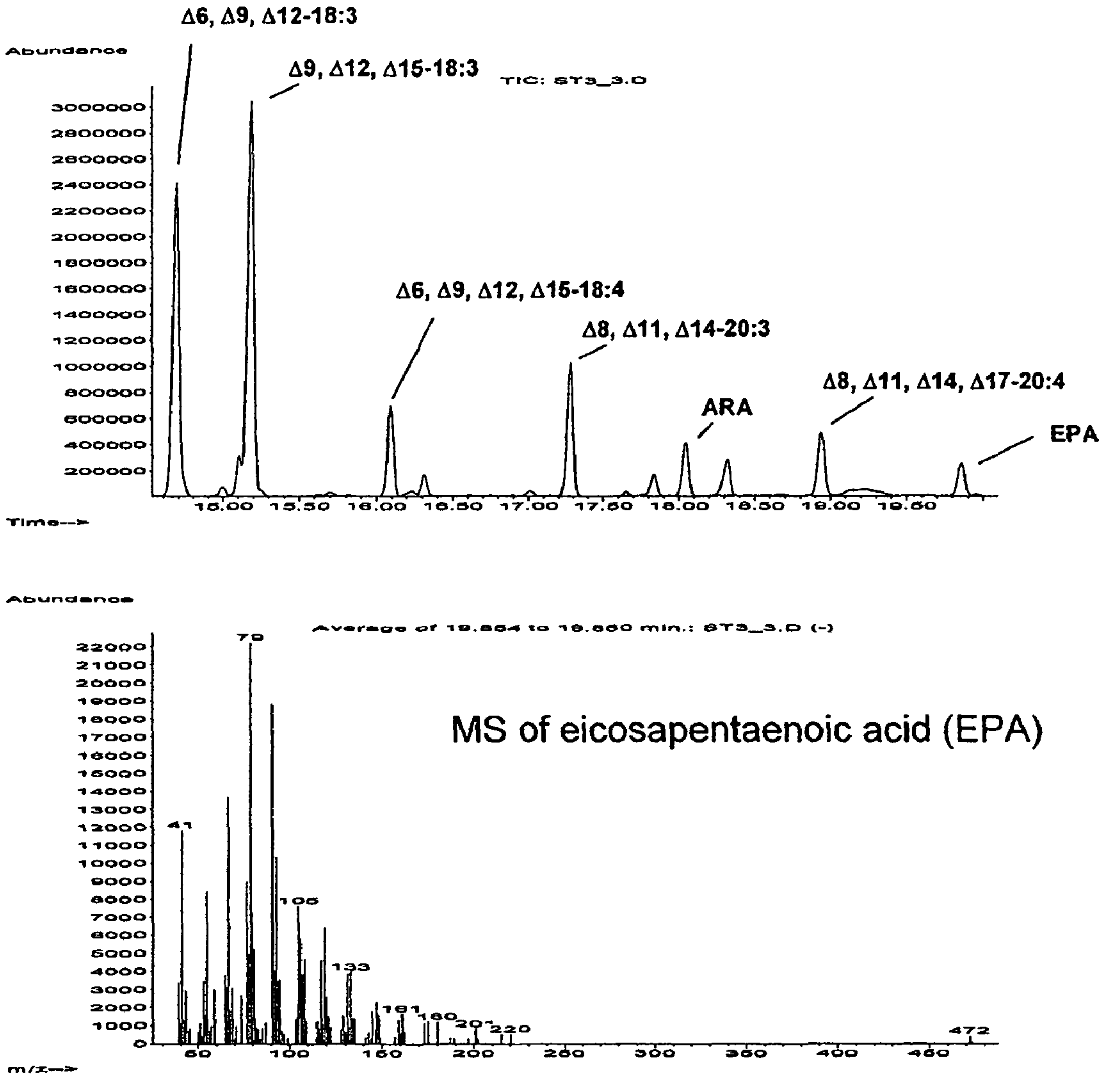

FIG. 21: Gas chromatogram profile of fatty acids, extracted from *S. cerevisiae* strain FS01446, harbouring a heterologous pathway including delta-9 desaturase, delta-12 desaturase, delta-6 desaturase, delta-6 elongase, delta-5 desaturase and omega-3 desaturase and corresponding mass spectrogram of eicosapentaenoic acid.

Figure 22:
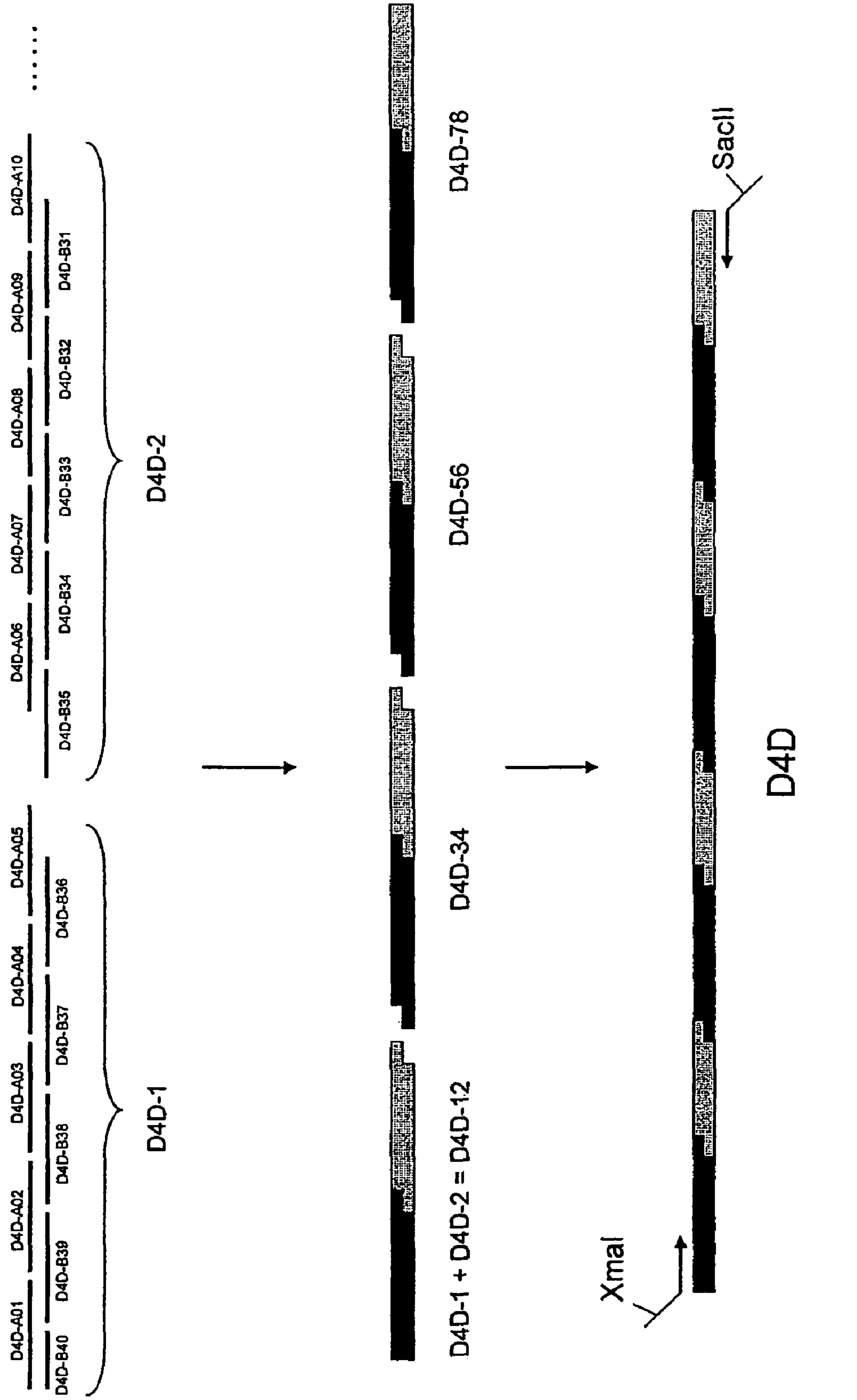

FIG. 22: Method used for assembly of synthetic gene encoding delta-4 desaturase, codon optimized for expression in *Saccharomyces cerevisiae.*

Figure 23:
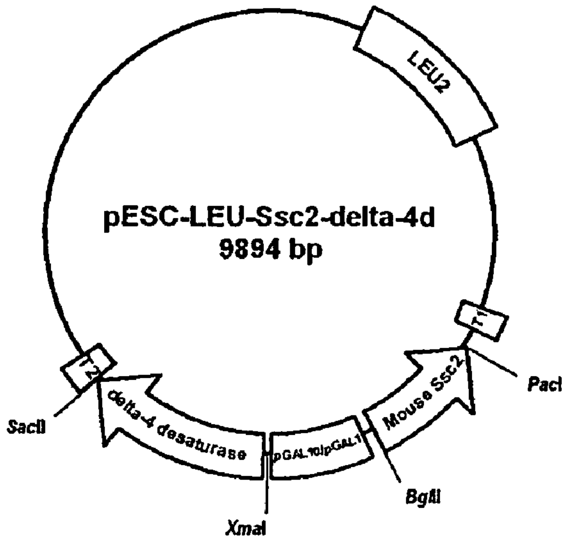

FIG. 23: Plasmid map over pESC-LEU-Ssc2-delta-4d

Figure 24:
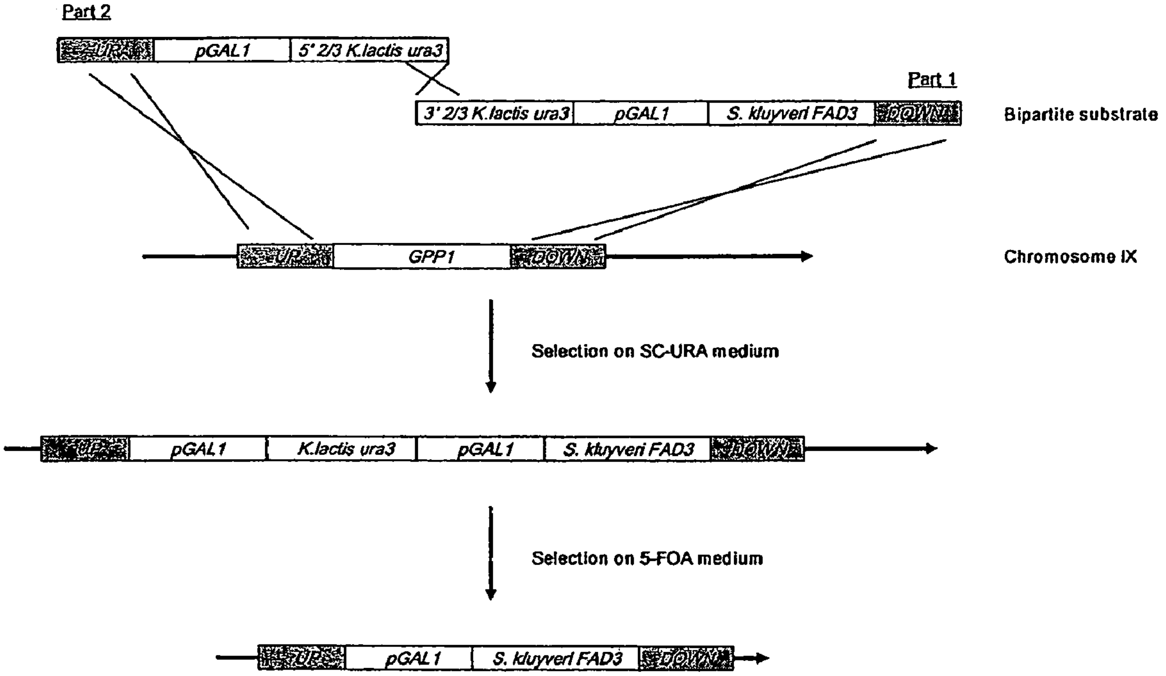

FIG. 24: Strategy for integration of *Saccharomyces kluyveri* FAD3, encoding an omega-3 desaturase, into the genome of *Saccharomyces cerevisiae.*

SEQUENCE ORIGIN

SEQ ID NO: 1 is a nucleotide sequence of from *Mortierella alpina* encoding a delta-9 desaturase SEQ ID NO: 2 is a nucleotide sequence of from *Cryptococcus curvatus* encoding a delta-9 desaturase SEQ ID NO: 3 is a nucleotide sequence of from *Histoplasma capsulatus* encoding a delta-9 desaturase SEQ ID NO: 4 is a nucleotide sequence of from *Trichoplusia ni* encoding a delta-9 desaturase SEQ ID NO: 5 is a nucleotide sequence of from *Mortierella alpina* encoding a delta-12 desaturase SEQ ID NO: 6 is a nucleotide sequence of from *Mucor rouxii* encoding a delta-12 desaturase SEQ ID NO: 7 is a nucleotide sequence of from *Mucor circinelloides* encoding a delta-12 desaturase SEQ ID NO: 8 is a nucleotide sequence of from *Aspergillus fumigatus* encoding a delta-12 desaturase SEQ ID NO: 9 is a nucleotide sequence of from *Cryptococcus curvatus* encoding a delta-12 desaturase SEQ ID NO: 10 is a nucleotide sequence of from *Caenorhabditis elegans* encoding a delta-12 desaturase SEQ ID NO: 11 is a nucleotide sequence of from *Mortierella alpina* encoding a delta-6 desaturase SEQ ID NO: 12 is a nucleotide sequence of from *Mucor rouxii* encoding a delta-6 desaturase SEQ ID NO: 13 is a nucleotide sequence of from *Borago officinalis* encoding a delta-6 desaturase SEQ ID NO: 14 is a nucleotide sequence of from *Anemone levellei* encoding a delta-6 desaturase SEQ ID NO: 15 is a nucleotide sequence of from *Caenorhabditis elegans* encoding a delta-6 desaturase SEQ ID NO: 16 is a nucleotide sequence of from *Mortierella alpina* encoding a delta-6 elongase SEQ ID NO: 17 is a nucleotide sequence of from *Physcomitrella patens* encoding a delta-6 elongase SEQ ID NO: 18 is a nucleotide sequence of from *Caenorhabditis elegans* encoding a delta-6 elongase SEQ ID NO: 19 is a nucleotide sequence of from mouse encoding a delta-6 elongase SEQ ID NO: 20 is a nucleotide sequence of from *Thraustochytrium aureum* encoding a delta-6 elongase SEQ ID NO: 21 is a nucleotide sequence of from *Phytophthora infestans* encoding a delta-6 elongase SEQ ID NO: 22 is a nucleotide sequence of from *Mortierella alpina* encoding a delta-5 desaturase SEQ ID NO: 23 is a nucleotide sequence of from *Phytophthora megasperma* encoding a delta-5 desaturase SEQ ID NO: 24 is a nucleotide sequence of from *Thraustochytrium* sp. ATCC 21685 encoding a delta-5 desaturase SEQ ID NO: 25 is a nucleotide sequence of from *Caenorhabditis elegans* encoding a delta-5 desaturase SEQ ID NO: 26 is a nucleotide sequence of from *Pythium irregulare* encoding a delta-5 desaturase SEQ ID NO: 27 is a nucleotide sequence of from *Phaeodactylum tricornutum* encoding a delta-5 desaturase SEQ ID NO: 28 is a nucleotide sequence of from mouse encoding a delta-5 elongase SEQ ID NO: 29 is a nucleotide sequence of from human encoding a delta-5 elongase SEQ ID NO: 30 is a nucleotide sequence of from *Caenorhabditis elegans* encoding an omega-3 desaturase SEQ ID NO: 31 is a nucleotide sequence of from *Petroselinum crispum* encoding an omega-3 desaturase SEQ ID NO: 32 is a nucleotide sequence of from *Arabidopsis thaliana* encoding an omega-3 desaturase SEQ ID NO: 33 is a nucleotide sequence of from *Brassica napus* encoding an omega-3 desaturase SEQ ID NO: 34 is a nucleotide sequence of from *Glycine soya* encoding an omega-3 desaturase SEQ ID NO: 35 is a nucleotide sequence of from *Thraustochytrium aureum* encoding a delta-4 desaturase SEQ ID NO: 36 is a nucleotide sequence of from *Euglena gracilis* encoding a delta-4 desaturase SEQ ID NO: 37 is a nucleotide sequence of from *Isochrysis galbana* encoding a delta-9 elongase SEQ ID NO: 38 is a nucleotide sequence of from *Euglena gracilis* encoding a delta-8 desaturase SEQ ID NO: 39 is the amino acid sequence encoded by SEQ ID NO:1

SEQ ID NO: 40 is the amino acid sequence encoded by SEQ ID NO:2

SEQ ID NO: 41 is the amino acid sequence encoded by SEQ ID NO:3

SEQ ID NO: 42 is the amino acid sequence encoded by SEQ ID NO:4

SEQ ID NO: 43 is the amino acid sequence encoded by SEQ ID NO:5

SEQ ID NO: 44 is the amino acid sequence encoded by SEQ ID NO:6

SEQ ID NO: 45 is the amino acid sequence encoded by SEQ ID NO:7

SEQ ID NO: 46 is the amino acid sequence encoded by SEQ ID NO:8

SEQ ID NO: 47 is the amino acid sequence encoded by SEQ ID NO:9

SEQ ID NO: 48 is the amino acid sequence encoded by SEQ ID NO:10

SEQ ID NO: 49 is the amino acid sequence encoded by SEQ ID NO:11

SEQ ID NO: 50 is the amino acid sequence encoded by SEQ ID NO:12

SEQ ID NO: 51 is the amino acid sequence encoded by SEQ ID NO:13

SEQ ID NO: 52 is the amino acid sequence encoded by SEQ ID NO:14

SEQ ID NO: 53 is the amino acid sequence encoded by SEQ ID NO:15

SEQ ID NO: 54 is the amino acid sequence encoded by SEQ ID NO:16

SEQ ID NO: 55 is the amino acid sequence encoded by SEQ ID NO:17

SEQ ID NO: 56 is the amino acid sequence encoded by SEQ ID NO:18

SEQ ID NO: 57 is the amino acid sequence encoded by SEQ ID NO:19

SEQ ID NO: 58 is the amino acid sequence encoded by SEQ ID NO:20

SEQ ID NO: 59 is the amino acid sequence encoded by SEQ ID NO:21

SEQ ID NO: 60 is the amino acid sequence encoded by SEQ ID NO:22

SEQ ID NO: 61 is the amino acid sequence encoded by SEQ ID NO:23

SEQ ID NO: 62 is the amino acid sequence encoded by SEQ ID NO:24

SEQ ID NO: 63 is the amino acid sequence encoded by SEQ ID NO:25

SEQ ID NO: 64 is the amino acid sequence encoded by SEQ ID NO:26

SEQ ID NO: 65 is the amino acid sequence encoded by SEQ ID NO:27

SEQ ID NO: 66 is the amino acid sequence encoded by SEQ ID NO:28

SEQ ID NO: 67 is the amino acid sequence encoded by SEQ ID NO:29

SEQ ID NO: 68 is the amino acid sequence of a delta-5 elongase from *Pavlova*

SEQ ID NO: 69 is the amino acid sequence encoded by SEQ ID NO:30

SEQ ID NO: 70 is the amino acid sequence encoded by SEQ ID NO:31

SEQ ID NO: 71 is the amino acid sequence encoded by SEQ ID NO:32

SEQ ID NO: 72 is the amino acid sequence encoded by SEQ ID NO:33

SEQ ID NO: 73 is the amino acid sequence encoded by SEQ ID NO:34

SEQ ID NO: 74 is the amino acid sequence encoded by SEQ ID NO:35

SEQ ID NO: 75 is the amino acid sequence encoded by SEQ ID NO:36

SEQ ID NO: 76 is the amino acid sequence of a delta-4 desaturase from *Isochrysis galbana*

SEQ ID NO: 77 is the amino acid sequence of a delta-4 desaturase from *Schizochytrium aggregatum*

SEQ ID NO: 78 is the amino acid sequence encoded by SEQ ID NO:37

SEQ ID NO: 79 is the amino acid sequence encoded by SEQ ID NO:38

SEQ ID NO: 80 is a nucleotide sequence from *Sordaria macrospora* encoding subunit 1 of ATP:citrate lyase SEQ ID NO: 81 is the amino acid sequence encoded by SEQ ID NO: 80

SEQ ID NO: 82 is a nucleotide sequence from *Sordaria macrospora* encoding subunit 2 of ATP:citrate lyase SEQ ID NO: 83 is the amino acid sequence encoded by SEQ ID NO: 82

SEQ ID NO: 84 is a synthetic nucleotide sequence encoding a delta-4 desaturase, codon-optimized for expression in *S. cerevisiae*

SEQ ID NO: 85 is a synthetic nucleotide sequence encoding a delta-9 elongase, codon-optimized for expression in *S. cerevisiae*

SEQ ID NO: 86 is a synthetic nucleotide sequence encoding a delta-8 desaturase, codon-optimized for expression in *S. cerevisiae*

SEQ ID NO: 87 is a nucleotide sequence from *Saccharomyces kluyveri* encoding an omega-3 desaturase SEQ ID NO: 88 is the amino acid sequence encoded by SEQ ID NO: 87

SEQ ID NO: 89 is a nucleotide sequence from *Mortierella alpina* encoding an omega-3 desaturase SEQ ID NO: 90 is the amino acid sequence encoded by SEQ ID NO: 89

SEQ ID NO: 92 is the amino acid sequence encoded by SEQ ID NO: 91

SEQ ID NO: 93 is a nucleotide sequence from *Aspergillus parasiticus* encoding a delta-12 desaturase SEQ ID NO: 94 is the amino acid sequence encoded by SEQ ID NO: 93

SEQ ID NO: 95 is a nucleotide sequence from *Pichia pastoris* encoding a delta-12 desaturase SEQ ID NO: 96 is the amino acid sequence encoded by SEQ ID NO: 95

SEQ ID NO: 97 is a nucleotide sequence from *Marchantia polymorpha* encoding a delta-6 desaturase SEQ ID NO: 98 is the amino acid sequence encoded by SEQ ID NO: 97

SEQ ID NO: 99 is a nucleotide sequence from *Cyprinus carpio* encoding a delta-6/delta-5 desaturase SEQ ID NO: 100 is the amino acid sequence encoded by SEQ ID NO: 99

SEQ ID NO: 101 is a nucleotide sequence from *Salmo salar* encoding a delta-6/delta-5 elongase SEQ ID NO: 102 is the amino acid sequence encoded by SEQ ID NO: 101

SEQ ID NO: 103 is a nucleotide sequence from *Marchantia polymorpha* encoding a delta-6 elongase SEQ ID NO: 104 is the amino acid sequence encoded by SEQ ID NO: 103

SEQ ID NO: 105 is a nucleotide sequence from *Salmo salar* encoding a delta-5 desaturase SEQ ID NO: 106 is the amino acid sequence encoded by SEQ ID NO: 105

SEQ ID NO: 107 is a nucleotide sequence from *Marchantia polymorpha* encoding a delta-5 desaturase SEQ ID NO: 108 is the amino acid sequence encoded by SEQ ID NO: 107

SEQ ID NO: 109 is a nucleotide sequence from *Pavlova lutheri* encoding a delta-4 desaturase SEQ ID NO: 110 is the amino acid sequence encoded by SEQ ID NO: 109

SEQ ID NO: 111 is a nucleotide sequence from *Saprolegna diclina* encoding a omega-3 desaturase SEQ ID NO: 112 is the amino acid sequence encoded by SEQ ID NO: 111

SEQ ID NO: 113 is a nucleotide sequence from *Saccharomyces kluyveri* encoding a delta-12 desaturase SEQ ID NO: 114 is the amino acid sequence encoded by SEQ ID NO: 113

DETAILED DESCRIPTION OF THE INVENTION

It should be understood that any feature and/or aspect discussed above in connection with the methods according to the invention apply by analogy to the uses. All patent and non-patent references cited in the present application, are hereby incorporated by reference in their entirety. As will be apparent, preferred features and characteristics of one aspect of the invention may be applicable to other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The present inventors have developed a novel, alternate and highly cost effective method for producing a polyunsaturated fatty acid by construction and engineering of non-plant host cells, especially microorganisms, for producing PUFAs with four or more double bonds from non-fatty acid substrates through heterologous expression of an oxygen requiring pathway.

The invention relates to the construction and engineering of such non-plant host cells for heterologous production of mono unsaturated fatty acids and PUFAs, including oleic acid, linoleic acid, alpha-linolenic, gamma-linoleic acid, dihomo-gamma-linolenic acid, arachidonic acid, 5,8,11,14,17-eicosapentaenoic acid (EPA), docosatetraenoic acid, stearidonic acid, eicosatetraenoic acid, 7,10,13,16,19-docosapentaenoic acid and 4,7,10,13,16,19-docosahexaenoic acid (DHA).

Figure 1:
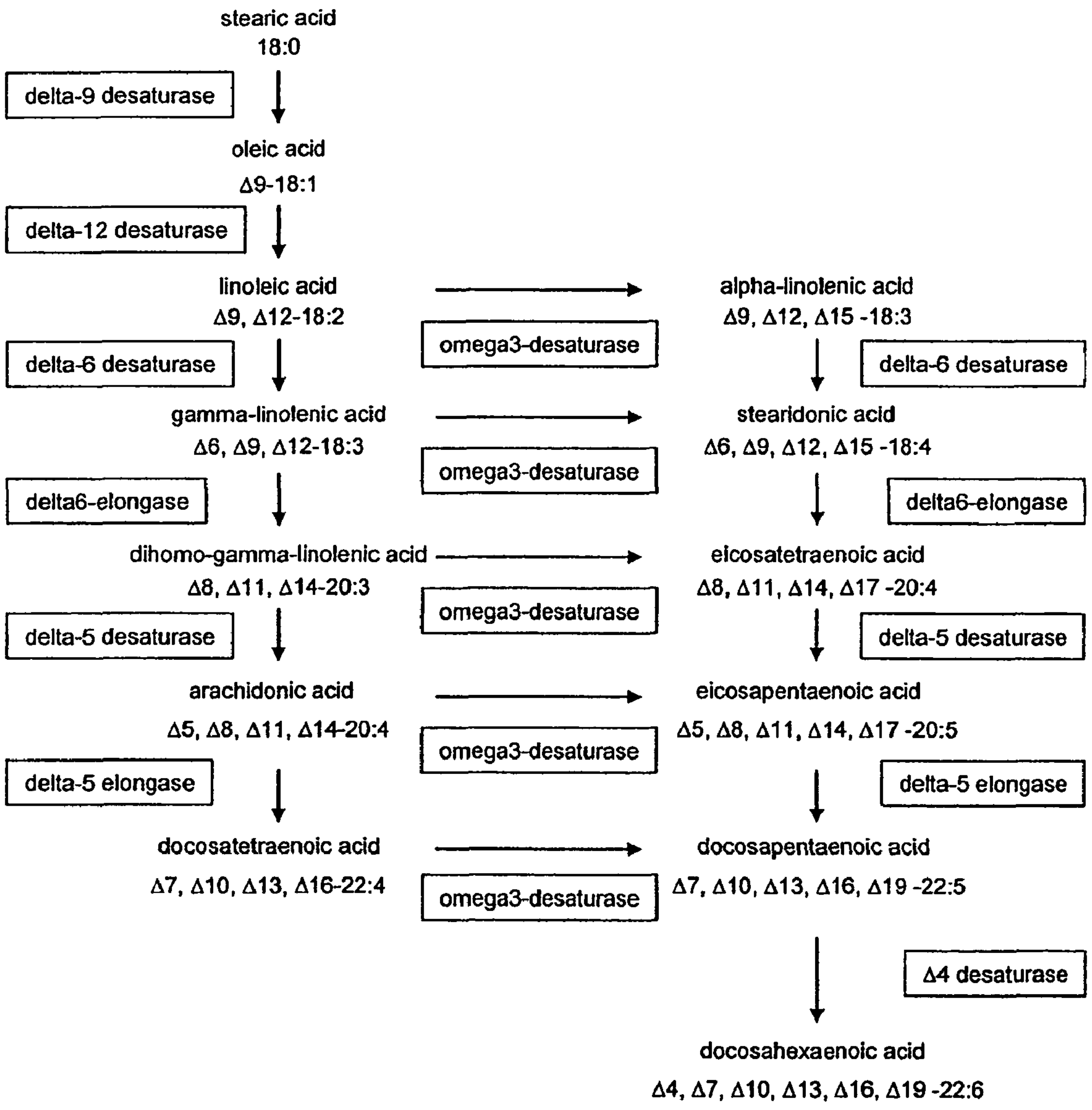
FIG. 1: Synthesis of polyunsaturated fatty acids in a genetically engineered microorganism (omega-6 delta/delta-6 and omega-3 delta/delta-6 pathway using delta-6 desaturase and delta-6 elongase)
Figure 2:
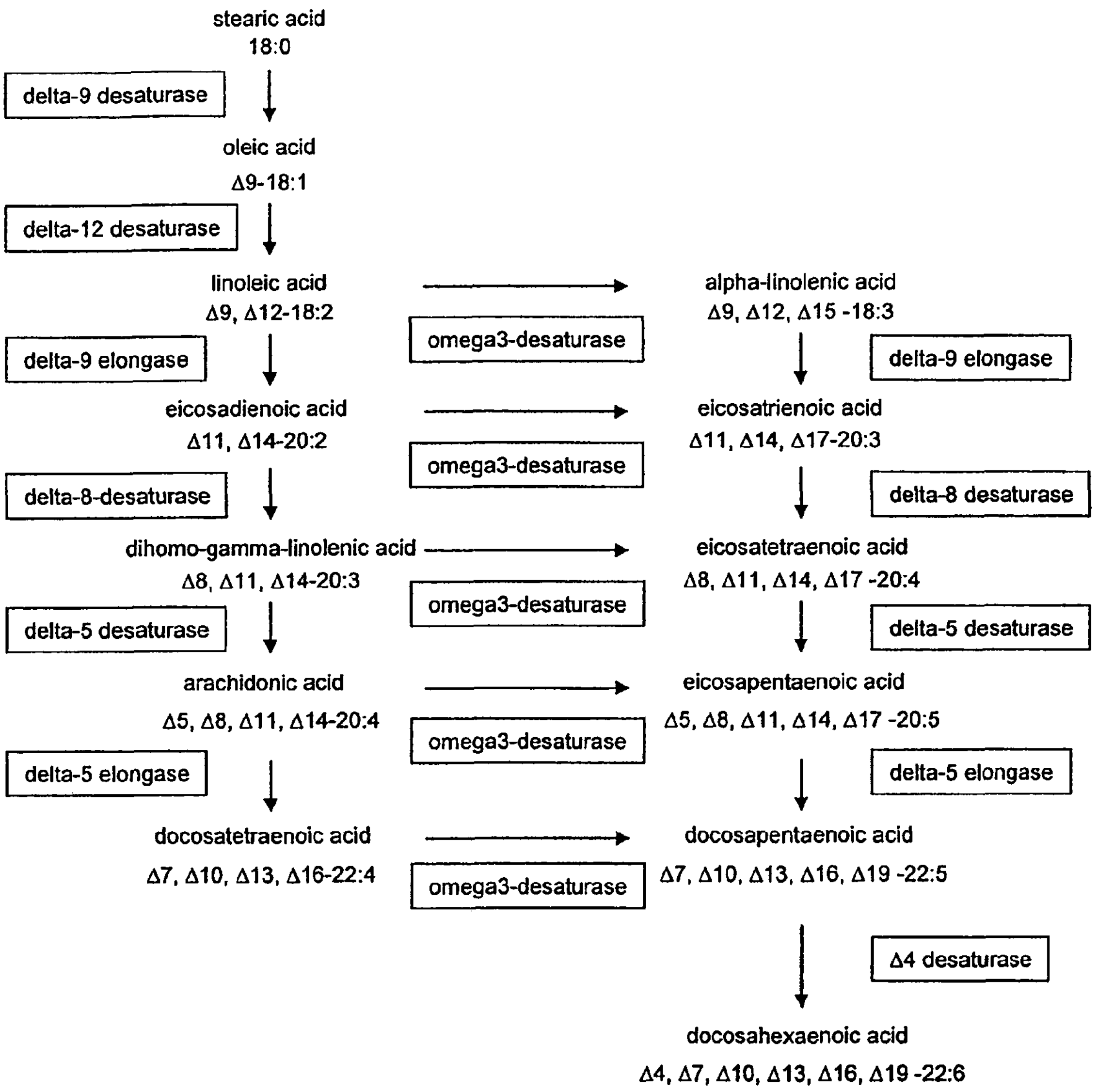
FIG. 2: Synthesis of polyunsaturated fatty acids in a genetically engineered microorganism (omega-6 delta/delta-8 and omega-3 delta/delta-8 pathway using delta-9 elongase and delta-8 desaturase)

The invention involves genetically modified non-plant host cells, especially microorganisms, containing a heterologous pathway from stearic acid to mono unsaturated fatty acids and PUFAs, e.g. oleic acid, arachidonic acid, DHA or EPA through expression of heterologous genes encoding the following enzymes delta-9 desaturase, delta-12 desaturase, delta-9 elongase, delta-8 desaturase, omega-3 desaturase, delta-6 desaturase, delta-6 elongase, delta-5 desaturase, delta-5 elongase, delta-4 desaturase or subsets hereof (FIG. 1 and FIG. 2).

Thus, in one aspect, the present invention provides a method for producing polyunsaturated fatty acids with four or more double bonds comprising heterologous expression of an oxygen requiring pathway in a non-plant host cell grown on a non-fatty acid substrate. In a particular preferred embodiment said non-fatty acid substrate is the exclusive carbon source.

In the present context the term "polyunsaturated fatty acid" relates to a long hydrocarbon chain composed of 18 or more carbon atoms having at least 4 double bonds and a terminal carboxylate group.

In a preferred embodiment the polyunsaturated fatty acid produced by the method of the present invention relates to polyunsaturated fatty acids with at least 4 double bonds, such as 4 double bonds, 5 double bonds or 6 double bonds.

As the skilled artisan would recognise, a fatty acid may be esterified to form triglycerides and/or phospholipids as well as sphingolipids. Thus, in one embodiment the present invention also relates to such esterified products. Furthermore, the fatty acid product of the present invention can be free fatty acids. Free fatty acids have a free carboxyl group, are not chemically connected to any other compound including triacylglycerides, phospholipids or sphingolipids, and can be present freely in any compartment of the cell.

By "expression", it is meant the production of a functional polypeptide through the transcription of a nucleic acid segment into mRNA and translation of the mRNA into a protein. By "heterologous expression", it is generally meant that a nucleic acid, not naturally present in the host genome, is present in the host cell and is operably linked to promoter and terminator nucleic acid sequences in a way so it is expressed in the host cell.

Also, in the present context heterologous expression further relates to the presence of a nucleic acid with a similar function to a naturally present nucleic acid, wherein the expression of said heterologous nucleic acid product changes the fatty acid composition.

For example, expression in yeast of a fungal delta-9 desaturase with different substrate specificity than the native yeast delta-9 desaturase changes the fatty acid composition of yeast (Example 36).

Said nucleic acid may be contained on an extrachromosomal nucleic acid construct or may be integrated in the host genome. Methods for isolation of nucleic acids for heterologous expression and preferred embodiments of heterologous expression are further described in details below.

By heterologous expression of a pathway is meant that several genes are expressed heterologously, whose gene products constitute steps in a pathway, not naturally present in the host.

An oxygen-requiring pathway shall mean that at least one of the enzymes in the pathway requires oxygen to function. For example the expression of nucleic acids coding for desaturase usually leads to a pathway that requires oxygen for activity as desaturases usually are oxygen-requiring enzymes.

In the present context, a "non-fatty acid substrate" relates to any substrate, but not a fatty acid, with two or more carbon atoms, such as but not limited to sugars, such as glucose, mannose, fructose, sucrose, galactose, lactose, erythrose, threose, ribose, glyceraldehyde, dihydroxyacetone, ribulose, cellobiose, starch, glycogen, trehalose, maltose, maltotriose, xylose, arabinose, stachyose, raffinose, or non-fermentable carbon source, such as but not limited to ethanol, lactate, acetate and glycerol.

Usually, a living organism needs a supply of many or all of the macroelements such as carbon, sulphur, phosphor, nitrogen, oxygen or hydrogen. An organism may grow on mixtures of different carbon sources, such as a fatty acid substrate and a non-fatty acid substrate. If a substrate or substrates is referred to an exclusive carbon or exclusive carbon sources, it is only that substrate or those substrates that is supplied to the organism as a carbon source. This shall not exclude other macroelements or other nutritional requirements, such as requirements for example for trace elements and vitamins. For example, if a non-fatty acid substrate is exclusively supplied as a carbon source. This means, it is only that non-fatty acid that is supplied as a carbon source without supplying another carbon source. However, this does not exclude other macroelements or other nutritional requirements.

In the present context the term "non-plant host cell" relates to host cells selected from the group consisting of microorganisms, animals, fungi, bacteria, invertea (insects) or protozoa. In particular, it relates to microscopic organisms, including bacteria, unicellular algae, protozoans and microscopic fungi, including yeast.

More specifically, the microorganism may be a fungus, and more specifically a filamentous fungus belonging to the genus of *Aspergillus*, e.g. *A. niger, A. awamori, A. oryzae, A. nidulans*, a yeast belong to the genus of *Saccharomyces*, e.g. *S. cerevisiae, S. kluyveri, S. bayanus, S. exiguus, S. sevazzi, S. uvarum*, a yeast belonging to the genus *Kluyveromyces*, e.g. *K. lactis K. marxianus* var. *marxianus, K. thermotolerans*, a yeast belonging to the genus *Candida*, e.g. *C. utilis, C. tropicalis, C. albicans, C. lipolytica, C. versatilis*, a yeast belonging to the genus *Pichia*, e.g. *P. stipidis, P. pastoris, P. sorbitophila*, or other yeast genus, e.g. *Cryptococcus, Debaromyces, Hansenula, Pichia, Yarrowia, Zygosaccharomyces* or *Schizosaccharomyces*, but are not limited to these examples. Concerning other microorganisms a non-exhaustive list of suitable filamentous fungi is supplied: a species belonging to the genus *Penicillium, Rhizopus, Fusarium, Fusidium, Gibberella, Mucor, Mortierella, Trichoderma*, among others.

Concerning bacteria a non-exhaustive list of suitable bacteria is given as follows: a species belonging to *Bacillus*, a species belonging to the genus *Escherichia*, a species belonging to the genus *Lactobacillus*, a species belonging to the genus *Corynebacterium*, a species belonging to the genus *Acetobacter*, a species belonging to the genus *Acinetobacter*, a species belonging to the genus *Pseudomonas*, etc. The preferred microorganisms of the invention may be *S. cerevisiae, A. niger, Escherichia coli* or *Bacillus subtilis*.

In a presently preferred embodiment the preferred microorganisms of the invention is *S. cerevisiae* for a number of reasons. *S. cerevisiae* is a well know model organism, and has undergone tremendous research for thousands of years, its physiology is well understood, and analytical tools are available to invenstigate the metabolism at any level, such as the genome level, the transcript level, the protein level, the metabolite level and the flux level. Hence this allows rapidly the development of metabolic engineering strategies and therefore the identification of efficient genetic engineering targets in order to improve the PUFA yield and production rates. Besides this, *Saccharomyces cerevisiae* has GRAS status, and fermentation technology is well established. The constructed and engineered microorganism can be cultivated using commonly known processes, including chemostat, batch, fed-batch cultivations, etc.

In a specific aspect, the invention relates to a method for producing polyunsaturated fatty acids with four or more double bonds comprising heterologous expression of an oxygen requiring pathway in a non-plant host cell grown on a non-fatty acid substrate, with the proviso that said method does not comprise combining the heterologous expression of nucleotide sequences encoding delta-12 desaturase, delta-6 desaturase, delta-6 elongase, and delta-5 desaturase in a host cell.

In a preferred embodiment, a method for producing polyunsaturated fatty acids with four or more double bonds is provided comprising heterologous expression of an oxygen requiring pathway in a non-plant host cell grown on a non-fatty acid substrate, wherein said heterologous expression increases the content of each individual specific polyunsaturated fatty acid of particularly ARA, EPA and DHA to more than 2% of the total fatty acid content. The content of intermediate PUFAs on the biosynthetic pathway towards ARA, EPA or DHA can be more than 2% but does not need to be more than 2%. The increase of PUFA content is described in more details below.

One aspect of the present invention relates to simultaneous heterologous expression of at least 4 specific genes for production of PUFAs.

Thus, in one embodiment the present invention relates to a method for producing polyunsaturated fatty acids with four or more double bonds comprising heterologous expression of an oxygen requiring pathway in a *Saccharomyces cerevisiae* grown on a non-fatty acid substrate, wherein the heterologous expression comprises combining heterologous expression of nucleotide sequences encoding delta-12 desaturase, delta-6 desaturase, delta-6 elongase, and delta-5 desaturase.

In another embodiment the present invention relates to a method for producing polyunsaturated fatty acids with four or more double bonds comprising heterologous expression of an oxygen requiring pathway in a *Saccharomyces cerevisiae* grown on a non-fatty acid substrate, wherein the heterologous expression comprises combining heterologous expression of nucleotide sequences encoding delta-12 desaturase, delta-9 elongase, delta-8 desaturase, and delta-5 desaturase.

Specifically, one embodiment describes a method for producing a polyunsaturated fatty acid comprising the steps of (a) isolating at least 4 nucleotide sequences, each having identity of at least 75% to one of the nucleotide sequence selected from the group consisting of SEQ ID NO: 1-38;
(b) constructing a vector comprising said isolated nucleotide sequences of step (a);
(c) transforming the vector of step (b) into a host cell for a time and under conditions sufficient for expression of proteins encoded by said isolated nucleotide sequences of step (a);
(d) exposing said host cell to a non-fatty acid substrate, whereby said non-fatty acid substrate is converted by said host into a desired polyunsaturated fatty acid product.

and obtaining said polyunsaturated fatty acid.

More specifically, one embodiment describes a method for producing a polyunsaturated fatty acid comprising the steps of (a) isolating at least 4 nucleotide sequences encoding delta-12 desaturase, delta-6 desaturase, delta-6 elongase, and delta-5 desaturase
(b) constructing one or more vectors comprising said isolated nucleotide sequences of step (a) and/or integrating said isolated nucleotide sequences into the genome of *Saccharomyces cerevisiae;*
(c) optionally, transforming said vector(s) of step (b) into a *Saccharomyces cerevisiae* for a time and under conditions sufficient for expression of proteins encoded by said isolated nucleotide sequences of step (a);
(d) growing said *Saccharomyces cerevisiae* on a non-fatty acid substrate, whereby said non-fatty acid substrate is converted by said host into a desired polyunsaturated fatty acid product and obtaining said polyunsaturated fatty acid.

Another embodiment describes a method for producing a polyunsaturated fatty acid comprising the steps of (a) isolating at least 4 nucleotide sequences encoding delta-12 desaturase, delta-9 elongase, delta-8 desaturase, and delta-5 desaturase
(b) constructing one or more vectors comprising said isolated nucleotide sequences of step (a) and/or integrating said isolated nucleotide sequences into the genome of *Saccharomyces cerevisiae;*
(c) optionally, transforming said vector(s) of step (b) into a *Saccharomyces cerevisiae* for a time and under conditions sufficient for expression of proteins encoded by said isolated nucleotide sequences of step (a);
(d) growing said *Saccharomyces cerevisiae* on a non-fatty acid substrate, whereby said non-fatty acid substrate is converted by said host into a desired polyunsaturated fatty acid product and obtaining said polyunsaturated fatty acid.

As mentioned elsewhere, the heterologous expression may further comprise heterologous expression of a nucleotide sequence encoding delta-9 desaturase, delta-5 elongase, omega-3 desaturase, and/or delta-4 desaturase.

Specifically, wherein SEQ ID NO: 1-4 encode delta-9 desaturases, wherein SEQ ID NO: 5-10, 93, 95, 113 encode delta-12 desaturases, wherein SEQ ID NO: 11-15, 97, 99 encode delta-6 desaturases, wherein SEQ ID NO: 16-21, 101, 103 encode delta-6 elongases, wherein SEQ ID NO: 22-27, 105, 107 encode delta-5 desaturases, wherein SEQ ID NO: 30-34, 87, 89, 111 encode omega-3 desaturases, wherein SEQ ID NO: 19, SEQ ID NO: 19, 28-29, 101 encode delta-5 elongases wherein SEQ ID NO: 35-36, 109 encode delta-4 desaturases, wherein SEQ ID NO: 37 encode delta-9 elongase and wherein SEQ ID NO: 38 encode delta-8 desaturase.

In one embodiment, the present invention relates to a method for producing a polyunsaturated fatty acid comprising combining the heterologous expression of genes encoding delta-12 desaturase, delta-6 desaturase, delta-6 elongase, and delta-5 desaturase in a host cell.

In another embodiment the invention relates to a method for producing polyunsaturated fatty acids with four or more double bonds comprising heterologous expression of an oxygen requiring pathway in a *Saccharomyces cerevisiae* host cell grown on exclusively non-fatty acid substrates as carbon sources, which is the exclusive carbon source.

The expression of said four genes allows the production of arachidonic acid and/or one or more of its intermediate precursors in host cells that endogenously only produce fatty acids of up to 18 carbon atoms of length with up to one double bond.

Furthermore, expression of said pathway generally improves the production of arachidonic acid in a host cell and can also lead to improved production of one or more of its intermediate precursors. A general advantage of this method is that it allows the use of non-fatty acid substrates, such as sugars. However, fatty acid-containing substrates, such as oils derived from, for example, plants, animals or microorganisms, can also be used.

In another embodiment of the present invention, a method for producing a polyunsaturated fatty acid is provided, comprising combining the heterologous expression of genes encoding delta-12 desaturase, delta-9 elongase, delta-8 desaturase, and delta-5 desaturase in a host cell.

The expression of said four genes allows the production of arachidonic acid and or one or more of its intermediate precursors in host cells that endogenously produces only fatty acids of up to 18 carbon atoms of length with up to one double bond.

Besides this, expression of said pathway generally improves the production of arachidonic acid and/or one or more of its intermediate precursors in a host cell. A general advantage of this method is that it allows the use of non-fatty acid substrates, such as sugars. However, fatty acid-containing substrates, such as oils derived for example from plants, animals or microorganisms, can also be used.

In a third embodiment, the present invention relates to a method for producing polyunsaturated fatty acids comprising combining the heterologous expression of genes encoding delta-12 desaturase, delta-6 desaturase, delta-6 elongase, delta-5 desaturase and delta-5 elongase in a host cell.

The expression of said five genes allows the production of docosatetraenoic acid, more specifically omega-6 docosatetraenoic acid and/or one or one more of its intermediate precursors in host cells that endogenously produce only fatty acids of up to 18 carbon atoms of length with up to one double bond.

Furthermore, expression of said pathway generally improves the production of omega-6 docosatetraenoic acid in a host cell and can also lead to improved production of one or more of its intermediate precursors. A general advantage of this method is that it allows the use of non-fatty acid substrates, such as sugars. However, fatty acid-containing substrates, such as oils derived from, for example, plants, animals or microorganisms, can also be used.

In another embodiment, the present invention relates to a method for producing a polyunsaturated fatty acid comprising combining the heterologous expression of genes encoding delta-12 desaturase, delta-9 elongase, delta-8 desaturase, delta-5 desaturase and delta-5 elongase in a host cell.

The expression of said five genes allows the production of docosatetraenoic acid, more specifically omega-6 docosatetraenoic acid and or one or more of its intermediate precursors in host cells that endogenously produce only fatty acids of up to 18 carbon atoms of length with up to one double bond.

Furthermore, expression of said pathway generally improves the production of omega-6 docosatetraenoic acid in a host cell and can also lead to improved production of one or more of its intermediate precursors. A general advantage of this method is that it allows the use of non-fatty acid substrates, such as sugars. However, fatty acid-containing substrates, such as oils derived from, for example, plants, animals or microorganisms, can also be used.

In a further embodiment, the present invention relates to a method for producing a polyunsaturated fatty acid comprising combining the heterologous expression of genes encoding delta-12 desaturase, delta-6 desaturase, delta-6 elongase, delta-5 desaturase and omega-3 desaturase in a host cell.

The expression of said five genes allows not only the production of omega-6 fatty acids, but also the production of omega-3 fatty acids, simultaneously or not, in host cells that endogenously only produce fatty acids of up to 18 carbon atoms of length with up to one double bond. In particular, the expression of said five genes allows the production of eicosapentaenoic acid in said host cells.

Furthermore, the expression of said five genes generally improves the production of eicosapentaenoic acid and/or one or more of its intermediate precursors, including arachidonic acid, in a host cell. A general advantage of this method is that it allows the use of non-fatty acid substrates, such as sugars. However, fatty acid-containing substrates, such as oils derived from, for example, plants, animals or microorganisms, can also be used.

In yet another embodiment, the present invention relates to a method for producing a polyunsaturated fatty acid comprising combining the heterologous expression of genes encoding delta-12 desaturase, delta-9 elongase, delta-8 desaturase, and delta-5 desaturase and omega-3 desaturase in a host cell.

The expression of said five genes allows not only the production of omega-6 fatty acids, but also the production of omega-3 fatty acids, simultaneously or not, in host cells that endogenously produce only fatty acids of up to 18 carbon atoms of length with up to one double bond. In particular, the expression of said five genes allows the production of eicosapentaenoic acid in said host cells.

Furthermore, the expression of said five genes generally improves production of eicosapentaenoic acid and/or one or more of its intermediate precursors, including arachidonic acid, in a host cell. A general advantage of this method is that it allows the use of non-fatty acid substrates, such as sugars. However, fatty acid-containing substrates, such as oils derived from, for example, plants, animals or microorganisms, can also be used.

In a further embodiment, the present invention relates to a method for producing a polyunsaturated fatty acid comprising combining the heterologous expression of genes encoding delta-12 desaturase, delta-6 desaturase, delta-6 elongase, delta-5 desaturase, omega-3 desaturase and delta-5 elongase in a host cell.

The expression of said six genes allows not only the production of omega-6 fatty acids, but also the production of omega-3 fatty acids, simultaneously or not, in host cells that endogenously only produce fatty acids of up to 18 carbon atoms of length with up to one double bond. In particular, it allows the production of docosapentaenoic acid in said host cells.

Furthermore, the expression of said six genes generally improves production of docosapentaenoic acid and/or one or more of its intermediate precursors, including docosatetraenoic acid, in a host cell. A general advantage of this method is that it allows the use of non-fatty acid substrates, such as sugars. However, fatty acid-containing substrates, such as oils derived from, for example, plants, animals or microorganisms, can also be used.

In another embodiment, the present invention relates to a method for producing a polyunsaturated fatty acid comprising combining the heterologous expression of genes encoding delta-12 desaturase, delta-9 elongase, delta-8 desaturase, delta-5 desaturase omega-3 desaturase and delta-5 elongase in a host cell.

The expression of said six genes allows not only the production of omega-6 fatty acids, but also the production of omega-3 fatty acids, simultaneously or not, in host cells that endogenously produce only fatty acids of up to 18 carbon atoms of length with up to one double bond. In particular, it allows the production of docosapentaenoic acid in said host cells.

Furthermore, the expression of said six genes generally improves production of docosapentaenoic acid and/or one or more of its intermediate precursors, including docosatetraenoic acid, in a host cell. A general advantage of this method is that it allows the use of non-fatty acid substrates, such as sugars. However, fatty acid-containing substrates, such as oils derived from, for example, plants, animals or microorganisms, can also be used.

In another embodiment, the present invention relates to a method for producing a polyunsaturated fatty acid comprising combining the heterologous expression of genes encoding delta-12 desaturase, delta-6 desaturase, delta-6 elongase, delta-5 desaturase, omega-3 desaturase, delta-5 elongase and delta-4 desaturase in a host cell.

The expression of said seven genes allows not only the production of omega-6 fatty acids, but also the production of omega-3 fatty acids, simultaneously or not, in host cells that endogenously produce only fatty acids of up to 18 carbon atoms of length with up to one double bond. In particular, it allows the production of docosahexaenoic acid in said host cells.

Furthermore, the expression of said seven genes generally improves the production of docosahexanenoic acid and/or one or more of its intermediate precursors, including docosatetraenoic acid, in a host cell. A general advantage of this method is that it allows the use of non-fatty acid substrates, such as sugars. However, fatty acid-containing substrates, such as oils derived from, for example, plants, animals or microorganisms, can also be used.

In another embodiment, the present invention relates to a method for producing a polyunsaturated fatty acid comprising combining the heterologous expression of genes encoding delta-12 desaturase, delta-9 elongase, delta-8 desaturase, delta-5 desaturase omega-3 desaturase, delta-5 elongase and delta-4 desaturase in a host cell.

The expression of said seven genes allows not only the production of omega-6 fatty acids, but also the production of omega-3 fatty acids, simultaneously or not, in a host that endogenously produces only fatty acids of up to 18 carbon atoms of length with up to one double bond. In particular, it allows the production of docosahexaenoic acid in said host cells.

Furthermore, the expression of said seven genes generally improves production of docosahexanenoic acid and/or one or more of its intermediate precursors, including docosatetraenoic acid, in a host cell. A general advantage of this method is that it allows the use of non-fatty acid substrates, such as sugars. However, fatty acid-containing substrates, such as oils derived for example from plants, animals or microorganisms, can also be used.

In another preferred embodiment, a method according to the present invention is provided, wherein any one of the different combinations of heterologous expression described above further comprises heterologous expression of a gene encoding a delta-9 desaturase that preferentially uses stearic acid as substrate. Expression of said gene encoding a stearic acid specific delta-9 desaturase allows a shift in the fatty acid composition from palmitoleic acid towards oleic acid as compared to an unmodified host cell. Expression of said gene in combination with one of the pathways described above for production of polyunsaturated fatty acids therefore further improves the production of polyunsaturated fatty acids.

In a particularly preferred embodiment, the present invention relates to a method for producing polyunsaturated fatty acids with four or more double bonds comprising heterologous expression of an oxygen requiring pathway in a *Saccharomyces cerevisiae* host cell grown on a non-fatty acid substrate or non-fatty acid substrates which is/are the exclusive carbon sources, wherein the combined heterologous expression consists of heterologous expression of nucleotide sequences encoding delta-12 desaturase, delta-6 desaturase, delta-6 elongase, and delta-5 desaturase.

In another particular preferred embodiment, the present invention relates to a method for producing polyunsaturated fatty acids with four or more double bonds comprising heterologous expression of an oxygen requiring pathway in a *Saccharomyces cerevisiae* host cell grown on a non-fatty acid substrate which is the exclusive carbon source, wherein the combined heterologous expression consists of heterologous expression of nucleotide sequences encoding delta-12 desaturase, delta-9 elongase, delta-8 desaturase, and delta-5 desaturase.

A further particular preferred embodiment relates to a method according to the present invention, wherein the combined heterologous expression further comprises heterologous expression of a nucleotide sequence encoding delta-5 elongase, omega-3 desaturase, and/or delta-4 desaturase.

Another further particular preferred embodiment relates to a method according to the present invention, wherein said combined heterologous expression further comprises heterologous expression of a nucleotide sequence encoding a delta-9 desaturase.

Substrate

The fermentation substrate for the production of PUFAs according to the present aspect maybe any complex medium or defined medium e.g. containing sugars, such as glucose, mannose, fructose, sucrose, galactose, lactose, erythrose, threose, ribose, glyceraldehyde, dihydroxyacetone, ribulose, cellobiose, starch, glycogen, trehalose, maltose, maltotriose, xylose, arabinose, stachyose, raffinose, or non-fermentable carbon sources, such as ethanol, acetate, lactate, or glycerol, or oils, such as oils derived from plants, animals or microorganisms or fatty acids, such as butyric acid, caproic acid, caprylic acid, capric acid, lauric acid, myristic acid, palmitic acid, stearic acid, arachidic acid, palmitoleic acid, oleic acid, elaidic acid, cis-vaccenic acid, linoleic acid, alpha-linolenic, gamma-linoleic acids, dihomo-gamma-linolenic acid, arachidonic acid, EPA, 7,10,13,16,19-docosapentaenoic acid and 4,7,10,13,16,19-docosahexaeonic acid DHA.

In the present context the term “host cell” relates to host cells selected from the group consisting of micro-organisms, animals, fungi, bacteria, invertea (insects), plants or protozoa. In particular, it relates to microscopic organisms, including bacteria, viruses, unicellular algae, protozoans and microscopic fungi including yeast. In a presently preferred embodiment the host cell is a non-plant host cell as described above.

More specifically, the microorganism may be a fungus, and more specifically a filamentous fungus belonging to the genus of *Aspergillus*, e.g. *A. niger, A. awamori, A. oryzae, A. nidulans*, a yeast belong to the genus of *Saccharomyces*, e.g. *S. cerevisiae, S. kluyveri, S. bayanus, S. exiguus, S. sevazzi, S. uvarum*, a yeast belonging to the genus *Kluyveromyces*, e.g. *K. lactis K. marxianus* var. *marxianus, K. thermotolerans*, a yeast belonging to the genus *Candida*, e.g. *C. utilis, C. tropicalis, C. albicans, C. lipolytica, C. versatilis*, a yeast belonging to the genus *Pichia*, e.g. *P. stipidis, P. pastoris, P. sorbitophila*, or other yeast genus, e.g. *Cryptococcus, Debaromyces, Hansenula, Pichia, Yarrowia, Zygosaccharomyces* or *Schizosaccharomyces*. Concerning other microorganisms a non-exhaustive list of suitable filamentous fungi is supplied: a species belonging to the genus *Penicillium, Rhizopus, Fusarium, Fusidium, Gibberella, Mucor, Mortierella, Trichoderma*, among others.

Concerning bacteria a non-exhaustive list of suitable bacteria is given as follows: a species belonging to *Bacillus*, a species belonging to the genus *Escherichia*, a species belonging to the genus *Lactobacillus*, a species belonging to the genus *Corynebacterium*, a species belonging to the genus *Acetobacter*, a species belonging to the genus *Acinetobacter*, a species belonging to the genus *Pseudomonas*, etc., that are well known in the art.

The preferred microorganisms of the invention may be *S. cerevisiae, A. niger, Escherichia coli* or *Bacillus subtilis*. The constructed and engineered microorganism can be cultivated using commonly known processes, including chemostat, batch, fed-batch cultivations, etc.

Thus, in one preferred embodiment, the present invention relates to a method for producing a polyunsaturated fatty acid comprising combining heterologous expression of genes encoding various desaturases and elongases in a host cell as described herein, wherein said host cell is selected from the group consisting of plants, micro-organisms, animals, fungi, bacteria, invertea (insects) or protozoa.

In a particular preferred embodiment, the present invention relates to a method for producing a polyunsaturated fatty acid comprising combining heterologous expression of genes encoding various desaturases and elongases in a host cell as described herein, wherein said host cell is a fungus, and preferably, wherein said fungus is a filamentous fungus or a yeast.

In one embodiment said yeast is selected from the group of the genus *Saccharomyces, Kluyveromyces, Candida, Pichia, Cryptococcus, Debaromyces, Hansenula, Yarrowia, Zygosaccharomyces Schizosaccharomyces, Lipomyces*. In a preferred embodiment said yeast is *Saccharomyces cerevisiae*. In another embodiment said filamentous fungus is selected from the group of the genus *Aspergillus, Penicillium, Rhizopus, Fusarium, Fusidium, Gibberella, Mucor, Mortierella* or *Trichoderma*.

In further embodiment said *Aspergillus* is selected from the species *Aspergillus niger, Aspergillus awamori, Aspergillus oryzae* or *Aspergillus nidulans*. And in a presently most preferred embodiment, said host is *Aspergillus niger.*

In another preferred embodiment, the present invention relates to a method for producing a polyunsaturated fatty acid comprising combining heterologous expression of genes encoding various desaturases and elongases in a host cell as described i herein, wherein said host is a bacterium.

In one embodiment, said bacterium is selected from the group of *Bacillus, Escherichia, Lactobacillus, Corynebacterium, Acetobacter, Acinetobacter*, or *Pseudomonas*. In a presently most preferred embodiment said bacterium is *Bacillus subtilis*. In another presently most preferred embodiment said one host cell is *Escherichia coli.*

In a presently preferred embodiment, the present invention relates to a genetically modified *Saccharomyces cerevisiae* capable of producing polyunsaturated fatty acids with four or more double bonds when grown on a non-fatty acid substrate.

In a presently most preferred embodiment, the present invention relates to a genetically modified *Saccharomyces cerevisiae* according to the invention, wherein said *Saccharomyces cerevisiae* is capable of producing polyunsaturated fatty acids with four or more double bonds when grown on a non-fatty acid substrate as the exclusive carbon source.

Polyunsaturated Fatty Acid

In the context of the present invention, a polyunsaturated fatty acid relates to a chemical compound with a long hydrocarbon chain composed of 18 or more carbon atoms having at least 4 double bonds and a terminal carboxylate group, having at least 5 double bonds and a terminal carboxylate group or having 6 double bonds and a terminal carboxylate group.

When applying the specific heterologous genes described above several intermediate products may be formed, and thus such intermediate products are included in the present invention. However, in some or many cases some or all of the intermediate products may be present at low levels that may not be easy to detect.

In the present context these intermediate products could be oleic acid, linoleic acid, gamma-linolenic acid, dihomo-gamma-linoleic acid, eicosadienoic acid, particularly, eicosadienoic acid with double bonds in position 11 and 14, eicosatrienoic acid, particularly, eicosatrienoic acid with double bonds in position 11, 14, and 17, arachidonic acid, docosatetraenoic acid, particularly docosatetraenoic acid with double bonds at position 7, 10, 13, 16, alpha-linoleic acid, stearidonic acid, eicosatetraenoic acid, particularly eicosatetraenoic acid with double bonds in position 8, 11, 14 and 17, eicosapentaenoic acid, particularly eicosaoentaenoic acid with double bonds in position 5, 8, 11, 14 and 17 or docosapentaenoic acid.

In one preferred embodiment, a method according to the present invention is provided, wherein the polyunsaturated fatty acid comprises at least 4 double bonds, such as 4 double bonds, such as 5 double bonds and such as 6 double bonds. In another preferred embodiment, said polyunsaturated fatty acid is produced from a non-fatty acid substrate.

In one preferred embodiment, said polyunsaturated fatty acid is produced from a fatty acid substrate with less than 4 double bonds in host cells originally devoid of endogenous expression of at least one of the enzymes selected from the group consisting of delta-12 desaturase, delta-6 desaturase, delta-6 elongase, delta-5 desaturase, omega-3 desaturase, delta-5 elongase and delta-4 desaturase.

In another preferred embodiment the polyunsaturated fatty acid is selected from the group consisting of arachidonic acid, eicosapentaenoic acid and docosahexaenoic acid. In one preferred embodiment, said polyunsaturated fatty acid is arachidonic acid.

Specifically, a method for producing arachidonic acid is provided comprising (a) isolating a nucleotide sequence having at least 75% identity to at least one of the nucleotide sequences set forth in SEQ ID NO: 5-10, 93, 95, 113 isolating another nucleotide sequence having at least 75% identity to at least one of the nucleotide sequences set forth in SEQ ID NO: 11-15, 97, 99 isolating a third nucleotide sequence having at least 75% identity to at least one of the nucleotide sequences set forth in SEQ ID NO: 16-21, 101, 103 and isolating a fourth nucleotide sequence having at least 75% identity to at least one of the nucleotide sequences set forth in SEQ ID NO: 22-27, 99, 105, 107.

(b) constructing at least one vector comprising said isolated nucleotide sequences of step (a);

(c) transforming the vector(s) of step (b) into a host cell for a time and under conditions sufficient for expression of proteins encoded by said isolated nucleotide sequences of step (a)

(d) exposing said host cell, to a non-fatty acid substrate, whereby said non-fatty acid substrate is converted by said host into a desired polyunsaturated fatty acid product.

and obtaining said arachidonic acid.

Or, alternatively, the present invention relates to a method for producing arachidonic acid comprising (a) isolating a nucleotide sequence having at least 75% identity to at least one of the nucleotide sequences set forth in SEQ ID NO: 5-10, 93, 95, 113 isolating another nucleotide sequence having at least 75% identity to the nucleotide sequence set forth in SEQ ID NO: 37, isolating a third nucleotide sequence having at least 75% identity to the nucleotide sequence set forth in SEQ ID NO: 38 and isolating a fourth nucleotide sequence having at least 75% identity to at least one of the nucleotide sequences set forth in SEQ ID NO: 22-27, 99, 105, 107

(b) constructing at least one vector comprising said isolated nucleotide sequences of step (a);

(c) transforming the vector(s) of step (b) into a host cell for a time and under conditions sufficient for expression of proteins encoded by said isolated nucleotide sequences of step (a)

(d) exposing said host cell, to a non-fatty acid substrate, whereby said non-fatty acid substrate is converted by said host into a desired polyunsaturated fatty acid product.

and obtaining said arachidonic acid.

In another preferred embodiment, said polyunsaturated fatty acid is eicosapentaenoic acid.

Specifically, a method for producing eicosapentaenoic acid is provided comprising (a) isolating a nucleotide sequence having at least 75% identity to at least one of the nucleotide sequences set forth in SEQ ID NO: 5-10, 93, 95, 113 isolating another nucleotide sequence having at least 75% identity to at least one of the nucleotide sequences set forth in SEQ ID NO: 11-15, 97, 99 isolating a third nucleotide sequence having at least 75% identity to at least one of the nucleotide sequences set forth in SEQ ID NO: 16-21, 101, 103 isolating a fourth nucleotide sequence having at least 75% identity to at least one of the nucleotide sequences set forth in SEQ ID NO: 22-27, 99, 105, 107 and isolating a fifth nucleotide sequence having at least 75% identity to at least one of the nucleotide sequences set forth in SEQ ID NO: 30-34, 87, 89, 111;

(b) constructing at least one vector comprising said isolated nucleotide sequences of step (a);

(c) transforming the vector(s) of step (b) into a host cell for a time and under conditions sufficient for expression of proteins encoded by said isolated nucleotide sequences of step (a)

(d) exposing said host cell, to a non-fatty acid substrate, whereby said non-fatty acid substrate is converted by said host into a desired polyunsaturated fatty acid product.

and obtaining said eicosapentaenoic acid.

Or, alternatively, a method for producing eicosapentaenoic acid in provided comprising (a) isolating a nucleotide sequence having at least 75% identity to at least one of the nucleotide sequences set forth in SEQ ID NO: 5-10, 93, 95, 113 isolating another nucleotide sequence having at least 75% identity to the nucleotide sequence set forth in SEQ ID NO: 37, isolating a third nucleotide sequence having at least 75% identity to the nucleotide sequences set forth in SEQ ID NO: 38, isolating a fourth nucleotide sequence having at least 75% identity to at least one of the nucleotide sequences set forth in SEQ ID NO: 22-27, 99, 105, 107 and isolating a fifth nucleotide sequence having at least 75% identity to at least one of the nucleotide sequences set forth in SEQ ID NO: 30-34, 87, 89, 111;

(b) constructing at least one vector comprising said isolated nucleotide sequences of step (a);

(c) transforming the vector(s) of step (b) into a host cell for a time and under conditions sufficient for expression of proteins encoded by said isolated nucleotide sequences of step (a)

(d) exposing said host cell, to a non-fatty acid substrate, whereby said non-fatty acid substrate is converted by said host into a desired polyunsaturated fatty acid product.

and obtaining said eicosapentaenoic acid.

In one preferred embodiment, said polyunsaturated fatty acid is docosahexanoic acid.

Specifically, a method for producing docosahexaenoic acid is provided comprising (a) isolating a nucleotide sequence having at least 75% identity to at least one of the nucleotide sequences set forth in SEQ ID NO: 5-10, 93, 95, 113 isolating another nucleotide sequence having at least 75% identity to at least one of the nucleotide sequences set forth in SEQ ID NO: 11-15, 97, 99 isolating a third nucleotide sequence having at least 75% identity to at least one of the nucleotide sequences set forth in SEQ ID NO: 16-21, 101, 103 isolating a fourth nucleotide sequence having at least 75% identity to at least one of the nucleotide sequences set forth in SEQ ID NO: 22-27, 99, 105, 107 isolating a fifth nucleotide sequence having at least 75% identity to at least one of the nucleotide sequences set forth in SEQ ID NO: 30-34, 87, 89, 111 isolating a sixth nucleotide sequence having at least 75% identity to at least one of the nucleotide sequences set forth in SEQ ID NO: 19, 28, 29, 101 and isolating a seventh nucleotide sequence having at least 75% identity to at least one of the nucleotide sequences set forth in SEQ ID NO: 35-36, 109;

(b) constructing at least one vector comprising said isolated nucleotide sequences of step (a);

(c) transforming the vector(s) of step (b) into a host cell for a time and under conditions sufficient for expression of proteins encoded by said isolated nucleotide sequences of step (a)

(d) exposing said host cell, to a non-fatty acid substrate, whereby said non-fatty acid substrate is converted by said host into a desired polyunsaturated fatty acid product, and obtaining said docosahexaenoic acid.

Or, the present invention also relates to a method for producing docosahexaenoic acid comprising (a) isolating a nucleotide sequence having at least 75% identity to at least one of the nucleotide sequences set forth in SEQ ID NO: 5-10, 93, 95, 113 isolating another nucleotide sequence having at least 75% identity to the nucleotide sequence set forth in SEQ ID NO: 37, isolating a third nucleotide sequence having at least 75% identity the nucleotide sequence set forth in SEQ ID NO: 38, isolating a fourth nucleotide sequence having at least 75% identity to at least one of the nucleotide sequences set forth in SEQ ID NO: 22-27, 99 105, 107 isolating a fifth nucleotide sequence having at least 75% identity to at least one of the nucleotide sequences set forth in SEQ ID NO: 30-34, 87, 89, 111 isolating a sixth nucleotide sequence having at least 75% identity to at least one of the nucleotide sequences set forth in SEQ ID NO: 19, 28, 29, 101 and isolating a seventh nucleotide sequence having at least 75% identity to at least one of the nucleotide sequences set forth in SEQ ID NO: 35-36, 109;

(b) constructing at least one vector comprising said isolated nucleotide sequences of step (a);

(c) transforming the vector(s) of step (b) into a host cell for a time and under conditions sufficient for expression of proteins encoded by said isolated nucleotide sequences of step (a)

(d) exposing said host cell, to a non-fatty acid substrate, whereby said non-fatty acid substrate is converted by said host into a desired polyunsaturated fatty acid product, and obtaining said docosahexaenoic acid.

In yet another preferred embodiment, said polyunsaturated fatty acid is docosapentaenoic acid.

Specifically, a method for producing docosapentaenoic acid is provided comprising (a) isolating a nucleotide sequence having at least 75% identity to at least one of the nucleotide sequences set forth in SEQ ID NO: 5-10, 93, 95, 113 isolating another nucleotide sequence having at least 75% identity to at least one of the nucleotide sequences set forth in SEQ ID NO: 11-15, 97, 99 isolating a third nucleotide sequence having at least 75% identity to at least one of the nucleotide sequences set forth in SEQ ID NO: 16-21, 101, 103 isolating a fourth nucleotide sequence having at least 75% identity to at least one of the nucleotide sequences set forth in SEQ ID NO: 22-27, 99, 105, 107 isolating a fifth nucleotide sequence having at least 75% identity to at least one of the nucleotide sequences set forth in SEQ ID NO: 19, 28, 29, 101 and isolating a sixth nucleotide sequence having at least 75% identity to at least one of the nucleotide sequences set forth in SEQ ID NO: 30-34, 87, 89, 111;

(b) constructing at least one vector comprising said isolated nucleotide sequences of step (a);

(c) transforming the vector(s) of step (b) into a host cell for a time and under conditions sufficient for expression of proteins encoded by said isolated nucleotide sequences of step (a)

(d) exposing said host cell, to a non-fatty acid substrate, whereby said non-fatty acid substrate is converted by said host into a desired polyunsaturated fatty acid product, and obtaining said docosapentenoic acid.

In one preferred embodiment, the polyunsaturated fatty acid is docosatetraenoic acid.

Specifically, the present invention relates to a method for producing docosatetraenoic acid comprising (a) isolating a nucleotide sequence having at least 75% identity to at least one of the nucleotide sequences set forth in SEQ ID NO: 5-10, 93, 95, 113 isolating another nucleotide sequence having at least 75% identity to at least one of the nucleotide sequences set forth in SEQ ID NO: 11-15, 97, 99 isolating a third nucleotide sequence having at least 75% identity to at least one of the nucleotide sequences set forth in SEQ ID NO: 16-21, 101, 103 isolating a fourth nucleotide sequence having at least 75% identity to at least one of the nucleotide sequences set forth in SEQ ID NO: 22-27, 99, 105, 107 and isolating a fifth nucleotide sequence having at least 75% identity to at least one of the nucleotide sequences set forth in SEQ ID NO: 19, 28, 29, 101;

(b) constructing at least one vector comprising said isolated nucleotide sequences of step (a);

(c) transforming the vector(s) of step (b) into a host cell for a time and under conditions sufficient for expression of proteins encoded by said isolated nucleotide sequences of step (a)

(d) exposing said host cell, to a non-fatty acid substrate, whereby said non-fatty acid substrate is converted by said host into a desired polyunsaturated fatty acid product, and obtaining said docosatetraenoic acid.

In one embodiment, the present invention relates to the use of specific nucleotide sequences encoding delta-12 desaturases, more specifically SEQ ID NOs 5-10, 93, 95, 113, which encode the amino acid sequences SEQ ID NOs 43-48. Usually these delta-12 desaturase-encoding nucleotide sequences are used together with at least 3 or more additional nucleotides sequences. The minimum three additional sequences are either nucleotide sequences encoding delta-6 desaturase, delta-5 elongase, and delta-5 desaturase, or nucleotide sequences encoding delta-9 elongase, delta-8 desaturase and delta-5 desaturase. Additional sequences can be selected from sequences that are supplied in table 1. The same embodiment also relates to any delta-12 desaturase-encoding nucleotide sequence comprising or having at least 75% identity to any one of the nucleotide sequences SEQ ID NOs 5-10.

Specifically, a nucleotide sequence encoding a delta-12 desaturase is selected from the group consisting of a) the nucleotide sequences set forth in SEQ ID NOs 5-10, 93, 95 and 113; and b) nucleotide sequences having at least 75% identity to the nucleotide sequences set forth in SEQ ID NO: 5-10, 93, 95 and 113.

In the present context "delta-12 desaturase" relates to an enzyme that is capable of converting oleic acid to linoleic acid and the meaning shall not exclude other functionality of said enzyme.

In one embodiment, the present invention relates to use of a specific nucleotide sequence encoding delta-9 elongase, more specifically SEQ ID NO 37, which encode the amino acid sequence SEQ ID NO 79. Usually this delta-9 elongase-encoding nucleotide sequence is used together with at least 3 or more additional nucleotide sequences. The minimum three additional sequences are nucleotide sequences encoding delta-12 desaturase, delta-8 desaturase and delta-desaturase. Additional sequences can be selected from sequences that are supplied in table 1. The same embodiment also relates to any delta-9 elongase-encoding nucleotide sequence that comprise or has at least 75% identity to the nucleotide sequence SEQ ID NO 37.

In the present context "delta-9 elongase" relates to an enzyme that is capable of converting linoleic acid to eicosadienoic acid and/or alpha linoleic acid to eicosatrienoic acid and the meaning shall not exclude other functionality of said enzyme.

In one embodiment, the present invention relates to the use of specific nucleotide sequences encoding delta-9 desaturases, more specifically SEQ ID NOs 1-4, which encode the amino acid sequences SEQ ID NOs 39-42. Usually these delta-9 desaturase-encoding nucleotide sequences are used together with at least 4 or more additional nucleotide sequences. The minimum four additional sequences are either nucleotide sequences encoding delta-12 desaturase, delta-9 desaturase, delta-8 desaturase and delta-5 desaturase, or nucleotide sequences encoding delta-12 desaturase, delta-6 desaturase, delta-6 elongase and delta-5 desaturase. Additional sequences can be selected from sequences that are supplied in table 1. The same embodiment also relates to any delta-9 desaturase-encoding nucleotide sequence comprising or having at least 75% identity to any one of the nucleotide sequences SEQ ID NOs 1-4.

Specifically, a nucleotide sequence encoding a delta-9 desaturase is selected from the group consisting of a) the nucleotide sequences set forth in SEQ ID NOs 1-4; and b) nucleotide sequences having at least 75% identity to the nucleotide sequences set forth in SEQ ID NOs 1-4.

In the present context "delta-9 desaturase" relates to an enzyme that is capable of converting stearic acid to oleic acid and/or palmitic acid to palmitoleic acid, and the meaning shall not exclude other functionality of said enzyme.

In one embodiment, the present invention relates to the use of a specific nucleotide sequence encoding a delta-8 desaturases, more specifically SEQ ID NO 38, which endcodes the amino acid sequence SEQ ID NO 79. Usually delta-8 desaturase-encoding nucleotide sequences are used together with at least 3 or more additional nucleotides sequences. The minimum three additional sequences are nucleotide sequences encoding delta-12 desaturase, delta-9 elongase, and delta-5 desaturase. Additional sequences can be selected from sequences that are supplied in table 1. The same embodiment also relates to any delta-8 desaturase nucleotide sequence comprising or having at least 75% identity to the nucleotide sequence SEQ ID NO 38.

In the present context "delta-8 desaturase" relates to an enzyme capable of converting eicosadienoic acid to dihomo-gamma linolenic acid or eicosatrienoic acid to eicosatrienoic acid and the meaning shall not exclude other functionality of said enzyme.

In one embodiment, the present invention relates to use of specific nucleotide sequences encoding delta-6 desaturases, more specifically SEQ ID NOs 11-15, 97 and 99, which encode the amino acid sequences SEQ ID NOs 49-53, 98 and 100. Usually these delta-6 desaturase-encoding nucleotide sequences are used together with at least 3 or more additional nucleotide sequences. The minimum three additional sequences are nucleotide sequences encoding delta-12 desaturase, delta-6 elongase, and delta-5 desaturase. Additional sequences can be selected from sequences supplied in table 1. The same embodiment also relates to delta-6 desaturase-encoding nucleotide sequences comprising or having at least 75% identity to the nucleotide sequences SEQ ID NOs 11-15, 97 and 99.

Specifically, a nucleotide sequence encoding a delta-6 desaturase is selected from the group consisting of a) the nucleotide sequences set forth in SEQ ID NOs 11-15, 97 and 99; and
b) nucleotide sequences having at least 75% identity to any one of the nucleotide sequences set forth in SEQ ID NOs 11-15, 97 and 99.

In the present context "delta-6 desaturase" is an enzyme capable of converting linoleic acid to gamma-linolenic acid and/or alpha-linolenic to stearidonic acid and the meaning shall not exclude other functionality of said enzyme.

In one embodiment, the present invention relates to use of specific nucleotide sequences encoding delta-6 elongases, more specifically SEQ ID NOs 16-21, 101 and 103, which encode the amino acid sequences SEQ ID NOs 54-59, 102 and 104. Usually these delta-6 elongase-encoding nucleotide sequences are used together with at least 3 or more additional nucleotides sequences. The minimum three additional sequences are nucleotide sequences encoding delta-12 desaturase, delta-6 desaturase, and delta-5 desaturase. Additional sequences can be selected from sequences that are supplied in table 1. The same embodiment also relates to delta-6 elongase-encoding nucleotide sequences that comprise or have at least 75% identity to the nucleotide sequences SEQ ID NOs 16-21, 101 and 103.

Specifically, a nucleotide sequence encoding a delta-6 elongase is selected from the group consisting of a) the nucleotide sequences set forth in SEQ ID NOs 16-21, 101 and 103; and
b) nucleotide sequences having at least 75% identity to the nucleotide sequences set forth in SEQ ID NOs 16-21, 101 and 103.

In the present context "delta-6 elongase" relates to an enzyme capable of converting gamma-linoleic acid to dihomo-gamma-linolenic acid and/or stearidonic acid to eicosatetraenoic acid, and the meaning shall not exclude other functionality of said enzyme.

In one embodiment, the present invention relates to use of specific nucleotide sequences encoding delta-5 desaturases, more specifically SEQ ID NOs 22-27, 99, 105 and 107, which encode the amino acid sequences SEQ ID NOs 60-65, 100, 106 and 108. Usually these delta-5 desaturase-encoding nucleotide sequences are used together with at least 3 or more additional nucleotide sequences. The minimum three additional sequences are nucleotide sequences encoding delta-12 desaturase, delta-6 desaturase, and delta-6 elongase. Additional sequences can be selected from sequences that are supplied in table 1. The same embodiment also relates to delta-5 desaturase-encoding nucleotide sequences that comprise or have at least 75% identity to the nucleotide sequences SEQ ID NOs 22-27, 99, 105 and 107.

Specifically, a nucleotide sequence encoding a delta-5 desaturase is selected from the group consisting of a) the nucleotide sequences set forth in SEQ ID NO: 22-27, 99, 105 and 107; and
b) nucleotide sequences having at least 75% identity to the nucleotide sequences set forth in SEQ ID NO: 22-27, 99, 105 and 107.

In the present context "delta-5 desaturase" relates to an enzyme capable of converting dihomo-gamma-linolenic acid to arachidonic and/or eicosatetraenoic acid to eicosapentaenoic acid and the meaning shall not exclude other functionality of said enzyme.

In one embodiment, the present invention relates to use of specific nucleotide sequences encoding delta-5 elongases, more specifically SEQ ID NOs 19, 28-29 and 101, which encode the amino acid sequences SEQ ID NOs 66-67 and 102. In addition, it relates to nucleotide sequences encoding the amino acid sequence SEQ ID NO 68. Usually these delta-5 elongase-encoding nucleotide sequences are used together with at least 4 or more additional nucleotides sequences. The minimum four additional sequences are either nucleotide sequences encoding delta-12 desaturase, delta-6 desaturase, delta-6 elongase and delta-5 desaturase, or nucleotide sequences encoding delta-12 desaturase, delta-9 elongase, delta-8 desaturase and delta-5 desaturase. Additional sequences can be selected from sequences supplied in table 1. The same embodiment also relates to delta-5 elongase-encoding nucleotide sequences that comprise or have at least 75% identity to the nucleotide sequences SEQ ID NOs 19, 28-29 and 101 and to nucleotide sequences that encode amino acid sequences having at least 75% identity to SEQ ID NO 68.

Specifically, a nucleotide sequence encoding a delta-5 elongase is selected from the group consisting of a) the nucleotide sequences set forth in SEQ ID NOs 19, 28-29 and 101; and
b) nucleotide sequences having at least 75% identity to the nucleotide sequences set forth in SEQ ID NOs 19, 28-29 and 101; and
c) nucleotide sequences encoding amino acid sequences that have at least 75% identity to SEQ ID NO 68.

In the present context "delta-5 elongase" relates to an enzyme capable of converting arachidonic acid to docosatetraenoic acid and/or eicosapentaenoic acid to docosapentaenoic acid and the meaning shall not exclude other functionality of said enzyme.

In one embodiment, the present invention relates to the use of specific nucleotide sequences encoding delta-4 desaturases, more specifically SEQ ID NOs 35-36 and 109, which encode the amino acid sequences SEQ ID NOs 74-75 and 110. In addition, it relates to nucleotide sequences encoding the amino acid sequences SEQ ID NOs 76-77. Usually these delta-4 desaturase-encoding nucleotide sequences are used together with at least 4 or more additional nucleotides sequences. The minimum four additional sequences are either nucleotide sequences encoding delta-12 desaturase, delta-6 desaturase, delta-6 elongase and delta-5 desaturase, or nucleotide sequences encoding delta-12 desaturase, delta-9 elongase, delta-8 desaturase and delta-5 desaturase. Additional sequences can be selected from sequences supplied in table 1. The same embodiment also relates to delta-4 desaturase nucleotide sequences that comprise or have at least 75% identity to the nucleotide sequences SEQ ID NOs 35-36 and 109 and to nucleotide sequences that encode amino acid sequences having at least 75% identity to SEQ ID NOs 76-77.

Specifically, a nucleotide sequence encoding a delta-4 desaturase is selected from the group consisting of a) the nucleotide sequences set forth in SEQ ID NO: 35-36 and 109; and b) nucleotide sequences having at least 75% identity to the nucleotide sequences set forth in SEQ ID NOs 35-36 and 109; and c) nucleotide sequences encoding amino acid sequences that have at least 75% identity to SEQ ID NOs 76-77.

In the present context "delta-4 desaturase" relates to an enzyme capable of converting docosapentaenoic acid to docosahexaenoic acid and the meaning shall not exclude other functionality of said enzyme.

In one embodiment, the present invention relates to the use of specific nucleotide sequences encoding omega-3 desaturases, more specifically SEQ ID NOs 30-34, 87, 89 and 111, which encode the amino acid sequences SEQ ID NO 69-73, 88, 90 and 112. Usually these omega-3 desaturase-encoding nucleotide sequences are used together with at least 4 or more additional nucleotides sequences. The minimum four additional sequences are either nucleotide sequences encoding delta-12 desaturases, delta-6 desaturases, delta-6 elongase and delta-5 desaturase, or nucleotide sequences encoding delta-12 desaturase, delta-9 elongase, delta-8 desaturase and delta-5 desaturase. Additional sequences can be selected from sequences supplied in table 1. The same embodiment also relates to omega-3 desaturase-encoding nucleotide sequences that comprise or have at least 75% identity to the nucleotide sequences SEQ ID NOs 30-34, 87, 89 and 111.

Specifically, a nucleotide sequence encoding an omega-3 desaturase is selected from the group consisting of a) the nucleotide sequences set forth in SEQ ID NOs 30-34, 87, 89 and 111; and b) nucleotide sequences having at least 75% identity to the nucleotide sequences set forth in SEQ ID NOs 30-34, 87, 89 and 111.

In the present context "omega-3 desaturase" relates to an enzyme capable of converting linoleic acid to alpha-linolenic acid, gamma-linolenic acid to stearidonic acid, eicosadieonic acid to eicosatrienoic acid, dihomo-gamma-linolenic acid to eicosatetraenoic acid, arachidonic acid to eicosapentaenoic acid, and docosatetraenoic acid to docosapentaenoic acid or subsets of theses capabilities, and the meaning shall not exclude other functionality of said enzyme.

As commonly defined (se e.g. Encyclopaedia of Life Sciences, Nature Publishing Group, 2000) "identity" is here defined as sequence identity between genes or proteins at the nucleotide or amino acid level, respectively. Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

One may manually align the sequences and manually count the number of identical amino acids. Alternatively, alignment of two sequences for the determination of percent identity can be accomplished using a mathematical algorithm. A preferred, non-limiting example of a mathematical algorithm that can be utilised for the comparison of two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into 15 the NBLAST and XBLAST programs of Altschul, et al. (1990) J. Mol. Biol. 215:403-410. BLAST nucleotide searches can be performed with the NBLAST program, score=100, wordlength=12, to obtain nucleotide sequences homologous to a nucleic acid molecules of the invention. BLAST protein searches can be performed with the XBLAST program, score=50, wordlength=3 to obtain amino acid sequences homologous to a protein molecule of the invention. To obtain gapped alignments for comparison purposes, Gapped BLAST can be utilised as described in Altschul et al. (1997) Nucleic Acids Res. 25:3389-402. Alternatively, PSI-Blast can be used to perform an iterated search which detects distant relationships between molecules. When utilising the NBLAST, XBLAST, and Gapped BLAST programs, the default parameters of the respective programs can be used. See ncbi.nlm.nih.gov. Alternatively, sequence identity can be 25 calculated after the sequences have been aligned e.g. by the program of Pearson W. R and D. J. Lipman Proc Natl Acad Sci USA 85:2444-2448, (1998) in the EMBL database. See ncbi.nlm.gov/cgi-bin/BLAST. Generally, the default settings with respect to e.g. "scoring matrix" and "gap penalty" can be used for alignment. In the context of the present invention, the BLASTN and PSI BLAST default settings can be advantageous. The percent identity between two sequences can be determined using techniques similar to those described above, with or without allowing gaps. In calculating percent identity, only exact matches are counted.

The technology described within the present invention relates to genetically engineered non-plant host cells and host cells that produces PUFAs from e.g. non-fatty acid substrates, such as sugar sources or combined fermentation substrates as described above.

The genetically transformed cells particularly harbour a heterologous oxygen-requiring pathway from stearic acid to PUFAs by expression of the following heterologous enzymes delta-9 desaturase, delta-12 desaturase, delta-9 elongase, delta-8 desaturase omega-3 desaturase, delta-6 desaturase, delta-6 elongase, delta-5 desaturase, delta-5 elongase, delta-4 desaturase or subsets hereof.

Delta-9 desaturase catalyses the reaction from palmitic acid to palimitoleic acid as well as the reaction from stearic acid to oleic acid. Delta-12 desaturase catalyzes the reaction from oleic acid to linoleic acid, which initiates the omega-6 pathway, linoleic acid is converted to gamma-linolenic acid by the action of delta-6 desaturase. Gamma-linolenic acid is elongated by two methyl groups by delta-6 elongase to form dihomo-gamma-linolenic, which is desaturated by delta-5 desaturase to arachidonic acid.

Alternatively, arachidonic acid can be produced from linoleic acid via the action of delta-9 elongase, delta-8 desaturase and delta-5 desaturase. Linoleic acid is elongated by delta-9 elongase to form eicosadienoic acid, which is converted to dihomo-gamma-linolenic acid via the action of delta-8 desaturase, and finally arachidonic acid is formed from dihomo-gamma-linolenic acid through the action of delta-5 desaturase. For both alternatives, arachidonic acid can be elongated by delta-5 elongase to form Δ7, Δ10, Δ13, Δ16-docosatetraenoic acid.

Omega-3 desaturase converts linoleic acids to alpha-linoleic acid, the starting point of the omega-3 pathway. Omega-3 desaturases are often highly unspecific and can convert gamma-linoleic acid to stearidonic acid, eicosadienoic acid to eicosatrienoic acid, dihomo-gamma-linolenic acid to eicosatetraenoic acid, arachidonic acid to EPA and docosatetraenoic acid to docosapentaenoic acid. The omega-3 pathway uses the same enzymes as the omega-6 pathway plus a delta-4 desaturase. Delta-6 desaturase catalyzes the reaction from alpha-linoleic acid to stearidonic acid, which is further converted by delta-6 elongase to eicosatetraenoic acid. Alternatively, eicosatetraenoic acid can be produced from alpha-linolenic acid via the action of delta-9 elongase and delta-8 desaturase. Delta-9 elongase catalyzes the reaction from alpha-linolenic acid to eicosatrienoic acid, and delta-8 desaturase catalyses the reaction from eicosatrienoic acids to eicososatetraenoic acid. Desaturation of eicosatetraenoic acid by delta-5 desaturase leads to EPA. EPA is converted via delta-5 elongase to docosapentaenoic acid, which itself is desaturated by delta-4 desaturase to form DHA.

The heterologous genes can be isolated from any living organism, including fungi, plants, animals, algae and marine protists, amoeba and bacteria, that harbours pathways to oleic acid, linoleic acid, alpha-linolenic, gamma-linoleic acids, dihomo-gamma-linolenic acid, arachidonic acid, stearidonic acid, eicosatetraenoic acid, EPA, 7,10,13,16,19-docosapentaenoic acid, docosatetraeonic acid or DHA.

A non-exhaustive list of organisms that have such pathways leading to fatty acids with one or more double bond are bacteria such as but not limited to, *Spirulina* spp., *Synechocystis*, etc. fungi such as *Mortiella alpina, Mucor rouxii, Mucor circinelloides, Aspergillus fumigatus*, etc., plants like *Petroselinum crispum, Arabidopsis thaliana, Brassica napus, Glycine max, Zea mays, Ricinus communis, Corylus avellana, Phaeodactylum tricornutum*, etc., are the animals such as *Caenorhabditis elegans, Homo sapiens, Mus musculus, Rattus norvegicus, Lepidoptera*, etc., and the like algae such as *Schizochytrium, Thraustochytrium* sp., *Phaeodactylum tricornutum*, etc., and amoeba, such as *Dictyostelium discoideum*, etc.

The expression of delta-12 desaturase has been reported in a wide range of different organisms including but not limited to, *Mortierella alpina, Mucor rouxii, Mucor circinelloides, Aspergillus fumigatus, Helianthus annuus, Petroselinum crispum, Arabidopsis thaliana, Brassica napus, Glycine max, Zea mays, Ricinus communis, Corylus avellana, Phaeodactylum tricornutum, C. elegans, Calendula officinalis* and cotton, but are not limited to these examples (WO9411516, US6025172, U.S. 2003/0180802, U.S. 2003/0172398, U.S. 2003/0074694, U.S. 2003/066104, U.S. Pat. No. 6,372,965, U.S. Pat. No. 6,441,278, WO200185968-A2, WO200179499-A1, U.S. Pat. No. 6,372,965-B1, WO200114538-A).

Delta-6 desaturases can be found at least in the following organisms *Mortierella alpina, Mucor rouxii, Mucor circinelloides, Pythium irregulare, Borago officinalis, Ceratodon purpureus, Physcomitrella patens, Anemone leveillei, Phaeodactylum tricornutum, Tetrahymena, Caenorhabditis elegans, Primulaceae, Homo sapiens, Castor*, evening primrose, *Synechocystis, Spirulina* spp., *Physcomitrella patens* (WO 9927111, U.S. 2002/0170090, WO 03/072784, U.S. Pat. No. 6,492,108, U.S. Pat. No. 6,686,186, U.S. 2002/0151019, U.S. 2002/0108147, WO 02/081702, WO200272028-A2, U.S. Pat. No. 6,355,861-B1, WO200144485-A, JP2001095588-A, WO200120001-A, WO200102591-A, WO200104636-A, JP2001095588-A, WO200175069-A1). Delta-6 elongases have been identified among others in the following organisms *Mortierella alpina, Physcomitrella patens, Caenorhabditis elegans, Mortiella Alpina, Homo sapiens, C. elegans, Mus musculus, T. aureum, Pavlova, Thraustochytrium aureum, Phytophthora infestans* (U.S. Pat. No. 6,403,349, WO 03/102138, U.S. 2003/0177508, WO200244320-A, WO200208401-A, WO200159128-A, DE10005973-A1, WO200055330-A, WO2003064638-A2).

Delta-9 elongases have been isolated from *Isochrysis galbana* (WO02077213, Qi et al. 2004) and delta-8 desaturases from *Euglena gracilis* (Wallis and Browse 1999). Delta-5 desaturases have been isolated from *Mortierella alpina, Phytophthora megasperma, Physcomitrella patens, Phaeodactylum tricornutum, Thraustochytrium* sp. ATCC 2165, *Caenorhabditis elegans, Dictyostelium discoideum, Schizochytrium, Thraustocytrium aureum, Saprolegnia diclina, Isochrysis galbana, Phytophthora megasperma, Homo sapiens*, rat, *Euglena*, among others (U.S. Pat. No. 5,972,664, WO9933958, WO9846765, WO 02/081668, WO2003012092-A, U.S. Pat. No. 6,428,990-B1, U.S. Pat. No. 6,432,684-B1, WO200234940-A, WO200040705-A, WO200034439-A, WO200104636-A, WO2003012092-A).

Omega-3 desaturases can be isolated from plants, fungi, and nematodes, such as *Petroselinum crispum, Brassica napus, Arabidopsis thaliana, Glycine soya, Saprolegnia diclina, Caenorhabditis elegans* (i.e. U.S. Pat. No. 6,194,167, U.S. 20030196217, Yadav et al. 1993, Kirsch et al. 1997) or from *Saccharomyces kluyveri.*

Delta-5 elongase have been found among others in mouse, *Homo sapiens, Caenorhabditis elegans, Thraustochytrium aureum*, (i.e. U.S. 2003/0177508 and WO200208401-A) and Delta-4 desaturase can be isolated from fungi, algae and marine protists including *Thraustochytrium* sp., *Euglena gracilis, Thraustochytrium aureum, Saprolegnia diclina, Isochrysis galbana*, etc. but are not limited to these organisms (i.e. WO 02/090493, WO200226946-A, Qiu et al. 2001, Meyer et al. 2003).

In one embodiment, the present invention describes the simultaneous heterologous expression of genes encoding delta-12 desaturase, delta-6 desaturase, delta-6 elongase and delta-5 desaturase in a microorganism, which leads to the production of PUFAs, and in particular production of arachidonic acid from non-fatty acid substrates. The genes can be expressed on a single plasmid or several plasmids, such as one plasmid, two plasmids, three plasmids, four plasmids, five plasmids, six plasmids, seven plasmids, eight plasmids, nine plasmids, or ten plasmids or more. The use of a single plasmid carrying several heterologous genes, for example four genes, is advantageous because it ensures that the cells that carry the plasmid contain all heterologous genes. In contrast if several plasmids are used, a fraction of the cell population will contain only one of the plasmids and thus will not express the full heterologous pathway. However, the number of heterologous genes that can be expressed from a single plasmid is limited by the increased size of the plasmid; large plasmids tend to be less stable in the cell than small plasmids, which leads to poorer expression from large plasmids. A presently preferred embodiment therefore involves expression of one or two heterologous genes per plasmid.

Furthermore, it describes the simultaneous heterologous expression of genes encoding delta-12 desaturase, omega-3 desaturase, delta-6 desaturase, delta-6 elongase and delta-5 desaturase in a microorganism, which results in production of EPA and other PUFAs from non-fatty acid substrates.

The invention also describes the simultaneous heterologous expression of genes encoding delta-12 desaturase, omega-3 desaturase, delta-6 desaturase, delta-6 elongase, delta-5 desaturase, delta-5 elongase and delta-4 desaturase in a microorganism, which results in production of DHA from non-fatty acid substrates.

The invention describes an additional expression of a delta-9 desaturase. The production of PUFAs in microorganism can be improved by expression of delta-9 desaturases that are more specific for the production of oleic acid rather than palmitoleic acid (FIG. 2). Recently, two delta-9 desaturases from *M. alpina*, ole1 and ole2, have been cloned. Both genes complement yeast Δole1 mutants, which cannot grow without supplementation of 16:1 and 18:1 fatty acids in the medium. Both *M. alpina* delta-9 desaturases shift the fatty acid content from 16:1 desaturated fatty acid towards 18:1 desaturated fatty acid (oleic acid) in yeast. The oleic acid content of the Δole1 yeast expressing *M. alpina* ole1 was 53.6% of total lipid, compared to 21.6% in wild-type *S. cerevisiae* (Wongwathanarat et al., 1999). The present invention shows that expression of a heterologous delta-9 desaturase together with the heterologous PUFA biosynthetic pathway can increase production of PUFA in yeast. For example, the expression of *Mortierella alpina* ole1 together with a *Mortierella alpina* delta-12 desaturase in yeast increases the production of linoleic acid, for example by the factor of 5 or any multiples thereof.

By "gene" is meant a nucleotide sequence, also referred to as DNA or RNA sequence, which encodes a specific protein. Nucleotide sequences encoding described PUFA desaturases and elongases can be isolated from their natural sources using standard procedures known in the art. One such procedure comprises isolation of total RNA, reverse transcription using Oligo(dT) or random primers followed by PCR amplification using sequence-specific primers. Novel PUFA desaturase- and elongase encoding nucleotide sequences can likewise be isolated by known procedures. Preferentially, these are based on sequence homology and comprise, for example, PCR using degenerate primers and screening of DNA or cDNA libraries by colony hybridization using radiolabeled polynucleotide probes. Alternatively, the isolation methods are based on the function of the polypeptide encoded by the polynucleotide. For example, a cDNA expression library is generated from a PUFA-producing organism and screened for desaturation or elongation of PUFA substrates.

PCR (Polymerase Chain Reaction) is a technique for the synthesis of large quantities of specific DNA sequences that is based on repeated cycles of in vitro replication of DNA template by a temperature-tolerant DNA polymerase (Mullis et al., Cold Spring Harbor Symp. Quant. Biol. 51: 263-273 (1986); European Patent Application 50424; European Patent Application 84796; European Patent Application 258017: European Patent Application 237362; European Patent Application 201184; U.S. Pat. No. 4,683,202; U.S. Pat. No. 4,582,788; U.S. Pat. No. 4,683,194). The technique utilizes sets of specific in vitro synthesized oligonucleotides, termed primers, which anneal to complementary sequences on the template DNA and prime DNA synthesis by DNA polymerase. Amplification is achieved by applying several cycles (normally 20-50) of melting of the double-stranded template at high temperature, annealing of the primers, and DNA replication. For amplification of known sequences, primers are usually designed to match the template sequence exactly. However, desired features, such as specific restriction sites, can be introduced into the resulting DNA fragment through the design of the primers. Moreover, a specific 5' tail sequence can be included in the primer sequence, which later allows fusion of the PCR-product to a DNA fragment containing a matching 3' end sequence.

PCR using degenerate primers can be used to amplify a novel DNA sequence with sequence homology to known DNA sequences. The primers are then designed to match DNA regions of high homology, as deduced from multiple alignments of known sequences. The primers are allowed to contain different bases at certain positions, such that the primer used in the PCR reaction is actually a mix of oligonucleotides with different sequences. A portion of the oligonucleotides in the mix anneal to the target sequence, allowing amplification of the template.

Techniques for manipulation of nucleic acids encoding PUFA enzymes such as subcloning nucleic acid sequences encoding polypeptides into expression vectors, labeling probes, DNA hybridization, and the like are described generally in Sambrook et al., Molecular cloning: A laboratory manual ($2^{nd}$ ed.), Vols. 1-3, Cold Spring Harbor Laboratory Press (1989). Following isolation of a desired gene, it can be sequenced using known methods.

Once a desired nucleotide sequence has been isolated, it can be expressed in a host cell. For the purpose of expressing a heterologous nucleic acid in a host cell, it is operably linked to a promoter and a terminator sequence using standard cloning techniques or standard in vitro procedures, such as fusion by PCR.

The term "promoter" refers to a DNA sequence capable of controlling the expression of a gene. The promoter sequence consists of proximal and more distal elements located upstream of the gene. The more distal elements are often referred to as enhancers. Promoter sequences can also be located within the transcribed portion of the DNA sequence, and/or downstream of the transcribed sequences. The "terminator sequence", also called the 3' non-coding sequence refer to DNA sequences located downstream of a gene and include polyadenylation recognition sequences and other sequences encoding regulatory signals capable of affecting mRNA processing or gene expression. The promoter and terminator sequences used for heterologous expression can be derived from the native sequence of the heterologous gene. More often, the promoter and terminator sequences are taken from a highly expressed DNA sequence of the host cell. For example, suitable promoter sequences for expression in *Saccharomyces cerevisiae* include the constitutive promoters of TDH3, ADH1, TPI1, ACT1 GPD and PGI or the promoter of any constitutively and highly transcribed yeast gene and the galactose-inducible promoters of GAL1, GAL10 and GAL7. Also contemplated by the present invention are other yeast inducible promoters, such as but not limited to, the CUP1 metallothionein promoter, which enables gene expression in the presence of heavy metals, such as copper (Karin M, et al, (1984) Proc Natl Acad Sci USA 81(2): 337-41. The MET15 promoter can also be used when repression of genes is desired. Suitable bacterial promoter sequences are for example the promoter and operator region of the *E. coli* tryptophan biosynthetic pathway as described by Yanofsky (1984) *J. Bacteriol.,* 158:1018-1024 and the promoter of phage lambda (Pλ) as described by Herskowitz and Hagen, (1980) *Ann. Rev. Genet.,* 14:399-445. A large number of terminator sequences are known and have been found to be satisfactory in a variety of hosts from the same and different genera and species. A heterologous polynucleotide, operably linked to a promoter and a terminator sequence, is hereafter termed an expression cassette.

The term operably linked refers to the association of a gene with a sequence that controls its expression on a single nucleic acid fragment. For example, a promoter is operably linked with a coding sequence when it is capable of regulating the expression of that coding sequence.

Constructs containing heterologous genes of interest can be introduced into the host by standard techniques. These techniques include transformation, such as for example, in *S. cerevisiae*, lithium acetate transformation, spheroplasting, and use of a kar1Δ15 mutant (Georgieva, B. et al, (2002) Meth. Enzymol. 350: 278-89), protoplast fusion, lipofection, transfection, transduction, conjugation, infection, bolistic impact, electroporation, or any other method that introduces the foreign DNA into the host cell. For simplicity, a host cell manipulated in this way will be referred to as “transformed”, “recombinant” or “genetically modified”. The construct that is introduced into the host cell contains in addition to the expression cassette a marker gene, which allows identification of transformed cells and, in the case of extrachromosomal expression, also prevents the cell from losing the construct. Preferably, the marker gene encodes a conditionally essential gene, which has been deleted in the host genome. Examples of the latter are, in yeast, the URA3 gene, the TRP1 gene, the HIS3 gene and the LEU2 gene, which restore the ability of the ura3, trp1, his3 or leu2 mutant yeast cell to produce the essential compounds uracil, tryptophane, histidine and leucine, respectively. Recombinant yeast cells can therefore be selected and maintained on medium lacking these factors. Alternatively, the marker gene can confer resistance to an antibiotic, allowing selection and maintenance of recombinant cells in medium containing the antibiotic.

TABLE 1

Examples of desaturases and elongases, useful for heterologous PUFA production.

| Enzyme | Source | Reference | SEQ ID NO: (nucleotide) | SEQ ID NO: (amino acid) |
|---|---|---|---|---|
| delta-9 desaturase | *Mortierella alpina* | present patent application | 1 | 39 |
| | *Cryptococcus curvatus* | Meesters et al. 1996 Yeast 12: 723-730 | 2 | 40 |
| | *Histoplasma capsulatus* | Gargano et al. 1995 Lipids 30: 899-906 | 3 | 41 |
| | *Trichoplusia ni* | Liu et al. 1999 Insect Biochem Mol Biol 29: 435-443 | 4 | 42 |
| delta-12 desaturase | *Mortierella alpina* | present patent application | 5 | 43 |
| | *Mucor rouxii* | Passorn et al. 1999 Biochem Biophys Res Commun 263: 47-51 | 6 | 44 |
| | *Mucor circinelloides* | BAB69056, GenBank December 2000 | 7 | 45 |
| | *Aspergillus fumigatus* | CAE47978, GenBank December 2003 | 8 | 46 |
| | *Cryptococcus curvatus* | AAS78627, Pubmed March 2004 | 9 | 47 |
| | *Caenorhabditis elegans* | US 2003/0172398 | 10 | 48 |
| | *Aspergillus parasiticus* | Wilson et al. 2004 Microbiology 150: 2881-2888 | 93 | 94 |
| | *Pichia pastoris* | AAX20125, Pubmed March 2005 | 95 | 96 |
| | *Saccharomyces kluyveri* | Watanabe et al. 2004 Biosci Biotechnol Biochem 68: 721-727 | 113 | 114 |
| delta-6 desaturase | *Mortierella alpina* | present patent application | 11 | 49 |
| | *Mucor rouxii* | Laoteng et al. 2000 Biochem Biophys Res Commun 279: 17-22 | 12 | 50 |
| | *Borago officinalis* | Sayanova et al. 1997 Proc Natl Acad Sci USA 94: 4211-4216. | 13 | 51 |
| | *Anemone leveillei* | Whitney et al. 2003 Planta 217: 983-92 | 14 | 52 |
| | *Caenorhabditis elegans* | WO 9927111 | 15 | 53 |
| | *Marchantia polymorpha* | Kajikawa et al. 2004 Plant Mol Biol 54: 335-352 | 97 | 98 |
| | *Cyprinus carpio* | Hastings et al. 2001 Proc Natl Acad Sci 98: 14304-14309 | 99 | 100 |
| delta-6 elongase | *Mortierella alpina* | present patent application | 16 | 54 |
| | *Physcomitrella patens* | WO0159128 | 17 | 55 |
| | *Caenorhabditis elegans* | WO200055330-A | 18 | 56 |
| | *Mus musculus* | WO200208401-A | 19 | 57 |
| | *Thraustochytrium aureum* | WO200208401-A | 20 | 58 |
| | *Phytophthora infestans* | WO2003064638-A2 | 21 | 59 |

TABLE 1-continued

Examples of desaturases and elongases, useful for heterologous PUFA production.

| Enzyme | Source | Reference | SEQ ID NO: (nucleotide) | SEQ ID NO: (amino acid) |
|---|---|---|---|---|
| | *Salmo salar* | Hastings et al. 2004 Mar Biotechnol 6: 463-474 | 101 | 102 |
| | *Marchantia polymorpha* | Kajikawa et al. 2004 Plant Mol Biol 54: 335-352 | 103 | 104 |
| delta-5 desaturase | *Mortierella alpina* | present patent application | 22 | 60 |
| | *Phytohphtora megasperma* | WO03012092 | 23 | 61 |
| | *Thraustochytrium* | WO200226946-A | 24 | 62 |
| | *Caenorhabditis elegans* | WO9933958 | 25 | 63 |
| | *Pythium irregulare* | WO200226946-A | 26 | 64 |
| | *Phaedodactylum. tricornutum* | US20040053379-A1 | 27 | 65 |
| | *Salmo salar* | Hastings et al. 2004 Mar Biotechnol 6: 463-474 | 105 | 106 |
| | *Marchantia polymorpha* | Kajikawa et al. 2004 Plant Mol Biol 54: 335-352 | 107 | 108 |
| | *Cyprinus carpio* | Hastings et al. 2001 Proc Natl Acad Sci 98: 14304-14309 | 99 | 100 |
| delta-5 elongase | *Mus musculus* | Tvrdik et al. 2000 J Cell Biol 149: 707-717 | 28 | 66 |
| | *Mus musculus* | WO200208401-A | 19 | 57 |
| | *Homo sapiens* | WO0244320 | 29 | 67 |
| | *Pavlova* | WO 03102138 | | 68 |
| | *Salmo salar* | Hastings et al. 2004 Mar Biotechnol 6: 463-474 | 101 | 102 |
| omega-3 desaturase | *Caenorhabditis elegans* | U.S. Pat. No. 6,194,167 | 30 | 69 |
| | *Petroselinum crispum* | Kirsch et al. 1997 Proc Natl Acad Sci USA 94: 2079-2084 | 31 | 70 |
| | *Arabidopsis thaliana* | Yadav et al. 1993 Plant Physiol 103: 467-476 | 32 | 71 |
| | *Brassica napus* | Yadav et al. 1993 Plant Physiol 103: 467-476 | 33 | 72 |
| | *Glycine soya* | Yadav et al. 1993 Plant Physiol 103: 467-476 | 34 | 73 |
| | *Mortierella alpina* | Sakuradani et al. 2005 Appl Microbiol Biotechnol 66: 648-654 | 89 | 90 |
| | *Saccharomyces kluyveri* | Oura et al. 2004 Microbiology 150: 1983-1990 | 87 | 88 |
| | *Saprolegnia diclina* | Pereira et al. 2004 Biochem J 378: 665-671 | 111 | 112 |
| delta-4 desaturase | *Thraustochytrium aureum* | WO200226946-A | 35 | 74 |
| | *Euglena gracilis* | Meyer et al. 2003 Biochemistry 42: 9779-9788 | 36 | 75 |
| | *Isochrysis galbana* | WO 02/090493 | | 76 |
| | *Schizochytrium aggregatum* | WO 02/090493 | | 77 |
| | *Pavlova lutheri* | Pereira et al. 2004 Biochem. J. 384: 357-366 | 109 | 110 |
| delta-9 elongase | *Isochrysis galbana* | WO2002077213_A2 | 37 | 78 |
| delta-8 desaturase | *Euglena gracilis* | WO200034439-A | 38 | 79 |

In one embodiment of the invention, the genes required for PUFA production are integrated into the genome of the host organism. Integration of heterologous polynucleotide sequences into the genome of *Saccharomyces cerevisiae* by homologous recombination is a well known, standard technique for genetic manipulation of *S. cerevisiae*. A linear DNA construct can be targeted for integration at any location in the yeast genome by fusing it to target sequences at the 5' end and at the 3' end. Upon transformation with the linear DNA construct, the DNA-double strand break repair pathway of yeast is activated, mediating homologous recombination between the target sequences of the linear DNA substrate and the corresponding sequences in the yeast genome. This results in integration of the linear DNA construct into the genome, and simultaneous looping out of any sequence between the two target sequences in the yeast genome. Depending on the purpose of the genetic manipulation, target sequences can be selected on each side of a yeast gene, resulting in knock-out of that gene, or adjacent to each other, resulting in disruption of the target sequence but otherwise leaving the genome intact.

The present invention involves the integration of several heterologous genes, encoding PUFA desaturases and elongases. Preferably, all expression cassettes necessary for the production of a specific PUFA are assembled on a single plasmid, which also contain a marker gene and a target sequence for integration. The target sequence is engineered to contain or naturally contains a unique restriction site, which allows linearization of the plasmid.

Following transformation of yeast with the linearized plasmid, the yeast cells are plated on selection medium as described herein and recombinant cells containing the heterologous DNA construct are identified.

Preferably, all expression cassettes necessary for the production of a specific PUFA are assembled on a single construct and are simultaneously integrated into the genome of the yeast cell. However, if expression of many heterologous genes is desired, it may be beneficial to place the individual genes on several, for example two, different constructs, targeted for integration at different sites in the host genome as described above. Following identification of the recombinant cells, the two separate chromosomal integrations can be combined by crossing of the recombinant strains. If necessary, each recombinant strain is first taken through an intermediate cross in order to introduce suitable genetic markers.

Crossing of strains is a traditional, widely used and very efficient method for combining different genotypes. In short, two haploid yeast strains of opposite mating type (i.e., for *S. cerevisiae*, mating types are denoted as MATa and MATalpha) are allowed to mate on rich medium, such as YPD. Usually, the haploid strains each display a different selectable phenotype, such as amino acid auxotrophy, allowing for diploids to be selected on double drop-out medium. Alternatively, the cells can be plated on rich medium following mating, and diploids are identified by inducing cells to undergo meiosis and sporulation by simply transferring a number of single colonies onto sporulation medium, such as, for example, medium containing potassium acetate as the sole carbon source, and monitoring sporulation by microscopy. Following sporulation of the diploids, the spores are dissected and the genotypes of the resulting haploid strains are scored using various methods, such as replica plating to suitable drop-out plates and by colony-PCR. Crossing of strains to combine different genotypes can also be advantageously accomplished by using a mutant that is defective for karyogamy, such as the kar1Δ15 mutant (Georgieva, B. et al (2002) Meth. Enzymol. 350: 278-89).

Preferably, different promoters are used in the construction of the several expression cassettes in the heterologous construct, so as to avoid further homologous recombination events to take place and loop out parts of the heterologous construct. Alternatively, a promoter sequence is placed in two copies on the same heterologous construct but in divergent directions so that a direct repeat is avoided.

Well-known methods for improving heterologous expression include codon-optimization of the heterologous nucleotide sequence. This is done by employing the host-preferred codons, as determined from codons of the highest frequency in highly expressed proteins of the host of interest. The coding sequence for a polypeptide having PUFA desaturase or elongase activity can be chemically synthesized in whole or in part using methods well established in the literature. Moreover, the nucleotide sequence surrounding the translational start-codon ATG has been found to influence gene expression in yeast. If the desired polypeptide is poorly expressed in yeast, the nucleotide sequence of the heterologous gene can be modified to include an efficient yeast translation initiation sequence to obtain optimal gene expression. This can be accomplished by standard techniques such as PCR-based site directed mutagenesis or by fusion to the initiation sequence of a highly expressed yeast gene.

Recombinant yeast strains containing heterologous pathways to PUFAs, such as arachidonic acid or DHA, can be grown in batch, fed batch or chemostat cultivation as described in example 10 in order to produce high amounts of PUFA-containing biomass. Following harvest of biomass, e.g. by centrifugation or filtration, and possible drying of the biomass to a suitable degree, it can be used as a functional food ingredient, for example as bakers yeast, yeast extract or as a flavour enhancer. The PUFA-containing biomass can also be used directly as a functional food, for example in tablets as an alternative to fish oil capsels.

Thus, the present invention also relates to food products, such as functional food products, wherein said food product has an increased content of polyunsaturated fatty acids when compared to a product produced by a cell, that is not modified for heterologous expression according to the present invention.

The yield of PUFA in a recombinant yeast can be improved via several strategies, some of which involve increasing the PUFA percentage of total fatty acid, and others that involve metabolic engineering of the host for increased fatty acid production.

One strategy that can be used for increasing the percentage PUFA in total fatty acid involves heterologous expression of a delta-9 desaturase with substrate specificity for stearic acid rather than palmitic acid. Expression of such a delta-9 desaturase shifts the fatty acid composition towards higher concentration of oleic acid, the precursor of the PUFA pathway, and results in increased PUFA production (see examples 9 and 12). Another strategy that can increase oleic acid content in yeast involves overexpression of the genes ELO1, ELO2 and/or ELO3, which encode fatty acid elongases. Overexpression of these genes may increase the concentration of fatty acids with 18 carbon atoms in relation to the concentration of fatty acids with 16 carbon atoms. Alternatively, a heterologous elongase with substrate specificity for palmitic acid or palmitoleic acid can be expressed in order to increase the availability of fatty acids with 18 carbon atoms.

Furthermore, the efficiency of expression of heterologous genes encoding enzymes in the PUFA pathway can be increased by optimizing the codons of the heterologous genes. Heterologous genes are likely to contain codons that are rare in the host organism, and the availability of the corresponding tRNAs may therefore be limiting for expression of the gene in question. In order to optimize the codons of a specific gene, the corresponding amino acid sequence is back-translated using the optimal codon frequency of the host. This can be done, for example, using the Backtranslation tool V2.0 program. The coding and non-coding strand of the codon-optimized gene can then be chemically synthesized in the form of overlapping oligonucleotides. To assemble the synthetic gene, the overlapping oligonucleotides are allowed to hybridize to each other and reconstitute the full, double-stranded nucleotide sequence, which can then be amplified by PCR.

Figure 3:
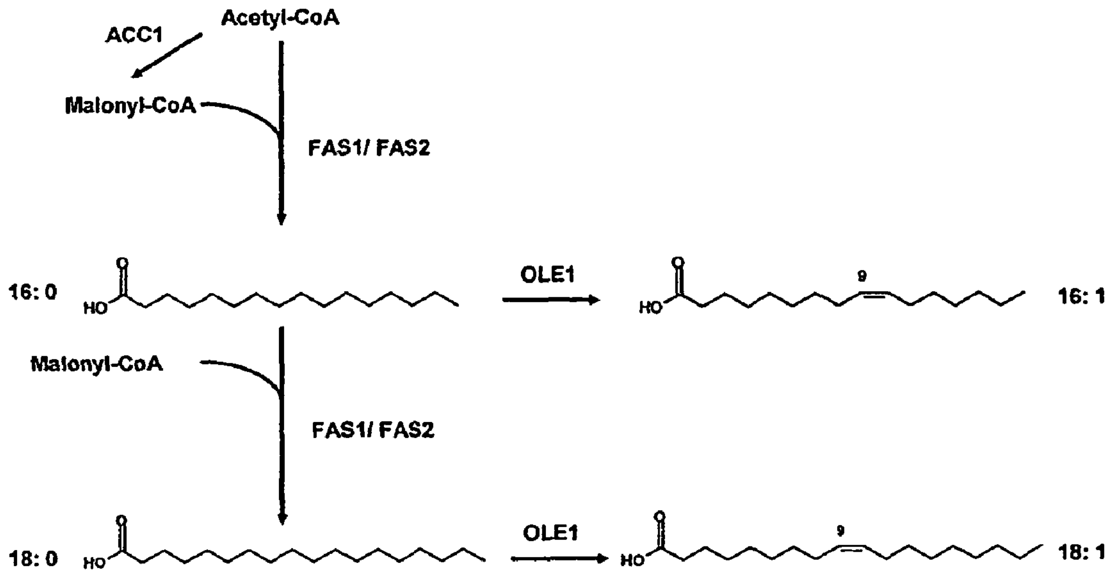
FIG. 3: Simplified view of fatty acid biosynthesis in *S. cerevisiae*
Figure 4:
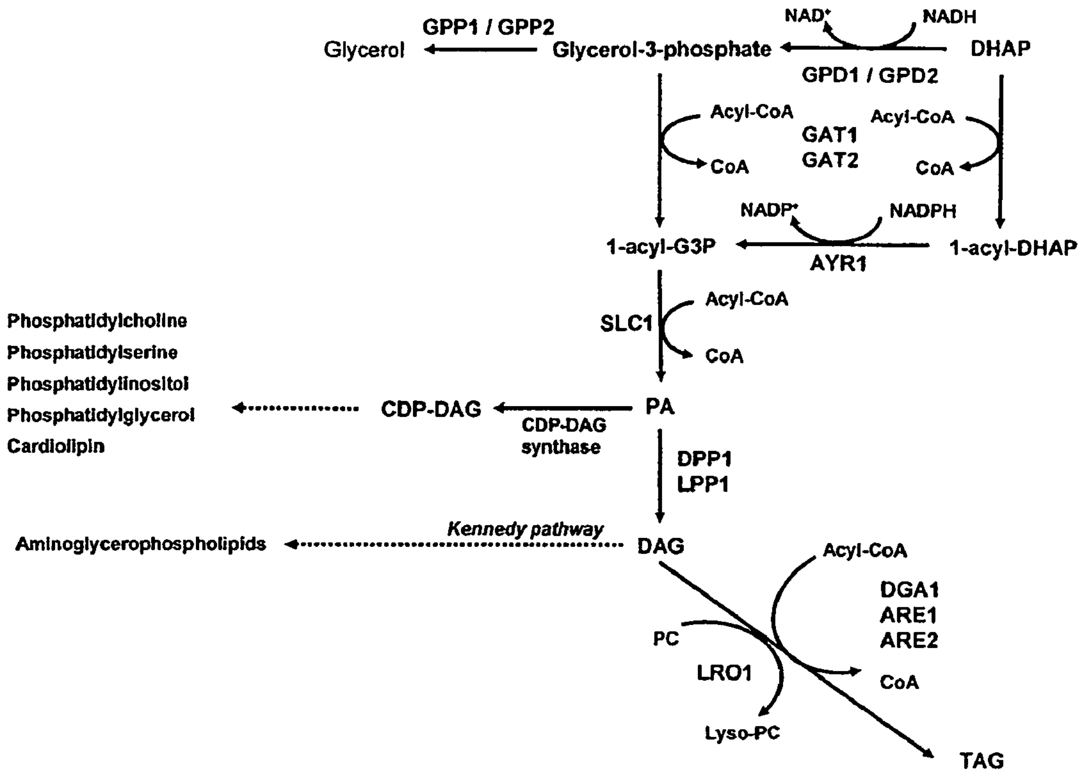
FIG. 4: Pathway to TAG and phospholipids in *Saccharomyces cerevisiae*. PA, phosphatidic acid; DAG, diacylglycerol; TAG, triacylglycerol.

In *S. cerevisiae*, fatty acid synthesis is carried out by the fatty acid synthase (FAS) complex (FIG. 3), which consists of a heteromultimeric complex of two multifunctional subunits (α and β). Overexpression of the α and β subunits, encoded by the yeast genes FAS2 and FAS1, respectively, can substantially increase the fatty acid content of *S. cerevisiae* and thereby the yield of PUFA on cell dry-weight.

Acetyl-CoA carboxylase catalyses the reaction from acetyl-CoA to malonyl-CoA and is encoded by the ACC1 gene product. Overexpression of ACC1 allows an increase in the malonyl-CoA pool, and thereby effecting more efficient fatty acid synthesis. Consequently, the lipid and PUFA yield in ACC1 overexpression mutants is increased (example 39).

Other targets for metabolic engineering include genes involved in the synthesis of the storage lipid triacylglycerol (TAG). In yeast, TAG synthesis is achieved by the action of enzymes encoded by the four genes DGA1, LRO1, ARE1 and ARE2 (Sandager et al. 2002 J Biol Chem 277: 6478-6482). Overexpression of these genes can therefore increase the content of TAG, and thereby total fatty acid content, of yeast. In particular, overexpression of DGA1, encoding an acyl-CoA:diacylglycerol acyltransferase, can increase the TAG content, as deletion of this gene alone results in approximately 60% decrease in the TAG content and approximately 40% decrease in the total lipid content (Sandager et al. 2002 J Biol Chem 277: 6478-6482) and example 29.

Furthermore, the cellular content of TAG and total lipid can be increased by increasing the availability of precursors needed for TAG synthesis. For example, the intracellular concentration of the main TAG precursor L-glycerol 3-phosphate can be increased more than 20 times in yeast by overexpressing GPD1, encoding glycerol 3-phosphate dehydrogenase, and deleting GPP1 and GPP2, which encode isoenzymes of glycerol 3-phosphatase (Nguyen et al. 2004 Met Eng 6: 155-163). Potentially the same strategy can be used overexpressing GPD2 or GPD1 and GPD2 together with a deletion of GPP1 and GPP2.

In order to produce more TAG, other target genes can be overexpressed such as genes involved in phosphatidic acid production. Here, synthesis of lysophosphatidic acid and phosphatidic acid can be increased by overexpression of GAT1 and SLC1 encoding L-glycerol 3-phosphate acyltransferase and 1-acylglycerol-3-phosphate acyltransferase, respectively. The phosphatidic acid pool is increased and more precursor is available to increase the levels of TAG (example 30). Other target genes include SPO14, a phospholipase D that catalyses the reaction of phosphatidylcholine to phosphatidic acid and choline (Xie, et al, (1988) Proc. Natl. Acad. Sci USA 95(21):12346-51.

Figure 5:
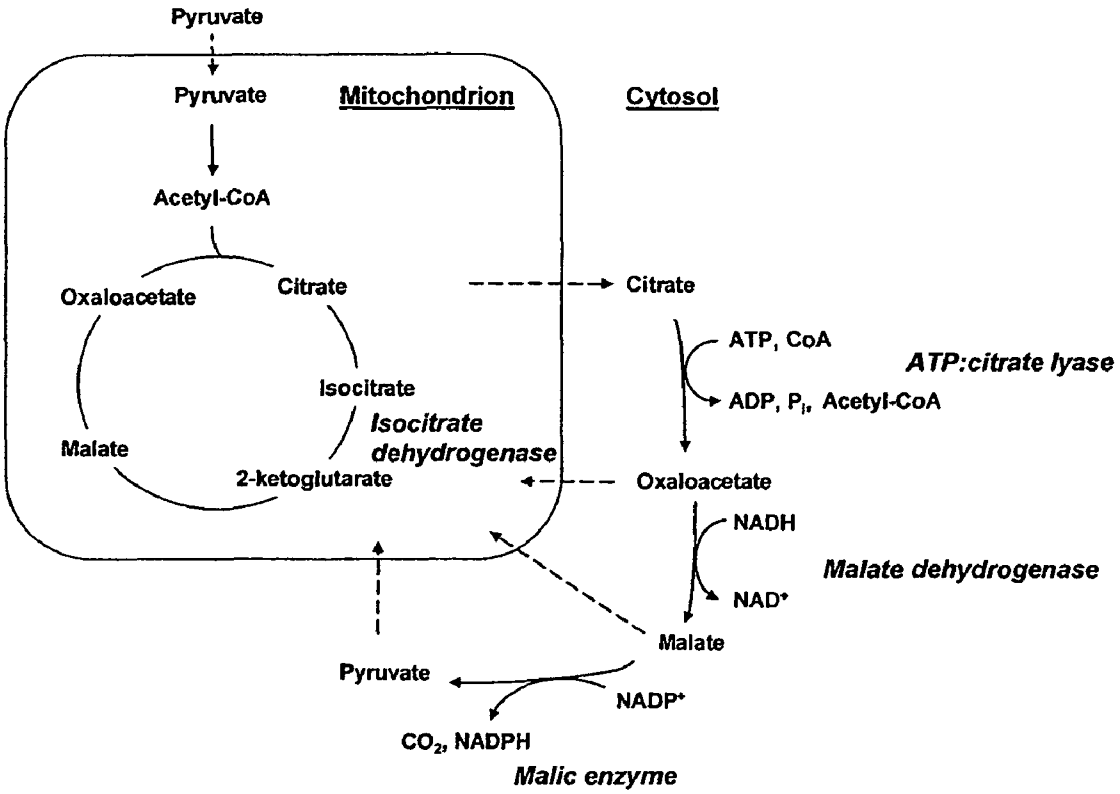
FIG. 5: Pathway to cytosolic acetyl-CoA in oleagineous yeast and fungi.

The availability of the main precursor for fatty acid synthesis, acetyl-CoA, can be increased by expressing a heterologous ATP:citrate lyase. ATP:citrate lyase is present in most oleaginous organisms but usually not in non-oleaginous yeast such as *Saccharomyces cerevisiae* and catalyzes the conversion of citrate into acetyl-CoA and oxaloacetate (FIG. 5). Furthermore, heterologous expression of an AMP-regulated isocitrate dehydrogenase is likely to lead to accumulation of citrate during conditions of nitrogen limitation (Ratledge 2002 Biochem Soc Trans 30:1047-1050). The combined expression of heterologous genes encoding ATP:citrate lyase and an isocitrate dehydrogenase whose activity is favoured by the presence of AMP can therefore lead to increased availability of acetyl-CoA and increased fatty acid production in the host cell.

It has been shown that overexpression of panthothenate kinase in *Escherichia coli* gives rise to higher CoA levels. Hence, overexpression of the putative panthothenate kinase in *Saccharomyces cerevisiae* encoded by YDR531W may allow an increase in the CoA pool in *Saccharomyces cerevisiae* and thereby increase production of acetyl-CoA.

Figure 6:
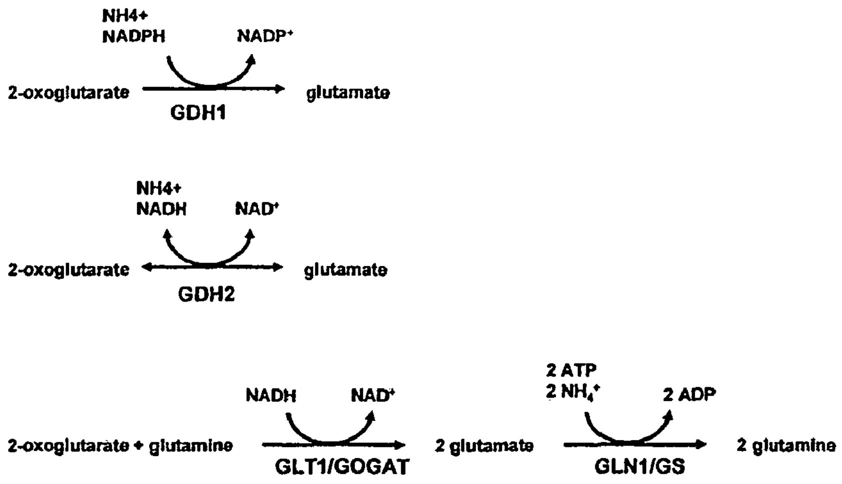
FIG. 6: Ammonia assimilation in *Saccharomyces cerevisiae*

Fatty acid synthesis by the FAS complex requires NADPH as a cofactor, and increased fatty acid production may therefore result in a redox imbalance in the cell, such that the availability of NADPH controls the rate of fatty acid production. Several strategies can be used to overcome this problem, including expression of a heterologous non-phosphorylating $NADP^+$ dependent glyceraldehyde 3-phosphate dehydrogenase (Bro et al. 2005 under review) and modification of the ammonium assimilation pathway (Nissen et al. 2002 Met Eng 2: 69-77). Overexpression of FAS1 and FAS2 can be combined with deletion of GDH1 and overexpression of either GDH2, encoding an NADH-dependent glutamate dehydrogenase, or GLT1 and GLN1, which encode the enzymes that constitute the GS-GOGAT pathway of ammonium assimilation (FIG. 6)

Figure 7:
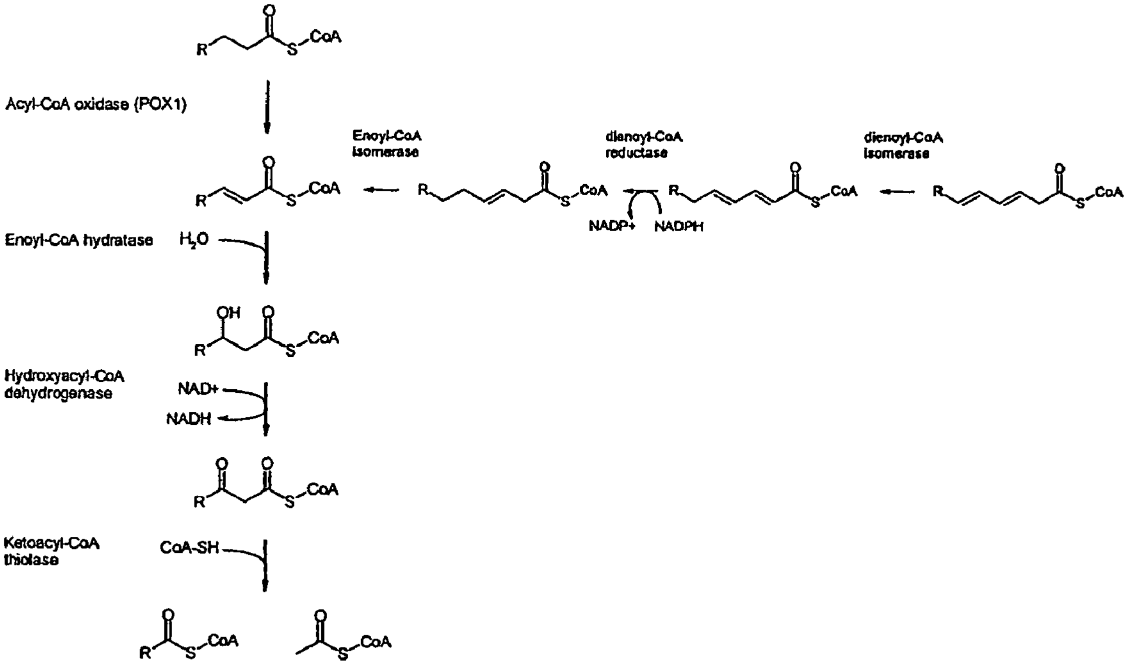
FIG. 7: Fatty acid degradation by beta-oxidation

The fatty acid yield can furthermore be increased by deleting the structural gene for fatty acid degradation, in yeast POX1 (FIG. 7). Such a deletion can be combined, for example, with the overexpression or integration of a heterologous steaoryl-CoA desaturase that is more specific in synthesizing oleic acid instead of palmitoleic acid, thus favoring the synthesis of PUFAs (FIG. 3) This can further be combined with overexpression of ACC1 to further enhance the production of PUFA and/or lipids.

Figure 8:
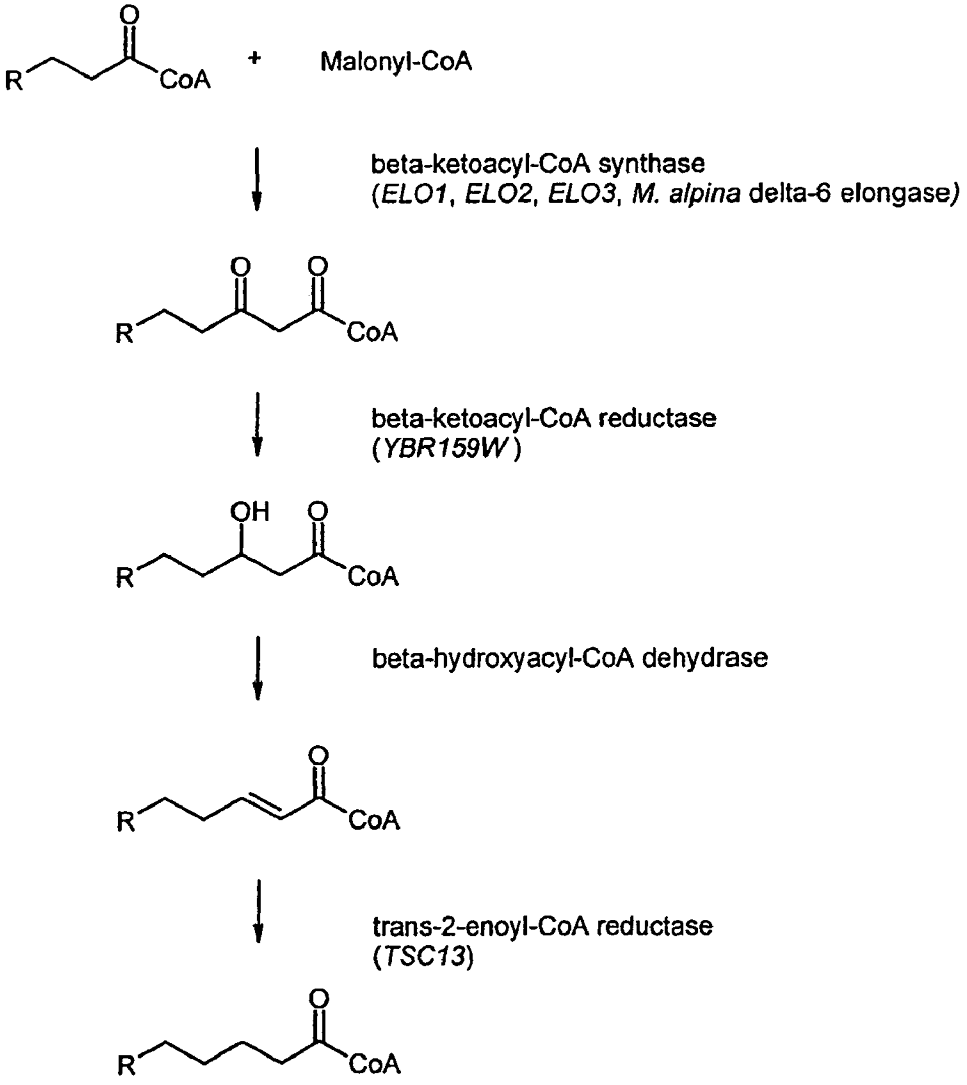
FIG. 8: Fatty acid elongation

Another possibility to improve the PUFA production or yield is to enhance the elongation PUFA. For example, the delta-6 elongase in the pathway to ARA performs a condensation reaction, where 18:3 is fused to a malonyl-CoA unit. However, the complete elongation of 18:3 to 20:3 additionally involves a keto group reduction, a dehydration and an enoyl reduction (FIG. 8). Since heterologous expression of delta-6 elongase in yeast results in elongation of 18:3, the three latter reactions must be catalyzed by endogenous yeast enzymes. The function of these enzymes in wild type yeast is the formation of very long chain fatty acids and the elongation of exogenous short chain fatty acids. A β-ketoacyl-CoA reductase is encoded by the gene YBR159W. The gene encoding the β-hydroxyacyl-CoA dehydrase has not been identified in yeast. The final step of fatty acid elongation, enoyl reduction, is catalyzed by the enzyme encoded by the TSC13 gene. To increase the elongation efficiency, YBR159W and TSC13 can therefore be overexpressed.

Lipid yield and/or PUFA content can also be improved further by combining the differents metabolic engineering strategies described above. This can be done by crossing of strains carrying different genetic modifications, for example as described in Examples 28, 35 and 36.

Overexpression of native yeast genes described above can be achieved by replacing the native promoter with a strong constitutive promoter, for example the TDH3 promoter, the ADH1 promoter, the ACT1 promoter, the TPI promoter or the GPD promoter, using an approach similar to the strategy used in the present invention for integration of *M. alpine* ole1 (example 7). Likewise, heterologous genes can be expressed through integration into the genome as described in example 7. Alternatively, native and heterologous genes can be expressed from plasmids such as the yeast episomal plasmids 2μ and CEN plasmids, or yeast integrating plasmids (i.e., YiP series), as described in examples 2-5. Deletion of yeast genes can be achieved by an approach similar to the one described in example 7. The different genetic alterations described in the present example can be combined by crossing of the recombinant strains or by combining chromosomal modifications with expression from vectors, which can result in an efficient engineered host for production of PUFAs.

The skilled addressee will recognize that simple expression of a heterologous PUFA pathway in bakers yeast is expected to result in a low content of arachidonic acid, as bakers yeast has a low content (approximately 10% of cell dry weight) of fatty acids. Furthermore, the fatty acids in bakers yeast primarily consists of fatty acids with 16 carbon atoms, and the most dominant mono-unsaturated fatty acid is palmitoleic acid, which can not serve as a precursor for synthesis of arachidonic acid. The result of simply expressing four genes encoding the enzymes of the pathway to arachidonic acid in *S. cerevisiae* is illustrated herein (Example 12) where expression of these four genes results in an arachidonic acid content of 0.8% of the fatty acids, or corresponding to less than 0.08% of the yeast dry weight.

Thus, the present invention relates to improvement of the PUFA content in the host organism through fermentation optimization (i.e. fermentation using nitrogen limitation, phosphor limitation, trace element limitation, NaCl limitation, myo-inositol limitation, etc.), e.g. decreasing the temperature and/or designing an optimal medium, or through improving the flux towards fatty acids by metabolic engineering, e.g. through overexpression of fatty acid synthases, overexpression of other enzymes involved in biosynthesis of the precursors for PUFAs, or codon optimization of the heterologous genes, or expression of heterologous enzymes involved in the biosynthesis of the precursor for PUFAs, i.e. oleic acid.

Thus, a preferred embodiment of the present invention relates to a method according to the present invention, wherein said host cell, such as *Saccharomyces cerevisiae* is cultivated in a myo-inositol deficient medium.

Growth on Myo-Inositol Deficient Medium

It is known that in some yeast species grown on media deficient in myo-inositol, the lipid yield is increase. Hence, it is of advantage to grow the genetically modified cells of this invention on a medium that is not supplemented with myo-inositol such that the lipid and PUFA yield is increased.

Codon Usage and Optimization

Codon usage can often differ among different species. For the expression of a heterologous protein from an organism that has a different codon usage it is of advantage to alter the codon usage of the heterologous protein to match that of the host cell. Thereby protein expression can be improved. For example, as compared to *Saccharomyces cerevisiae*, the codon usage is different in many fungi, such as *Mortierella alpina, Cryptococcus, curvatus*, and *Histoplasma capsulatus, Mucor rouxii, Mucor circinelloides, Aspergillus fumigatus Saccharomyces klyveri, Phytophthera megasperma, Pythium irregulare* and *Aspergillus parasiticus*, insects, such as *Trichoplusia ni*, mammals, such as *Mus musculus* and *Homo sapiens*, algae, such *Thraustocytrium aureum, Euglena gracilis, Isochrysis galbana, Saprilegnia diclian, Phaeodactylum tricornutum, Saprolegnia* and *Schizochytrium aggregatum* and *Pavlova lutheri*, worms, such as *Caenorhabditis elegans*, plants, such as *Arabidopsis thaliana, Brassica napus, Glycine soya, Borago officinalis, Anemone leveillei, Marchantia polymorpha, Physcomitrella patens, Petroselinum crispum* and *Phytophthora infestans*, fish, such as *Cyprinus carpio*, and *Salmo salar*. Hence, codon optimization of nucleotide sequences of the corresponding enzymes mentioned in Table 1 will increase PUFA production.

Thus, a preferred embodiment of the present invention relates to a method according to the present invention, wherein said heterologous nucleotide sequences are codon optimized for expression in *Saccharomyces cerevisiae.*

Furthermore, in one embodiment the present invention relates to a method according to the present invention, wherein said combined heterologous expression further comprises an over-expression of at least one of the genes selected from the group consisting of ACC1, YBR159W, ELO1, ELO2, ELO3, FAS1, FAS2, DGA1, LRO1, ARE1, ARE2, and GPD1.

Another embodiment relates to a method according to the present invention, wherein said combined heterologous expression further comprises a deletion of at least one of the genes selected from the group consisting of GPP1, GPP2 and POX1.

Another embodiment relates to a method according to the present invention, wherein said combined heterologous expression further comprises a heterologous expression of the nucleotide sequences encoding ATP:citrate lyase and/or an isocitrate dehydrogenase which is stimulated by AMP.

Another embodiment relates to a method according to the present invention, wherein said combined heterologous expression further comprises a heterologous expression of a nucleotide sequence encoding a non-phosphorylating NADP-dependent D-glyceraldehyde-3-phosphate dehydrogenase.

Another embodiment relates to a method according to the present invention, wherein said combined heterologous expression further comprises a deletion of the gene GDH1 and optionally an over-expression of at least one of the genes selected from the group consisting of GDH2, GLN1 and GLT1.

Another embodiment relates to a method according to the present invention, wherein said combined heterologous expression further comprises an over-expression of at least one of the genes selected from the group consisting of TSC13, GAT1, SLC1 and YDR531W.

Thus, in one embodiment, the present invention relates to methods, cells, and compositions relating to an improved polyunsaturated fatty acid content, wherein said heterologous expression increases the content of each individual specific polyunsaturated fatty acid, particularly ARA, EPA and DHA, to more than 2% of the total fatty acid content, such as 3% of the total fatty acid content, 4% of the total fatty acid content, 5% of the total fatty acid content, 6% of the total fatty acid content, 7% of the total fatty acid content, 8% of the total fatty acid content, 9% of the total fatty acid content, 10% of the total fatty acid content or more.

Thus, in one presently particular preferred embodiment, the method of the invention discloses heterologous expression which increases the content of arachidonic acid, eicosapentaenoic acid and/or docosahexaenoic acid to more than 2% of the total fatty acid content in the genetically modified *Saccharomyces cerevisiae* described herein.

In another embodiment the present invention relates methods, cells, and compositions relating to an improved polyunsaturated fatty acid content, wherein said heterologous expression increases the content of each individual specific polyunsaturated fatty acid to more than 0.1% of the yeast dry weight, such as 0.2% of the yeast dry weight, 0.3% of the yeast dry weight, 0.4% of the yeast dry weight, 0.5% of the yeast dry weight, 0.6% of the yeast dry weight, 0.7% of the yeast dry weight, 0.8% of the yeast dry weight, 0.9% of the yeast dry weight, 1% of the yeast dry weight, 2% of the yeast dry weight, 3 of the yeast dry weight, 4% of the yeast dry weight, 5% of the yeast dry weight or more.

The polynucleotides encoding PUFA desaturases and elongases can be expressed in the host organism from extrachromosomal elements. For extrachromosomal expression in e.g. yeast, high copy number plasmids, are preferred. Other yeast vectors include yeast replicating plasmids (YRps), such as the 2μ plasmid, which have a chromosomally derived replicating sequence and are propagated in medium copy-number (20 to 40 copies per cell), and yeast centromere plasmids (Ycps; also known as CEN plasmids), which have both a replication origin and a centromere sequence, ensuring stable segregation. Several yeast expression vectors with differing selection markers can be used in combination when the purpose is to express several heterologous genes. In addition, several heterologous genes can be expressed from the same plasmid, for example using the pESC vectors (Stratagene), which permit simultaneous, inducible expression from the divergent GAL1/GAL10 promoter sequence. A variety of prokaryotic expression systems can be used to express PUFA-synthesizing desaturases and elongases, including the pBR322 plasmid, the pUC plasmids and derivatives thereof. For expression in prokaryotes the heterologous genes are assembled in an artificial operon, meaning that a single promoter sequence controls the expression of a cluster of genes. Several genes encoding PUFA-synthesizing desaturases and elongases can be fused by PCR and subsequently be subcloned into a bacterial expression vector using standard techniques.

Thus, one aspect of the present invention relates to a vector comprising at least 4 isolated nucleotide sequences having at least 75% sequence identity to the nucleotide sequences selected from the group consisting of SEQ ID NO: 1-38.

As described in detail above, the combined expression of 4-7 heterologous nucleotide sequences should enable PUFA production. Thus, the vector can comprise nucleotide sequences encoding, for example, delta-12 desaturase, delta-6 desaturase, delta 6 elongase and delta-5 desaturase or, for example, delta-12 desaturase, delta-9 elongase, delta-8 desaturase and delta-5 desaturase. Alternatively the expression vector can, for example, comprise 7 genes encoding delta-12 desaturase, delta-6 desaturase, delta 6 elongase, delta-5 desaturase, omega-3 desaturase, delta-5 elongase and delta-4 desaturase.

Due to cross-feeding between cells, it is generally not expected that all cells in a population contain a specific plasmid construct, even though selection pressure is being applied. This effect is enhanced if several different vectors with different selection markers are used. Therefore, all genes required for PUFA production are preferably expressed from a single expression vector. However, as large vector constructs (i.e. vectors exceeding approximately 20 kb in size) may be unstably replicated and segregated in the host cell, it can also be beneficial to express the heterologous pathway from several, for example two, separate vectors.

As the skilled addressee would recognise, the individual nucleotide sequences can be expressed either from a single vector or from separate vectors. The skilled artisan is also well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression, and thus that multiple events must be screened in order to obtain strains displaying the desired expression level and pattern. Such screening may be accomplished by Southern analysis of DNA, Northern analysis of mRNA expression, Western analysis of protein expression, or phenotypic analysis, such as analysis of fatty acid composition that can be detected by methods such as but not limited to, high-performance liquid chromatography (HPLC), gas chromatography coupled to mass spectrometry (GC-MS), thin-layer chromatography, among others.

Preferably, the heterologous genes are expressed from several vectors. It can also be advantageous to express one or several heterologous genes in the PUFA pathway from a genomic location. For example, eicosapentaenoic acid can be produced in *S. cerevisiae* by expressing five heterologous genes encoding delta-12 desaturase, delta-6 desaturase, delta-6 elongase, delta-5 desaturase and omega-3 desaturase from in total three different vectors, and additionally expressing a heterologous delta-9 desaturase from a genomic location (Example 58).

As noted above, once the vector has been constructed, it may then be introduced into the host cell of choice by methods known to those of ordinary skill in the art including, for example, transfection, transformation and electroporation. The host cell is then cultured under suitable conditions permitting expression of the genes leading to the production of the desired PUFA, which is then recovered and purified.

In another aspect, the present invention relates to a genetically modified cell comprising a vector according to the present invention.

As indicated, a further embodiment of the present invention relates to a genetically modified cell, wherein expression of said isolated nucleotide sequences from said vector results in said cell producing a polyunsaturated fatty acid that is not produced in a wild-type of said host cell.

In one aspect the present invention relates to a composition comprising a polyunsaturated fatty acid produced by a genetically modified cell according to the present invention.

In a preferred embodiment the composition comprising a polyunsaturated fatty acid produced by a genetically modified *Saccharomyces cerevisiae* according to the present invention.

As exemplified below, compositions containing 25% PUFA in total fatty acid composition through heterologous expression of at least 4 genes can be achieved by the methods of the present invention.

Thus, in a presently preferred embodiment, the invention relates to a composition comprising at least 25% polyunsaturated fatty acid produced in total fatty acid composition by a genetically modified cell according to the invention.

However, even smaller amounts are of both economical and technical importance, thus the invention furthermore relates to a composition comprising at least 2% polyunsaturated fatty acid of the total fatty acid composition, such as 5% polyunsaturated fatty acid of the total fatty acid composition, such as 10% or more polyunsaturated fatty acid of the total fatty acid composition.

Indeed higher levels are even more preferred such as 25% polyunsaturated fatty acid of the total fatty acid composition, such as 30% polyunsaturated fatty acid of the total fatty acid composition, such as 35% polyunsaturated fatty acid of the total fatty acid composition, such as 40% polyunsaturated fatty acid of the total fatty acid composition, such as 45% polyunsaturated fatty acid of the total fatty acid composition, such as 50% polyunsaturated fatty acid of the total fatty acid composition, such as 55% polyunsaturated fatty acid of the total fatty acid composition, such as 60% polyunsaturated fatty acid of the total fatty acid composition, such as 65% polyunsaturated fatty acid of the total fatty acid composition, such as 70% polyunsaturated fatty acid of the total fatty acid composition, such as 75% polyunsaturated fatty acid of the total fatty acid composition, such as 80% polyunsaturated fatty acid of the total fatty acid composition, such as 85% polyunsaturated fatty acid of the total fatty acid composition, such as 90% polyunsaturated fatty acid of the total fatty acid composition, such as 95% polyunsaturated fatty acid of the total fatty acid composition, such as 97% polyunsaturated fatty acid v total fatty acid composition, such as 98% polyunsaturated fatty acid of the total fatty acid composition, such as 99% polyunsaturated fatty acid of the total fatty acid composition, such as 100% polyunsaturated fatty acid v total fatty acid composition, produced from a cell, such as a microorganism that expresses a heterologous pathway leading to mono unsaturated fatty acids and particularly PUFAs.

A composition in the context of the present invention shall mean a blend or mixture of compounds. In one embodiment said composition is an oil.

As described above the PUFA can be of various formations/formulations, thus in one embodiment said polyunsaturated fatty acid is in a formation of triacylglycerides. In another embodiment, said polyunsaturated fatty acids are in a formulation of phospholipids.

In a further embodiment said polyunsaturated fatty acids is in a formulation of free fatty acids.

There is now numerous data on the advantages of PUFA. Clinical evidence has been collected that shows that DHA and ARA are advantageous in the development of neural and retinal functions and could therefore be of benefit to babies to achieve improved memory and eyesight. In addition, preterm and young infants are actually unable to synthesize sufficient amounts of DHA and naturally receive PUFAs by breast milk. However, PUFAs have previously been absent in infant formula as well as in cow milk. DHA also reduces or eliminates the risk factor involved in various diseases like cardiovascular diseases and has some positive effects on hypertension, arthritis, arteriosclerosis and thrombosis. It is now established that both PUFAs are increasingly supplied in food, for example in infant formula, and also in pharmaceutical and cosmetics formulations. This increasing demand can be covered with the technology described within the present invention through the supply of PUFA such as an oil comprising triacylglycerides, phospholipids or free fatty acids (enriched in PUFA) that are produced in reproducibly high and constant quality by a genetically modified *Saccharomyces cerevisiae* that is capable of producing PUFAs with four or more double bonds when grown on a non-fatty acid substrate.

A general source of PUFAs is fish oil. However, the fatty acid content of fish oil varies during the fishing season and in some cases the fish oil may be contaminated because of environmental pollution. Besides this, fish oil has an obnoxious smell. Fish itself does not produce PUFA but takes it up usually through the consumption of algae. Nowadays, fish oil rich in PUFAs is produced from aquacultured fish. However, the PUFA content can vary depending on the diet that they are fed. Besides this, a shortage in high quality fish feed is expected and it is therefore of advantage to supplement fish feed with PUFA or simply with yeast or feed that is high in PUFA content.

Thus, one embodiment of the present invention relates to the use of a composition according to the present invention as an ingredient in a food product. Another embodiment relates to the use of a composition according to the present invention as an ingredient in a cosmetic product.

In a particular preferred embodiment, the present invention relates to the use of a composition according to the invention as an ingredient in feed.

In a presently most preferred embodiment, the present invention relates to the use of a genetically modified *Saccharomyces cerevisiae* according to the invention as an ingredient in feed.

The composition could be an oil containing polyunsaturated fatty acids, and the PUFAs can be in formation of triglycerides, phospholipids or free fatty acids.

The invention will now be further described by way of the following non-limiting examples.

EXAMPLES

Example 1

Isolation of Genes Encoding Delta-9 Desaturase, Delta-12 Desaturase, Delta-6 Desaturase, Delta-6 Elongase and Delta-5 Desaturase The fungus *Mortierella alpina* produces arachidonic acid via a pathway, where oleic acid is desaturated and elongated in turn by a delta-12 desaturase, a delta-6 desaturase, a delta-6 elongase and a delta-5 desaturase. The nucleotide sequences encoding these enzymes were amplified by PCR using first strand cDNA from *Mortierella alpina* CBS 608.70. In addition, the nucleotide sequence coding for the delta-9 desaturase of *M. alpina* was isolated. The defined primers used for the amplification were designed to match the published sequences of *M. alpina* genes encoding these enzymes.

The procedure was as follows:

*M. alpina* CBS 608.70 was cultivated in 100 ml GY medium (20 g/L glucose, 10 g/L yeast extract pH 6.0) at room temperature for 3 days. Biomass was collected by filtration and total RNA was isolated using Trizol reagent (Gibco BRL). Approximately 5 μg of RNA was used for reverse transcription (Superscript II RT, Invitrogen) using Oligo(dT) 12-18 as primer. After first strand cDNA synthesis, complementary RNA was removed by RNAse digestion. The cDNA was then used as template for PCR (Phusion enzyme, Finnzymes) using the following primers: 5'ATGGCAACTCCTCTTCCCCCCTCC 3' (SEQ ID NO: 115) and 5'CTATTCGGCCTTGACGTGGTCAGTGC 3' (SEQ ID NO: 116) for delta-9 desaturase; 5'AACCCTTTTTCAGGATGGCACC 3' (SEQ ID NO: 117) and 5'AAAGTTGTGTCCGGTAAATGCTTC 3' (SEQ ID NO: 118) for delta-12 desaturase; 3' GGACTAGTCCACCATGGCTGCTGCTCCCAGTGTGAGG 5' (SEQ ID NO: 119) and 3' CCATCGATGGCTTACTGTGCCTTGCCCATCTTGGAGG 5' (SEQ ID NO: 120) for delta-6 desaturase; 5'ATGGAGTCGATTGCGCCATTCC 3' (SEQ ID NO: 121) and 5'TTACTGCAACTTCCTTGCCTTCTCC3' (SEQ ID NO: 122) for delta-6 elongase; and 5'ATGGGTACGGACCAAGGAAAAACC3' (SEQ ID NO: 123) and 5'CTACTCTTCCTTGGGACGGAGTCC3' (SEQ ID NO: 124) for delta-5 desaturase. The resulting fragments of the expected sizes were excised from an agarose gel and purified using GFX-columns (Amersham).

Example 2

Construction of a Yeast Vector for Expression of Delta-12 Desaturase

The gene encoding delta-12 desaturase, isolated as described in Example 1, was reamplified by PCR using the primers 5'GACCTCGAGTAAGCTTATGGCACCTCCCAACACTATTG 3' (SEQ ID NO: 125) and 5'GCTAGCCGCGGTACCAATTACTTCTTGAAAAAGACC 3' (SEQ ID NO: 126). These primers introduced XhoI and NheI restriction sites at the 5' and 3' ends of the gene, respectively, and allowed ligation of the XhoI/NheI restricted PCR fragment into an XhoI/NheI digested pESC-TRP vector (Stratagene) to yield pESC-TRP-delta-12. The sequence of the gene encoding delta-12 desaturase (SEQ ID NO 5) was obtained by sequencing of two different clones of pESC-TRP-delta-12.

Example 3

Figure 9:
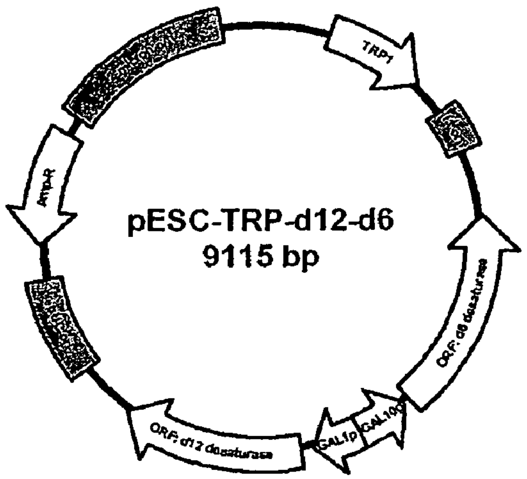
FIG. 9: Yeast vector for expression of genes encoding delta-12 desaturase and delta-6 desaturase and Yeast vector for expression of genes encoding delta-6 elongase and delta-5 desaturase.
Figure 9:
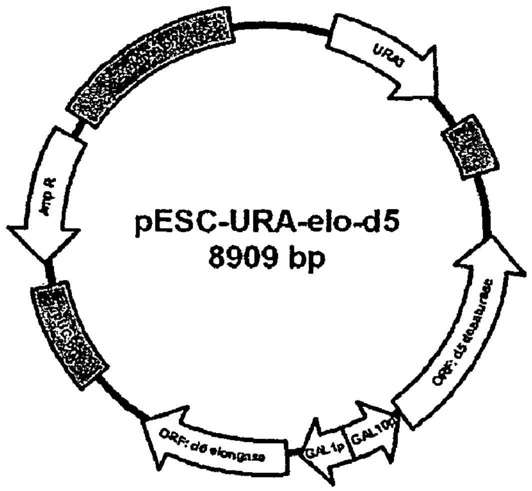

Construction of a Yeast Vector for Expression of Delta-12 Desaturase and Delta-6 Desaturase The gene encoding delta-6 desaturase was isolated as described in Example 1. The resulting PCR fragment contained SpeI and ClaI restriction sites at the 5' and 3' ends of the gene, respectively. The fragment was restricted with SpeI and ClaI and was ligated into SpeI/ClaI digested pESC-TRPdelta-12 (Example 2). The resulting plasmid, pESC-TRP-delta-12 delta-6, contained the genes encoding delta-12 desaturase and delta-6 desaturase under the control of the divergent GAL1/GAL10 promoter (FIG. 9A). The sequence of the gene encoding delta-6 desaturase (SEQ ID NO 11) was obtained by sequencing of two different clones.

Example 4

Construction of a Yeast Vector for Expression of Delta-6 Elongase

The gene encoding delta-6 elongase, isolated as described in Example 1, was reamplified by PCR using the primers 5' GACCTCGAGTAAGCTTATGGAGTCGATTGCGCC 3' (SEQ ID NO: 127) and 5' GCTAGCCGCGGTACCAATTACTGCAACTTCCTTGC 3' (SEQ ID NO: 128). These primers introduced HindIII and NheI restriction sites at the 5' and 3' ends of the gene, respectively, and allowed ligation of the HindIII/NheI restricted PCR fragment into a HindIII/NheI digested pESC-URA vector (Stratagene) to yield pESC-URA-elo. Two different clones of pESC-URA-elo were sequenced to obtain the sequence of the cloned gene (SEQ ID NO 16).

Example 5

Construction of a Yeast Vector for Expression of Delta-6 Elongase and Delta-5 Desaturase The gene encoding delta-5 desaturase, isolated as described in Example 1, was reamplified by PCR using the primers 5'CGCACTAGTATCGATATGGGTACGGACCAAGG 3' (SEQ ID NO: 129) and 5' TTAATTAAGAGCTCAGATCTTCTACTCTTCCTTGGGACG 3' (SEQ ID NO: 130). These primers introduced ClaI and SacI restriction sites at the 5' and 3' ends of the gene, respectively, and allowed ligation of the ClaI/SacI restricted PCR product into ClaI/SacI digested pESC-URA-elo (Example 4). The resulting plasmid, pESC-URA-elo-delta-5, contained the genes encoding delta-6 elongase and delta-5 desaturase under the control of the divergent GAL1/GAL10 promoter (FIG. 9B). The sequence of the gene encoding delta-5 desaturase (SEQ ID NO 22) was obtained by sequencing of two different clones of pESC-URA-elo-delta-5.

Example 6

Expression of the Pathway to Arachidonic Acid in Yeast

Yeast strains containing the appropriate genetic markers were transformed with the vectors described in Examples 2, 3, 4, and 5, separately or in combination. Transformants were selected on medium lacking uracil and tryptophane and subsequently streak purified on the same medium.

*S. cerevisiae* strain CEN.PK113-3C (MATa trp1) was transformed separately with the vector pESC-TRP-delta-12 (Example 2), yielding the strain FS01321, and with pESC-TRP-delta-12 delta-6 (Example 3), resulting in the strain FS01322. *S. cerevisiae* strain FS01267 (MATa trp1 ura3) was co-transformed with pESC-TRP-delta-12 delta-6 and pESC-URA-elo (Example 4), and the transformed strain was named FS01323. The same strain was also co-transformed with pESC-TRP-delta-12 delta-6 and pESC-URA-elo-delta-5 (Example 5), resulting in the strain FS01324.

Example 7

Replacement of Yeast OLE1 with *M. alpina* ole1

Figure 10:
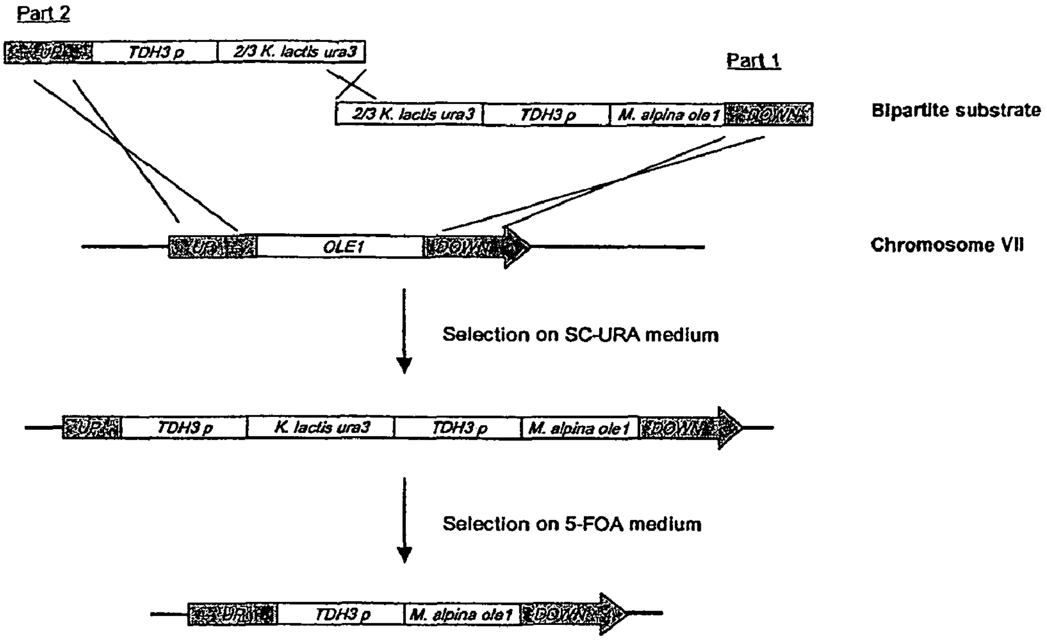
FIG. 10: Strategy for integration of *M. alpina* ole1 into the genome of *S. cerevisiae*

Replacement of the native *S. cerevisiae* OLE1 gene with the corresponding gene from *M. alpina* was carried out through homologous recombination with a bipartite substrate (FIG. 10). One part of the bipartite substrate consisted of two thirds (towards the 3'end) of *K. lactis* URA3, fused to the TDH3 promoter sequence, the *M. alpina* ole1 gene and a target sequence downstream of the native *S. cerevisiae* OLE1. The second part of the bipartite substrate consisted of a target sequence upstream of the native OLE1, fused to the TDH3 promoter sequence and two thirds (towards the 5' end) of *K. lactis* URA3. Following transformation with the bipartite substrate and selection on medium lacking uracil, transformants were obtained in which the native OLE1 had been knocked out and replaced with two copies of the TDH3 promoter sequence as a direct repeat on either side of the *K. lactis* URA3 marker gene and the *M. alpina* ole1 gene immediately downstream of the second TDH3 promoter repeat. A second recombination event, resulting in looping out of the selection marker, was selected for by replating transformants on medium containing 5'-fluoroorotic acid (5-FOA), which is toxic to cells expressing the URA3 gene. This resulted in a strain, in which the native *S. cerevisiae* OLE1 gene had been replaced with the *M. alpina* ole1 under the control of the TDH3 promoter. Suitable genetic markers were introduced into this strain by crossing it with a strain of opposite mating type and containing the desired marker, inducing sporulation, dissecting the spores, and scoring the genotypes of the novel haploid strains.

The procedure was as follows:

For construction of the first part of the bipartite gene targeting substrate, the *M. alpina* ole1 gene (SEQ ID NO 1), isolated as described in Example 1, was reamplified by PCR using the primers 5'ATGGCAACTCCTCTTCCCCCCTCC 3' (SEQ ID NO: 115) and 5'TTGTTATTGTAATGTGATACCTATTCGGCCTTGACGTGG 3' (SEQ ID NO: 131). A target sequence downstream of *S. cerevisiae* OLE1 was amplified by PCR using *S. cerevisiae* genomic DNA as template and the primers 5' GTATCACATTACAATAACAAAACTGCAAC 3' (SEQ ID NO: 132) and 5' ACCAGCATCTATTAAAGTAAAATACCG 3' (SEQ ID NO: 135). A third DNA fragment was generated by PCR using a plasmid, containing the TDH3 promoter sequence (−1 to −1067) downstream of the *K. lactis* URA3, as template and the primers 5' CTTGACGTTCGTTCGACTGATGAGC 3' (SEQ ID NO: 133) and 5' GGGGGGAAGAGGAGTTGCCATTTTGTTTGTTTATGTGTG 3' (SEQ ID NO: 134). These PCR fragments were then fused during two rounds of PCR. First, *M. alpina* ole1 was fused to the downstream target sequence using the primers 5'ATGGCAACTCCTCTTCCCCCCTCC 3' (SEQ ID NO: 115) and 5' ACCAGCATCTATTAAAGTAAAATACCG 3'(SEQ ID NO: 135). Second, the product of the first fusion reaction was fused to the *K. lactis* URA3/TDH3 promoter fragment using the primers 5'CTTGACGTTCGTTCGACTGATGAGC 3' (SEQ ID NO: 133) and 5' ACCAGCATCTATTAAAGTAAAATACCG 3'(SEQ ID NO: 135). This resulted in the fusion product 2/3URA3-TDH3p-ole1-DOWN, which constituted the first part of the bipartite gene targeting substrate.

For construction of the second part of the bipartite substrate, a target sequence upstream of the native *S. cerevisiae* OLE1 was amplified by PCR using *S. cerevisiae* genomic DNA as template and the primers 5' GCTGAAAAGATGATGTTCTGAGG 3' (SEQ ID NO: 136) and 5' AGTACATA- CAGGGAACGTCCGCGGTCTGCAGAGAAGGC 3'(SEQ ID NO: 137). A second PCR fragment was constructed using a plasmid, containing the TDH3 promoter sequence (−1 to −1067) upstream of the *K. lactis* URA3 gene, as template and the primers 5' GGACGTTCCCTGTATGTACTAAAAAT-GAAAGAAGCTTACCAG 3' (SEQ ID NO: 138) and 5' GAGCAATGAACCCAATAACGAAATC 3'(SEQ ID NO: 139). Finally, this fragment was fused to the upstream target sequence by PCR using the primers 5' GCTGAAAAGAT-GATGTTCTGAGG 3' (SEQ ID NO: 136) and 5' GAGCAAT-GAACCCAATAACGAAATC 3'(SEQ ID NO: 139), resulting in the fusion product UP-TDH3p-2/3URA3, which was the second part of the bipartite gene targeting substrate.

The yeast strain CEN.PK 113-5D (MATa ura3) was transformed with the linear substrates 2/3URA3-TDH3p-ole1-DOWN and UP-TDH3p-2/3URA3 and plated out on medium lacking uracil. Transformants were streak purified on the same medium and then transferred onto medium containing 5-FOA. Pop-out recombinants were streak purified on 5-FOA-containing medium and verified by colony PCR. The correct integration and absence of mutations in the TDH3 promoter and *M. alpina* ole1 (SEQ ID NO 1) was verified by sequencing of the modified region in two different transformants. The resulting strain, FS01309, had the genotype MATa OLE1::TDH3p-*M. alpina* ole1.

To introduce the TRP1 marker into FS01309, FS01309 was crossed with a trp1 strain of the same genetic background (CEN.PK) and opposite mating type. Diploids were selected on medium lacking uracil and tryptophane and transferred to sporulation medium. Following sporulation, spores were dissected using a Singer MSM microscope and micromanipulator dissection microscope. Tetrads were scored for auxotrophy by replica-plating to suitable drop-out plates and for the OLE1::TDH3p-*M. alpina* ole1 genotype by colony-PCR, using the primers 5' ATGGCAACTCCTCTTCCCCCCTCC 3' (SEQ ID NO: 115) and 5' AGACATTGAAATCCAAA-GAAGACTGAAGG 3' (SEQ ID NO: 140). Mating type was scored by replica-plating to a lawn of cells with either a or alpha mating type, incubating at 30° C. to allow mating, replica-plating to sporulation medium, and visualizing sporulation by illuminating plates under a 302 nm UV-light source. The haploid strains with the mating types MATa trp1 OLE1::TDH3p-*M. alpina* ole1 and MATa ura3 trp1 OLE1:TDH3p-*M. alpina* ole1 were named FS01315 and FS01316, respectively.

Example 8

Expression of the Pathway to Arachidonic Acid in Combination with a Heterologous Delta-9 Desaturase in Yeast Yeast strains, in which the native OLE1 was replaced with ole1 from *M. alpina* (Example 7) and containing the appropriate genetic markers, were transformed with the vectors described in Examples 2, 3, 4, and 5, separately or in combination. Transformants were selected on medium lacking uracil and tryptophane and streak purified on the same medium.

*S. cerevisiae* strain FS01315 (MATa trp1 OLE1::TDH3p-*M. alpina* ole1) was transformed separately with the vector pESC-TRP-delta-12 (Example 2), yielding the strain FS01326, and with pESC-TRP-delta-12 delta-6 (Example 3), resulting in the strain FS01327. *S. cerevisiae* strain FS01316 (MATa trp1 ura3 OLE1::TDH3p-*M. alpina* ole1) was co-transformed with pESC-TRP-delta-12 delta-6 and pESC-URA-elo (Example 4), and the transformed strain was named FS01328. The same strain was also co-transformed with pESC-TRP-delta-12 delta-6 and pESC-URAelo-delta-5 (Example 5), resulting in the strain FS01329.

Example 9

Fermentation with Recombinant Yeast Strains in Shake Flasks

Single yeast colonies were inoculated into 100 ml minimal medium (5 g/L glucose, 20 g/L galactose, 15 g/L (NH4) 2SO4, 1 g/L MgSO4.7H2O, 14.4 g/L KH2PO4, 1 mL/L vitamin solution, 1 mL/L trace metal solution, pH 6.5) in 500 ml baffled shake flasks. The vitamin solution contained: 50 mg/L biotin, 1 g/L calcium panthotenate, 1 g/L nicotinic acid, 25 g/L myo-inositol, 1 g/L thiamine HCl, 1 g/L pyridoxal HCl and 0.2 g/L para-aminobenzoic acid, while the trace metal solution contained: 15 g/L EDTA, 4.5 g/L $ZnSO_4.7H_2O$, 1 g/L $MnCl_2.2H_2O$, 0.3 g/L $CoCl_2.6H_2O$, 0.4 g/L $Na_2MoO_4.2H_2O$, 4.5 g/L $CaCl_2.2H_2O$, 3 g/L $FeSO_4.7H_2O$, 1 g/L $H_3BO_3$ and 0.1 g/L KI. For the ura3 strain FS01309, 100 ml/L of an amino acid cocktail (0.5 g/L histidine, 0.5 g/L tryptophane, 0.5 g/L uracil, 0.5 g/L leucine) was added to the medium by filtering through a 0.22 μm sterile filter. The cultures were incubated shaking (150 rpm) at 18 or 30° C. for 96 or 72 hours, respectively. Following incubation, the biomass was collected by filtration and the lipid composition was analyzed as described in Example 11.

Example 10

Fermentation with Recombinant Yeast Strains in Fermenters

The recombinant yeast strains can be grown in fermenters operated as batch, fed-batch or chemostat cultures.

Batch and Fed-Batch Cultivations

For the precultures, single yeast colonies are inoculated into 100 ml minimal medium in 500 ml baffled shake flasks as described in example 9 and incubated shaking (150 rpm) at 30° C. Exponentially growing precultures are used for inoculation of batch cultivations at a starting concentration of 1 mg DW/L. Batch cultivations can be carried out in laboratory fermenters (e.g. B. Braun Biotech, Melsungen, Germany) with a working volume of 2 L. For the cultivations can be used a defined medium containing: 40 g/L glucose or galactose; 5.0 g/L $(NH_4)_2SO_4$; 3.0 g/L $KH_2PO_4$; 0.5 g/L $MgSO_4.7H_2O$ is used; and trace metals and vitamins as described in example 9. Antifoam (300 μl/L, Sigma A-8436) is added to avoid foaming. The choice of carbon source is dependent on the promoters chosen for heterologous expression; for example, if the GAL1/GAL10 promoters are used, galactose is used as carbon source and if constitutive yeast promoters are used, glucose is generally chosen as carbon-source. The carbon source should be autoclaved separately from the minimal medium and afterwards added to the fermenter. Also, the vitamin and trace metal solutions are added to the fermenter by sterile filtration following autoclaving and cooling of the medium. Cultivations are performed at a fixed temperature, e.g. 18° C. or 30° C., with a stirrer speed of 600 rpm and with 1 vvm (volume air per volume liquid per minute) aeration. The pH is controlled at 5.0 by automatic addition of 4 M KOH. The bioreactors are fitted with cooled condensers, and the off-gas can be led to a gas analyser (INNOVA, Ballerup, Denmark) to measure the off-gas content of $CO_2$.

Chemostat Cultures

In chemostat cultures the cells can be grown in, for example, 1-L working-volume Applikon laboratory fermentors. In brief, the cultures are fed with a defined medium containing glucose or galactose as the growth-limiting nutrient (same medium as for the batch fermentations). The dilution rate (which equals the specific growth rate) in a steady-state culture can be set at different values, e.g. at 0.050 $h^{-1}$, 0.10 $h^{-1}$, 0.15 $h^{-1}$ or 0.20 $h^{-1}$. The temperature is set at a fixed value, e.g. 18° C. or 30° C., and the culture pH is set to 5.0. Aerobic conditions are maintained by spraying the cultures with air (e.g. 0.5 L/min). The dissolved-oxygen concentration, which is continuously monitored, e.g. with an Ingold model 34 100 3002 probe, is kept above 50% of air saturation.

Example 11

Analysis of PUFAs as Methyl Esters

Figure 11:
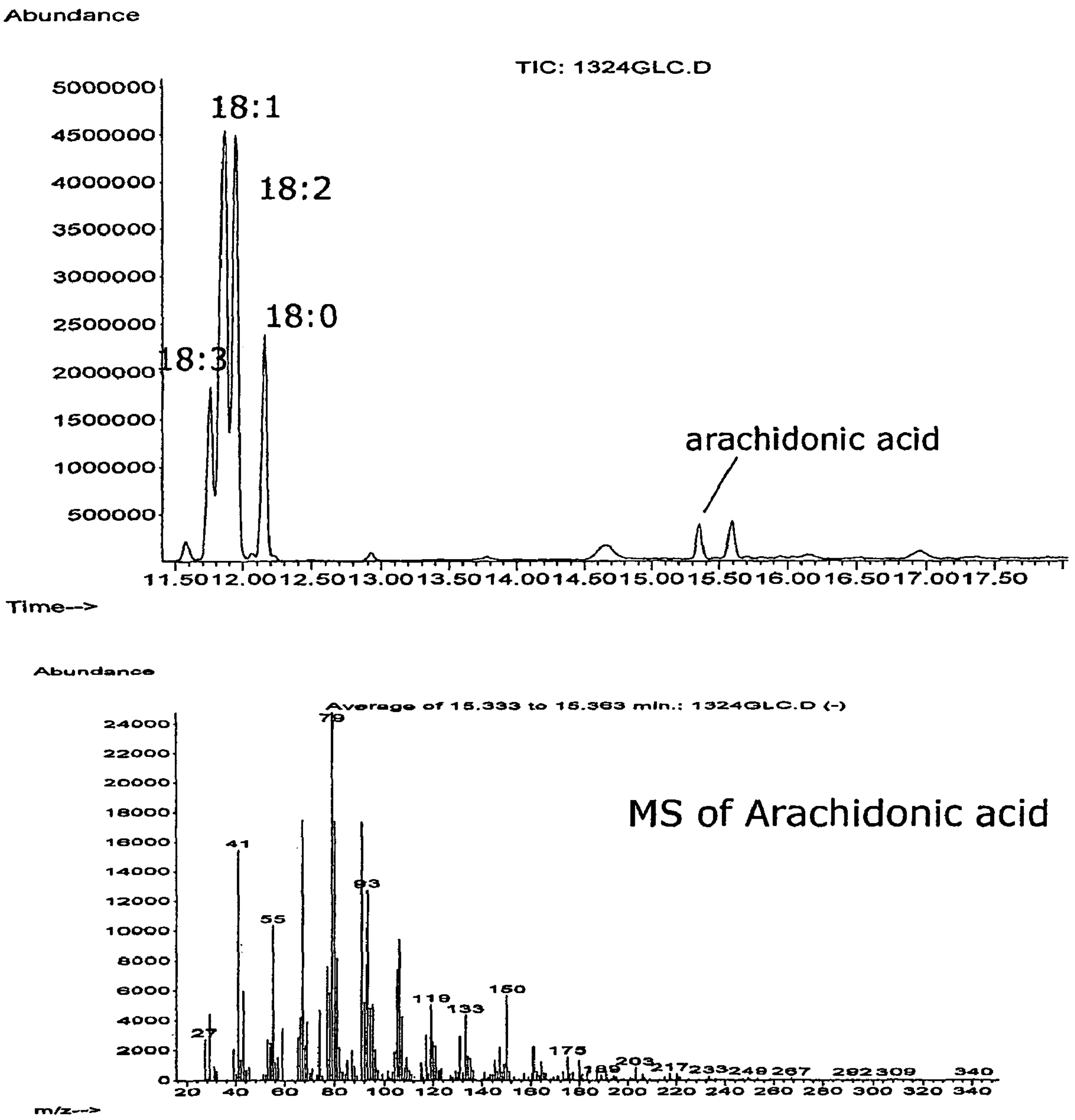
FIG. 11: Gas chromatogram profile of fatty acids, extracted from *S. cerevisiae* harbouring a heterologous pathway including delta-12 desaturase, delta-6 desaturase, delta-6 elongase and delta-5 desaturase and corresponding mass spectrogram of arachidonic acid
Figure 12:
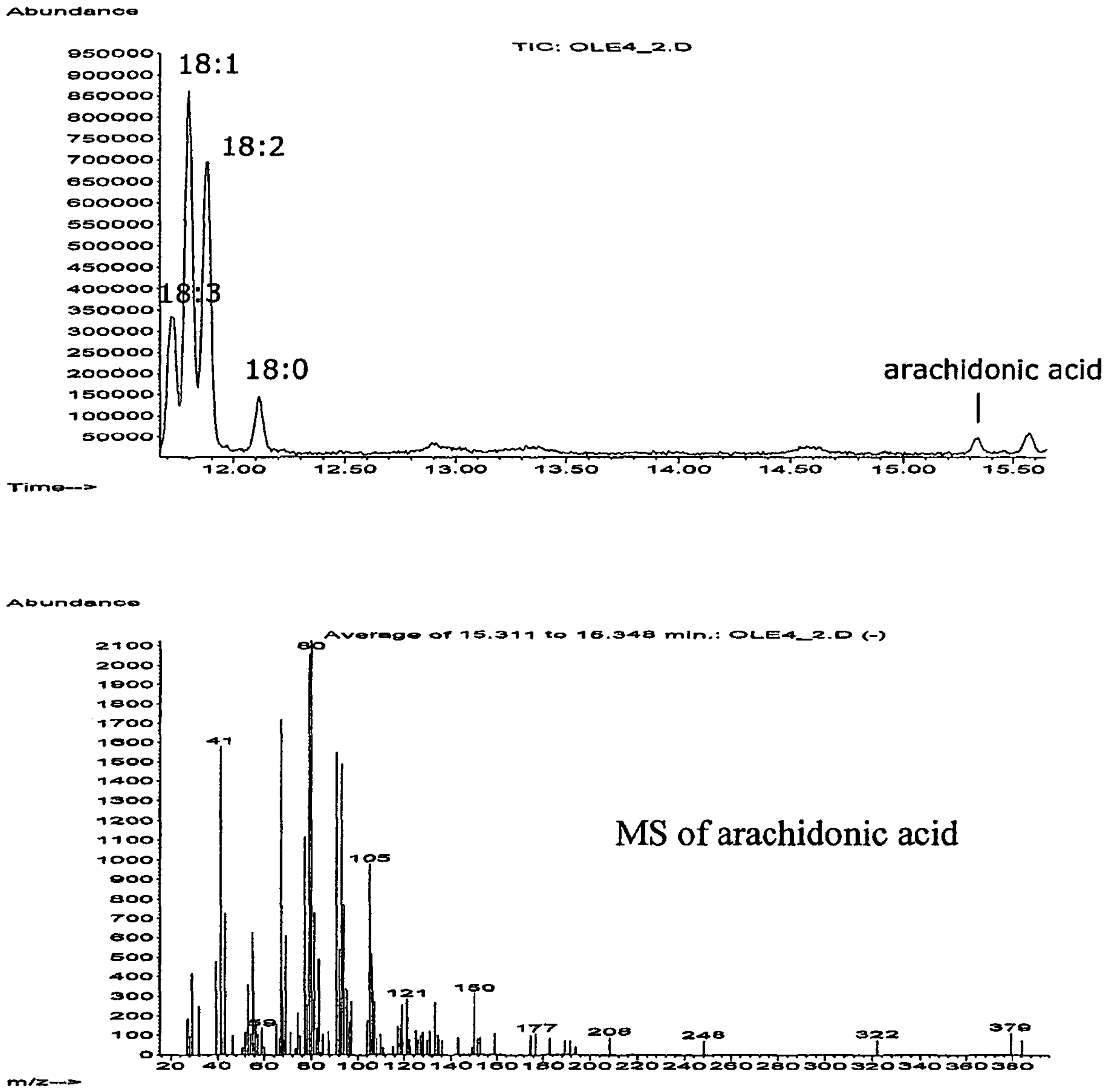
FIG. 12: Gas chromatogram profile of fatty acids, extracted from *S. cerevisiae* harbouring a heterologous pathway including delta-9 desaturase, delta-12 desaturase, delta-6 desaturase, delta-6 elongase and delta-5 desaturase and corresponding mass spectrogram of arachidonic acid

Cells are grown in 100 ml shake flasks using the minimal medium as described in example 9 until the carbon source is exhausted. The biomass is separated through centrifugation at 3000 rpm, and the lipids are extracted using 30 ml of a chloroform/methanol mixture (2:1, v:v) overnight. In the next step, the sample is filtrated, the solvent solution is washed with 6 ml NaCl and the sample is dried over nitrogen. To the lipids, 2 ml toluene and 2 ml 1% sulphuric acid in methanol are added, and the sample is left at 50° C. overnight for transesterification of the lipids. The sample is washed with 5 ml NaCl solution and vortexed. Extraction of methyl esters start with the addition of 5 ml hexane, then the sample is vortexed and the upper hexane phase is removed. Another 5 ml hexane is added and the extraction is continued. 4 ml sodium carbonate is added to the hexane, the sample is vortexed and the phases are separated through centrifugation at 2000 rpm for 2 min. The sample is dried using anhydrous sodium sulphate and the solution is filtrated and dried over nitrogen. To the dried sample 0.5 ml of hexane is added and the sample is ready for determination of methyl esters, which is conducted using a gas chromatograph coupled to mass selective detector (GC/MS). The GC/MS is a Hewlett Packard HP G1723A, gas chromatograph-quadruple mass selective detector (EI) operated at 70 eV. The column is a JW-1701, 30 m, 250 μm i.d., 0.15 μm film thickness. The MS is operated in SCAN Mode. The oven temperature is initially 170° C. and in the following risen to 220° C. at 4° C./min. The final temperature is held for 3 min. The flow through the column is 1 ml He/min. Injection volumes are 5 μl. The injector is driven at split of 100:1 splitless for all analyses. The temperature of the inlet is 300° C., the interface temperature 230° C., and the quadropule temperature 105° C. Detected fatty acid methyl esters are confirmed with the 1998 NIST Mass Spectral Database, and retention times are confirmed with standard fatty acid methyl esters. A typical gas chromatogram is shown in FIG. 11:

Example 12

Fatty Acid Compositions of Recombinant Yeast Strains

The recombinant yeast strain FS01324, expressing the *M. alpina* genes encoding delta-12 desaturase, delta-6 desaturase, delta-6 elongase and delta-5 desaturase, and the recombinant yeast strain FS01329, which in addition to the mentioned *M. alpina* genes also expresses the *M. alpina* ole1 gene, were cultivated as described in example 9 and the fatty acid composition was analyzed as described in example 11. A wild-type strain (FS01201) of the same genetic background was also included in the analysis as a reference. Strains FS01329 and FS01201 were cultivated at 30° C., while FS01324 was cultivated at 17° C.

The results of the analysis (Table 2) show that arachidonic acid was produced in both recombinant strains. As expected, the percentage of arachidonic acid was higher in FS01329 than in FS01324, i.e approximately two times higher. Furthermore, the ratio of stearic acid (18:1) to palmitoleic acid (16:1) was dramatically increased in the ole1 expressing strain FS01329.

TABLE 2

Fatty acid composition (% of total fatty acid) of the recombinant yeast strains FS01324 and FS01329, and of the wild-type strain FS01201.

| Fatty acid | FS01201 | FS01324 | FS01329 |
|---|---|---|---|
| 12:0 | 1.9 | 2.5 | 0.51 |
| 16:0 | 21.8 | 13.3 | 29.1 |
| 16:1 | 46.5 | 48.4 | 5.8 |
| 18:0 | 7.8 | 4.5 | 4.1 |
| 18:1 | 20.0 | 12.6 | 23.8 |
| 18:2 | — | 9.7 | 19.8 |
| 18:3 | — | 4.0 | 10.2 |
| 20:3 | — | — | 1.3 |
| 20:4 | — | 0.8 | 1.7 |
| Other | 2.1 | 4.2 | 3.7 |

Example 14

Integration of Genes Encoding Delta-12 Desaturase, Delta-6 Desaturase, Delta-6 Elongase and Delta-5 Desaturase into the Yeast Genome The genes encoding delta-12 desaturase, delta-6 desaturase, delta-6 elongase and delta-5 desaturase, isolated according to Example 1, are each placed downstream of a separate strong, constitutive yeast promoter (e.g. TDH3 promoter, ADH1 promoter, GPD promoter or TPI promoter) on an a single plasmid. The plasmid also contains a target sequence for integration into the yeast genome by homologous recombination and the *K. lactis* URA3 gene flanked by direct repeats. The target sequence is engineered to contain a unique restriction site to allow linearization of the plasmid.

Suitable yeast strains (e.g. a strain with the genotype MATa ura3 and a strain with the genotype MATa ura3 OLE1::TDH3p-*M. alpina* ole1) are transformed with the linearized plasmid, and transformants are selected on medium lacking uracil. After streak purification on the same medium, pop-out of the *K. lactis* URA3 marker is selected for on medium containing 5-FOA. Correct integration of the plasmid is verified by PCR and sequencing of the modified region. To introduce desired genetic features into the resulting strain, it is crossed to a suitable yeast strain of opposite mating type. Following selection of diploids, sporulation and dissection, the novel haploid strains are scored by the methods described in Example 7.

Example 15

Cloning of a Delta-5 Elongase into a Yeast Expression Vector

The mouse gene Ssc2 encodes a protein with sequence homology to a fatty acid elongase from yeast, ELO1p (Tvrdik et al. 2000). Expression of the gene in Human Embryonic Kidney 293 Cells, followed by in vitro assays of proteins extracted from these cells, has shown that the Ssc2 gene product can elongate 20:4 (n-6) and 20:5 (n-3), i.e. arachidonic acid and eicosapentaenoic acid (Moon et al. 2001).

Mouse Ssc2 (Tvrdik et al. 2000, Moon et al. 2001) was isolated by PCR using Mouse liver cDNA (Quick-Clone cDNA, Clontech) as template and the primers 5'GAA-GATCTCCACCATGGAGCAGCTGAAGGC-CTTTGATAATG 3' (SEQ ID NO: 141) and 5'CCTTAAT-TAAGGCTTATTGAGCCTTCTTGTCCGTCATGCCATTAGC 3' (SEQ ID NO: 142). These primers contained BglII and PacI restriction sites, allowing ligation of the BglII/PacI digested PCR fragment into BglII/PacI digested pESC-TRP vector, resulting in the vector pESC-TRP-delta-5elo.

Example 16

Cloning of a Omega3 Desaturase into a Yeast Expression Vector

C. elegans fat1 (Spychalla et al. 1997) is amplified from a C. elegans cDNA library (Stratagene) using a gene-specific forward primer containing a KpNI restriction site and a gene-specific reverse primer containing a NheI restriction site. The PCR product is digested with KpNI/NheI and ligated into KpNI/NheI digested pESC-TRP-delta-5elo vector (Example 15), yielding the vector pESC-TRP-delta-5elo-omega3.

Example 17

Cloning of a Delta-4 Desaturase into a Yeast Expression Vector

Thraustochytrium sp. ATCC 26185 is cultivated in a 500 ml shake flask containing 100 ml medium at room temperature with shaking. Following harvest of biomass, total RNA is isolated and used for cDNA preparation using Oligo(dT)12-18 as primer. Thraustochytrium Fad4 is amplified using the Thraustochytrium cDNA as template and gene-specific primers containing suitable restriction sites. The Fad4 gene is then ligated into a suitable yeast expression vector (e.g. a high-copy vector with HIS or LEU selection and a galactose-inducible or constitutive promoter).

Example 18

Expression of the Pathway to Docosahexaenoic Acid in Yeast

A yeast strain, containing genes encoding delta-12 desaturase, delta-6 desaturase, delta-6 elongase and delta-5 desaturase integrated in its genome (Example 14), is co-transformed with pESC-TRP-delta-5elo-omega-3 (Example 16) and an expression vector containing a gene encoding a delta-4 desaturase (Example 17).

Example 19

Integration of Genes Encoding Delta-5 Elongase, Omega-3 Desaturase and Delta-4 Desaturase into the Yeast Genome Genes encoding delta-5 elongase, omega-3 desaturase and delta-4 desaturase are each placed downstream of a separate strong, constitutive yeast promoter (e.g. TDH3 promoter, ADH1 promoter, GPD promoter or TPI promoter) on a single plasmid. The plasmid also contains a target sequence for integration into the yeast genome by homologous recombination and the K. lactis URA3 gene flanked by direct repeats. The target sequence is engineered to contain a unique restriction site to allow linearization of the plasmid. Suitable yeast strains are transformed with the linearized plasmid, and transformants are selected on medium lacking uracil. After streak purification on the same medium, pop-out of the K. lactis URA3 marker is selected for on medium containing 5-FOA. Correct integration of the plasmid is verified by PCR and sequencing of the modified region. In order to introduce desired genetic features into the resulting strain, it is crossed to a suitable yeast strain of opposite mating type. Following selection of diploids, sporulation and dissection, the novel haploid strains are scored by the methods described in Example 7.

Example 20

Construction of Vectors for PUFA Production in E. coli

The genes needed for PUFA production (e.g. genes encoding delta-12 desaturase, delta-6 desaturase, delta-6 elongase and delta-5 desaturase for arachidonic acid production) are fused by PCR such that the stop and start codons overlap each other. Suitable primers are used, such that unique restriction sites are introduced at the 5' end and 3' end of the fusion product. The fusion product is ligated into an E. coli expression vector (e.g. pTXB1, pBR322 or a pUC vector) downstream of the promoter, resulting in an artificial operon. More genes (e.g. delta-5 elongase, delta-3 desaturase, delta-4 desaturase) can be added to the operon, again using a PCR-fusion approach followed by insertion at the 3' end restriction site that was originally used for cloning of the cluster. Preferably, the expression system is based on a constitutive promoter, such as the bacteriophage gamma tandem promoter PR, PL or a strong constitutive E. coli promoter. Alternatively, the system is temperature-inducible, e.g. the bacteriophage gamma tandem promoter PR, PL is used in combination with the cI857 repressor, or IPTG-inducible, i.e the T7 promoter is used.

Example 21

Production of PUFAs in E. coli

An E. coli strain of appropriate genotype is transformed with an expression vector containing an artificial gene cluster with the genes required for production of a PUFA (Example 21) and recombinant cells are identified on selection medium, e.g. LB medium containing 5 mg/L ampicillin. Single colonies are inoculated into 100 ml medium, which can be 20 g/L glucose, 3 g/L $KH_2PO_4$, 7 g/L $K_2HPO_4$, 2 g/L $(NH_4)_2SO_4$ and 0.25 g/L $MgSO_4 \cdot 7H_2O$ supplemented with 5 mg·l$^{-1}$ ampicillin, in a baffled 500 ml shake flask. The cultures are incubated with 200 rpm shaking at 37° C. for 16-20 hours, until the carbon source is exhausted, and the biomass is harvested for analysis of fatty acid composition as described in example 11. If an IPTG-inducible promoter, such as the T7 promoter, is used, IPTG is added to the medium at a final concentration of 0.01-1 mM.

Example 22

General Molecular Biology Methods Used in Strain Construction

Standard recombinant DNA and molecular cloning techniques used in the Examples are well known in the art and are described by: Sambrook, J., Fritsch, E. F., and Maniatis, T. Molecular Cloning: A Laboratory Manual; Cold Spring Harbor Laboratory: Cold Spring Harbor, N.Y. (1989). Materials and methods suitable for the maintenance and growth of microbial cultures are well known in the art as described by, e.g. Manual of Methods for General Bacteriology (Gerhardt, P., Murray, R. G. E., Costilow, R. N., Nester, E. W., Wood, W. A., Krieg, N. R., and Briggs, G., Eds.) American Society for Microbiology: Washington, D.C. (1994). All chemicals and reagents used for maintenance and growth of cells were obtained from Sigma, DIFCO Laboratories or GIBCO/BRL unless specified otherwise. Restriction enzymes and DNA ligase was purchased from New England Biolabs. All PCR reactions were carried out using the Phusion polymerase (Finnzymes). Oligonucleotides and sequencing services were purchased from MWG Biotech, Ebersberg, Germany. Purification of DNA fragments was carried out using GFX-columns (Amersham) or the QiaexII purification kit (Qiagen).

*E. coli* DH5α cells were made competent by the Inoue method as described in Sambrook et al., supra. *E. coli* cells were typically grown at 37° C. in Luria Bertani (LB) medium, supplied with 50 mg/l ampicillin where necessary.

Yeast cells were typically grown at 30° C. in YPD medium or synthetic complete drop-out medium, and were made competent by a LiAc-based method (Sambrook et al., supra).

Genomic modifications (overexpression and deletion of genes, integration of heterologous genes) were performed by means of homologous recombination using PCR-generated targeting substrates and the *K. lactis* URA3 gene as a selectable marker, essentially as described in Erdeniz, N., Mortensen, U. H., Rothstein, R. (1997) Genome Res. 7:1174-83. Information on primer design for fusion PCR can be found in the same publication. Generally, fusion of DNA fragments was made possible by using primers with appropriately designed 5' overhangs for amplification of the original DNA fragments. In all cases, PCR-generated fragments were excised from a 1% agarose gel and purified before proceeding with fusion PCR. Transformants were generally selected on -URA plates, and pop-out of the *K. lactis* URA3 marker gene was selected for by plating on 5-FOA medium (5-fluoroorotic acid, 750 mg/l). Correct integration of promoters and heterologous genes was verified by PCR, always using one primer annealing to a sequence outside of the target sequence for integration and one primer annealing inside the sequence to be integrated. Gene deletions were also verified by PCR, using primers on both sides of the deleted gene. Generally, PCR-verification of genomic modifications was performed by means of colony-PCR. For colony-PCR, a small amount of cells was dispersed in 10 μl $H_2O$ and was placed at −80° C. for approximately 30 min, followed by 15 min. incubation at 37° C. The cell suspension was then used as template for PCR.

Methods for combining genetic features by crossing of strains used in Examples are well known and are, e.g., described in: Adams, A., Gottschling, D. E., Kaiser, C. A., and Stearns, T. Methods in Yeast Genetics: A Cold Spring Harbor Laboratory Course Manual, Cold Spring Harbor Laboratory Press, Cold Spring Harbor, N.Y. (1997). Typically, strains of opposite mating types were allowed to mate, diploids were selected and transferred to sporulation medium (20 g/l potassium acetate, 1 g/l glucose, 2.5 g/l yeast extract, pH 7.0) and were allowed to sporulate at 30° C. for approximately 3 days. The asci were dissected on a YPD plate using a Singer MSM microscope and micromanipulator dissection microscope. The mating types of the resulting tetrads were scored by replica-plating to a lawn of cells with either a or alpha mating type, incubating at 30° C. to allow mating, replica-plating to sporulation medium, and visualizing sporulation by illuminating plates under a 302 nm UV-light source. Auxotrophic markers were scored by replica plating to drop-out plates. Genetic modifications that could not be scored by phenotype were scored by colony-PCR. In general, the same primer sets that were used for verification of genomic integrations or knockouts were also used for colony-PCR scoring of tetrads (see above).

The genetic nomenclature used for describing the genotypes of the strains is as follows: Native yeast genes are written in capital letters, while deleted or mutated native yeast genes are written in small letters. Fungal genes are written in small letters, for example *M. alpina* ole1, *S. macrospora* acl1. Yeast promoters are indicated by a small p, for example pADH1, pTDH3 for the ADH1 and TDH3 promoters. Overexpressions of native yeast genes by the promoter-replacement method are indicated by the promoter name followed by the gene name, for example pADH1-FAS1, pTDH3-DGA1 for overexpression of FAS1 with the ADH1 promoter and overexpression of DGA1 with the TDH3 promoter. Disruption of native yeast genes are indicated by a double colon, for example pox1::pTDH3-*M. alpina* ole1, which means that the POX1 gene has been disrupted and that the TDH3 promoter and the *M. alpina* ole1 gene has been integrated in its place. Plasmids are written in brackets.

Example 23

Construction of pWAD1 and pWAD2

Figure 13:
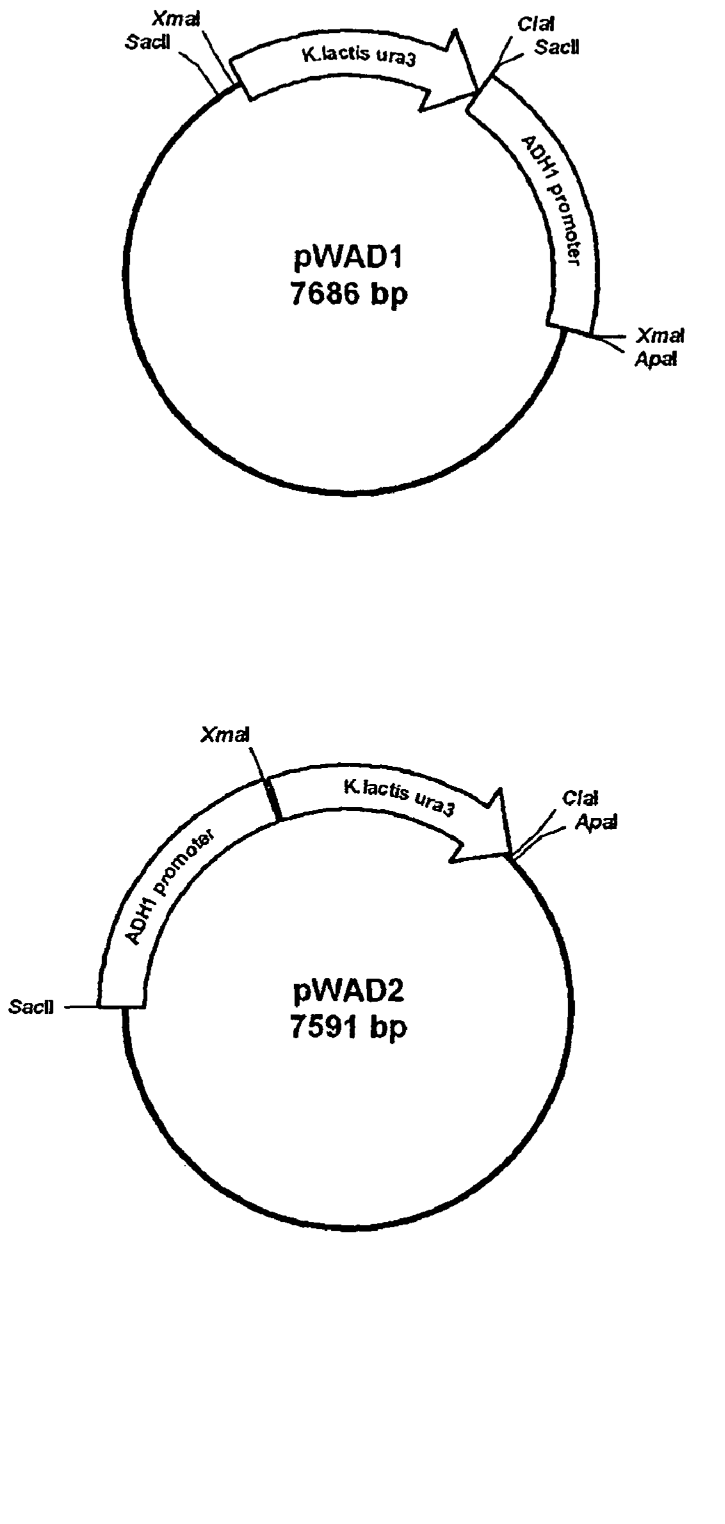
FIG. 13: Plasmid map over pWAD1, Plasmid map over pWAD2.

The two vectors pWAD1 and pWAD2 were used as templates for PCR in the construction of gene-targeting substrates for overexpression of genes with the ADH1 promoter. For construction of pWAD1 and pWAD2, the ADH1 promoter (consisting of the 1467 bp immediately upstream of the start codon of the ADH1 gene) was amplified from genomic yeast DNA using the primers 5' AAATCGATAACCGCGGAGGGGGATCGAAGAAATGATGG 3' (SEQ ID NO: 143) and 5' TTGGGCCCTTTCCCGGGTGTATATGAGATAGTTGATTGTATGC 3' (SEQ ID NO: 144). These primers introduced a ClaI and a SacII restriction site at the 5' end of the promoter sequence, and XmaI and ApaI restriction sites at the 3' end. For construction of pWAD1, the ADH1 promoter fragment was digested with ClaI and ApaI and was introduced into ClaI/ApaI digested pWJ716. This resulted in a plasmid construct, where the ADH1 promoter was placed immediately downstream of *K. lactis* URA3. Absence of mutations in the ADH1 promoter sequence was verified by sequencing of pWAD1. For construction of pWAD2, the ADH1 promoter fragment was released from pWAD1 through digestion with SacII and XmaI. The fragment was purified and was introduced into SacII/XmaI digested pWJ716. This resulted in a plasmid construct, where the ADH1 promoter was placed immediately upstream of *K. lactis* URA3. Plasmid maps of pWAD1 and pWAD2 are shown in FIG. 13. The plasmid pWJ716, carrying the *K. lactis* URA3 structural under the control of its native promoter and connected to its native terminator sequence, was a kind gift from Uffe H. Mortensen, Center for Microbial Biotechnology, Bio-Centrum DTU, Technical University of Denmark.

Example 24

Construction of pWJ716-TD1 and pWJ716-TD2

Figure 14:
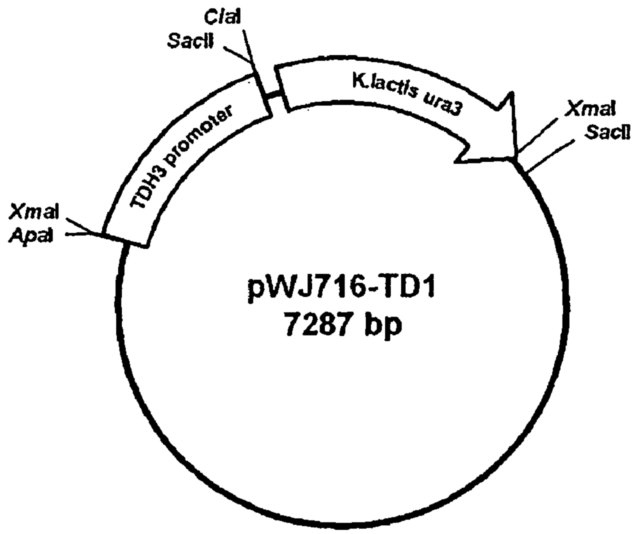
FIG. 14: Plasmid map over pWJ716-TD1 and Plasmid map over pWJ716-TD2.
Figure 14:
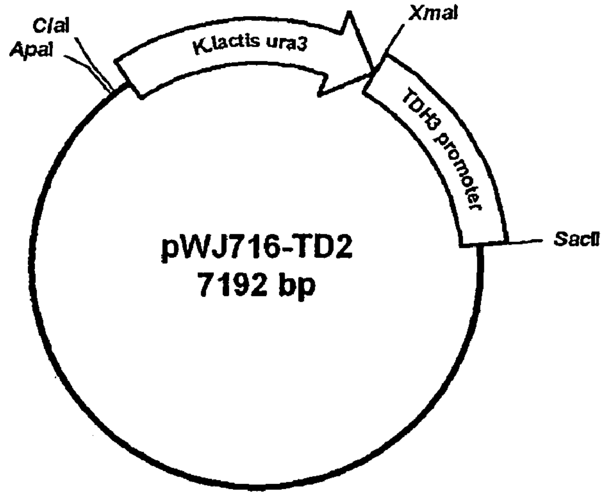

The two vectors pWJ716-TD1 and pWJ716-TD2 were used as templates for PCR in the construction of gene-targeting substrates for overexpression of genes with the TDH3 promoter. For construction of pWJ716-TD1 and pWJ716-TD2, the TDH3 promoter (consisting of the 1067 bp immediately upstream of the start codon of the TDH3 gene) was amplified from genomic yeast DNA using the primers 5'TTGGGCCCTTTCCCGGGTTTTGTTTGTTTATGTGTG 3' (SEQ ID NO: 145) and 5'AAATCGATAACCGCGGATGAAAGAAGCTTACCAG 3' (SEQ ID NO: 146). These primers introduced a ClaI and a SacII restriction site at the 5' end of the promoter sequence, and XmaI and ApaI restriction sites at the 3' end. For construction of pWJ716-TD1, the TDH3 promoter fragment was digested with ClaI and ApaI and was introduced into ClaI/ApaI digested pWJ716. This resulted in a plasmid construct, where the TDH3 promoter was placed immediately downstream of *K. lactis* URA3. Absence of mutations in the TDH3 promoter sequence was verified by sequencing of pWJ716-TD1. For construction of pWJ716-TD2, the TDH3 promoter fragment was released from pWJ716-TD1 through digestion with SacII and XmaI. The fragment was purified and was introduced into SacII/XmaI digested pWJ716. This resulted in a plasmid construct, where the TDH3 promoter was placed immediately upstream of *K. lactis* URA3. Plasmid maps of pWJ716-TD1 and pWJ716-TD2 are shown in FIG. 14.

Example 25

Overview of Genetically Modified Yeast Strains

A number of genetically modified yeast strains were constructed as described in the Examples. An overview of the strains mentioned in the Examples is given in Table 3. All modifications were made in the CEN.PK genetic background. The strains FS01267, FS01269 and FS01277 were obtained by crossing of the strains CEN.PK 110-1° C. and CEN.PK 113-6B, dissecting the asci of the resulting diploids and scoring the genotype of the resulting haploid strains.

TABLE 3

Overview of strains used or constructed in Examples. The table shows only genomic modifications; for strains expressing PUFA pathways from plasmids, see Table 4 and 11. SDG, Scientific research and Development GmbH, Oberusel, Germany; FS, Fluxome Sciences A/S

| Strain | Genotype | Source |
|---|---|---|
| CEN.PK 113-7D | MATa | SDG |
| CEN.PK 113-5D | MATa ura3 | SDG |
| CEN.PK 110-10C | MATalpha his3 | SDG |
| CEN.PK 113-6B | MATa ura3 trp1 leu2 | SDG |
| FS01267 | MATa trp1ura3 | FS |
| FS01269 | MATalpha trp1 | FS |
| FS01277 | MATa ura3 leu2 trp1 | FS |
| FS01309 | MATa ura3 ole1::pTDH3-*M. alpina* ole1 | Example 7 |
| FS01316 | MATa ura3 trp1 ole1::pTDH3-*M. alpina* ole1 | Example 7 |
| FS01351 | MATa ura3 pADH1-FAS1 | Example 26 |
| FS01352 | MATa ura3 pADH1-FAS2 | Example 26 |
| FS01342 | MATalpha trp1 pADH1-FAS1 | Example 26 |
| FS01372 | MATa ura3 trp1 pADH1-FAS1 pADH1-FAS2 | Example 26 |
| FS01392 | MATa ura3 trp1 pADH1-FAS1 pADH1-FAS2 pTPI1-ACC1 | Example 27 |
| FS01367 | MATa ura3 pox1::pTDH3-*M. alpina* ole1 | Example 28 |
| FS01368 | MAT alpha ura3 trp1 pox1::pTDH3-*M. alpina* ole1 | Example 28 |
| FS01344 | MATa ura3 pTDH3-DGA1 | Example 29 |
| FS01370 | MATa ura3 trp1 pTDH3-DGA1 | Example 29 |
| FS01425 | MATa ura3 trp1 pADH1-FAS1 pADH1-FAS2 pox1::pTDH3-*M. alpina* ole1-pADH1-*S. macrospora* acl1-pTDH3-*S. macrospora* acl2 | Example 33 |
| FS01395 | MATa ura3 trp1 pADH1-FAS1 pADH1-FAS2 pTPI1-GAT1 | Example 30 |
| FS01394 | MATa ura3 trp1 pADH1-FAS1 pADH1-FAS2 pTPI1-SLC1 | Example 30 |
| FS01393 | MATa ura3 trp1 pADH1-FAS1 pADH1-FAS2 pTPI1-YDR531W | Example 30 |
| FS01427 | MATa ura3 trp1 pADH1-FAS1 pADH1-FAS2 pADH1-YBR159W | Example 31 |
| FS01440 | MATa ura3 trp1 pADH1-FAS1 pADH1-FAS2 pADH1-TSC13 | Example 31 |
| FS01254 | MATalpha ura3 gdh1::loxP gdh2::PGKp-GDH2-KanMX3 | Example 35 |
| FS01398 | MATa ura3 trp1 pADH1-FAS1 pADH1-FAS2 gdh1::loxP gdh2::PGKp-GDH2-KanMX3 | Example 35 |
| FS01419 | MATa ura3 trp1 pADH1-FAS1 pADH1-FAS2 gdh1::loxP glt1::PGKp-GLT1-KanMX3 | Example 35 |
| FS01420 | MATalpha ura3 trp1 pADH1-FAS1 gdh1::loxP gln1::PGKp-GLN1-KanMX3 | Example 35 |
| FS01437 | MATa ura3 trp1 pADH1-FAS1 pADH1-FAS2 gdh1::loxP glt1::PGKp-GLT1-KanMX3 gln1::PGKp-GLN1-KanMX3 | Example 35 |

TABLE 3-continued

Overview of strains used or constructed in Examples. The table shows only genomic modifications; for strains expressing PUFA pathways from plasmids, see Table 4 and 11. SDG, Scientific research and Development GmbH, Oberusel, Germany; FS, Fluxome Sciences A/S

| Strain | Genotype | Source |
|---|---|---|
| FS01396 | MATa ura3 trp1 pADH1-FAS1 pADH1-FAS2 pox1::pTDH3-*M. alpina* ole1 | Example 36 |
| FS01408 | MATalpha ura3 trp1 pADH1-FAS1 pox1::pTDH3-*M. alpina* ole1 | Example 36 |
| FS01423 | MATa ura3 trp1 pADH1-FAS1 pADH1-FAS2 pTPI1-ACC1 pox1::pTDH3-*M. alpina* ole1 | Example 36 |
| FS01444 | MATalpha ura3 trp1 leu2 pox1::pTDH3-*M. alpina* ole1 | Example 57 |
| FS01460 | MATalpha ura3 trp1 leu2 pox1::pTDH3-*M. alpina* ole1 gpp1::pGAL1-*S. kluyveri* FAD3 | Example 61 |

Example 26

Overexpression of Fatty Acid Synthase (FAS)

Figure 15:
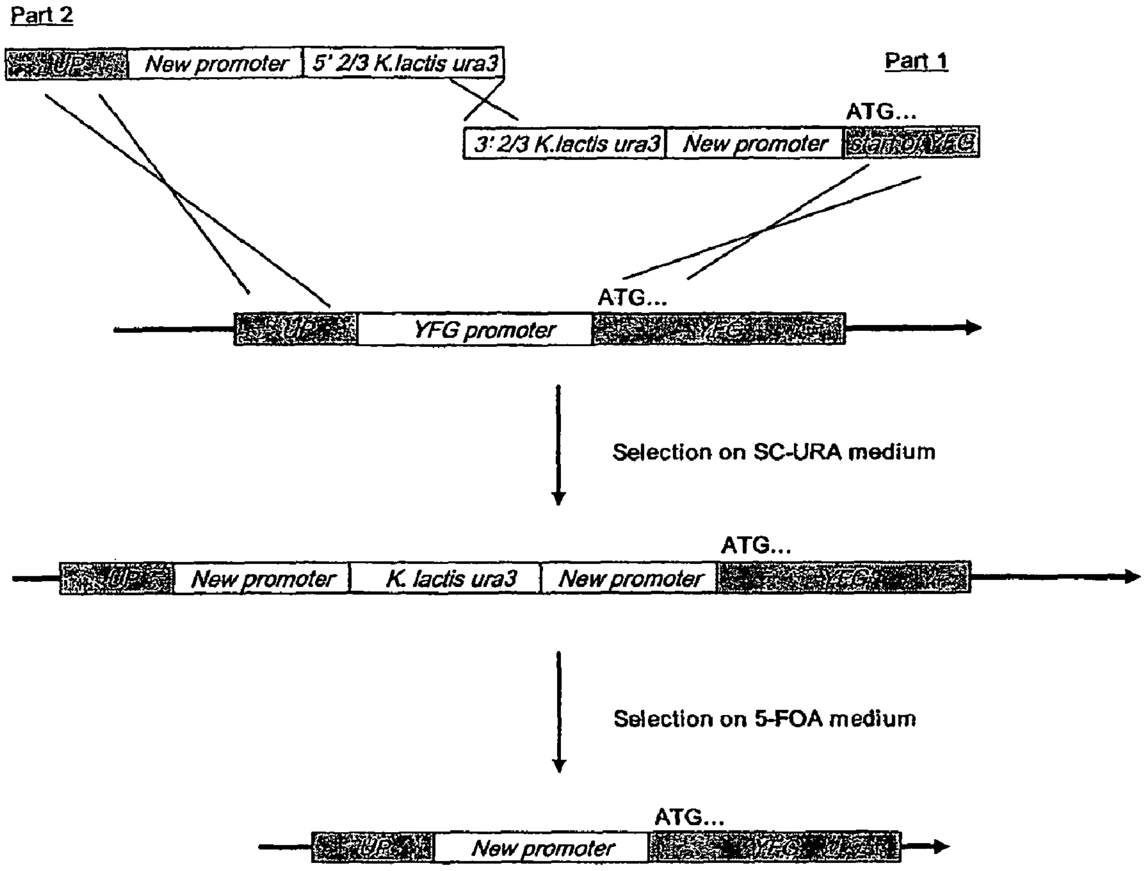
FIG. 15: Method used for overexpression of genes by promoter replacement. YFG, arbitrary gene to be overexpressed.

The two genes FAS1 and FAS2, encoding the beta and alpha subunits of the yeast fatty acid synthase, respectively, were overexpressed with a strong yeast promoter. This was done by replacing the native FAS1- and FAS2 promoters with the ADH1 promoter, using a promoter-replacement method based on a bipartite gene-targeting substrate (FIG. 15). The two genes were overexpressed separately and the modifications were subsequently combined through crossing of strains. For each of the overexpressions, one part of the bipartite substrate consisted of two thirds (towards the 3'end) of *K. lactis* URA3, fused to the ADH1 promoter sequence and a target sequence corresponding to the beginning of the gene to be overexpressed. The second part of the bipartite substrate consisted of a target sequence upstream of the gene to be overexpressed, fused to the ADH1 promoter sequence and two thirds (towards the 5' end) of *K. lactis* URA3. Following transformation with the bipartite substrate and selection on medium lacking uracil, transformants were obtained in which the native promoter had been knocked out and replaced with two copies of the ADH1 promoter sequence as a direct repeat on either side of the *K. lactis* URA3 marker gene. A second recombination event, resulting in looping out of the selection marker, was selected for by replating transformants on medium containing 5'-fluoroorotic acid (5-FOA), which is toxic to cells expressing the URA3 gene. This resulted in a strain, in which the native promoter had been replaced with the ADH1 promoter.

The procedure was as follows:

For construction of part 1 of the bipartite gene targeting substrates (FIG. 15), a fragment consisting of two thirds of *K. lactis* URA3 (towards the 3' end) and the ADH1 promoter was amplified from plasmid pWAD1. For overexpression of FAS1, the primer pair 5' CTTGACGTTCGTTCGACTGATGAGC 3' (SEQ ID NO: 133) and 5' TGGTCTTGTGGAGTAAGCGTCCATTGTATATGAGATAGTTGATTGTATGC 3' (SEQ ID NO: 147) was used for this amplification and for overexpression of FAS2, the primer pair 5' CTTGACGTTCGTTCGACTGATGAGC 3' (SEQ ID NO: 133) and 5' TTCTTGCTCAACTTCCGGCTTCATTGTATATGAGATAGTTGATTGTATGC 3' (SEQ ID NO: 148) was used. Furthermore, downstream target sequences, consisting of the beginning of FAS1 and FAS2, respectively, were amplified from genomic yeast DNA by PCR using the primer pair 5' ATGGACGCTTACTCCACAAGACCATTAAC 3' (SEQ ID NO: 149) and 5' TTGATATAGATCACGCAATTCTTCAAAGTAGTC 3' (SEQ ID NO: 150) for the FAS1 targeting sequence and the primer pair 5' ATGAAGCCGGAAGTTGAGCAAGAATTAGC 3' (SEQ ID NO: 151) and 5' ACTTCTTCAACTTGTGAGCAACCAAAACG 3' (SEQ ID NO: 152) for the FAS2 targeting sequence. Finally, the FAS1 and FAS2 downstream targeting sequences were fused to the fragment consisting of two thirds of *K. lactis* URA3 (towards the 3' end) and the ADH1 promoter. For FAS1, the primer pair 5'CTGACGTTCGTTCGACTGATGAGC 3' (SEQ ID NO: 133) and 5' TTGATATAGATCACGCAATTCTTCAAAGTAGTC 3' (SEQ ID NO: 150) was used for the fusion reaction and for FAS2, the primer pair 5'CTTGACGTTCGTTCGACTGATGAGC 3' (SEQ ID NO: 133) and 5' ACTTCTTCAACTTGTGAGCAACCAAAACG 3' (SEQ ID NO: 152) was used. The resulting fusion fragments 3' 2/3 *K. lactis* URA3-pADH1-DOWN (FAS1) and 3' 2/3 *K. lactis* URA3-pADH1-DOWN (FAS2) were part 1 of the bipartite targeting substrate used for FAS1 and FAS2 promoter replacement, respectively.

For construction of part 2 of the bipartite targeting substrate, a fragment consisting of the ADH1 promoter and two thirds of *K. lactis* URA3 towards the 5' end was first amplified by PCR using plasmid pWAD2 as template. The primers used for this amplification were 5' GGACGTTCCCTGTATGTACTAGGGGGATCGAAGAAATGATGG 3' (SEQ ID NO: 153) and 5' GAGCAATGAACCCAATAACGAAATC 3' (SEQ ID NO: 139). Next, upstream targeting sequences were amplified from genomic yeast DNA using the primers 5'CCGCTGTACTATGCGGTCTCGTCC 3' (SEQ ID NO: 154) and 5' AGTACATACAGGGAACGTCCGTATGCCAAAAATGCCAAAATGCC 3' (SEQ ID NO: 155) for the FAS1 upstream targeting sequence and 5' CAACTACAAGGAGGAGAATAAAGAGCAAGCC 3' (SEQ ID NO: 156) and 5' AGTACATACAGGGAACGTCCAACGACAACAACAACGACTACAATGATGG 3' (SEQ ID NO: 157) for the FAS2 upstream targeting sequence. The upstream targeting sequences were then fused to the previously constructed pADH1-5' 2/3 *K. lactis* URA3 fragment. The primers used for the fusion reaction were 5'CCGCTGTACTATGCGGTCTCGTCC 3' (SEQ ID NO: 154) and 5' GAGCAATGAACCCAATAACGAAATC 3' (SEQ ID NO: 139) for FAS1 and 5' CAACTACAAGGAGGAGAATAAAGAGCAAGCC 3' (SEQ ID NO: 156) and 5' GAGCAATGAACCCAATAACGAAATC 3' (SEQ ID NO: 139) for FAS2. The resulting fusion fragments UP(FAS1)-pADH1-5' 2/3 *K. lactis* URA3 and UP(FAS2)-pADH1-5' 2/3 *K. lactis* URA3 were part 2 of the bipartite targeting substrate used for FAS1 and FAS2 promoter replacement, respectively.

For FAS1 overexpression, the yeast strain CEN.PK 113-5D (MATa ura3) was transformed with the linear substrates UP(FAS1)-pADH1-5' 2/3 *K. lactis* URA3 and 3' 2/3 *K. lactis* URA3-pADH1-DOWN (FAS1). For FAS2 overexpression, the same parent strain was transformed with the linear substrates UP(FAS2)-pADH1-5' 2/3 *K. lactis* URA3 and 3' 2/3 *K. lactis* URA3-pADH1-DOWN (FAS2). Transformants were selected and streak-purified on medium lacking uracil and were then transferred to plates containing 5-FOA. Pop-out recombinants were streak-purified on 5-FOA-containing medium. The resulting strains had the genotypes MATa ura3 pADH1-FAS1 and MATa ura3 pADH1-FAS2 and were named FS01351 and FS01352, respectively. Correct integration of the ADH1 promoter and absence of PCR-generated mutations were verified by sequencing of the modified regions in both strains.

To combine overexpression of FAS1 and FAS2 in one strain, the FAS1 overexpressing mutant FS01351 (MATa ura3 pADH1-FAS1) was first crossed to the strain FS01269 (MATalpha trp1). Diploids were selected on medium lacking uracil and tryptophane and were then transferred on to sporulation medium. Following sporulation, the asci were dissected into ascospore tetrads. Presence of the pADH1-FAS1 modification in the resulting haploid strains was determined by colony PCR, and remaining genetic features were scored using standard methods. From the set of haploid strains derived from the cross, a strain with the genotype MATalpha trp1 pADH1-FAS1 was selected and named FS01342.

FS01342 (MATalpha trp1 pADH1-FAS1) was then crossed to FS01352 (MATa ura3 pADH1-FAS2) and diploids were selected on medium lacking uracil and tryptophane. Following transfer of the diploids to sporulation medium, asci were dissected into ascospore tetrads. Presence of the pADH1-FAS1 and pADH1-FAS2 modifications in the resulting haploid strains was determined by colony PCR, and remaining genetic features were scored using standard methods. From the set of haploid strains derived from the cross, a strain with the genotype MATa ura3 trp1 pADH1-FAS1 pADH1-FAS2 was selected and was named FS01372.

Example 27

Overexpression of ACC1

The yeast gene ACC1, encoding acetyl-CoA carboxylase, was overexpressed with a strong constitutive yeast promoter. This was done by replacing the native ACC1 promoter with the TPI1 promoter, using a promoter-replacement method based on a bipartite gene-targeting substrate (FIG. 15). One part of the bipartite substrate consisted of two thirds (towards the 3'end) of *K. lactis* URA3, fused to the TPI1 promoter sequence and a target sequence corresponding to the beginning of ACC1. The second part of the bipartite substrate consisted of a target sequence upstream of ACC1, fused to the TPI1 promoter sequence and two thirds (towards the 5' end) of *K. lactis* URA3. Following transformation with the bipartite substrate and selection on medium lacking uracil, transformants were obtained in which the native promoter had been knocked out and replaced with two copies of the TPI1 promoter sequence as a direct repeat on either side of the *K. lactis* URA3 marker gene. A second recombination event, resulting in looping out of the selection marker, was selected for by replating transformants on medium containing 5'-fluoroorotic acid (5-FOA), which is toxic to cells expressing the URA3 gene. This resulted in a strain, in which the native ACC1 promoter had been replaced with the TPI1 promoter.

In order to construct part 1 of the bipartite substrate, two thirds (towards the 3' end) of *K. lactis* ura3 was amplified from the plasmid pWJ716 using the primers 5' CTTGACGT-TCGTTCGACTGATGAGC 3' (SEQ ID NO: 133) and 5' CTGGAATTCGATGATGTAGTTTCTGG 3'(SEQ ID NO: 158). Moreover, the TPI1 promoter sequence was amplified from genomic yeast DNA using the primers 5' CTACAT-CATCGAATTCCAGCTACGTATGGTCATTTCTTCTTC 3' (SEQ ID NO: 159) and 5' TTTTTGATTAAAAT-TAAAAAAACTTTTTAGTTTATGTATGTGTTTTTTG 3' (SEQ ID NO: 160) and a downstream targeting sequence, consisting of the beginning of the ACC1 gene (i.e., the first 553 bp of the gene) was amplified from genomic yeast DNA using the primers 5' AGTTTTTTTAATTTTAAT-CAAAAAATGAGCGAAGAAAGCTTATTCGAGTC 3' (SEQ ID NO: 161) and 5' CACCTAAAGACCTCATG-GCGTTACC 3' (SEQ ID NO: 162). These three fragments were fused to each other in two rounds of PCR. First, the TPI1 promoter sequence was fused to the downstream targeting sequence, using the primers 5' CTACATCATCGAATTC-CAGCTACGTATGGTCATTTCTTCTTC 3' (SEQ ID NO: 159) and 5' CACCTAAAGACCTCATGGCGTTACC 3' (SEQ ID NO: 162). The resulting product was then fused to the fragment containing two thirds (towards the 3' end) of *K. lactis* URA3. The resulting fragment, 3' 2/3 *K. lactis* URA3-pTPI1-DOWN(ACC1) was part 1 of the bipartite gene targeting substrate.

In order to construct part 2 of the bipartite substrate, two thirds (towards the 5'end) of *K. lactis* URA3 was amplified from the plasmid pWJ716 using the primers 5' CGGTCTG-CATTGGATGGTGGTAAC 3' (SEQ ID NO: 163) and 5' GAGCAATGAACCCAATAACGAAATC 3' (SEQ ID NO: 139). The TPI1 promoter sequence was amplified from genomic yeast DNA using the primers 5'CTACATCATC-GAATTCCAGCTACGTATGGTCATTTCTTCTTC 3' (SEQ ID NO: 159) and 5'CACCATCCAATGCAGACCGTTT-TAGTTTATGTATGTGTTTTTTG 3' (SEQ ID NO: 164), and a target sequence upstream of ACC1 was amplified from genomic DNA using primers 5' TGTTCTGCTCTCT-TCAATTTTCCTTTC 3' (SEQ ID NO: 165) and 5' CTG-GAATTCGATGATG-TAGTTTCTAATTTTCTGCGCTGTTTCG 3'(SEQ ID NO: 166). These three fragments were fused in two rounds of PCR. First, the upstream targeting sequence was fused to the TPI1 promoter sequence, using the primers 5' TGTTCT-GCTCTCTTCAATTTTCCTTTC 3' (SEQ ID NO: 165) and 5'CACCATCCAATGCAGACCGTTTTAGTT-TATGTATGTGTTTTTTG 3'(SEQ ID NO: 164). The resulting fragment was then fused to the fragment containing two thirds (towards the 5' end) of *K. lactis* URA3, resulting in the fragment UP(ACC1)-pTPI1-5' 2/3 *K. lactis* URA3, which constituted part 2 of the bipartite gene targeting substrate.

Yeast strain FS01372 (MATa ura3 trp1 pADH1-FAS1 pADH1-FAS2) was transformed with the linear substrates UP(ACC1)-pTPI1-5' 2/3 *K. lactis* URA3 and 3' 2/3 *K. lactis* URA3-pTPI1-DOWN(ACC1). Transformants were selected and streak-purified on medium lacking uracil and were then transferred to plates containing 5-FOA. Pop-out recombinants were streak-purified on 5-FOA-containing medium. The resulting strain had the genotype MATa ura3 trp1 pADH1-FAS1 pADH1-FAS2 pTPI1-ACC1 and was named FS01392. Correct integration of the TPI1 promoter was checked by colony PCR.

Example 28

Integration of *M. alpina* ole1 at the POX1 Locus in *S. cerevisiae*

Figure 16:
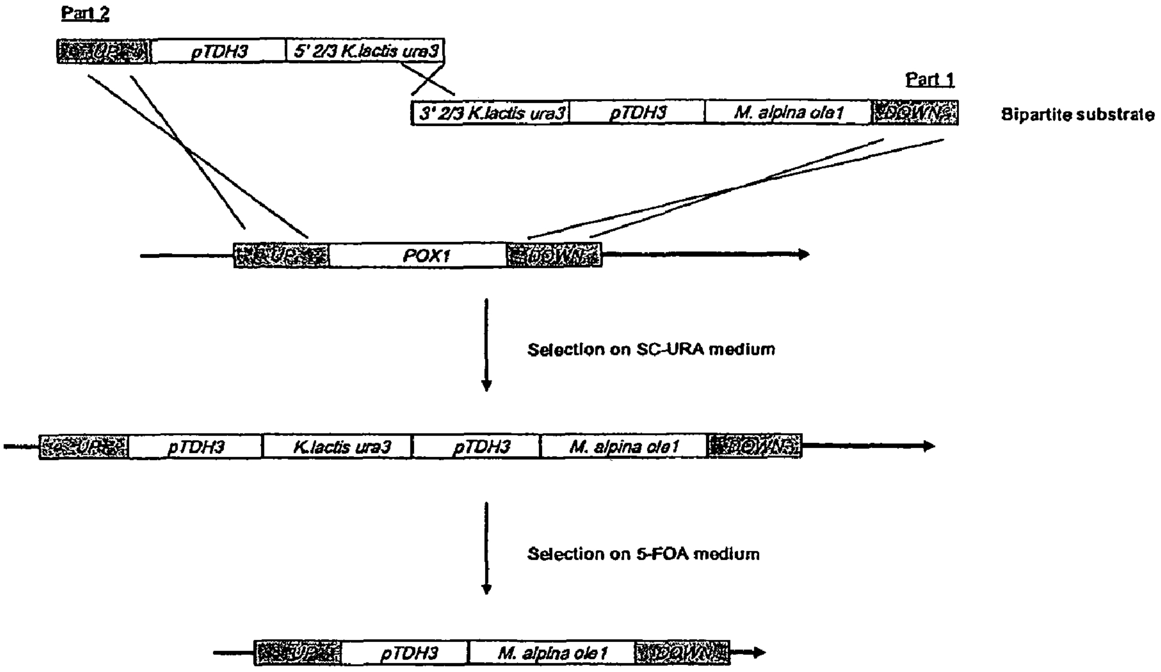
FIG. 16: Strategy for integration of *M. alpina* ole1 into the genome of *S. cerevisiae* at the POX1 locus

The *M. alpina* ole1 gene, encoding a delta-9 desaturase, was integrated into the genome of *S. cerevisiae* and was placed under the control of the yeast TDH3 promoter. The TDH3 promoter and the *M. alpina* ole1 gene were integrated at the locus of POX1, encoding the first enzyme in the beta-oxidation pathway, resulting in knockout of this gene. The integration was carried out through homologous recombination using a bipartite gene targeting substrate (FIG. 16). One part of the bipartite substrate consisted of two thirds (towards the 3' end) of *K. lactis* URA3, fused to the TDH3 promoter sequence, the *M. alpina* ole1 gene and a target sequence downstream of POX1. The second part of the bipartite substrate consisted of a target sequence upstream of POX1, fused to the TDH3 promoter sequence and two thirds (towards the 5' end) of *K. lactis* URA3. Following transformation with the bipartite substrate and selection on medium lacking uracil, transformants were obtained in which POX1 had been knocked out and replaced with two copies of the TDH3 promoter sequence as a direct repeat on either side of the *K. lactis* URA3 marker gene and the *M. alpina* ole1 gene immediately downstream of the second TDH3 promoter repeat. A second recombination event, resulting in looping out of the selection marker, was selected for by replating transformants on medium containing 5'-fluoroorotic acid (5-FOA), which is toxic to cells expressing the URA3 gene. This resulted in a strain, in which the POX1 gene had been replaced with the *M. alpina* ole1 under the control of the TDH3 promoter.

The procedure was as follows:

For construction of part 1 of the bipartite gene targeting substrates (FIG. 16), a fragment consisting of two thirds of *K. lactis* URA3 (towards the 3' end) followed by the TDH3 promoter was amplified by PCR from plasmid pWJ716-TD1, using primers 5' CTTGACGTTCGTTCGACTGATGAGC 3' (SEQ ID NO: 133) and 5' GGGGGGAAGAGGAGTTGCCATTTTGTTTGTTTATGTGTG 3' (SEQ ID NO: 134). Furthermore, the *M. alpina* ole1 gene (SEQ ID NO 1), isolated as described in Example 1, was reamplified by PCR using the primers 5'ATGGCAACTCCTCTTCCCCCCTCC 3' (SEQ ID NO: 115) and 5'TTGTTATTGTAATGTGATACCTATTCGGCCTTGACGTGG 3'(SEQ ID NO: 131), and a targeting sequence downstream of POX1 was amplified from genomic yeast DNA by PCR using the primers 5' GTATCACATTACAATAACAATTCCTTCGAACCCTCTGTTTTGC 3' (SEQ ID NO: 166) and 5' TTAGAGCTTCATTCCAACAAGTGCC 3' (SEQ ID NO: 167). These three fragments were then fused by two rounds of PCR. First, the *M. alpina* ole1 gene was fused to the downstream targeting sequence, using the primers 5'ATGGCAACTCCTCTTCCCCCCTCC 3' (SEQ ID NO: 115) and 5' TTAGAGCTTCATTCCAACAAGTGCC 3'(SEQ ID NO: 167). The resulting fragment was then fused to the fragment containing two thirds of *K. lactis* URA3 (towards the 3' end) followed by the TDH3 promoter. The resulting fragment, 3' 2/3 *K. lactis* URA3-pTDH3-*M. alpina* ole1-DOWN(POX1), constituted part 1 of the bipartite targeting substrate.

For construction of the second part of the bipartite substrate, a target sequence upstream of POX1 was amplified by PCR using *S. cerevisiae* genomic DNA as template and the primers 5' AATTCGGTAAATTCAATGGGTAGG 3' (SEQ ID NO: 168) and 5' TTAGTACATACAGGGAACGTCCGTAAATATAGGGCTTAAAATGTGTCAGG 3'(SEQ ID NO: 169). Furthermore, a fragment consisting of the TDH3 promoter followed by two thirds of *K. lactis* URA3 (towards the 5' end) was amplified by PCR using plasmid pWJ716-TD2 as template. The primers used for this amplification were 5' GGACGTTCCCTGTATGTACTAAAAATGAAAGAAGCTTACCAG 3' (SEQ ID NO: 138) and 5' GAGCAATGAACCCAATAACGAAATC 3' (SEQ ID NO: 139). These two fragments were then fused by PCR using the primers 5' AATTCGGTAAATTCAATGGGTAGG 3' (SEQ ID NO: 168) and 5' GAGCAATGAACCCAATAACGAAATC 3' (SEQ ID NO: 139), resulting in the fragment UP(POX1)-pTDH3-5' 2/3 *K. lactis* URA3, which constituted part 2 of the bipartite targeting substrate.

The yeast strain CEN.PK 113-5D (MATa ura3) was transformed with the linear substrates UP(POX1)-pTDH3-5' 2/3 *K. lactis* URA3 and 3' 2/3 *K. lactis* URA3-pTDH3-*M. alpina* ole1-DOWN(POX1) and plated out on medium lacking uracil. Transformants were selected and streak-purified on medium lacking uracil and were then transferred to plates containing 5-FOA. Pop-out recombinants were streak-purified on 5-FOA-containing medium. The resulting strain had the genotype MATa ura3 pox1::pTDH3-*M. alpina* ole1 and was named FS01367. Correct integration of the TDH3 promoter and *M. alpina* ole1 and absence of PCR-generated mutations was verified by sequencing of the modified region.

To combine pox1::pTDH3-*M. alpina* ole1 modification with the appropriate genetic markers, FS01367 (MATa ura3 pox1::pTDH3-*M. alpina* ole1) was crossed to FS01269 (MATalpha trp1). Diploids were selected on medium lacking uracil and tryptophane and were then transferred on to sporulation medium. Following sporulation, the asci were dissected into ascospore tetrads. Presence of the pox1::pTDH3-*M. alpina* ole1 modification in the resulting haploid strains was determined by colony PCR, and remaining genetic features were scored using standard methods. From the set of haploid strains derived from the cross, a strain with the genotype MAT alpha ura3 trp1 pox1::pTDH3-*M. alpina* ole1 was selected and named FS01368.

Example 29

Overexpression of DGA1

The yeast gene DGA1, encoding diacylglycerol acyltransferase, was overexpressed with a strong constitutive yeast promoter. This was done by replacing the native DGA1 promoter with the TDH3 promoter, using a promoter-replacement method based on a bipartite gene-targeting substrate (FIG. 15). One part of the bipartite substrate consisted of two thirds (towards the 3'end) of *K. lactis* URA3, fused to the TDH3 promoter sequence and a downstream targeting sequence corresponding to the beginning of DGA1. The second part of the bipartite substrate consisted of a target sequence upstream of DGA1, fused to the TDH3 promoter sequence and two thirds (towards the 5' end) of *K. lactis* URA3. Following transformation with the bipartite substrate and selection on medium lacking uracil, transformants were obtained in which the native promoter had been knocked out and replaced with two copies of the TDH3 promoter sequence as a direct repeat on either side of the *K. lactis* URA3 marker gene. A second recombination event, resulting in looping out of the selection marker, was selected for by replating transformants on medium containing 5'-fluoroorotic acid (5-FOA), which is toxic to cells expressing the URA3 gene.

This resulted in a strain, in which the native DGA1 promoter had been replaced with the TDH3 promoter.

The procedure was as follows:

For construction of part 1 of the bipartite gene targeting substrates (FIG. 15), a fragment consisting of two thirds of *K. lactis* ura3 (towards the 3' end) followed by the TDH3 promoter was amplified by PCR from plasmid pWJ716-TD1, using primers 5' CTTGACGTTCGTTCGACTGATGAGC 3' (SEQ ID NO: 133) and 5' TTTGTTTGTTTATGTGTGTT-TATTCGAAACTAAG 3'(SEQ ID NO: 170). Furthermore, a downstream targeting sequence, corresponding to the beginning of DGA1, was amplified by PCR from genomic yeast DNA by PCR using the primers 5' CGAATAAACACACAT-AAACAAACAAAATGTCAGGAACATTCAATGATATA 3' (SEQ ID NO: 171) and 5' GTTTTAAATTGACAGTTT-TAATCAAACTTATAGGG 3'(SEQ ID NO: 172). These fragments were then fused by PCR using the primers 5'CTTGACGTTCGTTCGACTGATGAGC 3' (SEQ ID NO: 133) and 5' GTTTTAAATTGACAGTTTTAATCAAACT-TATAGGG 3'(SEQ ID NO: 172). The resulting fragment, 3' 2/3 *K. lactis* URA3-pTDH3-DOWN(DGA1), constituted part 1 of the bipartite targeting substrate.

For construction of the second part of the bipartite substrate, a target sequence upstream of DGA1 was amplified by PCR using *S. cerevisiae* genomic DNA as template and the primers 5' TTTTGGCTGTTGTTCCAGGTCGTAGG 3' (SEQ ID NO: 173) and 5' AGTACATACAGGGAACGTC-CGATAAACAGGAAAAAAAAAAAAACTTTGGCG 3' (SEQ ID NO: 174). Furthermore, a fragment consisting of the TDH3 promoter followed by two thirds of *K. lactis* URA3 (towards the 5' end) was amplified by PCR using plasmid pWJ716-TD2 as template. The primers used for this amplification were 5' GGACGTTCCCTGTATGTACTAAAAAT-GAAAGAAGCTTACCAG 3' (SEQ ID NO: 138) and 5' GAGCAATGAACCCAATAACGAAATC 3' (SEQ ID NO: 139). These two fragments were then fused by PCR using the primers 5' TTTTGGCTGTTGTTCCAGGTCGTAGG 3'(SEQ ID NO: 173) and 5' GAGCAATGAACCCAATAAC-GAAATC 3' (SEQ ID NO: 139), resulting in the fragment UP(DGA1)-pTDH3-5' 2/3 *K. lactis* URA3, which constituted part 2 of the bipartite targeting substrate.

The yeast strain FS01202 (MATa ura3) was transformed with the linear substrates UP(DGA1)-pTDH3-5' 2/3 *K. lactis* URA3 and 3' 2/3 *K. lactis* URA3-pTDH3-DOWN(DGA1) and plated out on medium lacking uracil. Transformants were selected and streak-purified on medium lacking uracil and were then transferred to plates containing 5-FOA. Pop-out recombinants were streak-purified on 5-FOA-containing medium. The resulting strain had the genotype MATa ura3 pTDH3-DGA1 and was named FS01344. Correct integration of the TDH3 promoter and absence of PCR-generated mutations was verified by sequencing of the modified region.

To combine DGA1 overexpression with the appropriate genetic markers, FS01344 (MATa ura3 pTDH3-DGA1) was crossed to FS01269 (MATalpha trp1). Diploids were selected on medium lacking uracil and tryptophane and were then transferred on to sporulation medium. Following sporulation, the asci were dissected into ascospore tetrads. Presence of the pTDH3-DGA1 modification in the resulting haploid strains was determined by colony PCR, and remaining genetic features were scored using standard methods. From the set of haploid strains derived from the cross, a strain with the genotype MATa ura3 trp1 pTDH3-DGA1 was selected and named FS01370.

Example 30

Overexpression of GAT1, SLC1 and YDR531W

The yeast genes GAT1, encoding glycerol-3-phosphate acyltransferase, SLC1, encoding 1-acyl-sn-gylcerol-3-phosphate acyltransferase, and YDR531W, putatively encoding pantothenate kinase, were all overexpressed with the strong constitutive TPI1 promoter using a promoter-replacement method based on a bipartite gene-targeting substrate (FIG. 15). For each of the overexpressions, the first part of the bipartite substrate consisted of two thirds (towards the 3'end) of *K. lactis* URA3, fused to the TPI1 promoter sequence and a target sequence corresponding to the beginning of the gene to be overexpressed. The second part of the bipartite substrate consisted of a target sequence upstream of the gene to be overexpressed, fused to the TPI1 promoter sequence and two thirds (towards the 5' end) of *K. lactis* URA3. Following transformation with the bipartite substrate and selection on medium lacking uracil, transformants were obtained in which the native promoter had been knocked out and replaced with two copies of the TPI1 promoter sequence as a direct repeat on either side of the *K. lactis* URA3 marker gene. A second recombination event, resulting in looping out of the selection marker, was selected for by replating transformants on medium containing 5-FOA. In the pop-out recombinants, the native promoters had thus been replaced with the TPI1 promoter, resulting in overexpression of GAT1, SLC1 and YDR531W, respectively.

In order to construct part 1 of the bipartite substrate, two thirds (towards the 3'end) of *K. lactis* URA3 was amplified from the plasmid pWJ716 using the primers 5' CTTGACGT-TCGTTCGACTGATGAGC 3' (SEQ ID NO: 133) and 5' CTGGAATTCGATGATGTAGTTTCTGG 3' (SEQ ID NO: 158). Moreover, the TPI1 promoter sequence was amplified from genomic yeast DNA using the primers 5' CTACAT-CATCGAATTCCAGCTACGTATGGTCATTTCTTCTTC 3' (SEQ ID NO: 159) and 5' TTTTTGATTAAAAT-TAAAAAAACTTTTTAGTTTATGTATGTGTTTTTTG 3' (SEQ ID NO: 160). Downstream target sequences, consisting of the beginning of GAT1, SLC1 and YDR531W, respectively, were then amplified from genomic yeast DNA. The primer pair 5' AGTTTTTTTAATTTTAATCAAAAAAT-GTCTGCTCCCGCTGCC 3' (SEQ ID NO: 175) and 5' AAC-CTTTTCGTAAAGTTCACTGG 3' (SEQ ID NO: 176) was used for amplification of the GAT1 downstream targeting, the primer pair 5' AGTTTTTTTAATTTTAATCAAAAAAT-GAGTGTGATAGGTAGGTTCTTG 3' (SEQ ID NO: 225) and 5' AGGAAAAACCCATAGAGCACG 3' (SEQ ID NO: 177) was used for amplification of the SLC1 targeting sequence, and the primer pair 5' AGTTTTTTTAATTTTAAT-CAAAAAATGCCGCGAATTACTCAAG 3' (SEQ ID NO: 178) and 5' GACTAGAAGGTATGGGTAGATAGCC 3' (SEQ ID NO: 179) was used for amplification of the YDR531W targeting sequence. Each of the GAT1, SLC1 and YDR531W downstream target sequences were then fused to the TPI promoter by PCR, using the forward primer 5' CTA-CATCATCGAATTCCAGCTACGTATGGT-CATTTCTTCTTC 3' (SEQ ID NO: 226) and the reverse primers 5' AACCTTTTCGTAAAGTTCACTGG 3' (SEQ ID NO: 176) (for fusion to the GAT1 targeting sequence), 5' AGGAAAAACCCATAGAGCACG 3' (SEQ ID NO: 177) (for fusion to the SLC1 targeting sequence) or 5' GACTA- GAAGGTATGGGTAGATAGCC 3' (SEQ ID NO: 179) (for the YDR531W targeting sequence). Finally, the resulting fusion fragments were fused to the fragment consisting of two thirds (towards the 3'end) of *K. lactis* URA3 by PCR using the forward primer 5' CTTGACGTTCGTTCGACTGATGAGC 3' (SEQ ID NO: 133) and the reverse primers 5' AAC-CTTTTCGTAAAGTTCACTGG 3' (SEQ ID NO: 176) (for fusion to the GAT1 targeting sequence), 5' AGGAAAAAC-CCATAGAGCACG 3' (SEQ ID NO: 177) (for fusion to the SLC1 targeting sequence) or 5' GACTAGAAGGTATGGG-TAGATAGCC 3' (SEQ ID NO: 179) (for the YDR531W targeting sequence). The resulting fragments, 3' 2/3 *K. lactis* URA3-pTPI1-DOWN(GAT1), 3' 2/3 *K. lactis* URA3-pTPI1-DOWN(SLC1) and 3' 2/3 *K. lactis* URA3-pTPI1-DOWN (YDR531W) constituted part 1 of the bipartite gene targeting substrate used for GAT1 and SLC1 overexpression, respectively.

In order to construct part 2 of the bipartite substrate, two thirds (towards the 5'end) of *K. lactis* URA3 was amplified from the plasmid pWJ716 using the primers 5' CGGTCTG-CATTGGATGGTGGTAAC 3' (SEQ ID NO: 163) and 5' GAGCAATGAACCCAATAACGAAATC 3' (SEQ ID NO: 139), and the TPI1 promoter sequence was amplified from genomic yeast DNA using the primers 5' CTACATCATC-GAATTCCAGCTACGTATGGTCATTTCTTCTTC 3' (SEQ ID NO: 159) and 5' CACCATCCAATGCAGACCGTTT-TAGTTTATGTATGTGTTTTTTG 3' (SEQ ID NO: 164). Furthermore, target sequences upstream of GAT1, SLC1 and YDR531W were amplified from genomic yeast DNA by PCR using the primer pair 5' GGTAAAGAAAACTA-CAAATCTGGG 3' (SEQ ID NO: 180) and 5' CTGGAAT-TCGATGATGTAGAAGCTGCCACTTCTTCAGGG 3' (SEQ ID NO: 181) for the GAT1 target sequence, the primer pair 5' TTGCTTTAAACATCTGTCCAAGAC 3' (SEQ ID NO: 182) and 5' CTGGAATTCGATGATGTAGCCTTCAC-CTTAAACCCTTCC 3' (SEQ ID NO: 183) for the SLC1 target sequence, and the primer pair 5' TGTCTTC-CTATTTTCTCTGACCC 3' (SEQ ID NO: 184) and 5' CTG-GAATTCGATGATGTAGTCGCATGCACTCAATTGG 3' (SEQ ID NO: 185) for the YDR531W target sequence. Each of the GAT1, SLC1 and YDR531W upstream target sequences were then fused to the TPI promoter by PCR, using the reverse primer 5' CACCATCCAATGCAGACCGTTT-TAGTTTATGTATGTGTTTTTTG 3' (SEQ ID NO: 164) and the forward primers 5' GGTAAAGAAAACTA-CAAATCTGGG 3' (SEQ ID NO: 180) (for fusion to the GAT1 targeting sequence) 5' TTGCTTTAAACATCTGTC-CAAGAC 3' (SEQ ID NO: 182) (for fusion to the SLC1 targeting sequence), or 5' TGTCTTCCTATTTTCTCT-GACCC 3' (SEQ ID NO: 184) (for fusion to the YDR531W target sequence). Finally, the resulting fusion fragments were fused to the fragment consisting of two thirds (towards the 5'end) of *K. lactis* URA3 by PCR using the reverse primer 5' GAGCAATGAACCCAATAACGAAATC 3' (SEQ ID NO: 139) and the forward primers 5' GGTAAAGAAAACTA-CAAATCTGGG 3' (SEQ ID NO: 180) (for fusion to the GAT1 targeting sequence), 5' TTGCTTTAAACATCTGTC-CAAGAC 3' (SEQ ID NO: 182) (for fusion to the SLC1 targeting sequence), or 5' TGTCTTCCTATTTTCTCT-GACCC 3' (SEQ ID NO: 184) (for fusion to the YDR531W target sequence).

The resulting fragments, UP(GAT1)-pTPI1-5' 2/3 *K. lactis* URA3, UP(SLC1)-pTPI1-5' 2/3 *K. lactis* URA3 and UP(YDR531W)-pTPI1-5' 2/3 *K. lactis* URA3 constituted part 2 of the bipartite gene targeting substrate used for GAT1, SLC1 and YDR531W overexpression, respectively.

For GAT1 overexpression, the yeast strain FS01372 (MATa ura3 trp1 pADH1-FAS1 pADH1-FAS2) was transformed with the linear substrates UP(GAT1)-pTPI1-5' 2/3 *K. lactis* URA3 and 3' 2/3 *K. lactis* URA3-pTPI1-DOWN (GAT1). Similarly, for SLC1 overexpression, FS01372 was transformed with the linear substrates UP(SLC1)-pTPI1-5' 2/3 *K. lactis* URA3 and 3' 2/3 *K. lactis* URA3-pTPI1-DOWN (SLC1) and for YDR531W overexpression, FS01372 was transformed with the linear substrates UP(YDR531W)-pTPI1-5' 2/3 *K. lactis* URA3 and 3' 2/3 *K. lactis* URA3-pTPI1-DOWN(YDR531W). Transformants were selected and streak-purified on medium lacking uracil and were then transferred to plates containing 5-FOA. Pop-out recombinants were streak-purified on 5-FOA-containing medium. The resulting strains had the genotypes MATa ura3 trp1 pADH1-FAS1 pADH1-FAS2 pTPI1-GAT1, MATa ura3 trp1 pADH1-FAS1 pADH1-FAS2 pTPI1-SLC1, and MATa ura3 trp1 pADH1-FAS1 pADH1-FAS2 pTPI1-YDR531W and were named FS01395, FS01394 and FS01393, respectively. Correct integration of the TPI1 promoter was verified by colony-PCR in all strains.

Example 31

Overexpression of YBR159W and TSC13

The yeast genes YBR159W, encoding beta-ketoacyl-CoA synthase, and TSC13, encoding trans-2-enoyl-CoA reductase, were both overexpressed with the strong constitutive ADH1 promoter using a promoter-replacement method based on a bipartite gene-targeting substrate (FIG. 15). For each of the overexpressions, the first part of the bipartite substrate consisted of two thirds (towards the 3'end) of *K. lactis* URA3, fused to the ADH1 promoter sequence and a target sequence corresponding to the beginning of the gene to be overexpressed. The second part of the bipartite substrate consisted of a target sequence upstream of the gene to be overexpressed, fused to the ADH1 promoter sequence and two thirds (towards the 5' end) of *K. lactis* URA3. Following transformation with the bipartite substrate and selection on medium lacking uracil, transformants were obtained in which the native promoter had been knocked out and replaced with two copies of the ADH1 promoter sequence as a direct repeat on either side of the *K. lactis* URA3 marker gene. A second recombination event, resulting in looping out of the selection marker, was selected for by replating transformants on medium containing 5-FOA. In the pop-out recombinants, the native promoters had thus been replaced with the ADH1 promoter, resulting in overexpression of YBR159W and TSC13, respectively.

The procedure was as follows:

For construction of part 1 of the bipartite gene targeting substrates (FIG. 15), a fragment consisting of two thirds of *K. lactis* URA3 (towards the 3' end) and the ADH1 promoter was amplified from plasmid pWAD1 using the primers 5' CTTGACGTTCGTTCGACTGATGAGC 3'(SEQ ID NO: 133) and 5'TGTATATGAGATAGTTGATTGTATGC 3'(SEQ ID NO: 186). Furthermore, downstream target sequences, consisting of the beginning of YBR159W and TSC13, respectively, were amplified by PCR from genomic yeast DNA using the primer pair 5' TACAATCAACTATCTCATATA-CAATGACTTTTATGCAACAGCTTCAAGAG 3' (SEQ ID NO: 187) and 5' GACCAACATTATTGACCAAAACGG 3' (SEQ ID NO: 188) for the YBR159W targeting sequence and the primer pair 5' GCATACAATCAACTATCTCATATA-CAATGCCTATCACCATAAAAAGCC 3' (SEQ ID NO: 189) and 5' GGAAGCCGTAGCCAAAGTAACC 3' (SEQ ID NO: 190) for the TSC13 targeting sequence. Finally, the YBR159W and TSC13 downstream targeting sequences were fused to the fragment consisting of two thirds of *K. lactis* URA3 (towards the 3' end) and the ADH1 promoter by PCR. For YBR159W, the primer pair 5'CTTGACGTTCGTTC-GACTGATGAGC 3' (SEQ ID NO: 133) and 5' GACCAACATTATTGACCAAAACGG 3' (SEQ ID NO: 188) was used for the fusion reaction and for TSC13, the primer pair 5'CTGACGTTCGTTCGACTGATGAGC 3' (SEQ ID NO: 133) and 5' GGAAGCCGTAGCCAAAG-TAACC 3' (SEQ ID NO: 190) was used. The resulting fusion fragments 3' 2/3 *K. lactis* URA3-pADH1-DOWN (YBR159W) and 3' 2/3 *K. lactis* URA3-pADH1-DOWN (TSC13) were part 1 of the bipartite targeting substrate used for YBR159W and TSC13 promoter replacement, respectively.

For construction of part 2 of the bipartite targeting substrate, a fragment consisting of the ADH1 promoter and two thirds of *K. lactis* URA3 towards the 5' end was first amplified by PCR using plasmid pWAD2 as template. The primers used for this amplification were 5' GGACGTTCCCTGTATGTAC-TAGGGGGATCGAAGAAATGATGG 3' (SEQ ID NO: 153) and 5' GAGCAATGAACCCAATAACGAAATC 3'(SEQ ID NO: 139). Next, upstream targeting sequences were amplified from genomic yeast DNA using the primer pair 5' GAAAAAATCATTGGATGCCC 3' (SEQ ID NO: 191) and 5' AGTACATACAGGGAACGTCCAACGCTTT-TATTCGTGAAATCTC 3' (SEQ ID NO: 192) for the YBR159W upstream targeting sequence and the primer pair 5' GTTATTGAAAGCAATGGGCAAC 3' (SEQ ID NO: 193) and 5' AGTACATACAGGGAACGTCCAAT-TCAAAATATGTATCTCTCTC 3' (SEQ ID NO: 227) for the TSC13 upstream targeting sequence. The upstream targeting sequences were then fused to the previously constructed pADH1-5' 2/3 *K. lactis* URA3 fragment. The reverse primer used for the fusion reactions was 5' GAGCAATGAAC-CCAATAACGAAATC 3' (SEQ ID NO: 139) and the forward primers were 5' GAAAAAATCATTGGATGCCC 3' (SEQ ID NO: 191) (for the YBR159W target sequence) or and 5' GTTATTGAAAGCAATGGGCAAC 3' (SEQ ID NO: 193) (for the TSC13 target sequence). The resulting fusion fragments UP(YBR159W)-pADH1-5' 2/3 *K. lactis* URA3 and UP(TSC13)-pADH1-5' 2/3 *K. lactis* URA3 were part 2 of the bipartite targeting substrate used for YBR159W and TSC13 promoter replacement, respectively.

For YBR159W overexpression, the yeast strain FS01372 (MATa ura3 trp1 pADH1-FAS1 pADH1-FAS2) was transformed with the linear substrates UP(YBR159W)-pADH1-5' 2/3 *K. lactis* URA3 and 3' 2/3 *K. lactis* URA3-pADH1-DOWN (YBR159W). Similarly, for TSC13 overexpression, FS01372 was transformed with the linear substrates UP(TSC13)-pADH1-5' 2/3 *K. lactis* URA3 and 3' 2/3 *K. lactis* URA3-pADH1-DOWN (TSC13). Transformants were selected and streak-purified on medium lacking uracil and were then transferred to plates containing 5-FOA. Pop-out recombinants were streak-purified on 5-FOA-containing medium. The resulting strains had the genotypes MATa ura3 trp1 pADH1-FAS1 pADH1-FAS2 pADH1-YBR159W and MATa ura3 trp1 pADH1-FAS1 pADH1-FAS2 pADH1-TSC13 and were named FS01427 and FS01440, respectively. Correct integration of the ADH1 promoter was verified by colony-PCR in both strains.

Example 32

Isolation of Genes Encoding Subunits of a Fungal ATP:Citrate Lyase

Fungal ATP:citrate lyases consist of two subunits, encoded by separate genes. In the oleaginous yeast *Sordaria macrospora* these two subunits are encoded by the genes acl1 and acl2 (Minou et al. 2000 Curr Genet 37:189-193). The coding sequences of *S. macrospora* acl1 and acl2 were isolated by PCR from first strand cDNA from *S. macrospora* CBS 957.73 as template. The defined primers used for the amplification were designed to match the published coding sequences of acl1 (SEQ ID NO 80) and acl2 (SEQ ID NO 82). The procedure was as follows:

*S. macrospora* CBS 957.73 was cultivated in 100 ml YEPA medium (1% yeast extract, 2% peptone and 2% acetate, pH 6.0) shaking at 100 rpm at room temperature for 4 days. Biomass was collected by filtration and total RNA was isolated using Trizol reagent (Gibco BRL). 5 μg of RNA was used for reverse transcription (Superscript II RT, Invitrogen) using Oligo(dT)12-18 as primer. After first strand cDNA synthesis, complementary RNA was removed by RNAse digestion. The cDNA was then used as template for PCR (Phusion enzyme, Finnzymes) using the following primers:

5' GCATACAATCAACTATCTCATATACAAT-GCCTTCCGCAACTAGCACC 3' (SEQ ID NO: 194) and 5' TTGTTATTGTAATGTGATACT-TAAATTTGGACCTCAACACGACC 3' (SEQ ID NO: 195) for acl1;

5' TTAGGCCTGGAACTCCACCGCAC 3' (SEQ ID NO: 196) and 5' CGAATAAACACACATAAACAAACAAAAT-GTCTGCGAAGAGCATC 3' (SEQ ID NO: 197) for acl2. The resulting fragments of the expected sizes were excised from an agarose gel and purified using GFX-columns (Amersham).

Example 33

Integration of Genes Encoding Subunits of a Fungal ATP:Citrate Lyase into the Genome of *S. cerevisiae*

Figure 17:
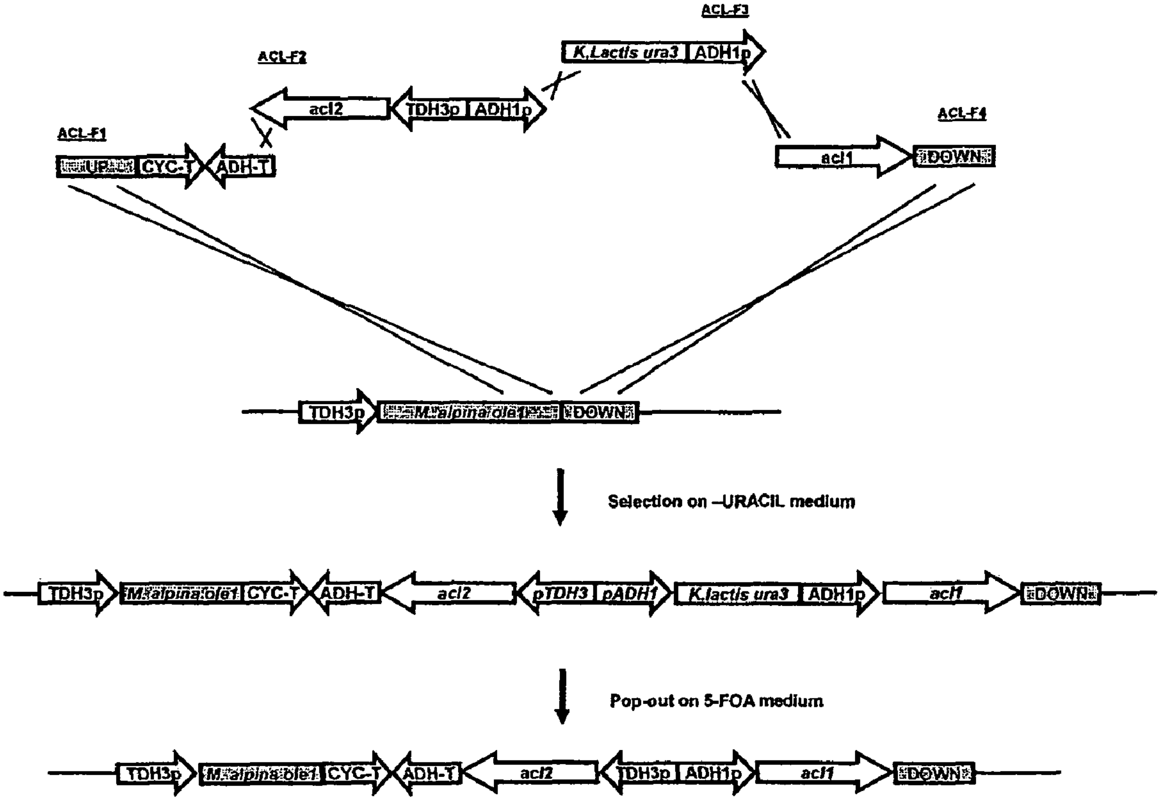
FIG. 17: Strategy for integration of *Sordaria macrospora* acl1 and acl2 into the genome of *Saccharomyces cerevisiae.*

The strategy used for integrating the two subunits of ATP: citrate lyase (acl1 and acl2) is shown in FIG. 17. As parent strain for integration into the genome, FS01396, a strain that carries the *M. alpina* ole1 gene integrated at the POX1 locus, was chosen. The acl1 and acl2 genes were integrated downstream of the *M. alpina* ole1 gene in this strain, using a gene targeting substrate consisting of four linear fragments: ACL-F1, ACL-F2, ACL-F3 and ACL-F4. ACL-F1 contained the upstream targeting sequence for directing the substrate to the correct position in the genome, in addition to the CYC terminator sequence in forward orientation and the ADH1 terminator sequence in reverse orientation. ACL-F1 additionally contained a 3' sequence of 20 bp which was identical to the 5' end of ACL-F2. ACL-F2 contained the acl2 gene in reverse orientation under the control of the TDH3 promoter, fused to the ADH1 promoter in forward orientation. ACL-F2 additionally contained a 3' sequence of 20 bp that was identical to the 5' end of ACL-F3. ACL-F3 consisted of the complete *K. lactis* URA3 marker gene in forward orientation followed by the ADH1 promoter sequence in forward orientation. ACL-F4 consisted of the acl1 gene in forward orientation, fused to the downstream targeting sequence used for directing the substrate to the correct position in the genome. In addition, ACL-F4 contained a 5' sequence of 20 bp that was identical to the 3' end of ACL-F3.

The overlapping sequences at the 3' end of ACL-F1 and 5' end of ACL-F2, the 3' end of ACL-F2 and 5' end of ACL-F3, and between the 3' end of ACL-F3 and the 5' end of ACL-F4 allowed assembly of the complete gene targeting substrate in vivo by the homologous recombination mechanisms of *S. cerevisiae*. Thus, FS01396 was transformed with the four linear substrates ACL-F1, ACL-F2, ACL-F3 and ACL-F4, and integration of the complete gene targeting substrate at the intended genomic location was selected for by plating out the transformed on medium lacking uracil. This resulted in a strain in which the complete targeting substrate was integrated immediately downstream of *M. alpina* ole1, in a way so that the *M. alpina* ole 1 was now connected to the CYC1 terminator. Moreover, the acl2 gene was placed under the control of the TDH3 promoter and was connected to the ADH1 terminator sequence, all in reverse direction. The marker gene *K. lactis* URA3 was integrated in forward direction and was flanked by the ADH1 promoter as a direct repeat on either side of the marker. Finally, the acl1 gene was placed under the control of the ADH1 promoter and immediately upstream of the POX1 terminator sequence, corresponding to the downstream targeting sequence (FIG. 17). The *K. lactis* URA3 marker gene was then looped out by replating transformants on 5-FOA medium.

The procedure was as follows:

For construction of the fragment ACL-F1, an upstream targeting sequence, corresponding to the 5' end of *M. alpina* ole1, was first amplified by PCR using genomic DNA as template and the primers 5'CAACGCTATCCGCTTTTACCAGT 3' (SEQ ID NO: 198) and 5' CTATTCGGCCTTGACGTGGTCAGTGC 3'(SEQ ID NO: 116). Furthermore, a fragment containing the CYC1 and ADH1 terminators in reverse orientation was amplified by PCR using plasmid p300 as template and using the primers 5' GCACTGACCACGTCAAGGCCGAATAGCCGCTCTAACCGAAAAGGAAGG 3' (SEQ ID NO: 199) and 5' GTGCGGTGGAGTTCCAGGCCTAACGAATTTCTTATGATTTATGATTTTTA 3' (SEQ ID NO: 200). The two fragments were then fused by PCR using the primers 5' CAACGCTATCCGCTTTTACCAGT 3' (SEQ ID NO: 198) and GTGCGGTGGAGTTCCAGGCCTAACGAATTTCTTATGATTTATGATTTTTA 3' (SEQ ID NO: 200), resulting in the fragment ACL-F1.

For construction of the fragment ACL-F2, a fragment containing the TDH3 promoter in reverse direction and the ADH1 promoter in forward direction was amplified by PCR using as template the plasmid pESC-URA-elo-delta-5-AT (Example 34) and using the primers 5' TTTGTTTGTTTATGTGTGTTTATTCGAAACTAAG 3' (SEQ ID NO: 170) and 5' GTTACCACCATCCAATGCAGACCGTGTATATGAGATAGTTGATTGTATGC 3' (SEQ ID NO: 201). The resulting fragment was fused by PCR to the acl2 gene, isolated as described in example X, using the primers 5' TTAGGCCTGGAACTCCACCGCAC 3' (SEQ ID NO: 196) and 5' GTTACCACCATCCAATGCAGACCGTGTATATGAGATAGTTGATTGTATGC 3' (SEQ ID NO: 201). The resulting fusion fragment was ACL-F2.

For construction of the fragment ACL-F3, a fragment containing the complete *K. lactis* URA3 marker gene upstream of the ADH1 promoter was amplified by PCR from plasmid pWAD2 using the primers 5'CGGTCTGCATTGGATGGTGGTAAC 3' (SEQ ID NO: 163) and 5' TGTATATGAGATAGTTGATTGTATGC 3' (SEQ ID NO: 186). The resulting fragment constituted ACL-F3.

For construction of the fragment ACL-F4, a downstream targeting sequence, corresponding to the POX1 terminator sequence, was amplified by PCR from genomic DNA using the primers 5' GTATCACATTACAATAACAATTCCTTCGAACCCTCTGTTTTGC 3' (SEQ ID NO: 166) and 5' TTAGAGCTTCATTCCAACAAGTGCC 3' (SEQ ID NO: 167). The resulting fragment was fused to the acl1 gene, isolated as described in example 32, using the primers 5' GCATACAATCAACTATCTCATATACAATGCCTTCCGCAACTAGCACC 3' (SEQ ID NO: 194) and 5' TTAGAGCTTCATTCCAACAAGTGCC 3' (SEQ ID NO: 167).

The yeast strain FS01396 (MATa ura3-52 trp1 pox1::pTDH3-*M. alpina* ole1 pADH1-FAS1 pADH1-FAS2, Example 36) was transformed with the linear fragments ACL-F1, ACL-F2, ACL-F3 and ACL-F4. Transformants were selected and streak-purified on medium lacking uracil and were then transferred to plates containing 5-FOA. Pop-out recombinants were streak-purified on 5-FOA-containing medium. The resulting strain had the genotype MATa ura3 trp1 pADH1-FAS1 pADH1-FAS2 pox1::pTDH3-mole1-pADH1-*S. macrospora* acl1-pTDH3-*S. macrospora* acl2 and was named FS01425. Correct assembly of the complete gene targeting substrate and integration at the correct genomic location was verified by colony-PCR.

Example 34

Construction of Plasmid pESC-URA-elo-delta-5-AT

The plasmid pESC-URA-elo-delta-5-AT contains short versions of the TDH3 and ADH1 promoters in replacement of the divergent GAL10/GAL1 promoter of pESC-URA-elo-delta-5. Short versions (fragments corresponding to 674 and 439 bp upstream of the TDH3 and ADH1 start codons, respectively) of the TDH3 and ADH1 promoters were amplified by PCR using genomic yeast DNA as template and the primer pair 5' AAGCGGCCGCTTTTGTTTGTTTATGTGTGTTTATTCG 3' (SEQ ID NO: 202) and 5' AAATGGAAAAAGGGTAGTGAAAAGTTTATCATTATCAATACTGCCATTTC 3' (SEQ ID NO: 203) for pTDH3 amplification and the primer pair 5' TTTCACTACCCTTTTTCCATTTGCCATC 3' (SEQ ID NO: 204) and 5' TTCCCGGGTGTATATGAGATAGTTGATTGTATGC 3' (SEQ ID NO: 205) for pADH1 amplification. The two promoter fragments were then fused by PCR using the primers 5' AAGCGGCCGCTTTTGTTTGTTTATGTGTGTTTATTCG 3' (SEQ ID NO: 202) and 5' TTCCCGGGTGTATATGAGATAGTTGATTGTATGC 3' (SEQ ID NO: 205). This resulted in a fragment consisting of the short version of the TDH3 and ADH1 promoters in divergent orientation, containing a NotI restriction site at the 5' end and an XmaI restriction site at the 3' end. Following restriction with NotI and XmaI, the fragment was introduced into NotI/XmaI digested pESC-URA-elo-delta-5. This resulted in plasmid pESC-URA-elo-delta-5-AT, in which the divergent GAL10/GAL1 promoter had been replaced by a divergent TDH3/ADH1 promoter. Absence of PCR-generated mutations in pESC-URA-elo-delta-5-AT was verified by sequencing of the pTDH3/pADH1 promoter sequences.

Example 35

Combining Ammonium Assimilation Modifications with FAS Overexpression

Deletion of the GDH1 gene and overexpression of either the GDH2 gene or the GLN1 and GLT1 genes leads to an altered co-factor dependency of the ammonium assimilation pathway of yeast, and strains carrying these modifications are likely to contain an increased availability of NADPH that can be used for fatty acid synthesis. Deletion of GDH1 and overexpression of GDH2 was therefore combined with overexpression of FAS1 and FAS2. Similarly, GDH1 deletion and overexpression of GLN1 and GLT1 was also combined with overexpression of FAS1 and FAS2. This was performed by crossing of strains containing the ammonium assimilation modifications to a strain containing the FAS1 and FAS2 overexpressions. Following sporulation of the resulting diploids, sporulation and dissection of asci, novel haploid strains were identified that carried the desired genetic modifications. The CEN.PK strains used in the present Example carrying the mentioned ammonium assimilation modifications were derived from the strains CEN.MS1-10C T1 and CEN.MS5-3A, which were kind gifts from Margarida Moreira dos Santos, Center for Microbial Biotechnology, Bio-Centrum DTU, Technical University of Denmark. The procedure was as follows:

To combine GDH1 deletion and GDH2 overexpression with FAS1 and FAS2 overexpression, the yeast strain FS01254 (MATalpha ura3 gdh1::loxP gdh2::PGKp-GDH2-KanMX3) was crossed to strain FS01372 (MATa ura3 trp1 pADH1-FAS1 pADH1-FAS2, Example 26). Diploids were selected on medium lacking uracil and tryptophane and were then transferred on to sporulation medium. Following sporulation, the asci were dissected into ascospore tetrads. Presence of the modification gdh2::PGKp-GDH2-KanMX3 in the resulting haploid strains was determined by replica plating to geniticin-containing plates. Presence of the gdh1::loxP knockout, the pADH1-FAS1 overexpression and the pADH1-FAS2 overexpression were determined by colony PCR using appropriate primers, and remaining genetic features were scored using standard methods. From the set of haploid strains derived from the cross, a strain with the genotype MATa ura3 trp1 pADH1-FAS1 pADH1-FAS2 gdh1::loxP gdh2::PGKp-GDH2-KanMX3 was selected and named FS01398.

To combine FAS1 and FAS2 overexpression with GDH1 deletion, GLN1 overexpression and GLT1 overexpression, to consecutive crosses were performed. First, the strain FS01335 (MATalpha ura3 trp1 gdh1::loxP gln1::PGKp-GLN1-KanMX3 glt1::PGKp-GLT1-KanMX3) was crossed to FS01372 (MATa ura3 trp1 pADH1-FAS1 pADH1-FAS2). Diploids were identified by streaking out cells from the cross to single colonies, transferring a number of colonies to a master plate, and testing the ability of the selected colonies to sporulate on sporulation medium. Following sporulation, the asci were dissected into ascospore tetrads. Presence of the modifications gln1::PGKp-GLN1-KanMX3 and glt1::PGKp-GLT1-KanMX3 in the resulting haploid strains was determined by replica plating to geniticin-containing plates and by performing colony-PCR using appropriate primers. Presence of the gdh1::loxP knockout, the pADH1-FAS1 overexpression and the pADH1-FAS2 overexpression were determined by colony PCR, and the mating types were scored using standard methods. From the set of haploid strains derived from the cross, the two strains FS01419 (MATa ura3 trp1 pADH1-FAS1 pADH1-FAS2 gdh1::loxP glt1::PGKp-GLT1-KanMX3) and FS01420 (MATalpha ura3 trp1 pADH1-FAS1 gdh1::loxP gln1::PGKp-GLN1-KanMX3) were selected.

Second, FS01419 and FS01420 were crossed and diploids were selected as described above for the FS01335×FS01372 cross. Following sporulation, the asci were dissected into ascospore tetrads. Presence of the modifications gln1::PGKp-GLN1-KanMX3 and glt1::PGKp-GLT1-KanMX3 in the resulting haploid strains was determined by replica plating to geniticin-containing plates. Presence of the pADH1-FAS2 overexpression was determined by colony PCR, and the mating types were scored using standard methods. From the set of haploid strains derived from the cross, the strain FS01437 (MATa ura3 trp1 pADH1-FAS1 pADH1-FAS2 gdh1::loxP glt1::PGKp-GLT1-KanMX3 gln1::PGKp-GLN1-KanMX3) was selected. The presence of the gdh1::loxP deletion and the pADH1-FAS2 overexpression in strain FS01437 was verified by colony PCR.

Example 36

Combining pox1::pTDH3-*M. alpina* ole1 Modification with FAS Overexpression and ACC1 Overexpression To combine the genomic integration of *M. alpina* ole1 with overexpression of FAS1 and FAS2, FS01368 (MATalpha ura3 trp1 pox1::pTDH3-*M. alpina* ole1, Example 28) was crossed to FS01372 (MATa ura3 trp1 pADH1-FAS1 pADH1-FAS2, Example 26). Diploids were identified by streaking out cells from the cross to single colonies, transferring a number of colonies to a master plate, and testing the ability of the selected colonies to sporulate on sporulation medium. Following sporulation, the asci were dissected into ascospore tetrads. Presence in the resulting haploid strains of the pADH1-FAS1 and pADH1-FAS2 overexpressions and presence of the pox1:: pTDH3-*M. alpina* ole1 modification were determined by colony PCR using appropriate primers, and the mating types were scored using standard methods. From the set of haploid strains derived from the cross, a strain with the genotype MATa ura3 trp1 pADH1-FAS1 pADH1-FAS2 pox1::pTDH3-*M. alpina* ole1 was selected and named FS01396. Furthermore, a strain with the genotype MATalpha ura3 trp1 pADH1-FAS1 pox1::pTDH3-*M. alpina* ole1 was selected and named FS01408.

To further combine genomic integration of *M. alpina* ole1, overexpression of FAS1, and overexpression of FAS2 with ACC1 overexpression, FS01408 (MATalpha ura3 trp1 pADH1-FAS1 pox1::pTDH3-*M. alpina* ole1, derived as described above) was crossed to FS01392 (MATa ura3 trp1 pADH1-FAS1 pADH1-FAS2 pTPI1-ACC1, Example 27). Diploids were selected as described above for the FS01368×FS01372 cross and were transferred to sporulation medium. Following sporulation, the asci were dissected into ascospore tetrads. Presence in the resulting haploid strains of the pADH1-FAS2 and pTPI1-ACC1 overexpressions and presence of the pox1:: pTDH3-*M. alpina* ole1 modification were determined by colony PCR using appropriate primers, and the mating types were scored using standard methods. From the set of haploid strains derived from the cross, a strain with the genotype MATa ura3 trp1 pADH1-FAS1 pADH1-FAS2 pTPI1-ACC1 pox1::pTDH3-*M. alpina* ole1 was selected and named FS01423.

Example 37

Expression of Pathway to Arachidonic Acid in Genetically Modified Yeast

To express the pathway to arachidonic acid in the modified strain backgrounds described in the previous Examples, the engineered strains were co-transformed with the plasmids pESC-TRP-delta-12 delta-6 and pESC-URA-elo-delta-5. An overview of the strains resulting from the transformations is shown in Table 4.

TABLE 4

Summary of arachidonic acid producing strains, their genotypes and parent strains.

| Strain | Genotype | Parent |
|---|---|---|
| FS01373 | MATa ura3 trp1 pADH1-FAS1 pADH1-FAS2 [pESC-TRP-delta-12 delta-6] [pESC-URA-elo-delta-5] | FS01372 |
| FS01413 | MATa ura3 trp1 pADH1-FAS1 pADH1-FAS2 pTPI1-ACC1 [pESC-TRP-delta-12 delta-6] [pESC-URA-elo-delta-5] | FS01392 |
| FS01369 | MAT alpha ura3 trp1 pox1::pTDH3-*M. alpina* ole1 [pESC-TRP-delta-12 delta-6] [pESC-URA-elo-delta-5] | FS01368 |
| FS01371 | MATa ura3 trp1 pTDH3-DGA1 [pESC-TRP-delta-12 delta-6] [pESC-URA-elo-delta-5] | FS01370 |
| FS01417 | MATa ura3 trp1 pADH1-FAS1 pADH1-FAS2 pox1::*M. alpina* ole1 [pESC-TRP-delta-12 delta-6] [pESC-URA-elo-delta-5] | FS01396 |
| FS01414 | MATa ura3 trp1 pADH1-FAS1 pADH1-FAS2 pTPI1-YDR531W [pESC-TRP-delta-12 delta-6] [pESC-URA-elo-delta-5] | FS01393 |
| FS01415 | MATa ura3 trp1 pADH1-FAS1 pADH1-FAS2 pTPI1-SLC1 [pESC-TRP-delta-12 delta-6] [pESC-URA-elo-delta-5] | FS01394 |
| FS01416 | MATa ura3 trp1 pADH1-FAS1 pADH1-FAS2 pTPI1-GAT1 [pESC-TRP-delta-12 delta-6] [pESC-URA-elo-delta-5] | FS01395 |
| FS01418 | MATa ura3 trp1 pADH1-FAS1 pADH1-FAS2 gdh1::loxP gdh2::PGKp-GDH2-KanMX3 [pESC-TRP-delta-12 delta-6] [pESC-URA-elo-delta-5] | FS01398 |
| FS01429 | MATa ura3 trp1 pADH1-FAS1 pADH1-FAS2 pTPI1-ACC1 pox1::*M. alpina* ole1 [pESC-TRP-delta-12 delta-6] [pESC-URA-elo-delta-5] | FS01423 |
| FS01430 | MATa ura3 trp1 pADH1-FAS1 pADH1-FAS2 pox1::pTDH3-mole1-pADH1-*S. macrospora* acl1-pTDH3-*S. macrospora* acl2 [pESC-TRP-delta-12 delta-6] [pESC-URA-elo-delta-5] | FS01425 |
| FS01431 | MATa ura3 trp1 pADH1-FAS1 pADH1-FAS2 pADH1-YBR159W [pESC-TRP-delta-12 delta-6] [pESC-URA-elo-delta-5] | FS01427 |
| FS01439 | MATa ura3 trp1 pADH1-FAS1 pADH1-FAS2 gdh1::loxP glt1::PGKp-GLT1-KanMX3 gln1::PGKp-GLN1-KanMX3 [pESC-TRP-delta-12 delta-6] [pESC-URA-elo-delta-5] | FS01437 |
| FS01442 | MATa ura3 trp1 pADH1-FAS1 pADH1-FAS2 pADH1-TSC13 [pESC-TRP-delta-12 delta-6] [pESC-URA-elo-delta-5] | FS01440 |

Example 38

Fatty Acid Compositions of Arachidonic Acid Producing Yeast Strains in Shake Flasks The reference strain FS01324 (MATa ura3 trp1 [pESC-TRP-delta-12 delta-6] [pESC-URA-elo-delta-5]) and the metabolically engineered strains FS01373, FS01413, FS01369, FS01371, FS01417, FS01414, FS01415, FS01416, FS01418, FS01429, FS01430, FS01431, FS01439 and FS01442 (Example 37) were cultured in shake flasks at 17° C. as described in example 9. Following depletion of carbon source, lipids were extracted and the fatty acid compositions of the strains were analyzed as described in Example 45. The results of the analysis are shown in Table 5. All samples were analyzed on a SP-X column, which gives full separation of the peaks. For comparison, the results shown in Example 12 (Table 2) were obtained using a JW-1701 column, which does not give complete separation of the peaks, and thereby results in overestimation of the area percentage of the smaller peaks.

The introduction of *M. alpina* ole1, encoding a fungal delta-9 desaturase with higher specificity towards 18:0 than 16:0, resulted in a decreased level of 16:1 and a corresponding increase in 18:1 and PUFAs (FS01369, Table 5a). The content of arachidonic acid was approximately doubled in FS01369 compared to the reference strain FS01324 (0.63% compared to 0.28% of total fatty acid).

Overexpression of FAS1 and FAS2 (strain FS01373) or FAS1, FAS2 and ACC1 (strain FS01413) resulted in a slight increase in ARA content compared to the reference strain FS01324 (Table 5a). In the strain FS01417, FAS1 and FAS2 overexpression was combined with expression of *M. alpina* ole1. The fatty acid composition of this strain was similar to the composition of strain FS01369 (carrying the *M. alpina* ole1 as the sole genomic modification).

Overexpression of YDR531W, putatively encoding pantothenate kinase, in strain FS01414 did not lead to significant alterations of the fatty acid composition compared to the reference strain. GAT1, SLC1 and DGA1, all encoding acyltransferases involved in TAG synthesis, were overexpressed separately (strain FS01416, FS01415 and FS01371, respectively). For all of these three genes, overexpression resulted in decreased levels of arachidonic acid (Table 5a, 5b). In addition, for overexpression of SLC1 and GAT1, the 16:1 content was increased by 10% of total FA.

The strain FS01418, carrying a deletion of GDH1 and overexpressing GDH2 in addition to FAS1 and FAS2, contained decreased amounts of arachidonic acid compared to FS01373 (overexpressing FAS1 and FAS2) (Table 5b). The strain FS01439, carrying a deletion of GDH1 and overexpressing GLN1 and GLT1 in addition to overexpression of FAS1 and FAS2, contained 0.44% arachidonic acid compared to 0.39% in FS01373.

The strain FS01430 carries the two genes encoding subunits of ATP:citrate lyase from the oleagineous fungus *Sordaria macrospora* under the control of strong constitutive yeast promoters. In addition, it overexpresses FAS1, FAS2 and *M. alpina* ole1. Typical for the strains expressing *M. alpina* ole1, the content of 16:1 was decreased in this strain compared to the reference strain FS01324. FS01430 had a higher 18:1 and 18:2 content, and a slightly increased ARA content compared to its parent strain FS01417 (overexpressing FAS1, FAS2 and *M. alpina* ole1).

In the strain FS01431, the gene YBR159W, encoding β-ketoacyl-CoA reductase, was overexpressed in a FAS1/FAS2 overexpressing background. FS01431 did not show an increased ARA content compared to the strain FS01373 (overexpressing FAS1 and FAS2), but instead contained increased levels of 16:1 (Table 5b). However, the elongation of 18:3 to 20:3 was improved from 19% conversion in FS01373 to 25% conversion in FS01431, calculated as 100×(20:3+20:4)/(18:3+20:3+20:4).

TABLE 5a

Fatty acid composition (% of total fatty acid) of metabolically engineered strains expressing the pathway to arachidonic acid, analyzed in shake flasks.

| Fatty acid | FS01324 | FS01369 | FS01373 | FS01413 | FS01417 | FS01414 | FS01415 | FS01416 |
|---|---|---|---|---|---|---|---|---|
| 12:0 | 1.07 | 1.63 | 1.25 | 1.44 | 7.30 | 1.63 | 1.17 | 1.43 |
| 16:0 | 19.03 | 19.87 | 16.53 | 15.50 | 21.21 | 15.16 | 14.28 | 13.00 |
| Δ9-16:1 | 40.11 | 28.33 | 39.69 | 39.49 | 27.05 | 39.65 | 50.03 | 51.21 |
| 16:2 | 3.50 | 2.83 | 4.78 | 3.28 | 1.86 | 6.35 | 5.35 | 5.65 |
| 18:0<br>stearic acid | 8.81 | 4.55 | 8.37 | 4.86 | 4.62 | 5.14 | 4.12 | 3.82 |
| 16:3 | 0.72 | 0.72 | 1.30 | 0.81 | 0.48 | 2.20 | 1.56 | 1.65 |
| Δ9-18:1<br>oleic acid | 12.31 | 18.19 | 12.10 | 11.64 | 17.74 | 12.26 | 9.71 | 9.23 |
| Δ9, Δ12-18:2<br>linoleic acid | 8.00 | 10.81 | 9.74 | 7.07 | 8.24 | 8.50 | 7.69 | 7.13 |
| Δ6, Δ9, Δ12-18:3<br>gamma-linolenic acid | 2.97 | 5.52 | 3.77 | 2.66 | 6.35 | 4.07 | 3.18 | 3.93 |
| Δ8, Δ11, Δ14-20:3<br>di-homo-gamma-linolenic acid | 0.34 | 1.55 | 0.51 | 0.28 | 1.53 | 0.47 | 0.27 | 0.23 |
| Δ5, Δ8, Δ11, Δ14-20:4<br>arachidonic acid | 0.28 | 0.63 | 0.39 | 0.41 | 0.35 | 0.35 | 0.25 | 0.15 |
| Others | 2.86 | 5.37 | 1.56 | 12.56 | 3.27 | 4.24 | 2.39 | 2.57 |
| Sum | 100 | 100 | 100 | 100 | 100 | 100 | 100 | 100 |

TABLE 5b

Fatty acid composition (% of total fatty acid) of metabolically engineered strains expressing the pathway to arachidonic acid, analyzed in shake flasks.

| Fatty acid | FS01371 | FS01418 | FS01430 | FS01431 | FS01442 | FS01439 | FS01429 |
|---|---|---|---|---|---|---|---|
| 12:0 | 1.51 | 0.98 | 0.94 | 0.09 | 0.57 | 1.02 | 1.40 |
| 16:0 | 17.20 | 15.14 | 18.12 | 11.47 | 19.76 | 13.27 | 21.47 |
| Δ9-16:1 | 41.53 | 41.73 | 27.58 | 50.28 | 33.84 | 33.62 | 26.42 |
| 16:2 | 3.79 | 4.44 | 1.48 | 2.96 | 7.51 | 7.84 | 2.44 |
| 18:0 | 4.98 | 6.79 | 2.93 | 4.61 | 7.56 | 7.24 | 4.41 |
| 16:3 | 1.01 | 0.61 | 0.24 | 0.67 | 0.88 | 1.06 | 0.17 |
| Δ9-18:1<br>oleic acid | 14.56 | 11.98 | 28.07 | 17.05 | 8.76 | 11.40 | 23.16 |
| Δ9, Δ12-18:2<br>linoleic acid | 7.58 | 8.49 | 14.02 | 7.93 | 11.74 | 16.87 | 15.43 |
| Δ6, Δ9, Δ12-18:3<br>gamma-linolenic acid | 3.65 | 2.03 | 3.80 | 2.74 | 2.70 | 4.08 | 1.77 |
| Δ8, Δ11, Δ14-20:3<br>di-homo-gamma-linolenic acid | 0.39 | 0.19 | 0.81 | 0.49 | 2.02 | 0.63 | 0.72 |
| Δ5, Δ8, Δ11, Δ14-20:4<br>arachidonic acid | 0.14 | 0.17 | 0.50 | 0.43 | 0.75 | 0.44 | 0.25 |
| Others | 3.67 | 7.45 | 1.52 | 1.27 | 3.92 | 2.54 | 2.36 |

In the strain FS01442, the gene TSC13, encoding trans-2-enoyl-CoA reductase, was overexpressed in a FAS1/FAS2 overexpressing background. This resulted in a marked increase in arachidonic acid content, from 0.39% of total fatty acid in FS01373 (overexpressing FAS1 and FAS2) to 0.75% of total fatty acid in FS01442 (overexpressing FAS1, FAS2 and TSC13). The increase in arachidonic acid content was due to increased elongation efficiency, from 19% conversion in FS01373 to 51% conversion in FS01431, calculated as 100×(20:3+20:4)/(18:3+20:3+20:4).

Example 39

Lipid Yields of Arachidonic Acid Producing Yeast Strains in Shake Flasks

The reference strain FS01324 (MATa ura3 trp1 [pESC-TRP-delta-12 delta-6] [pESC-URA-elo-delta-5]) and the metabolically engineered strains FS01373, FS01413, FS01369, FS01371, FS01417, FS01414, FS01415, FS01416, FS01418, FS01429, FS01430, FS01431 and FS01439 (Example 37) were cultured at 17° C. as described in Example 9. Lipids were extracted and quantified as described in Example 44. The lipid yields, biomass yields and arachidonic acid yields of the modified strains are summarized in Table 6.

TABLE 6

Lipid yield, biomass yield and arachidonic acid yield in arachidonic acid producing strains, analyzed in shake flasks. The yield of arachidonic acid on carbon-source was calculated under the assumption that fatty acids constitute 70% (w/w) of lipids. Lipids were extracted shortly after depletion of the carbon source for all strains except the strains marked by an asterisk (*); for these strains lipids were extracted at mid-exponential phase.

| Strain | Lipid yield (% of dw) | arachidonic acid (% of FA) | Biomass yield (g dw/g hexose) | arachidonic acid yield (mg/g hexose) |
|---|---|---|---|---|
| FS01324 | 12.8 ± 1.9 | 0.31 | 0.36 | 0.10 |
| FS01369* | 9.9 ± 1.1 | 0.63 | n.a. | n.a. |
| FS01373 | 11.4 ± 0.3 | 0.47 | 0.34 | 0.13 |
| FS01413 | 16.8 ± 0.8 | 0.41 | 0.33 | 0.16 |
| FS01417 | 20.1 ± 0.14 | 0.35 | 0.28 | 0.14 |
| FS01414 | 17.0 ± 0.8 | 0.35 | 0.33 | 0.14 |
| FS01415 | 17.5 ± 0.3 | 0.25 | 0.33 | 0.10 |
| FS01416 | 17.8 ± 0.3 | 0.15 | 0.35 | 0.07 |
| FS01418 | 17.0 ± 1.5 | 0.17 | 0.26 | 0.05 |
| FS01430 | 16.8 ± 0.6 | 0.50 | 0.30 | 0.18 |
| FS01431 | 12.8 ± 0.2 | 0.43 | 0.29 | 0.11 |
| FS01371* | 8.9 ± 1.2 | 0.14 | n.a. | n.a. |
| FS01439* | 16.5 ± 3.5 | 0.44 | n.a. | n.a. |
| FS01429* | 10.3 ± 1.1 | 0.25 | n.a. | n.a. |
| FS01442* | 8.6 ± 1.2 | 0.75 | n.a. | n.a. |

According to this analysis, overexpression of FAS1 and FAS2 alone (strain FS01373) did not result in increased lipid yield compared to the reference strain FS01324. However, FAS1/FAS2 overexpression combined with other modifications (overexpression of either ACC1, YDR531W, SLC1, GAT1 or *S. macrospora* acl1 and acl2, POX1 deletion and *M. alpina* ole1 overexpression, GDH1 deletion combined with GDH2 overexpression, GDH1 deletion combined with GLN1 and GLT1 overexpression) did result in increased lipid yield compared to the reference strain. The most successful strain in terms of arachidonic acid yield on carbon source was FS01430 (overexpressing FAS1, FAS2, *S. macrospora* acl1 and acl2, and *M. alpina* ole1). This strain produced 0.18 mg arachidonic acid/g hexose, compared to 0.10 mg/g hexose in the reference strain FS01324.

Example 40

Chemostat Fermentations

Continuous cultivations were performed in Braun Biostat B fermenters (Braun Biotech International). Cells from a 48 h shake flask culture in defined minimal medium (Verduyn et al., 1990) were used for inoculation of 1.0 l medium to an $OD_{600}$ of 0.2 as measured by using a Hitachi U-1100 spectrophotometer (Tokyo, Japan). The fermentations were carried out at 17° C. and at pH 5.0, controlled by 2M KOH. Foaming was avoided by the addition of 100 μl Antifoam 204 (Sigma-Aldrich, St Louis, Mo.) per liter medium. Aerobic conditions were obtained by sparging the fermentor with sterile air at a flow rate of 1.5-2.5 l/min to ensure that the dissolved oxygen concentration was above 60%. The stirring speed was kept at 800 rpm and the carbon dioxide content of outflowing gas was measured with a Brüel and Kjær acoustic gas analyzer (Brüel & Kjær, Denmark). Following depletion of the carbon source, level controlled continuous fermentation mode at a dilution rate of 0.05 $h^{-1}$ was applied.

Example 41

Growth Media Used in Chemostat Fermentations

Carbon-limited media with glucose or ethanol as carbon source contained: 12.5 g/l glucose or 10 g/l ethanol, 5 g/l $(NH_4)_2SO_4$, 3 g/l $KH_2PO_4$, 0.5 g/l $MgSO_4.7H_2O$, 1 ml/l vitamin solution and 1 ml/l trace metal solution. Nitrogen-limited media with glucose or ethanol as carbon source contained: 40 g/l glucose or 30 g/l ethanol, 2 g/l $(NH_4)_2SO_4$, 4 g/l $K_2SO_4$, 3 g/l $KH_2PO_4$, 0.5 g/l $MgSO_4$*$7H_2O$, 1 ml/l vitamin solution and 1 ml/l trace metal solution. The glucose/galactose carbon-limited minimal medium contained: 2.5 g/l glucose, 10 g/l galactose, 5 g/l $(NH_4)_2SO_4$, 3 g/l $KH_2PO_4$, 0.5 g/l $MgSO_4.7H_{20}$, 1 ml/l vitamin solution and 1 ml/l trace metal solution. For all media described above, the vitamin solution contained: 50 mg/L biotin, 1 g/L calcium panthotenate, 1 g/L nicotinic acid, 25 g/L myo-inositol, 1 g/L thiamine HCl, 1 g/L pyridoxal HCl and 0.2 g/L para-aminobenzoic acid, while the trace metal solution contained: 15 g/L EDTA, 4.5 g/L $ZnSO_4.7H_2O$, 1 g/L $MnCl_2.2H_2O$, 0.3 g/L $CoCl_2.6H_2O$, 0.4 g/L $Na_2MoO_4.2H_2O$, 4.5 g/L $CaCl_2.2H_2O$, 3 g/L $FeSO_4.7H_2O$, 1 g/L $H_3BO_3$ and 0.1 g/L KI. The improved myo-inositol deficient medium contained no myo-inositol but was otherwise identical to the glucose/galactose carbon-limited minimal medium.

Example 42

HPLC Analysis

Glucose, galactose, ethanol, glycerol, acetate, succinate, and pyruvate concentrations in the culture broth were determined by column liquid chromatography (CLC) using a Dionex Summit CLC system (Dionex, Sunnyvale, Calif.) after removing the cells from the culture broth via centrifugation. An Aminex HPX-87H column (BioRad, Hercules, Calif.) was used at 60° C. with a Waters 410 Differential refractive index detector (Millipore, Milford, Mass.) and a Waters 486 Tuneable Absorbance Detector (UV detector) set at 210 nm. The two detectors were connected in series. As mobile phase 5 mM $H_2SO_4$ was used at a flow rate of 0.6 ml/min.

Example 43

Biomass Dry Weight Determination

The cell dry weight was determined by filtering a known volume of the culture broth through a pre-weighed 0.45 μm Supor membrane (Pall Corporation, Ann Arbor, Mich.) filter. After washing with 1 volume of distilled water and drying in microwave oven for 15 minutes at 150 W, the filter was weighed again.

Example 44

Total Lipid Analysis

For analysis of total lipid yield, the biomass was separated through centrifugation for 5 minutes at 5000 rpm. The biomass was re-dissolved in 10 ml distilled water and the resulting cell suspension was broken using the glass bead method to generate cell extract.

The cell extract was prepared by addition of 1 ml glass beads with a particle size of 250-500 μm (Sigma-Aldrich, St Louis, Mo.) to 1 ml cell suspension in a micro tube with screw cap (Sarstedt, Germany). For each cell suspension 6 tubes were processed. The tubes were shaken at level 4 for 20 seconds in a FastPrep FP120 instrument (Qbiogene, France). This was done in total 6 rounds for each tube with a 5 minutes intervening cooling of the tubes on ice after 3 rounds. The cell extracts were combined in 2 ml eppendorf tubes by transferring 600 μl cell extract to generate 3 eppendorf tubes each containing 1.2 ml glass bead free cell extract. 1 ml of the cell extract was transferred into a glass tube with screw cap containing 20 ml chloroform/methanol 2:1. The tube was sparged with nitrogen then closed immediately and placed on a rotary mixer and the total lipid extraction was performed over night. This was done in triplicates. The extract was then filtered through a Whatman filter (Whatman International, England) and the collected solvent was washed with 4 ml NaCl and finally dried over nitrogen in pre-weighed 10 ml glass tubes. The tubes with dry lipid fraction were weighed and the lipid yield was determined by calculating the lipid dry weight divided by the dry weight of the biomass in 1 ml of the initial cell suspension.

Example 45

Transesterification of Lipids and GC-MS Analysis

Dry lipid was generated as for the determination of total lipid (Example 44) and was dissolved in 1 ml toluene and 2 ml 1% sulphuric acid in methanol was added. The tube was closed after mixing and sparging with nitrogen and left at 50° C. over night for transesterification of the lipids. The sample was then washed with 5 ml 5% NaCl solution. Methyl esters were subsequently extracted twice by adding 5 ml hexane, vortexing the sample and collecting the organic upper phase. The organic phase was washed with 4 ml 2% sodium carbonate and the organic phase was collected again. Trace of water phase was removed by adding anhydrous sodium sulphate and filtering the sample through a Whatman filter paper (Whatman International, England) to remove the sodium sulphate. The hexane phase was then dried under a stream of nitrogen. When dry, the sample was redissolved in 0.5 ml of hexane containing 0.01% butylated hydroxytoluene (BHT) (Sigma-Aldrich, St Louis, Mo.) for protection of double bonds was added and the sample was analyzed for methyl esters. The analysis was performed using a gas chromatograph coupled to mass selective detector (GC/MS). The GC/MS system was a Hewlett Packard HP G1723A with a gas chromatograph-quadruple mass selective detector (EI) operated at 70 eV. The column used was Supelco Sp™-2380. The MS was operated in SCAN Mode. The oven temperature was initially 170° C. and in the following risen to 220° C. at 4° C./min. The final temperature was held for 15 min. The flow through the column was 0.6 ml He/min. Injection volumes were 1-5 μl. The injector was driven at split of 100:1 splitless for all analyses. The temperature of the inlet was 300° C., the interface temperature 230° C., and the quadropule temperature 105° C. Detected fatty acid methyl esters were confirmed with the 1998 NIST Mass Spectral Database, and retention times were confirmed with standard fatty acid methyl esters.

Example 46

Analysis of Arachidonic Acid Producing Yeast Strains in Continuous Fermentation

The reference strain FS01324 (MATa ura3 trp1 [pESC-TRP-delta-12 delta-6] [pESC-URA-elo-delta-5]) and the metabolically engineered strains FS01373 and FS01413 (Example 37) were grown in chemostat cultivations as described in Example 40. The medium was glucose/galactose carbon-limited minimal medium as described in Example 41. At steady state, samples were taken for HPLC analysis, analysis of biomass dry-weight, lipid yield and fatty acid composition as described in the above Examples. A summary of the analysis is shown in Table 7.

TABLE 7

Arachidonic acid content (% of total fatty acid), lipid yield (% of biomass dry-weight), biomass yield (g dry-weight/g hexose), arachidonic acid yield on biomass (mg arachidonic acid/g biomass dry-weight) and arachidonic acid yield on carbon source (mg arachidonic acid/g hexose) of arachidonic acid producing yeast strains analyzed in continuous fermentation with standard carbon-limited minimal medium. The yield of arachidonic acid on carbon-source was calculated under the assumption that fatty acids constitute 70% (w/w) of lipids.

| Strain | 20:4 (% of FA) | Lipid yield (% of dw) | Biomass yield (g/g) | 20:4 yield on biomass (mg/g) | 20:4 yield on c-source (mg/g) |
|---|---|---|---|---|---|
| FS01324 | 1.1 | 15.0 ± 0.6 | 0.43 | 1.17 | 0.50 |
| FS01373 | 1.0 | 15.3 ± 0.5 | 0.42 | 1.03 | 0.44 |
| FS01413 | 0.8 | 12.1 ± 2.9 | 0.56 | 0.64 | 0.36 |

All strains had a higher content of arachidonic acid in chemostat cultivations than previously shown in shake flask cultures. However, the genetically modified strains FS01373 and FS01413 did not have improved lipid yields relative to the reference strain FS01324 in carbon-limited chemostat cultures.

Example 47

Medium Optimization for Increased Arachidonic Acid Yield

The wild-type strain CEN.PK 113-7D, the reference strain FS01324 (MATa ura3 trp1 [pESC-TRP-delta-12 delta-6]

[pESC-URA-elo-delta-5]), and the metabolically engineered strains FS01373, FS01413, FS01417 and FS01430 (Example 37) were grown in chemostat cultivations as described in Example 40. The medium used in these experiments was an improved carbon-limited minimal medium, which contained no myo-inositol (Example 41). At steady state, samples were taken for HPLC analysis, analysis of biomass dry-weight, lipid yield and fatty acid composition as described in the above Examples. A summary of the analysis is shown in Table 8.

TABLE 8

Arachidonic acid content (% of total fatty acid), lipid yield (% of biomass dry-weight), biomass yield (g dry-weight/g hexose), arachidonic acid yield on biomass (mg arachidonic acid/g biomass dry-weight) and arachidonic acid yield on carbon source (mg arachidonic acid/g hexose) of arachidonic acid producing yeast strains analyzed in continuous fermentation with myoinositol-deficient, carbon-limited minimal medium. The yield of arachidonic acid on carbon-source was calculated under the assumption that fatty acids constitute 70% (w/w) of lipids.

| Strain | 20:4 (% of FA) | Lipid yield (% of dw) | Biomass yield (g/g) | 20:4 yield on biomass (mg/g) | 20:4 yield on c-source (mg/g) |
|---|---|---|---|---|---|
| CEN.PK | 0 | 8.4 ± 2.5 | 0.67 | 0 | 0 |
| FS01324 | 0.8 | 10.4 ± 1.0 | 0.75 | 0.58 | 0.43 |
| FS01373 | 1.2 | 11.7 ± 1.0 | 0.67 | 1.01 | 0.68 |
| FS01413 | 1.5 | 10.4 ± 0.2 | 0.68 | 1.09 | 0.74 |
| FS01430 | 2.7 | 8.6 ± 0.7 | 0.58 | 1.62 | 0.72 |
| FS01417 | 3.5 | 8.0 ± 0.8 | 0.45 | 1.93 | 1.12 |

Figure 18:
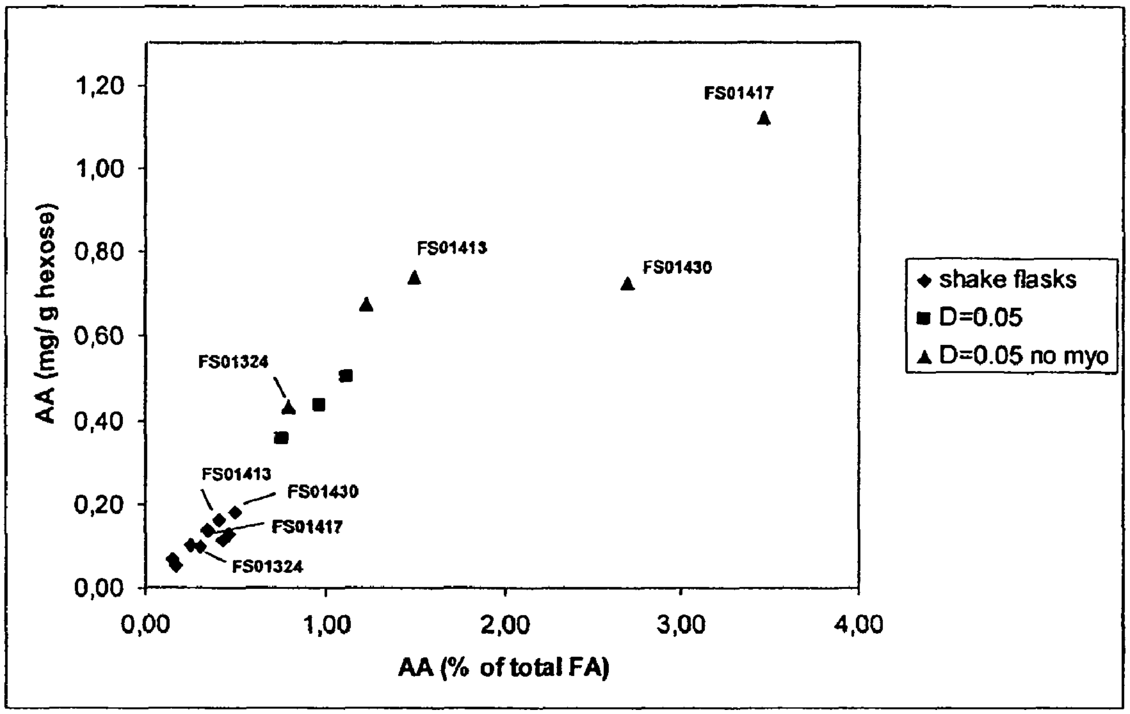
FIG. 18: Overview of the performance of genetically modified strains of *Saccharomyces cerevisiae*: yield of arachidonic acid on carbon source plotted against percentage arachidonic acid of total fatty acid.

In myo-inositol deficient, carbon-limited medium, the metabolically engineered strains FS01324, FS01373, FS01413, FS01430 and FS01417 all contained higher levels of arachidonic acid than the reference strain FS01324. In particular, the strain FS01417 contained 3.5% arachidonic acid of total fatty acid, compared to 0.8% in the reference strain FS01324. An overview of the performance of the genetically engineered strains is shown in FIG. 18.

Example 48

Medium Optimization for Increased Total Lipid Yield

In contrast to the results of shake flask experiments (Example 39), the modified strains did not have increased lipid yields relative to the reference strain in the chemostat cultivations of Examples 46 and 47. This is probable to be due to that the experiments were carried out under carbon-limitation, which is not optimal for lipid accumulation. It is therefore likely that the metabolically engineered strains will show increased lipid yields relative to the reference strain when analyzed under conditions that promote lipid accumulation. To optimize the chemostat conditions for lipid accumulation, the wild-type strain CEN.PK 113-7D was grown in chemostat as described in Example 40 in different medium compositions. The media used in these experiments were either i) carbon-limited with glucose as carbon source, ii) nitrogen-limited with glucose as carbon source, iii) carbon-limited with ethanol as carbon-source or iiii) nitrogen-limited with ethanol as carbon source (Example 41). At steady state, samples were taken for HPLC analysis, analysis of biomass dry-weight and lipid yield as described in the above Examples. A summary of the analysis is shown in Table 9.

TABLE 9

Biomass yield and lipid yield of the wild-type strain CEN.PK 113-7D grown in chemostat with i) carbon-limited medium with glucose as carbon source, ii) nitrogen-limited medium with glucose as carbon source, iii) carbon-limited medium with ethanol as carbon-source or iii) nitrogen-limited medium with ethanol as carbon source.

| Medium | Lipid yield (% of dw) |
|---|---|
| i) C-lim, glc | 7 |
| ii) N-lim, glc | 14 |
| iii) C-lim, EtOH | 10 |
| iiii) N-lim, EtOH | 10 |

The analysis showed that the lipid yield in chemostat cultivation with *S. cerevisiae* can be approximately doubled by using a nitrogen-limited, rather than glucose-limited, medium.

Example 49

Analysis of Arachidonic Acid Producing Yeast Strains in Continuous Fermentation with Optimized Growth Medium The reference strain FS01324 (MATa ura3 trp1 [pESC-TRP-delta-12 delta-6] [pESC-URA-elo-delta-5]) and the engineered strains FS01373, FS01413, FS01369, FS01371, FS01417, FS01414, FS01415, FS01416, FS01418, FS01429, FS01430, FS01431, FS01439 and FS01442 (Example 37) are grown in continuous cultivations using nitrogen-limited, myo-inositol deficient medium. At steady state, samples are taken for HPLC analysis, analysis of biomass dry-weight, lipid yield and fatty acid composition as described in the above Examples. The use of nitrogen-limited medium is anticipated to lead to higher lipid yields and therefore increased arachidonic acid yields. In addition, the strains carrying genetic modifications aimed at improving lipid yield are likely to have even higher lipid yields than the reference strain in nitrogen-limited medium.

Example 50

Figure 19:
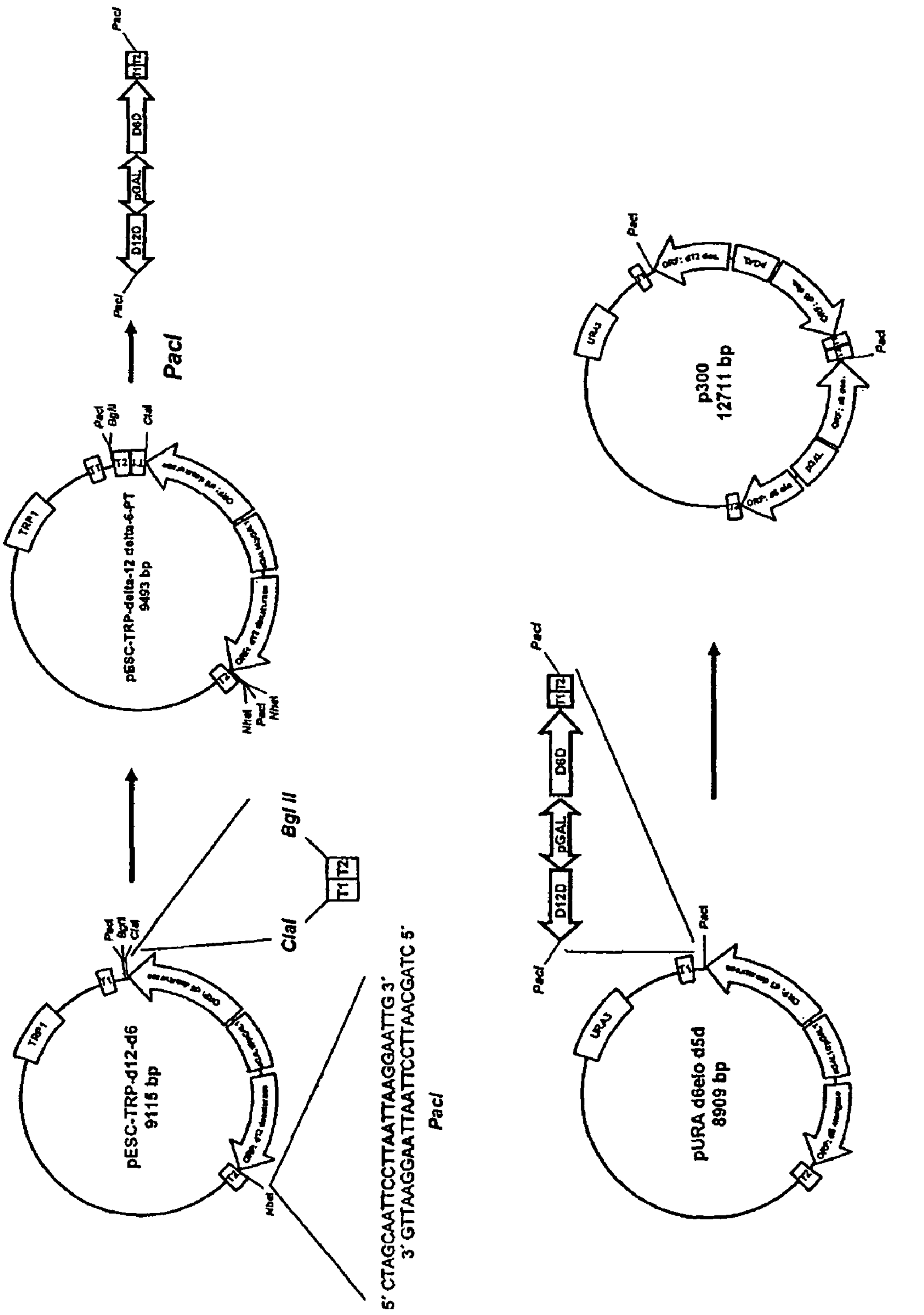
FIG. 19: Construction of plasmid p300 (SEQ ID NOS: 206 and 224)

Construction of p300, a Single Yeast Expression Vector Containing Genes Encoding Delta-12 Desaturase, Delta-6 Desaturase, Delta-6 Elongase and Delta-5 Desaturase To reduce the number of plasmids needed for expression of PUFA pathways, the four genes required for arachidonic acid production (*M. alpina* genes encoding −12 desaturase, delta-6 desaturase, delta-6 elongase and delta-5 desaturase) were placed on a single plasmid, p300. The strategy used for construction of p300 is shown in FIG. 19. First, a second PacI restriction site was introduced into pESC-TRP-delta-12 delta-6 at the NheI restriction site. For this purpose, the palindromic synthetic oligonucleotide 5'CTAGCAATTCCTTAATTAAGGAATTG 3' (SEQ ID NO: 206) was used. This oligonucleotide anneals to itself, resulting in a double-stranded DNA fragment containing a PacI restriction site and overhangs at both ends that match the NheI restriction site. The fragment was cloned into the NheI restriction site of pESC-TRP-delta-12 delta-6, resulting in the plasmid pESC-TRP-delta-12 delta-6-PacI. Next, a fragment containing the ADH1 and CYC1 terminator sequences in back-to-back orientation was introduced into pESC-TRP-delta-12 delta-6-

PacI. To construct the ADH1-CYC1-terminator fragment, the ADH1 terminator was amplified by PCR using the primers 5' TGTTCTCGAGAAGGTGTTGAGCGACCT-CATGCTATACCTGAGAAAG 3' (SEQ ID NO: 207) and 5' CCATCGATGGCGAATTTCTTATGATTTATGATTTTTA 3' (SEQ ID NO: 208) and the CYC1 terminator was amplified by PCR using the primers 5' GAAGATCTTC-CCGCTCTAACCGAAAAGGAAGG 3' (SEQ ID NO: 209) and 5' AACACCTTCTCGAGAACACTTC-GAGCGTCCCAAAACC 3' (SEQ ID NO: 210), using pESC-URA as template for both reactions. Following purification of the ADH1 and CYC1 terminator fragments, they were fused by PCR using the primers 5' GAAGATCTTC-CCGCTCTAACCGAAAAGGAAGG 3' (SEQ ID NO: 209) and 5' CCATCGATGGCGAATTTCTTATGATT-TATGATTTTTA 3' (SEQ ID NO: 208). The ClaI and BglII restriction sites included in these primers allowed introduction of the ADH1-CYC1-terminator fragment into ClaI/BglII digested pESC-TRP-delta-12 delta-6-PacI, resulting in the plasmid pESC-TRP-delta-12 delta-6-PacI-T. Absence of mutations in the terminator sequences was verified by sequencing of pESC-TRP-delta-12 delta-6-PacI-T. To construct the plasmid p300, pESC-TRP-delta-12 delta-6-PacI-T was digested with PacI, resulting in release of an insert containing the *M. alpina* gene encoding delta-12 desaturase, the divergent GAL1/GAL10 promoter, the *M. alpina* gene encoding delta-6 desaturase, the ADH1 terminator and the CYC terminator (FIG. 19). The insert was purified and introduced into PacI digested pESC-URA-elo-delta-5, resulting in plasmid p300. The correct orientation of the pESC-TRP-delta-12 delta-6-PacI-T-derived insert in p300 was verified by restriction analysis.

Example 51

Cloning of an Omega-3 Desaturase from *A. thaliana* into a Yeast Expression Vector The *A. thaliana* FAD3 gene (SEQ ID NO 32), encoding an omega-3 desaturase, was amplified from an *A. thaliana* cDNA preparation (Plant normal Tissue First strand cDNA/*Arabidopsis*, Gentaur Molecular Products) using the primers 5' GGTCTCGAGCCACCATGGTTGTTGC-TATGGACCAAC 3' (SEQ ID NO: 211) and 5' GGGGTAC-CATTAATTGATTTTAGATTTGTCAGAAGCGTAA 3' (SEQ ID NO: 212). These primers introduce XhoI and KpNI restriction sites at the 5' and 3' end of the gene, respectively. The *A. thaliana* FAD3 gene was introduced into XhoI/KpNI digested pESC-TRP, resulting in the plasmid pESC-TRP-Aro3. Absence of mutations in *A. thaliana* FAD3 was verified by sequencing of pESC-TRP-Aro3.

Example 52

Cloning of Omega-3 Desaturase from *Saccharomyces kluyveri* into a Yeast Expression Vector The *S. kluyveri* FAD3 gene (SEQ ID NO 87), encoding an omega-3 desaturase, was amplified from a preparation of genomic DNA from *S. kluyveri* Y159 using the primers 5' GGTCTCGAGCCACCATGTCTATTGAAACAGTCGG 3' (SEQ ID NO: 213) and 5' GGCCGCGGATCATTGACTG-GAACCATCTT 3' (SEQ ID NO: 214). These primers introduce XhoI and SacII restriction sites at the 5' and 3' end of the gene, respectively. The *S. kluveri* FAD3 gene was introduced into XhoI/SacII digested pESC-TRP, resulting in the plasmid pESC-TRP-SK33. Absence of mutations in *S. kluveri* FAD3 was verified by sequencing of pESC-TRP-SK33.

Example 53

Expression of Omega-3 Desaturase from *S. kluyveri* and Evaluation of p300

Yeast strain FS01267 (MATa trp1 ura3) was co-transformed with plasmids p300 and pESC-TRP-SK33. Transformants were selected on medium lacking uracil and tryptophane and were streak purified on the same medium. The transformed strain was named FS01432. FS01432 was grown in a shake flask as described in example 9 and the fatty acid composition was analyzed as described in Example 45. The fatty acid compositions of FS01432, the reference strain FS01324 and *S. kluyveri* Y159 are shown in Table 10.

The results of the analysis showed that strain FS01432, expressing the pathway to arachidonic acid and the omega-3 desaturase from *S. kluyveri*, contained alpha-linoleic acid and small amounts of stearidonic acid. The alpha-linolenic acid content in this strain was higher than the gamma-linolenic acid content, indicating that the omega-3 desaturase from *S. kluyveri* desaturates linoleic acid more efficiently than the delta-6 desaturase from *M. alpina*.

TABLE 10

Fatty acid composition (% of total fatty acid) of strain FS01324 (MATa ura3 trp1 [pESC-TRP-delta-12 delta-6] [pESC-URA-elo-delta-5]), FS01432 (MATa ura3 trp1 [p300] [pESC-TRP-SK33]) and *S. kluyveri* Y159.

| Fatty acid | FS01324 | FS01432 | *S. kluyveri* Y159 |
|---|---|---|---|
| 12:0 dodecanoic acid | 1.1 | 1.2 | |
| 16:0 palmitic acid | 19.0 | 15.3 | 23.9 |
| Δ9-16:1 palmitoleic acid | 40.1 | 46.1 | 20.5 |
| 16:2 | 3.5 | 1.7 | |
| 18:0 stearic acid | 8.8 | 4.8 | 4.8 |
| 16:3 | 0.7 | | |
| Δ9-18:1 oleic acid | 12.3 | 20.9 | 31.7 |
| Δ9, Δ12-18:2 linoleic acid | 8.0 | 3.4 | 14.7 |
| Δ6, Δ9, Δ12-18:3 gamma-linolenic acid | 3.0 | 0.4 | |
| Δ9, Δ12, Δ15-18:3 alpha-linolenic acid | | 2.2 | 4.4 |
| Δ6, Δ9, Δ12, Δ15-18:4 stearidonic acid | | 0.1 | |
| Δ8, Δ11, Δ14-20:3 di-homo-gamma-linolenic acid | 0.3 | 0.03 | |
| Δ5, Δ8, Δ11, Δ14-20:4 arachidonic acid | 0.3 | | |
| Others | 2.8 | 3.9 | |
| Sum | 100 | 100 | 100 |

Comparing the fatty acid composition of FS01324 (expressing the pathway to ARA from two plasmids) and FS01432 (expressing the pathway to ARA from a single plasmid), it can be observed that the conversion of the initial substrate oleic acid into linoleic acid and intermediates downstream of linoleic acid is less efficient in FS01432 than FS01324. Thus, FS01432 contains only 6.1% fatty acids with two or more double bonds compared to 11.6% in FS01324. This decrease is also reflected in the higher content of oleic acid in FS01432 compared to FS01324. In conclusion, it appears that expression from plasmid p300 is less efficient than expression from the original plasmids pESC-TRP-delta-12 delta-6 and pESC-URA-elo-delta-5.

Example 54

Construction of the Vector pESC-LEU-SK33

Figure 20:
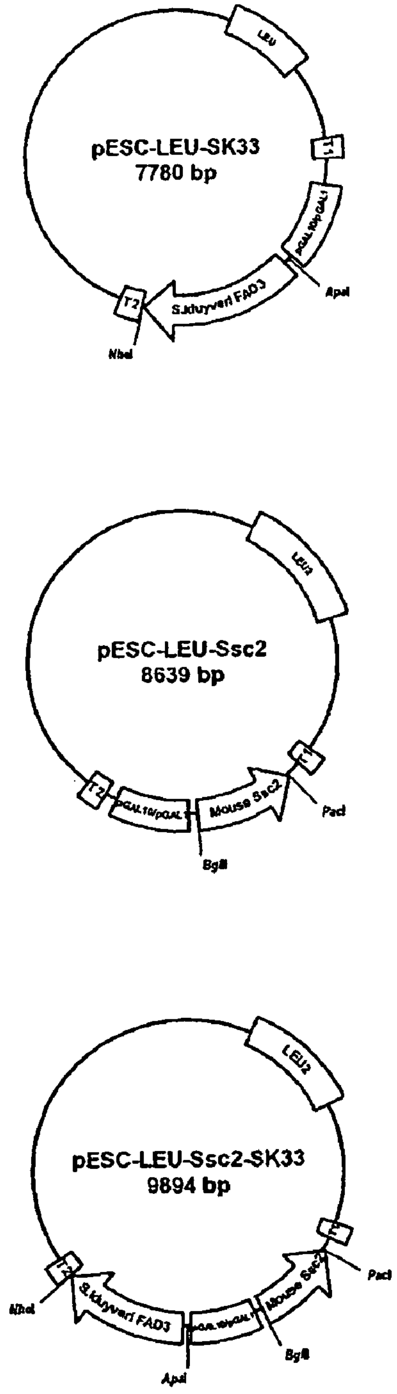
FIG. 20: Plasmid map over pESC-LEU-SK33.

To construct vector pESC-LEU-SK33, *S. kluyveri* FAD3 was released from pESC-TRP-SK33 (Example 52) by digestion with ApaI and NheI and was introduced into ApaI/NheI digested pESC-LEU, resulting in the plasmid pESC-LEU-SK33 (FIG. 20A). Correct insertion of *S. kluyveri* FAD3 was verified by restriction analysis.

Example 55

Construction of the Vector pESC-LEU-Ssc2

To construct vector pESC-LEU-Ssc2, mouse Ssc2 was released from pESC-TRP-delta-5elo (Example 15) by digestion with BglII and PacI and was introduced into BglII/PacI digested pESC-LEU, resulting in the plasmid pESC-LEU-Ssc2 (FIG. 20B). Correct insertion of mouse Ssc2 was verified by restriction analysis.

Example 56

Construction of the Vector pESC-LEU-Ssc2-SK33

To construct vector pESC-LEU-Ssc2-SK33, *S. kluyveri* FAD3 was released from pESC-TRP-SK33 (Example 52) by digestion with ApaI and NheI and was introduced into ApaI/NheI digested pESC-LEU-Ssc2 (Example 55), resulting in the plasmid pESC-LEU-Ssc2-SK33 (FIG. 20C). Correct insertion of *S. kluyveri* FAD3 was verified by restriction analysis.

Example 57

Introducing leu2 Mutation in pox1::pTDH3-*M. alpina* ole1 Background

To enable expression of a PUFA pathway from three plasmids, carrying URA3, TRP1 and LEU2 markers, respectively, in a strain carrying the *M. alpina* ole1 integrated into its genome, a leu2 mutation was introduced into this strain background. For this purpose, FS01368 (MATalpha ura3 trp1 pox1::pTDH3-*M. alpina* ole1) was crossed to FS01277 (MATa ura3 leu2 trp1). Diploids were identified by streaking out cells from the cross to single colonies, transferring a number of colonies to a master plate, and testing the ability of the selected colonies to sporulate on sporulation medium. Following sporulation, the asci were dissected into ascospore tetrads and the genotypes were scored. Presence of the pox1::pTDH3-*M. alpina* ole1 modification was determined by colony PCR using appropriate primers. From the set of haploid strains derived from the cross, a strain with the genotype MATalpha ura3 trp1 leu2 pox1::pTDH3-*M. alpina* ole1 was selected and named FS01444.

Example 58

Expression of the Pathways to Eicosapentaenoic Acid, Docosatetraenoic Acid and Docosapentaenoic Acid in *S. cerevisiae*

To express the pathways to eicosapentaenoic acid, docosatetraenoic acid and docosapentaenoic acid in *S. cerevisiae*, the plasmids constructed in Examples 54-56 were introduced into yeast together with the two plasmids pESC-TRP-delta-12 delta-6 and pESC-URA-elo-delta-5, resulting in the strains FS01446, FS01447 and FS01448 (Table 11).

TABLE 11

Genotypes of the strains FS01369, FS01446, FS01447 and FS01448

| Strain | Genotype | Parent |
|---|---|---|
| FS01369 | MAT alpha ura3 trp1 pox1::pTDH3-*M. alpina* ole1 [pESC-TRP-delta-12 delta-6] [pESC-URA-elo-delta-5] | FS01368 |
| FS01446 | MATalpha ura3 trp1 leu2 pox1::pTDH3-*M. alpina* ole1 [pESC-TRP-delta-12 delta-6] [pESC-URA-elo-delta-5] [pESC-LEU-SK33] | FS01444 |
| FS01447 | MATalpha ura3 trp1 leu2 pox1::pTDH3-*M. alpina* ole1 [pESC-TRP-delta-12 delta-6] [pESC-URA-elo-delta-5] [pESC-LEU-Ssc2] | FS01444 |
| FS01448 | MATalpha ura3 trp1 leu2 pox1::pTDH3-*M. alpina* ole1 [pESC-TRP-delta-12 delta-6] [pESC-URA-elo-delta-5] [pESC-LEU-Ssc2-SK33] | FS01444 |

The strains FS01446, FS01447 and FS01448 and FS01369 were first cultured in shake flasks with 150 rpm shaking at 17° C. in defined minimal medium containing 5 g/l glucose and 20 g/l galactose. Following depletion of glucose and while the cells were in exponential growth on galactose, 1 ml of each culture was transferred to a new shake flask containing 100 ml minimal medium with 20 g/l galactose as the sole carbon source. The cells were then cultured at 17° C. 150 rpm shaking until depletion of the carbon source, the biomass was harvested, lipids were extracted as described in example X and the fatty acid composition was analyzed as described in example X. The fatty acid compositions of the strains are summarized in Table 12.

TABLE 12

Fatty acid composition (% of total fatty acid) of strains FS01369, FS01446, FS01447 and FS01448.

| Fatty acid | FS01369 | FS01446 | FS01447 | FS01448 |
|---|---|---|---|---|
| 12:0 | 0.57 | 0.55 | 0.70 | 0.73 |
| 16:0 | 23.04 | 21.06 | 21.66 | 19.41 |
| Δ9-16:1 | 19.39 | 20.01 | 18.37 | 20.43 |
| 18:0 | 4.06 | 3.66 | 3.69 | 3.71 |
| Δ9-18:1 | 20.14 | 25.02 | 19.75 | 29.91 |
| Δ9, Δ12-18:2 | 18.63 | 14.86 | 21.76 | 13.05 |
| Δ6, Δ9, Δ12-18:3 | 6.90 | 3.32 | 6.18 | 3.41 |
| Δ8, Δ11, Δ14-20:3 | 2.52 | 1.37 | 2.84 | 1.80 |
| Δ5, Δ8, Δ11, Δ14-20:4 | 1.10 | 0.54 | 1.13 | 0.52 |
| Δ9, Δ12, Δ15-18:3 | — | 4.27 | — | 2.28 |
| Δ6, Δ9, Δ12, Δ15-18:4 | — | 0.81 | — | 0.46 |

TABLE 12-continued

| Fatty acid composition (% of total fatty acid) of strains FS01369, FS01446, FS01447 and FS01448. | | | | |
|---|---|---|---|---|
| Fatty acid | FS01369 | FS01446 | FS01447 | FS01448 |
| Δ8, Δ11, Δ14, Δ17-20:4 | — | 0.67 | — | 0.50 |
| Δ5, Δ8, Δ11, Δ14, Δ17-20:5 | — | 0.33 | — | 0.19 |
| Others | 3.67 | 3.52 | 3.91 | 3.60 |
| Sum | 100 | 100 | 100 | 100 |

The analysis showed that FS01446 and FS01448, both strains expressing *S. kluyveri* FAD3, produced eicosapentaenoic acid (Table 12, FIG. 21). However, expression of mouse Ssc2 in FS01447 and FS01448 did not result in the expected elongation of 20:4 into 22:4 (or 20:5 into 22:5).

Example 59

Codon-Optimization and Assembly of Synthetic Delta-4 Desaturase from *Thraustochytrium*

The sequence of *Thraustochytrium* delta-4 desaturase (SEQ ID NO 35) was codon-optimized for expression in *S. cerevisiae* and was assembled from synthetic oligonucleotides. The procedure was as follows:

The *Thraustochytrium* nucleotide sequence encoding a delta-4 desaturase was codon-optimized for expression in *S. cerevisiae* using the Backtranslation tool (Entelechon) with the "discard codons below 50% theroretical ratio"-option. The codon-optimized gene (SEQ ID NO 84) was then assembled from chemically synthesized oligo nucleotides. The method used for assembly of the gene is shown in FIG. 22. Sense- and antisense oligonucleotides were designed to cover the complete sequence of the gene, and were designed in a way so that a 20 bp overlap was achieved for each complementary sense and antisense oligonucleotide (FIG. 22). The sense oligonucleotides were each 40 bp of length and were number D4D-A01 to D4D-A39 consecutively from the 5' end to the 3' end of the sense strand. Similarly, the antisense oligonucleotides were numbered D4D-B01 to D4D-40 consecutively from the 5' end to the 3' end of the antisense strand. First, 200 bp-pieces of double stranded DNA were assembled by mixing five sense oligonucleotides with their 5 complementary antisense oligonucleotides. For example, 100 pmol of each of the oligonucleotides D4D-01, D4D-02, D4D-03, D4D-04 and D4D-05, D4D-B40, D4D-39, D4D-38, D4D-37 and D4D-36 were mixed in a volume of 50 μl. The oligonucleotide mix was then loaded on a 2% agarose gel together with a size marker, and the smear around the size of 200 bp was excised from the gel and was purified. The purified mix was then used as template in a PCR reaction using oligonucleotides D4D-A01 and D4D-B36 as primers, which resulted in amplification of the desired 200 bp fragment, named D4D-1. In analogy, the remaining part of the gene was assembled in 200 bp pieces, named D4D-2 to D4D-8 (FIG. 22). Next, the eight 200 bp-fragments were fused by PCR to four fragments of 400 bp, named D4D-12, D4D-34, D4D-56 and D4D-78. These fragments were then fused by PCR to form two fragments of 800 bp, and finally the two 800 bp-fragments were fused to form the full gene. The final fusion PCR reaction was carried out using the primers 5' ATCCCGGGACCATGACAGTTGGTTACGATGAGG 3' (SEQ ID NO: 215) and 5' ATCCGCGGTTATGCTGCTCTTTGCCAACTTTCG 3' (SEQ ID NO: 216), which introduced XmaI and SacII restriction sites at the 5' end and 3' end of the gene, respectively.

Example 60

Cloning of Synthetic Delta-4 Desaturase into a Yeast Expression Vector

The synthetically assembled gene encoding delta-4 desaturase (Example 59) was digested with XmaI and SacII and was introduced into XmaI/SacII digested pESC-LEU-Ssc2, resulting in the plasmid pESC-LEU-Ssc2-delta-4d (FIG. 23).

Example 61

Integration of *S. kluyveri* FAD3 into the genome of *S. cerevisiae*

The *S. kluyveri* FAD3 gene, encoding an omega-3 desaturase was integrated into the genome of *S. cerevisiae* and was placed under the control of the yeast GALL promoter. The GALL promoter and the *S. kluyveri* FAD3 gene were integrated at the locus of GPP1, resulting in knockout of this gene (see also Example 66). The integration was carried out through homologous recombination using a bipartite gene targeting substrate (FIG. 24). One part of the bipartite substrate consisted of two thirds (towards the 3'end) of *K. lactis* URA3, fused to the GALL promoter sequence, the *S. kluyveri* FAD3 gene and a target sequence downstream of GPP1. The second part of the bipartite substrate consisted of a target sequence upstream of GPP1, fused to the GALL promoter sequence and two thirds (towards the 5' end) of *K. lactis* URA3. Following transformation with the bipartite substrate and selection on medium lacking uracil, transformants were obtained in which GPP1 had been knocked out and replaced with two copies of the GALL promoter sequence as a direct repeat on either side of the *K. lactis* URA3 marker gene and the *S. kluyveri* FAD3 gene immediately downstream of the second GALL promoter repeat. A second recombination event, resulting in looping out of the selection marker, was selected for by replating transformants on medium containing 5'-fluoroorotic acid (5-FOA), which is toxic to cells expressing the URA3 gene. This resulted in a strain, in which the GPP1 gene had been replaced with the *S. kluyveri* FAD3 under the control of the GALL promoter.

The procedure was as follows:

For construction of the first part of the bipartite gene targeting substrate, a fragment containing the GALL promoter immediately upstream of *S. kluyveri* FAD3 was amplified from plasmid pESC-TRP-SK33 (see example X for construction of pESC-TRP-SK33), using the primers 5' ACTACATCATCGAATTCCAGAACGAATCAAATTAACAACCATAG 3' (SEQ ID NO: 217) and 5' TCATTGACTGGAACCATCTT 3' (SEQ ID NO: 218). A target sequence downstream of *S. cerevisiae* GPP1 was amplified by PCR using *S. cerevisiae* genomic DNA as template and the primers 5' AAGATGGTTCCAGTCAATGATAAGGATGACTTGTTGAAATGGTAA 3' (SEQ ID NO: 219) and 5'CCACAAGACTGTTTCCAGAGC 3' (SEQ ID NO: 220). A third DNA fragment, consisting of two-thirds of *K. lactis* URA3 towards the 3' end, was generated by PCR using as template a plasmid containing the *K. lactis* URA3 and the primers 5' CTTGACGTTCGTTCGACTGATGAGC 3' (SEQ ID NO: 133) and 5'CTGGAATTCGATGATGTAGTTTCTGG 3' (SEQ ID NO: 158). These PCR fragments were then fused during two rounds of PCR. First, the fragment containing the GALL promoter and the *S. kluyveri*

FAD3 was fused to the downstream target sequence using the primers 5' ACTACATCATCGAATTCCAGAACGAATCAAATTAACAACCATAG 3' (SEQ ID NO: 217) and 5' CCACAAGACTGTTTCCAGAGC 3' (SEQ ID NO: 220). Second, the product of the first fusion reaction was fused to the 3' 2/3 *K. lactis* URA3 fragment using the primers 5' CTTGACGTTCGTTCGACTGATGAGC 3' (SEQ ID NO: 133) and 5'CCACAAGACTGTTTCCAGAGC 3'(SEQ ID NO: 220). This resulted in the fusion product 2/3URA3-pGAL1-*S. kluyveri* FAD3-DOWN, which constituted the first part of the bipartite gene targeting substrate.

For construction of the second part of the bipartite substrate, a target sequence upstream of GPP1 was amplified by PCR using *S. cerevisiae* genomic DNA as template and the primers 5' ATGGCATGGCCCCGAAGG 3' (SEQ ID NO: 221) and 5' CTGGAATTCGATGATGTAGTTTGAACGAAAATGAACAAGACG 3'(SEQ ID NO: 222). The GAL1 promoter was amplified by PCR using pESC-TRP-SK33 as template and the primers 5' ACTACATCATCGAATTCCAGAACGAATCAAATTAACAACCATAG 3' (SEQ ID NO: 217) and 5' CCACCATCCAATGCAGACCGCGGGGTTTTTTCTCCTTGAC 3' (SEQ ID NO: 223). A third fragment, consisting of two thirds of *K. lactis* URA3 towards the 5' end, was generated by PCR using the primers 5'CGGTCTGCATTGGATGGTGGTAAC 3' (SEQ ID NO: 163) and 5' GAGCAATGAACCCAATAACGAAATC 3' (SEQ ID NO: 139), and a plasmid containing the *K. lactis* URA3 as template. These PCR fragments were then fused during two rounds of PCR. First, the GALL promoter was fused to the upstream targeting sequence using the primers 5' ATGGCATGGCCCCGAAGG 3' (SEQ ID NO: 221) and 5' CCACCATCCAATGCAGACCGCGGGGTTTTTTCTCCTTGAC 3' (SEQ ID NO: 223). Second, the product of the first fusion reaction was fused to the 5' 2/3 *K. lactis* URA3 fragment using the primers 5' ATGGCATGGCCCCGAAGG 3' (SEQ ID NO: 221) and 5' GAGCAATGAACCCAATAACGAAATC 3' (SEQ ID NO: 139). This resulted in the fusion product UP-pGAL1-2/3URA3, which constituted the second part of the bipartite gene targeting substrate.

The yeast strain FS01444 (MATalpha ura3 trp1 leu2 pox1::pTDH3-mole1, Example 57) is transformed with the linear substrates 2/3URA3-pGAL1-*S. kluyveri* FAD3-DOWN and UP-pGAL1-2/3URA3 and plated out on medium lacking uracil. Transformants are streak purified on the same medium and then transferred onto medium containing 5-FOA. Pop-out recombinants are streak purified on 5-FOA-containing medium and are verified by colony PCR. The resulting strain has the genotype MATalpha ura3 trp1 leu2 pox1::pTDH3-mole1 gpp1::pGAL1-*S. kluyveri* FAD3 and is named FS01460.

Example 62

Expression of the Pathway to Docosahexaenoic Acid

To express the full pathway to docosahexaenoic acid, FS01460 (MATalpha ura3 trp1 leu2 pox1::pTDH3-mole1 gpp1::pGAL1-*S. kluyveri* FAD3, Example 61) is co-transformed with the plasmids pESC-TRP-delta-12 delta-6, pESC-URA-elo-delta-5 and pESC-LEU-Ssc2-delta-4d. Transformants are selected and streak-purified on medium lacking uracil, tryptophane and leucine. The transformed strain is then cultivated under suitable conditions for induction of the GAL promoters (e.g. Example 9, Example 49), and the fatty acid composition is analyzed as described in Example 45.

Example 63

Overexpression of LRO1

The acyltransferase encoded by LRO1 in *S. cerevisiae* catalyses the transfer of an acyl chain from position 2 in phosphatidylcholine to diacylglycerol, resulting in the formation of triacylglycerol. Since polyunsaturated fatty acid desaturation takes place mainly on position 2 of phosphatidylcholine (Domergue, F. et al. (2003) J Biol Chem 278: 35115-35126), overexpression of LRO1 is likely to result in increased incorporation of polyunsaturated fatty acid into triacylglycerol and overall increased polyunsaturated fatty acid content. LRO1 is overexpressed with a strong yeast promoter, for example the TDH3, ADH1, TPI1 or HXT7 promoter using a using a promoter-replacement method based on a bipartite gene-targeting substrate (FIG. 15)), as described in e.g. Example 26 and Example 30.

Example 64

Overexpression of ARE1 and ARE2

The acyltransferases encoded by ARE1 and ARE2 in *S. cerevisiae* catalyze the addition of an acyl chain to diacylglycerol to form triacylglycerol. Overexpression of ARE1 and ARE2 may result in increased lipid yield and overall increased polyunsaturated fatty acid content. ARE1 and ARE2 are overexpressed with strong yeast promoters, for example the TDH3, ADH1, TPI1 or HXT7 promoters using a using a promoter-replacement method based on a bipartite gene-targeting substrate (FIG. 15), as described in e.g. Example 26 and Example 30.

Example 65

Overexpression of ELO1, ELO2 and ELO3

The yeast genes ELO1, ELO2 and ELO3 encode fatty acid elongases. The elongase encoded by ELO1 is responsible for elongation of C14 fatty acids to C16 species (Toke et al. (1996) J Biol Chem 271: 18413-18422), ELO2 encodes an elongase involved in synthesis of saturated and monounsaturated fatty acid of up to 24 carbon atoms in length, and ELO3 encodes an elongase with a broad substrate range (Oh, C.-S. et al. (1997) J Biol Chem 272: 17376-17384). Overexpression of these elongases may contribute to increased contents of C18 fatty acids, the substrates for the polyunsaturated fatty acid pathway, and thereby result in increased production of polyunsaturated fatty acids. ELO1, ELO2 and ELO3 are overexpressed with strong yeast promoters, for example the TDH3, ADH1, TPI1 or HXT7 promoters using a using a promoter-replacement method based on a bipartite gene-targeting substrate (FIG. 15), as described in e.g. Example 26 and Example 30.

Example 66

Overexpression of GPD1 and Deletion of GPP1 and GPP2

The universal precursor for lipid synthesis is glycerol-3-phosphate, which is formed from dihydroxyacetonephosphate by the action of NAD-dependent glycerol-3-phosphate dehydrogenase, in yeast encoded by GPD1. Glycerol-3-phosphate either enter the lipid synthesis pathway or it can be dephosphorylated to form glycerol by the action of glycerol- 3-phosphatases encoded by GPP1 and GPP2. By overexpressing GPD1 and deleting GPP1 and GPP2, the availability of glycerol-3-phosphate can be increased (Nguyen, H. T. T. et al. (2004) Metab Eng. 6, 155-163). By combining these modifications with overexpression of the FAS complex and acyltransferases in the lipid synthesis pathway, it is likely that the lipid yield and polyunsaturated fatty acid yield can be improved.

GPD1 is overexpressed with a strong yeast promoter, for example the TDH3, ADH1, TPI1 or HXT7 promoter, using a using a promoter-replacement method based on a bipartite gene-targeting substrate (FIG. 15), as described in e.g. Example 26 and Example 30.

GPP1 and GPP2 are deleted using a bipartite gene-targeting substrate with *K. lactis* URA3 as a recyclable marker. One part of the bipartite substrate consists of two thirds (towards the 3'end) of *K. lactis* URA3, followed by a short sequence R, and a target sequence downstream of GPP1 or GPP2, respectively. The second part of the bipartite substrate consists of a target sequence upstream of GPP1 or GPP2, respectively, fused to the short sequence R and two thirds (towards the 5' end) of *K. lactis* URA3. Following transformation with the bipartite substrate and selection on medium lacking uracil, transformants are obtained in which GPP1 or GPP2, respectively, have been knocked out and replaced with two copies of the short sequence R as a direct repeat on either side of the *K. lactis* URA3 marker gene. A second recombination event, resulting in looping out of the selection marker, is selected for by replating transformants on medium containing 5'-fluoro-orotic acid (5-FOA), which is toxic to cells expressing the URA3 gene. In the resulting strains, GPP1 and GPP2 have been deleted and replaced with the short sequence R. Alternatively, GPP1 and GPP2 are used as the loci for integration of heterologous genes, resulting in deletion of these genes, e.g. as described in Example 66.

The GPD1 overexpression and the GPP1 and GPP2 deletions are performed in a pADH1-FAS1 pADH1-FAS2 pTPI1-ACC1 pox1::pTDH3-*M. alpina* ole1 strain background. Following construction of the GPD1 overexpression, GPP1 and GPP2 deletion strain, these modifications are combined with overexpression of acyltransferases in the lipid biosynthetic pathway (e.g. overexpression of GAT1, SLC1 and DGA1 or LRO1) through crossing of strains.

Example 67

Expression of a Heterologous $NADP^+$ Dependent Glyceraldehyde 3-Phosphate Dehydrogenase Expression of the *Streptococcus mutans* GapN gene (SEQ ID NO: 91), encoding an $NADP^+$ dependent glyceraldehyde 3-phosphate dehydrogenase, increases the availability of cytosolic NADPH for fatty acid synthesis. Integration of the *S. mutans* GapN into the genome of *S. cerevisiae* is combined with overexpression of FAS1, FAS2 and ACC1.

The *S. mutans* GapN gene is integrated into the genome of *S. cerevisiae* and is placed under the control of the yeast ADH1 promoter. The ADH1 promoter and the *S. mutans* GapN gene are integrated at the locus of GPP2, resulting in knockout of this gene (see also Example 66). The integration is carried out through homologous recombination using a bipartite gene targeting substrate, using the same principle methods as described for the integration of *M. alpina* ole1 (Example 28).

Example 68

Combining Genetic Modifications in a Single Strain

Genetic modifications that lead to improved lipid yields and/or polyunsaturated fatty acid yields are combined by crossing of strains or by repeating the promoter replacement procedure in different strain backgrounds. For example, overexpression of FAS1, FAS2, and ACC1 is combined with overexpression of GAT1, SLC1, and DGA1 and/or LRO1.

Example 69

Codon-Optimization and Assembly of Synthetic Delta-9 Elongase from *Isochrysis galbana* and Synthetic Delta-8 Desaturase from *Euglena gracilis*

The sequences encoding *Isochrysis galbana* delta-9 elongase (SEQ ID NO 37) and *Euglena gracilis* delta-8 desaturase (SEQ ID NO 38) are codon-optimized for expression in *S. cerevisiae* using the Backtranslation tool (Entelechon) with the "discard codons below 50% theroretical ratio"-option. The codon-optimized genes (SEQ ID NO 85 and SEQ ID NO 86, respectively) are then assembled from chemically synthesized oligo nucleotides, in principle as described for the assembly of a synthetic gene encoding delta-4 desaturase (Example 59).

Example 70

Cloning of Synthetic Delta-9 Elongase and Delta-8 Desaturase into Yeast Expression Vectors The codon-optimized gene encoding a delta-9 elongase (SEQ ID NO 85, Example 70) is cloned into the yeast expression vector pESC-TRP-delta-12 (Example 2), resulting in the vector pESC-TRP-delta-12 delta-9e. Furthermore, the vectors pESC-URA-elo-delta-5 is digested with suitable restriction enzymes resulting in the release of the *M. alpina* delta-6 elongase encoding gene from this plasmid. The linearized plasmid is purified and the codon-optimized delta-8 desaturase (SEQ ID NO 86, Example 71) is introduced in the place of the *M. alpina* delta-6 elongase. The resulting plasmid is named pESC-URA-delta-8 delta-5.

Example 71

Expression of the Pathway to Arachidonic Acid via Codon-Optimized Delta-9 Elongase and Delta-8 Desaturase A suitable yeast strain (e.g. FS01267, FS01368, FS01408 or FS01423) is co-transformed with plasmids pESC-TRP-delta-12 delta-9e and pESC-URA-delta-8 delta-5. The resulting strain is cultivated under suitable conditions for induction of the GAL promoters (e.g. Example 9, Example 49), and the fatty acid composition is analyzed as described in Example 45.

Example 72

Expression of the Pathway to Eicosapentaenoic Acid via Codon-Optimized Delta-9 Elongase and Delta-8 Desaturase A suitable yeast strain (e.g. FS01277 or FS01444) is co-transformed with plasmids pESC-TRP-delta-12 delta-9e (Example 70), pESC-URA-delta-8 delta-5 (Example 70) and pESC-LEU-SK33 (Example 54). The resulting strain is cultivated under suitable conditions for induction of the GAL promoters (e.g. Example 9, Example 49), and the fatty acid composition is analyzed as described in Example 45.

Example 73

Expression of the Pathway to Docosatetraenoic Acid via Codon-Optimized Delta-9 Elongase and Delta-8 Desaturase A suitable yeast strain (e.g. FS01277 or FS01444) is co-transformed with plasmids pESC-TRP-delta-12 delta-9e (Example 70), pESC-URA-delta-8 delta-5 (Example 70) and pESC-LEU-Ssc2 (Example 55). The resulting strain is cultivated under suitable conditions for induction of the GAL promoters (e.g. Example 9, Example 49), and the fatty acid composition is analyzed as described in Example 45.

Example 74

Expression of the Pathway to Docosapentaenoic Acid via Codon-Optimized Delta-9 Elongase and Delta-8 Desaturase A suitable yeast strain (e.g. FS01277 or FS01444) is co-transformed with plasmids pESC-TRP-delta-12 delta-9e (Example 70), pESC-URA-delta-8 delta-5 (Example 70) and pESC-LEU-Ssc2-SK33 (Example 56). The resulting strain is cultivated under suitable conditions for induction of the GAL promoters (e.g. Example 9, Example 49), and the fatty acid composition is analyzed as described in Example 45.

Example 75

Expression of the Pathway to Docosahexaenoic Acid via Codon-Optimized Delta-9 Elongase and Delta-8 Desaturase The yeast strain FS01460 (Example 61) is co-transformed with plasmids pESC-TRP-delta-12 delta-9e (Example 70), pESC-URA-delta-8 delta-5 (Example 70) and pESC-pESC-LEU-Ssc2-delta-4d (Example 60). The resulting strain is cultivated under suitable conditions for induction of the GAL promoters (e.g. Example 9, Example 49), and the fatty acid composition is analyzed as described in Example 45.

Example 76

Codon-Optimization of Genes Encoding Delta-9 Desaturase, Delta-12 Desaturase, Delta-6 Desaturase, Delta-6 Elongase, Delta-5 Desaturase, Delta-5 Elongase and Omega-3 Desaturase The sequences of *M. alpina* delta-9 desaturase (SEQ ID NO 1), delta-12 desaturase (SEQ ID NO 5), delta-6 desaturase (SEQ ID NO 11), delta-6 elongase (SEQ ID NO 16) and delta-5 desaturase (SEQ ID NO 22), mouse delta-5 elongase (SEQ ID NO 28) and *S. kluyveri* omega-3 desaturase (SEQ ID NO 87) are codon-optimized for expression in *S. cerevisiae* and are assembled from synthetic oligonucleotides using the same principle as described for assembly of a synthetic gene encoding delta-4 desaturase (Example 59).

The invention is further described by the following numbered paragraphs:

1. A method for producing polyunsaturated fatty acids with four or more double bonds comprising heterologous expression of an oxygen requiring pathway in a *Saccharomyces cerevisiae* grown on a non-fatty acid substrate.
2. A method according to paragraph 1, wherein said non-fatty acid substrate is the exclusive carbon source.
3. A method according to any of paragraphs 1-2, wherein the heterologous expression comprises combining heterologous expression of nucleotide sequences encoding delta-12 desaturase, delta-6 desaturase, delta-6 elongase, and delta-5 desaturase.
4. A method according to any of paragraphs 1-2, wherein the heterologous expression comprises combining heterologous expression of nucleotide sequences encoding delta-12 desaturase, delta-9 elongase, delta-8 desaturase, and delta-5 desaturase.
5. A method according to any of the preceding paragraphs, wherein the combined heterologous expression further comprises heterologous expression of a nucleotide sequence encoding delta-5 elongase, omega-3 desaturase, and/or delta-4 desaturase.
6. A method according to any of the preceding paragraphs, wherein said combined heterologous expression further comprises heterologous expression of a nucleotide sequence encoding a delta-9 desaturase.
7. A method according to any of the preceding paragraphs, wherein said combined heterologous expression further comprises an over-expression of at least one of the genes selected from the group consisting of ACC1, YBR159W, ELO1, ELO2, ELO3, FAS1, FAS2, DGA1, LRO1, ARE1, ARE2, and GPD1.
8. A method according to any of the preceding paragraphs, wherein said combined heterologous expression further comprises a deletion of at least one of the genes selected from the group consisting of GPP1, GPP2 and POX1.
9. A method according to any of the preceding paragraphs, wherein said combined heterologous expression further comprises a heterologous expression of the nucleotide sequences encoding ATP:citrate lyase and/or an isocitrate dehydrogenase which is stimulated by AMP.
10. A method according to any of the preceding paragraphs, wherein said combined heterologous expression further comprises a heterologous expression of a nucleotide sequence encoding a non-phosphorylating NADP-dependent D-glyceraldehyde-3-phosphate dehydrogenase.
11. A method according to any of the preceding paragraphs, wherein said combined heterologous expression further comprises a deletion of the gene GDH1 and optionally an over-expression of at least one of the genes selected from the group consisting of GDH2, GLN1 and GLT1.
12. A method according to any of the preceding paragraphs, wherein said combined heterologous expression further comprises an over-expression of at least one of the genes selected from the group consisting of TSC13, GAT1, SLC1 and YDR531W.

13. A method according to any of the preceding paragraphs, wherein said heterologous nucleotide sequences are codon optimized for expression in *Saccharomyces cerevisiae.*

14. A method according to any of the preceding paragraphs, wherein said *Saccharomyces cerevisiae* is cultivated in a myo-inositol deficient medium.

15. A method according to any of the preceding paragraphs, wherein the polyunsaturated fatty acid is selected from the group consisting of arachidonic acid, eicosapentaenoic acid and docosahexaenoic acid.

16. A method according to any of the preceding paragraphs, wherein said heterologous expression increases the content of arachidonic acid, eicosapentaenoic acid and/or docosahexaenoic acid to more than 2% of the total fatty acid content in said *Saccharomyces cerevisiae*

17. A method according to any of paragraphs 3-16, wherein the nucleotide sequence encoding delta-12 desaturase is selected from the group consisting of a) the nucleotide sequences set forth in SEQ ID NOs 5-10, 93, 95, and 113; and b) nucleotide sequences having at least 75% identity to the nucleotide sequences set forth in SEQ ID NOs 5-10, 93, 95, and 113.

18. A method according to any of paragraphs 4-17, wherein the nucleotide sequence encoding delta-9 elongase is a nucleotide sequence comprising or having at least 75% identity to the nucleotide sequence of SEQ ID NO: 37.

19. A method according to any of paragraphs 6-18, wherein the nucleotide sequence encoding delta-9 desaturase is selected from the group consisting of a) the nucleotide sequences set forth in SEQ ID NO: 1-4; and b) nucleotide sequences having at least 75% identity to the nucleotide sequences set forth in SEQ ID NO: 1-4.

20. A method according to any of paragraphs 4-19, wherein the nucleotide sequence encoding delta-8 desaturase is a nucleotide sequence comprising or having at least 75% identity to the nucleotide sequence of SEQ ID NO: 38.

21. A method according to any of paragraphs 3-17 or 19, wherein the nucleotide sequence encoding delta-6 desaturase is selected from the group consisting of a) the nucleotide sequences set forth in SEQ ID NO: 11-15, 97, and 99; and b) nucleotide sequences having at least 75% identity to the nucleotide sequences set forth in SEQ ID NO: 11-15, 97, and 99.

22. A method according to any of paragraphs 3-17, 19 or 21, wherein the nucleotide sequence encoding delta-6 elongase is selected from the group consisting of a) the nucleotide sequences set forth in SEQ ID NO: 16-21, 101 and 103; and b) nucleotide sequences having at least 75% identity to the nucleotide sequences set forth in SEQ ID NO: 16-21, 101 and 103.

23. A method according to any of paragraphs 3-22, wherein the nucleotide sequence encoding delta-5 desaturase is selected from the group consisting of a) the nucleotide sequences set forth in SEQ ID NO: 22-27, 99, 105 and 107; and b) nucleotide sequences having at least 75% identity to the nucleotide sequences set forth in SEQ ID NO: 22-27, 99, 105 and 107.

24. A method according to any of paragraphs 3-23 wherein the nucleotide sequence encoding delta-5 elongase is selected from the group consisting of a) the nucleotide sequences set forth in SEQ ID NO: 19, 28, 29 and 101;

b) nucleotide sequences having at least 75% identity to the nucleotide sequences set forth in SEQ ID NO: 19, 28, 29 and 101; and c) nucleotide sequences encoding amino acid sequences that have at least 75% identity to SEQ ID NO 68.

25. A method according to any of paragraphs 3-24, wherein the nucleotide sequence encoding delta-4 desaturase is selected from the group consisting of a) the nucleotide sequences set forth in SEQ ID NO: 35-36 and 109;

b) nucleotide sequences having at least 75% identity to the nucleotide sequences set forth in SEQ ID NO: 35-36 and 109; and c) nucleotide sequences encoding amino acid sequences that have at least 75% identity to SEQ ID NOs 76-77.

26. A method according to any of paragraphs 2-25, wherein the nucleotide sequence encoding omega-3 desaturase is selected from the group consisting of a) the nucleotide sequences set forth in SEQ ID NO: 30-34, 87, 89 and 111; and b) nucleotide sequences having at least 75% identity to the nucleotide sequences set forth in SEQ ID NO: 30-34, 87, 89 and 111.

27. A method for producing a polyunsaturated fatty acid comprising the steps of (a) isolating at least 4 nucleotide sequences encoding delta-12 desaturase, delta-6 desaturase, delta-6 elongase, and delta-5 desaturase (b) constructing one or more vectors comprising said isolated nucleotide sequences of step (a) and/or integrating said isolated nucleotide sequences into the genome of *Saccharomyces cerevisiae;*

(c) optionally, transforming said vector(s) of step (b) into a *Saccharomyces cerevisiae* for a time and under conditions sufficient for expression of proteins encoded by said isolated nucleotide sequences of step (a);

(d) growing said *Saccharomyces cerevisiae* on a non-fatty acid substrate, whereby said non-fatty acid substrate is converted by said host into a desired polyunsaturated fatty acid product and obtaining said polyunsaturated fatty acid.

28. A method for producing a polyunsaturated fatty acid comprising the steps of (a) isolating at least 4 nucleotide sequences encoding delta-12 desaturase, delta-9 elongase, delta-8 desaturase, and delta-5 desaturase (b) constructing one or more vectors comprising said isolated nucleotide sequences of step (a) and/or integrating said isolated nucleotide sequences into the genome of *Saccharomyces cerevisiae;*

(c) optionally, transforming said vector(s) of step (b) into a *Saccharomyces cerevisiae* for a time and under conditions sufficient for expression of proteins encoded by said isolated nucleotide sequences of step (a);

(d) growing said *Saccharomyces cerevisiae* on a non-fatty acid substrate, whereby said non-fatty acid substrate is converted by said host into a desired polyunsaturated fatty acid product and obtaining said polyunsaturated fatty acid.

29. A method according to any of paragraphs 27-28, wherein the heterologous expression further comprises heterologous expression of a nucleotide sequence encoding delta-9 desaturase, delta-5 elongase, omega-3 desaturase, and/or delta-4 desaturase.

30. A genetically modified *Saccharomyces cerevisiae* capable of producing polyunsaturated fatty acids with four or more double bonds when grown on a non-fatty acid substrate.
31. A genetically modified *Saccharomyces cerevisiae* according to paragraph 30, wherein said *Saccharomyces cerevisiae* is capable of producing polyunsaturated fatty acids with four or more double bonds rown on a non-fatty acid substrate as the exclusive carbon source.
32. A composition comprising a polyunsaturated fatty acid produced by a genetically modified *Saccharomyces cerevisiae* according to any of paragraphs 30-31.
33. A composition comprising at least 25% polyunsaturated fatty acid in total fatty acid composition produced by a genetically modified cell according to any of paragraphs 30-31.
34. A composition according to any of paragraphs 32-33, wherein said composition is an oil.
35. A composition according to any of paragraphs 32-33, wherein said polyunsaturated fatty acid is incorporated in triacylglycerides.
36. A composition according to any of paragraphs 32-33, wherein said polyunsaturated fatty acids is incorporated in phospholipids.
37. A composition according to any of paragraphs 32-33, wherein said polyunsaturated fatty acids is in a form of free fatty acids.
38. Use of a composition according to any of paragraphs 32-37 as an ingredient in a food product.
39. Use of a composition according to any of paragraphs 32-37 as an ingredient in a cosmetic product.
40. Use of a composition according to any of paragraphs 32-37 as an ingredient in feed.
41. Use of a genetically modified *Saccharomyces cerevisiae* according to paragraph 29 as an ingredient in feed.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

REFERENCES

DE 10005973-A1
European Patent Application 50424
European Patent Application 84796
European Patent Application 258017
European Patent Application 237362
European Patent Application 201184
JP 2001095588-A
U.S. Pat. No. 4,683,202
U.S. Pat. No. 4,582,788
U.S. Pat. No. 4,683,194
U.S. Pat. No. 5,972,664
U.S. Pat. No. 6,025,172
U.S. Pat. No. 6,136,574
U.S. Pat. No. 6,194,167
U.S. Pat. No. 6,355,861-B1
U.S. Pat. No. 6,355,861
U.S. Pat. No. 6,372,965
U.S. Pat. No. 6,403,349
U.S. Pat. No. 6,428,990-B1
U.S. Pat. No. 6,432,684
U.S. Pat. No. 6,432,684-B1
U.S. Pat. No. 6,441,278
U.S. Pat. No. 6,492,108
U.S. Pat. No. 6,686,186
U.S. 98/07422
U.S. 98/07421
U.S. 98/07126
U.S. 2002/0170090
U.S. 2002/0151019
U.S. 2002/0108147
U.S. 2003/0177508
U.S. 2003/0180802
U.S. 2003/0172398
U.S. 20030196217
U.S. 2003/0074694
U.S. 2003/066104
WO 9411516
WO 9846765
WO 9927111
WO 9933958
WO 200040705-A
WO 200034439-A
WO 200055330-A
WO 2001/85968-A2
WO 200144485-A
WO 2001/79499-A1
WO 200120001-A
WO 200102591-A
WO 200104636-A
WO 200175069-A1
WO 2001/14538-A
WO 200159128-A
WO 02077213
WO 200208401-A
WO 02/081702
WO 02/081668
WO200208401-A
WO 02/090493
WO 200226946-A
WO 200234940-A
WO 2002/44320
WO 200272028-A2
WO 2003064638-A2
WO 2003012092-A
WO 03/012092
WO 03/072784
WO 03/102138
Adams, A., Gottschling, D. E., Kaiser, C. A., and Stearns, T. Methods in Yeast Genetics: A Cold Spring Harbor Laboratory Course Manual, Cold Spring Harbor Laboratory Press, Cold Spring Harbor, N.Y. (1997)
Altschul, S. F. et al. (1990) Basic local alignment search tool. J Mol. Biol. 215, 403-410
Altschul, S. F. et al. (1997) Gapped BLAST and PSI-BLAST: a new generation of protein database search programs. Nucleic Acids Res. 25, 3389-3402
Beaudoin, F., Michaelson, L. V., Hey, S. J., Lewis, M. J., Shewry, P. R., Sayanova, O., and Napier, J. A. (2000). Heterologous reconstitution in yeast of the polyunsaturated fatty acid biosynthetic pathway. Proc. Natl. Acad. Sci. U.S. A 97, 6421-6426.
Domergue, F., Abbadi, A., Ott, C., Zank, T. K., Zahringer, U., and Heinz, E. (2003). Acyl carriers used as substrates by the desaturases and elongases involved in very long-chain polyunsaturated fatty acids biosynthesis reconstituted in yeast. J Biol. Chem 278, 35115-35126.
Erdeniz, N., Mortensen, U. H., Rothstein, R. (1997) Cloning-free PCR-based allele replacement methods. Genome Res. 7:1174-83

Gargano S. et al. (1995) A temperature-sensitive strain of *Histoplasma capsulatum* has an altered delta 9-fatty acid desaturase gene. Lipids 30, 899-906.

Gerhardt, P., Murray, R. G. E., Costilow, R. N., Nester, E. W., Wood, W. A., Krieg, N. R., and Briggs, G., Eds. Manual of Methods for General Bacteriology. American Society for Microbiology: Washington, D.C. (1994)

Hastings, N., et al. (2004) Molecular cloning and functional characterization of fatty acyl desaturase and elongase cDNAs involved in the production of eicosapentaenoic and docosahexaenoic acids from alpha-linolenic acid in Atlantic salmon (*Salmo salar*). Mar Biotechnol 6, 463-474.

Hastings, N., et al. (2001) A vertebrate fatty acid desaturase with delta-5 and delta-6 activities. Proc Natl Acad Sci 98, 14304-14309.

Kajikawa, M., et al. (2004) Isolation and characterization of delta(6)-desaturase, an ELO-like enzyme and delta(5)-desaturase from the liverwort *Marchantia polymorpha* and production of arachidonic and eicosapentaenoic acids in the methylotrophic yeast *Pichia pastoris*. Plant Mol Biol 54, 335-352.

Karlin, S. and Altschul, S. F. (1990) Methods for assessing the statistical significance of molecular sequence features by using general scoring schemes. Proc Natl Acad Sci USA. 87, 2264-2268

Karlin, S. and Altschul, S. F. (1993) Applications and statistics for multiple high-scoring segments in molecular sequences. Proc Natl Acad Sci USA. 90, 5873-5877

Kirsch, C., et al. (1997) Rapid, transient, and highly localized induction of plastidial omega-3 fatty acid desaturase mRNA at fungal infection sites in *Petroselinum crispum*. Proc Natl Acad Sci USA 94, 2079-2084

Laoteng, K et al. (2000) Delta(6)-desaturase of *Mucor rouxii* with high similarity to plant delta(6) desaturase and its heterologous expression in *Saccharomyces cerevisiae*. Biochem Biophys Res Commun 279, 17-22

Liu, W., et al. (1999) Cloning and functional expression of a cDNA encoding a metabolic acyl-CoA delta-9 desaturase of the cabbage looper moth, *Trichoplusia ni*. Insect Biochem Mol Biol 29, 435-443.

Meesters P A and Eggink G. (1996) Isolation and characterization of a delta-9 fatty acid desaturase gene from the oleaginous yeast *Cryptococcus curvatus* CBS 570. Yeast 12:723-730.

Meyer, A., et al. (2003) Biosynthesis of docosahexaenoic acid in *Euglena gracilis*: Biochemical and molecular evidence for the involvement of a delta 4-fatty acyl group desaturase. Journal Biochemistry 42, 9779-9788

Nguyen, H. T. T. et al. (2004) Engineering of *Saccharomyces cerevisiae* for the production of L-glycerol 3-phosphate. Metab Eng. 6,155-163

Nissen, T. et al. (2000) Optimization of ethanol production in *Saccharomyces cerevisiae* by metabolic engineering of the ammonium assimilation. Metab Eng. 2, 69-77

Oh, C.-S., Toke, D. A., Mandala, S., Martin, C. E. (1997) ELO2 and ELO3, homologues of the *Saccharomyces cerevisiae* ELO1 gene, function in fatty acid elongation and are required for sphingolipid formation. J Biol Chem 272: 17376-17384

Oura, T., et al. (2004) *Saccharomyces kluyveri* FAD3 encodes an omega-3 fatty acid desaturase. Microbiology 150, 1983-1990.

Passorn, S et al. (1999) Heterologous expression of *Mucor rouxii* delta(12)-desaturase gene in *Saccharomyces cerevisiae*. Biochem Biophys Res Commun 263, 47-51

Pereira, S. L., et al. (2004) Identification of two novel microalgal enzymes involved in the conversion of the omega3-fatty acid, eicosapentaenoic acid, into docosahexaenoic acid. Biochem J 384, 357-366.

Pereira, S. L., et al. (2004) A novel omega3-fatty acid desaturase involved in the biosynthesis of eicosapentaenoic acid. *Biochem J* 378, 665-671.

Qi et al. (2004) Production of very long chain polyunsaturated omega-3 and omega-6 fatty acids in plants. Nat. Biotechnol. 16 May 2004 doi: 10.1038/nbt972

Ratledge, C. (2002) Regulation of lipid accumulation in oleaginous micro-organisms. Biochem Soc Trans 30, 1047-1050

Sakuradani, E., et al. (2005) A novel fungal omega3-desaturase with wide substrate specificity from arachidonic acid-producing *Mortierella alpina* 1S-4. Appl Microbiol Biotechnol 66, 648-654.

Sambrook et al. (1989) Molecular cloning: A laboratory manual ($2^{nd}$ ed.), Vols. 1-3, Cold Spring Harbor Laboratory Sandager, L. et al. (2002) Storage lipid synthesis is non-essential in yeast. J Biol. Chem. 277, 6478-6482

Sayanova, O. et al. (1997) Expression of a borage desaturase cDNA containing an N-terminal cytochrome b5 domain results in the accumulation of high levels of delta(6)-desaturated fatty acids in transgenic tobacco. Proc Natl Acad Sci USA 94, 4211-4216.

Sijtsma, L. and De Swaaf, M. E. (2004). Biotechnological production and applications of the omega-3 polyunsaturated fatty acid docosahexaenoic acid. Appl Microbiol. Biotechnol. 64, 146-153.

Toke, D. A. et al. (1996) Isolation and characterization of a gene affecting fatty acid elongation in *Saccharomyces cerevisiae*. J Biol Chem 271: 18413-18422

Tvrdik, P et al. (2000) Role of a new mammalian gene family in the biosynthesis of very long chain fatty acids and sphingolipids. J. Cell Biol. 149: 707-717.

Wallis, J. G. and Browse, J. (1999). The Delta8-desaturase of *Euglena gracilis*: an alternate pathway for synthesis of 20-carbon polyunsaturated fatty acids. Arch Biochem Biophys. 365, 307-16.

Watanabe, K., et al. (2004) Yeast Delta 12 fatty acid desaturase: gene cloning, expression, and function. Biosci Biotechnol Biochem 68, 721-727.

Whitney, H. M., et al. (2003) Functional charactyerisation of two cytochrome b5-fusion desaturases from *Anemone leveillei*: the unexpected identification of a fatty acid Delta6-desaturase. Planta 217, 983-92

Wilson, R. A., et al. (2004) Characterization of *Aspergillus parasiticus* odeA gene Microbiology 150, 2881-2888.

Wongwathanarat, P., Michaelson, L. V., Carter, A. T., Lazarus, C. M., Griffiths, G., Stobart, A. K., Archer, D. B., and MacKenzie, D. A. (1999). Two fatty acid delta9-desaturase genes, ole1 and ole2, from *Mortierella alpina* complement the yeast ole1 mutation. Microbiology 145 (Pt 10), 2939-2946.

Yadav, N. S et al. (1993) Cloning of higher plant omega-3 fatty acid desaturases. Plant Physiol 103: 467-476

Zhu, M., Yu, L. J., and Wu, Y. X. (2003). An in expensive medium for production of arachidonic acid by *Mortierella* alpina. J Ind. Microbiol. Biotechnol. 30, 75-79.

What is claimed is:

1. A genetically modified *Saccharomyces cerevisiae* capable of producing polyunsaturated fatty acids with four or more double bonds when grown on a non-fatty acid substrate, wherein said *Saccharomyces cerevisiae* comprises heterologous expression of nucleotide sequences encoding delta-12 desaturase, delta-6 desaturase, delta-6 elongase, delta-5 desaturase and delta-9 desaturase; wherein said heterologous expression increases the content of polyunsaturated fatty acids with four or more double bonds to more than 1.1% of the total fatty acid content in said *Saccharomyces cerevisiae*.

2. A genetically modified *Saccharomyces cerevisiae* capable of producing polyunsaturated fatty acids with four or more double bonds when grown on a non-fatty acid substrate, wherein said *Saccharomyces cerevisiae* comprises heterologous expression of nucleotide sequences encoding delta-12 desaturase, delta-9 elongase, delta-8 desaturase, delta-5 desaturase, and delta-9 desaturase, wherein said heterologous expression increases the content of polyunsaturated fatty acids with four or more double bonds to more than 1.1% of the total fatty acid content in said *Saccharomyces cerevisiae*.

3. A method for producing polyunsaturated fatty acids with four or more double bonds comprising heterologous expression of an oxygen requiring pathway in a *Saccharomyces cerevisiae* grown on a non-fatty acid substrate, wherein the heterologous expression comprises combining heterologous expression of nucleotide sequences encoding delta-12 desaturase, delta-6 desaturase, delta-6 elongase, delta-5 desaturase, and delta-9 desaturase, wherein said heterologous expression increases the content of polyunsaturated fatty acids with four or more double bonds to more than 1.1% of the total fatty acid content in said *Saccharomyces cerevisiae*.

4. A method for producing polyunsaturated fatty acids with four or more double bonds comprising heterologous expression of an oxygen requiring pathway in a *Saccharomyces cerevisiae* grown on a non-fatty acid substrate, wherein the heterologous expression comprises combining heterologous expression of nucleotide sequences encoding delta-12 desaturase, delta-9 elongase, delta-8 desaturase, delta-5 desaturase, and delta-9 desaturase, wherein said heterologous expression increases the content of polyunsaturated fatty acids with four or more double bonds to more than 1.1% of the total fatty acid content in said *Saccharomyces cerevisiae*.

5. A method according to claim 3 or 4, wherein the heterologous expression further comprises combining heterologous expression of nucleotide sequences encoding delta-5 elongase, omega-3 desaturase, and/or delta-4 desaturase.

6. A method according to claim 5, wherein said combined heterologous expression further comprises an over-expression of at least one of the genes selected from the group consisting of genes encoding the acetyl-CoA carboxylase designated ACC1, the β-ketoacyl-CoA reductase designated YBR159W, the fatty acid synthase a subunit designated FAS1, the fatty acid synthase β subunit designated FAS2, the enoyl reductase designated TSC13, the L-glycerol-phosphate acyltransferase designated GAT1, the 1-acylglycerol-3-phosphate acyltransferase designated SLC1 and the pantothenate kinase designated YDR531W; or wherein said combined heterologous expression further comprises a deletion of at least one of the genes selected from the group consisting of genes encoding the glyceraldehydes-3-phosphate dehydrogenase designated GDH1 and the peroxisomal acyl-CoA oxidase designated POX1, or wherein said combined heterologous expression further comprises a heterologous expression of nucleotide sequences encoding ATP:citrate lyase subunits.

7. A method according to claim 3 or 4, wherein said heterologous nucleotide sequences are codon optimized for expression in *Saccharomyces cerevisiae*; or wherein said *Saccharomyces cerevisiae* is cultivated in a myo-inositol deficient medium.

8. A method according to claim 3 or 4, wherein the polyunsaturated fatty acid is selected from the group consisting of arachidonic acid, eicosapentaenoic acid, and docosahexaenoic acid.

9. A method according to claim 6, wherein said heterologous expression increases the content of arachidonic acid, eicosapentaenoic acid, and/or docosahexaenoic acid to more than 3% of the total fatty acid content in said *Saccharomyces cerevisiae.*

10. A method for producing a polyunsaturated fatty acid comprising the steps of (a) isolating at least five nucleotide sequences encoding a delta-12 desaturase a delta-6 desaturase a delta-6 elongase, a delta-5 desaturase, and a delta-9 desaturase exogenous to *Saccharomyces cerevisiae,*

(b) constructing one or more vectors comprising said isolated nucleotide sequences of step (a) and/or integrating said isolated nucleotide sequences into the genome of *Saccharomyces cerevisiae;*

(c) growing said *Saccharomyces cerevisiae* on a non-fatty acid substrate, whereby said non-fatty acid substrate is converted by said host into a desired polyunsaturated fatty acid product and obtaining said polyunsaturated fatty acid, wherein heterologous expression of said five isolated nucleotide sequences increases the content of the polyunsaturated fatty acid to more than 1.1% of the total fatty acid content in said *Saccharomyces cerevisiae.*

11. A method for producing a polyunsaturated fatty acid comprising the steps of (a) isolating at least five nucleotide sequences encoding a delta-12 desaturase, a delta-9 elongase, a delta-8 desaturase, a delta-5 desaturase and a delta-9 desaturase exogenous to *Saccharomyces cerevisiae,*

(b) constructing one or more vectors comprising said isolated nucleotide sequences of step (a) and/or integrating said isolated nucleotide sequences into the genome of *Saccharomyces cerevisiae;*

(c) growing said *Saccharomyces cerevisiae* on a non-fatty acid substrate, whereby said non-fatty acid substrate is converted by said host into a desired polyunsaturated fatty acid product and obtaining said polyunsaturated fatty acid, wherein heterologous expression of said five isolated nucleotide sequences increases the content of the polyunsaturated fatty acid to more than 1.1% of the total fatty acid content in said *Saccharomyces cerevisiae.*

12. A method according to claim 10 or 11, wherein the heterologous expression further comprises heterologous expression of a nucleotide sequence encoding delta-9 desaturase, delta-5 elongase, omega-3 desaturase, and/or delta-4 desaturase.

13. A composition comprising a genetically modified *Saccharomyces cerevisiae* comprising a nucleotide sequence encoding each of an heterologous delta-12 desaturase, delta-6 desaturase, delta-6 elongase, delta-5 desaturase, and delta-9 desaturase, and having a polyunsaturated fatty acid content of more than 1.1% of the total fatty acid content, wherein the polyunsaturated fatty acid has four or more double bonds.

14. A composition according to claim 13, wherein the polyunsaturated fatty acid comprises arachidonic acid, eicosapentaenoic acid and/or docosahexaenoic acid.

15. The composition of claim 13, wherein the polyunsaturated fatty acid content is more than 3% of the total fatty acid content.

16. A food product comprising the composition of claim 13.

17. A cosmetic product comprising the composition of claim 13.

18. A feed comprising the composition of claim 13.

* * * * *

SEQUENCE LISTING

<160> NUMBER OF SEQ ID NOS: 227

<210> SEQ ID NO 1
<211> LENGTH: 1338
<212> TYPE: DNA
<213> ORGANISM: Mortierella alpina

<400> SEQUENCE: 1
atggcaactc ctcttccccc ctccttcgtc gtccctgcga cacagacgga gacccgcaga 60
gatcctctcc agcacgagga actgcccccct ctcttccccg agaaaatcac cgtctacaac 120
atctggagat atcttgacta caagcatgtt ttcggtctgg ggctgacgcc tttgatcgca 180
ctctacggtc tcttgacgac cgagatccag acgaagacgc tgatctggtc catcatctac 240
tactatgcta cgggactcgg catcacagca ggatatcatc gactctgggc ccatcgtgcc 300
tacaacgcag gacctgccat gagcttcgtg ctcgcattgc ttggcgccgg tgctgttgaa 360
ggatccatca agtggtggtc ccgcggccac cgtgctcacc atcgctggac cgataccgag 420
aaggacccct acagtgctca ccgcggactc ttcttctcgc atattggctg gatgctgatc 480
aagcgccctg gatggaagat cggccatgcc gatgtcgacg acctcaacaa gagcaaactc 540
gttcagtggc agcacaagaa ctaccttcct cttgttctca ttatgggcgt tgtcttcccc 600
acggttgtcg ctggactcgg ctggggcgac tggcgcggag gctacttctt tgctgctatt 660
cttcgtcttg tctttgttca ccacgccact ttctgtgtca actccctggc tcactggctt 720
ggtgatggac cctttgatga ccgccactct ccccgcgacc actttatcac tgccttcgtc 780
actttgggag aaggctacca caacttccac caccagttcc cccaggacta ccgcaacgct 840
atccgctttt accagtacga ccctaccaag tgggtcattg ccctctgtgc tttctttggc 900
ctcgctactc acctcaagac cttccctgag aacgaagtcc gcaagggtca gctccagatg 960
atcgagaagc gtgtcttgga gaagaagacc aagctccagt ggggcactcc cattgctgat 1020
ctgcccatcc tgagctttga agacttccag catgcctgca agaacgacaa caagaagtgg 1080
attctcctgg agggtgtcgt ctatgatgtt gccgacttta tgaccgagca ccctggtggt 1140
gagaagtaca tcaagatggg cgttggcaag gacatgaccg cagccttcaa tggcggtatg 1200
tacgatcaca gcaatgccgc gcgcaacttg ctgagcctga tgcgcgtcgc cgtcgttgag 1260
tttggaggtg aagttgaggc ccagaagaag aacccctcga tgcccatcta cggcactgac 1320
cacgtcaagg ccgaatag 1338

<210> SEQ ID NO 2
<211> LENGTH: 1482
<212> TYPE: DNA
<213> ORGANISM: Cryptococcus curvatus

<400> SEQUENCE: 2
atgtcggctt cgactgctac agcaccacca gcaacagctc cggctgttgc caaccctact 60
cctgctgctg cttctgcggc ggctgctgct ccagcagcca ccaaggacaa ggcagagacc 120
atcgaccccg aatccgagca ctttgtcgtc tcccagaact atgtcacccg cactgtggag 180
aacatgacaa tgctccctcc cgtcacctgg agcaaccttc tgcagaacat ccagtggatt 240
tcgttcactg cgctcactgt cccccccgcc atggccatct acggcctctg cactctcgag 300
ctccagcgca agactgtcat ctgggcgatc gtctactatt tcatgaccgg tctcggcatt 360
actgccggct accaccggct ctgggctcac cgcgcgtaca acgcgtccgc tcccctccag 420

-continued

```
tacttcctcg ctctgtgcgg cgctggctcc gtccagggct ccatcaagtg gtggtctcgc    480
ggccaccgcg cgcaccaccg ctacaccgac accaagctcg acccctactc tgcgcacgag    540
ggtttctggt gggcccacgt cggatggatg ctcgtcaagc cccgcggcaa gattggcgtc    600
gccgacattt ccgacctcag ccgcaacccc gtcgtcaagt ggcagcacaa caactatgtc    660
atgctcatgg tcctcatggg tcttgtcttc cccactcttg ttgccggcct cggctgggga    720
gactggaagg gtggcctgct tttcgctggt gccgctcgcc ttgttttcgt ccaccactcg    780
acgttctgcg tcaactcgct cgcccactgg ctcggtgaga ctccctttga caacaagcac    840
acccccaagg accactttat cactgcgctt gtgaccgtcg gcgagggcta ccacaacttc    900
caccaccagt tccccatgga cttccgcaac gccatcaagt ggtaccagta cgaccccacc    960
aagtggttca tctggaccat gtccaacgtc ggcctcgcct cgcacctcaa gaagttcccc   1020
gacaacgaga tcaagaaggg ccagtacacc atgaagctcc agatgctcca ggaacagtcc   1080
ggctccatcc agtggcccaa gcacagcaac gacctgcccg ttatttcttg ggaggacttc   1140
caggccgagg ccaaggagcg ctcccttgtg gctatccacg ggttcatcca cgactgctcc   1200
agcttcctcg aggaccaccc gggaggcatc cacctgatca agaaggccat cggcaccgac   1260
gcgaccactg ccttctttgg cggtgtgtac gaccactcga acgccgcgca caaccttctc   1320
gccatgatgc gtgttggtat cctcgacggc ggcatggagg tcgagtccct caagctcgag   1380
aacctccagc gctccatgtc tgtctcgtct atggagtcgg acgctgcgtc ctctgcctcg   1440
tcggtttccg tgtcttccat ctctccgagg tggccgcact ag                      1482
```

<210> SEQ ID NO 3
<211> LENGTH: 1431
<212> TYPE: DNA
<213> ORGANISM: Histoplasma capsulatus

<400> SEQUENCE: 3

```
atggctttaa acgaagcccc cacggcttcc ccagttgctg agacagctgc tggaggtaaa     60
gacgttgtca ctgatgctgc acgtcgcccc aactctgagc ccaagaaggt tcatatcaca    120
gatacgccga taactctggc aaactggcat aagcatatca gctggctcaa cgtcactctc    180
atcatcgcca tccccattta cggccttgtc caggcatact gggtcccctt acacctcaaa    240
actgctctat gggctgttgt gtactatttc atgactggac tcggtatcac tgccggatat    300
catcgtcttt gggcacactg ctcatattcc gccacattgc cactaaaaat atatcttgct    360
gctgttggag gtggtgctgt ggaagggtcc attagatggt gggctagagg ccaccgtgcc    420
caccaccgct ataccgacac agataaggac ccttactctg tccgcaaagg cctcctgtac    480
tcccacattg gttggatggt aatgaaacaa aacccgaaac gcatcggccg aaccgagatc    540
acagatctta atgaagaccc cgtcgttgtc tggcaacacc ggaactacct caaagtcgtc    600
attttcatgg gtatcgtctt ccccatgctc gtcagcggcc ttggctgggg cgactggttc    660
ggtggcttca tctatgccgg catcctccgt atcttcttcg tccaacaagc taccttctgc    720
gtcaactccc tcgcccactg gctaggtgac cagcccttcg atgaccgcaa ctccccacgc    780
gaccacatcg tcaccgccct cgtcaccctc ggcgaaggct accacaactt ccaccacgaa    840
ttcccctctg actaccgcaa cgccatcgaa tggcaccaat acgacccgac caaatggaca    900
atctggatct ggaagcagct tggtctcgcc tacgacctca agcagttccg cgccaacgag    960
atcgaaaagg gccgtgttca gcaactgcag aagaaaatcg accagcgccg cgcgaagctc   1020
```

-continued

```
gactggggca tcccgctcga gcaactcccc gtcattgaat gggacgacta cgtcgaccaa   1080

gctaagaacg gccgcggtct catcgccatt gccggtgtcg tccatgacgt cacggatttc   1140

atcaaggacc acccgggcgg taaagcgatg atcaactccg gtatcggcaa ggatgccact   1200

gccatgttta acggcggggt gtacaaccat tccaacgcag cgcacaatca gctgtcgacg   1260

atgcgggttg gggtcatccg tggcggctgt gaggtggaaa tttggaagcg agcacagaag   1320

gagaataagg aggtggagtc ggtgcgggat gaatatggga atcggatcgt gcgggcgggg   1380

gcgcaggtga cgaagatccc ggaacctatt actacagctg atgcagcgta g            1431
```

<210> SEQ ID NO 4
<211> LENGTH: 1439
<212> TYPE: DNA
<213> ORGANISM: Trichoplusia ni

<400> SEQUENCE: 4

```
gccagtcttc tgtggtgcgt ctgtaatcaa tcacatctta cgggaaaccc actggatgtt     60

ataattcgtg gatttaacgc gattccttac acttacatct ttctaaagat taccagacaa    120

tatgcctcct caagggcaaa ctggtggatc atgggtcctg tatgagacag acgctgtgaa    180

cacggacaca gatgcgccag tcatcgtgcc accatcagcc gagaagagag agtggaagat    240

agtatggaga aacgtcatcc tcatgggcat gttgcatata ggaggagtat atggtgctta    300

cctgttcctc acgaaagcaa tgtggctcac ggatctattc gcgttcttct tgtatttatg    360

ttcgggcctt ggcatcaccg ccggagcaca cagactctgg gcccacaagt cttacaaagc    420

gcgcttgcct ctcagacttt tgctcacact cttcaacaca ttggccttcc aagacgcagt    480

aattgactgg gcccgagacc atcgcatgca tcacaagtac tccgaaactg atgctgaccc    540

ccacaacgcg acccgaggat tcttcttctc ccacgtcggt tggttgctgg tcaggaaaca    600

cccgcagatc aaggccaaag gtcacaccat cgacctcagt gaccttaaga gtgaccccat    660

tcttcgtttc cagaagaagt actacttgac actgatgccc ctgatctgct tcatcttgcc    720

gagctacatt ccaaccctgt ggggtgaatc tgcgttcaac gcgttcttcg tatgctctat    780

attccgctac gtatacgtac tcaacgtcac ttggcttgtg aactccgccg cccacctgtg    840

gggcagcaag ccttacgaca agaacatcaa ccccgtggaa accagacccg tatcactcgt    900

agtactcggt gaaggattcc acaactacca tcacactttc ccttgggact acaaaactgc    960

agaactcggc gactactccc ttaacttcac caaaatgttc attgatttca tggccagtat   1020

cggatgggca tatgacctta agacagtctc gactgacgtc atccagaagc gcgtgaagag   1080

gaccggcgac ggtagccacg ctgtatgggg ctgggacgat cacgaggttc accaagagga   1140

caagaagtta gctgctataa tcaacccaga aaagactgaa taaccaaatt agtccataac   1200

acaattccat tagtttttag atcgacgggt gtatgcgtat tataccaatg tgagggaaat   1260

gtgataccag ttatatttta tttatttctt aattatttaa tttgacatga taatggttta   1320

tcaagacttt tagaattaat tattagattt ttaacaaaac aatgcccatc tgttttcatt   1380

cgacagaaaa taaaaataga ttttgttaaa aaaaaaaaaa aaaaaaaaaa aaaaaaaaa    1439
```

<210> SEQ ID NO 5
<211> LENGTH: 1206
<212> TYPE: DNA
<213> ORGANISM: Mortierella alpina

<400> SEQUENCE: 5

```
atggcacctc ccaacactat tgatgccggt ttgacccagc gccatatcag cacctcggcc     60
```

-continued

```
gccccaaact cggccaagcc caccttcgag cgcaactacc agctccctga gttcaccatc    120

aaggagatcc gagagtgcat ccctgcccat tgctttgagc gctctggtct tcgtggtctc    180

tgccacgttg ccattgatct gacctgggcc tcgctcttgt tcctggctgc aacccagatc    240

gacaagttcg agaacccctt gatccgctac ttggcctggc ctgtgtactg gatcatgcag    300

ggcattgtct gcaccggcat ctgggtattg gcccatgagt gcggtcatca gtcgttctcg    360

acctccaaga ccctcaacaa cactgttggc tggatcctgc actcgatgct cttggtccct    420

taccactcct ggagaatctc gcactcgaag caccacaagg ccactggcca catgactaag    480

gatcaggtct ttgttcccaa gacccgcacc caggttggct tgcctcccaa ggagagtgcc    540

gctgctaccg ttcaggagga ggaggacatg tcagtgcacc tggatgagga ggctcctatt    600

gtgactctgt tctggatggt gatccagttc ctgttcggct ggcccgcgta cctgattatg    660

aacgcctctg gtcaggacta tggccgctgg acctcgcatt tccacaccta ctcgcccatc    720

tttgaacccc gcaacttttt cgacattatc ctctcggatc tcggtgtgtt ggctaccctc    780

ggtgccttga tctacgcttc catgcagttg tcgctcttga ctgtgaccaa gtactacatt    840

atcccctacc tgtttgtcaa cttttggttg gtcctcatca cctttttgca gcacaccgac    900

cccaagctgc ctcattaccg tgagggtgcc tggaacttcc agcgtggagc tctctgcacg    960

gttgaccgct cgtttggcaa gttcttggac catatgttcc acggcattgt tcacacccat   1020

gtagcccatc acttgttctc gcagatgccg ttctaccatg ctgaggaagc cacataccat   1080

ctcaagaaac tgctgggaga gtactacatt tacgacgcat ccccgatcgt tgttgcggtc   1140

tggaagtcgt tccgggagtg ccgatttgtg gaggatcatg gagacgtggt ctttttcaag   1200

aagtaa                                                              1206
```

<210> SEQ ID NO 6
<211> LENGTH: 1191
<212> TYPE: DNA
<213> ORGANISM: Mucor rouxii

<400> SEQUENCE: 6

```
atggcaacca agagaaacgt tacctccaat gctcctgctg cagaagacat cagcatcagc     60

aacaaggctg tgattgatga agccattgaa agaaactggg agatccccaa tttcaccatc    120

aaggagatcc gtgatgctat cccagctcac tgtttccgtc gtgatacctt tagatccttt    180

acacatgttc ttcatgatat tatcatcatg cccatcttgg ccattggtgc ttcttacatt    240

gattccatcc ctaataccta tgctcgcatt gctctctggc ccttgtactg gatcgctcaa    300

ggtattgttg gcactggtgt ctgggtcatt ggtcatgaat gtggccatca agcattcagc    360

ccttcaaaga ctatcaataa tagcgttggt tacgttctcc acactgcttt attagtacct    420

tatcactcat ggagattctc tcactctaag catcataaag ccactggaca catgtcaaaa    480

gatcaggtct ttgtcccctc tactcgtaag gaatacggtt tgcctcctcg tgagcaagat    540

cctgaggttg atggacctca tgatgctctt gatgaagtcc cattgttgtc ttgtatcgca    600

tgttccttca atttaccttt ggctggcctc tttatctctt caccaatgtc tctggtcaag    660

attaccccgg ttgggcttct catttcaacc ccaagtgtgc tatctacgat tgaaaaccaa    720

ttctgggatg ttatgagctc caccgctggt gtccttggca tgattggttt cttggcttac    780

tgtggtcaag tcttggctct cttgctgtca tcaagtacta tgttattccc ctatttgaat    840

gttaactttt ggttggttct aatcacttac ttgcaacaca ctgatcccaa gttgcctcat    900
```

-continued

```
taccgtgaaa atgtttggaa cttccaacgc ggtgctgctt taactgttga tcgttcttat    960

ggcttcctcc tcgactactt ccatcatcac atttctgata ctcatgttgc tcaccatttc   1020

ttctccacca tgcctcacta ccacgctgaa gaagctactg ttcatatcaa gaaggctctt   1080

ggtaagcact accactgcga caacacacct gtccctatcg ccttgtggaa ggtctggaag   1140

agctgtcgtt ttgttgaaga tgagggcgat gttgtcttct ttaagaacta a            1191
```

<210> SEQ ID NO 7
<211> LENGTH: 1366
<212> TYPE: DNA
<213> ORGANISM: Mucor circinelloides

<400> SEQUENCE: 7

```
attttccttc tttctttgtt caggggccaa attaccacct taaattaaac attgccatgg     60

caaccaagag aaacgttacc tccaatgctc ctgctgcaga agacatcagc atcagcaaca    120

aggctgtgat tgatgaagcc attgaaagaa actgggagat ccccaatttc accatcaagg    180

agatccgtga tgctatccca gctcactgtt tccgtcgtga tacctttaga tcctttacac    240

atgttcttca tgatattatc atcatgtcca tcttggccat tggtgcttct tacattgatt    300

ccatccctaa tacctatgct cgcattgctc tctggccctt gtactggatc gctcaaggta    360

ttgttggcac tggtgtctgg gtcattggtc atgaatgtgg ccatcaagca ttcagccctt    420

caaagactat caataatagc gttggttacg ttctccacac tgctttatta gtaccttatc    480

actcatggag attctctcac tctaagcatc ataaagccac tggacacatg tcaaaagatc    540

aggtctttgt cccctctact cgtaaggaat acggtttgcc tcctcgtgag caagatcctg    600

aagttgatgg acctcatgat gctcttgatg aagctcccat tgttgtcttg tatcgcatgt    660

tccttcaatt tacctttggc tggcctcttt atctcttcac caatgtctct ggtcaagatt    720

accccggttg ggcttctcat ttcaacccca agtgtgctat ctacgatgaa aaccaattct    780

gggatgttat gagctccacc gctggtgtcc ttggcatgat tggtttcttg gcttactgtg    840

gtcaagtctt tggctctctt gctgtcatca agtactatgt tattccctat ttgaatgtta    900

acttttggtt ggttctaatc acttacttgc aacacactga tcccaagttg cctcattacc    960

gtgaaaatgt ttggaacttc caacgcggtg ctgctttaac tgttgatcgt tcttatggtt   1020

tcctcctcga ctacttccat catcacattt ctgacactca tgttgctcac catttcttct   1080

ccaccatgcc tcactaccac gctgaagaag ctactgttca tatcaagaag gctcttggta   1140

agcactacca ctgcgacaac actcctgtcc ctatcgcctt gtggaaggtc tggaagagtt   1200

gccgttttgt tgaagatgag ggcgatgttg tcttctttaa gaactaaaca tttaattatt   1260

tattttcttt ttatacatat atattctcta ctataaagca acccaaacat cttgcatcca   1320

aataaactat aacattctac ataaaaaaaa aaaaaaaaaa aaaaaa                  1366
```

<210> SEQ ID NO 8
<211> LENGTH: 1275
<212> TYPE: DNA
<213> ORGANISM: Aspergillus fumigatus

<400> SEQUENCE: 8

```
atggcttcgg atgccgagaa gaccagcagc aagatgattg acacctatgg taacgagttc     60

aaaattcccg attacaccat caagcagatc cgggatgcca tccctgctca ctgctaccaa    120

cgctcggctg ccacgagttt gtactatgtc ttccgggaca tggccatcct tgcgagtgtc    180

ttctatgtct tccacaacta tgtcaccccc gagaccgtgc cctccatgcc ggtgcgcgtc    240
```

-continued

```
gtcctgtgga ccatttatac cgtcgttcaa ggtctagtcg gcaccggtgt ttgggttctg    300
gcgcacgagt gcggtcacca ggctttctcc acttccaagg tcttgaacga cactgttgga    360
tggatctgcc actctcttct gctcgtccct tacttctcct ggaagatctc tcacggcaag    420
caccacaagg ccaccggtaa catcgctcgc gatatggtct tcgttcccaa gaccagggaa    480
gaatatgcca ctcgcatcgg tcgtgccgcc catgagctca gtgaattgat ggaggagacc    540
cccatcctga ccgcaaccaa cctcgttctt cagcagctgt tcggatggcc catgtacctc    600
ttgaccaatg ttaccggcca caacaaccac gagcggcagc ccgagggacg cggcaagggc    660
aagcggaacg gctactttgg tggtgtcaac cacttcaacc cttccagccc cctgtatgag    720
gccaaggatg ccaagctgat cgtcctgagc gatctcggtc tcttccttgt gggaagcctc    780
ctctactata tcggatcaac ctatggctgg ctcaacctcc ttgtctggta cggcattcct    840
tacctctggg taaaccactg gctcgttgcc atcactttcc ttcagcacac cgaccccacc    900
ctcccccact accagcctga ggcctgggat ttcactcgtg gagcagctgc tacaattgac    960
cgtgacttcg gcttcgtcgg tcgccacatc ttccacggca tcatcgagac ccacgttctt   1020
caccactatg tcagcaccat cccctttctac cacgctgatg aggccagcga ggccatccag   1080
aaggtcatgg gaccacacta ccgcagcgag gctcacaccg gctggactgg cttcctcaag   1140
gccctctgga ccagcgctcg cacctgccag tgggttgagc ccaccgaggg cgccaagggc   1200
gaaagccagt acgttctttt ctaccgcaac atcaacggca tcggtgtccc tcctgccaag   1260
attcccgcca aatag                                                    1275
```

<210> SEQ ID NO 9
<211> LENGTH: 1341
<212> TYPE: DNA
<213> ORGANISM: Cryptococcus curvatus

<400> SEQUENCE: 9

```
atgtctgccg ccaccctgcg ccagcgtaac gtcgacaagc caggtgctgc cgacaaggcc     60
gagctcctcc gtgaagccga ggacctcgag ctcaccgagg gccagaagtt tgtcgggccc    120
aactttaccg tcaagcagct cttggacgcc attcccgccc actgctacaa gcgctcggcg    180
ttcaagtcgt cgctttacgt cctccaggac tttgtcctcc tcgccgccct cgtctacggc    240
gcctaccaca ttgactcctt cttgagccgc ttcaaccttg gctcggttgc ccacaccgcc    300
gccaagatcg gcctctggtt cacctaccag gtccttgccg gcatggtcgg taccggtatc    360
tgggttatcg cccacgaatg cggccaccag gcctactccg agtccaagac gatcaacaac    420
gccgtcggct gggtcctcca ctcgatcctt cttgtgcctt accactcgtg gcgcatctcg    480
cacggccgtc accacgccgc caccggccac cttacccgtg acgaggtctt tgttccccgc    540
acccgcgagc agctcggcat ccaggccccc aagactgagg aggagaagaa gggcatcaac    600
gtccccgctt ggcgccaggc tgagcttcgt gaggccctcg aggagtcgcc tatcggtgcg    660
ctctacggtg ccatcctcca ccagctcttc ggctggccca tgtacctcat ccgcaacgcg    720
tccggccagc tctggtaccc caagatgacc aaccacttcc agccgtcgtc gatcatcttc    780
aagccctcgc acttctggca gatcattgct tcggacattg gtgttgttct caccgccgcc    840
gccctcggcg tctttgtcta ctaccgtggc tttgccgaga tggctcgcat ctacctcatc    900
ccctacctct gggtgaacca ctggcttgtc ttcatcacct tcctgcagca caccgacccc    960
gttctccccc actactcgga gaagacttgg acctttgccc gtggcgccct ggcgaccatt   1020
```

-continued gaccgcaact gcctcggccc cgtcggcccc tacctcttcc acggcatcac cgagacgcac 1080
gtcgcgcacc acacctcgtc gcgcatcccc cactacaacg cgtgggaggc gaccgaggcc 1140
ctcaagaagt tcctcggccc ccactaccac tacaaccccg agaacatgtt cgtgtccttc 1200
tggaaggccc accgctactg caagttcatc gaggcgggcg aagacgtcgc cttctaccgc 1260
aacgccgctg gtgtcgcgca gaaggtcggc atcatcgagg agaacggcgc ggtgtccgac 1320
tcgggcgtcg agcacaagta a 1341

<210> SEQ ID NO 10
<211> LENGTH: 1253
<212> TYPE: DNA
<213> ORGANISM: Caenorhabditis elegans

<400> SEQUENCE: 10
aaacttggcc cccgacgaag atgacaatcg ctacaaaagt gaacacaaat aaaaaggacc 60
ttgatacaat caaggtaccg gagcttccat cagtggcagc tgtcaaagca gcaatccctg 120
agcactgctt tgtcaaggat ccattgactt caatttcata tcttatcaag gattacgtac 180
ttctcgctgg tctctatttt gcagttccat acattgagca ttatctcgga tggatcgggc 240
ttcttggatg gtattgggca atgggaattg ttggatccgc attgttctgt gtgggtcatg 300
actgtggaca tggatcattc tccgattatg aatggctcaa tgatctttgt ggacatttgg 360
ctcatgctcc aattcttgct ccattctggc catggcaaaa gtctcataga caacatcatc 420
aatacacatc ccacgtggaa aaggataagg gacatccatg ggttactgag gaagactaca 480
ataatagaac tgctattgag aagtatttcg ctgtgattcc aatttccgga tggcttcgat 540
ggaatccaat ctacaccatc gtcggtcttc cagatggatc tcatttctgg ccatggtccc 600
ggctcttcga gactactgag gatcgtgtca agtgtgcagt ttctggagtt gcatgcgcta 660
tctgtgctta cattgccttt gtcctctgcg actattctgt ctacacattt gtcaagtact 720
actacattcc acttctcttc caaggactta ttctcgtcat tatcacatat cttcaacatc 780
agaatgagga tattgaggtc tacgaagctg atgagtgggg atttgtacgc ggacaaaccc 840
aaactatcga cagacactgg ggattcggac tcgacaacat catgcacaac attaccaacg 900
gtcacgtcgc ccatcacttc ttcttcacca aaatcccaca ttatcatctg ttggaggcaa 960
ctccagcaat caagaaagct cttgaaccac tgaaagacac tcaatacgga tacaaacgag 1020
aagtcaacta taactggttc ttcaagtatc ttcactacaa cgttaccctc gactatttga 1080
ctcataaagc aaagggtgtc ctgcaataca gaagtggagt tgaggctgca aaggctaaga 1140
aggctcaata aactacaaaa tctcctgaca cgtgttcatt ttttttgatt gccattttat 1200
gttataacca attttgaatt tgtttttgaa aattaattct cacatatttc aat 1253

<210> SEQ ID NO 11
<211> LENGTH: 1374
<212> TYPE: DNA
<213> ORGANISM: Mortierella alpina

<400> SEQUENCE: 11
atggctgctg ctcccagtgt gaggacgttt actcgggccg agattctgaa tgccgaggcc 60
ctgaatgaag gcaagaagga tgctgaggca cccttcctga tgatcatcga caacaaggtg 120
tacgatgtcc gcgagtttgt ccctgatcat cccggtggaa gtgtgattct cacgcacgtt 180
ggcaaggacg gcactgacgt ctttgacact ttccaccccg aggctgcttg ggagactctt 240
gccaactttt acgttggtga tattcatgag agcgaccgcg acatcaagaa tgatgacttt 300
gcggccgagg ttcgcaagct gcgtaccttg ttccagtctc ttggctacta cgattcttcc 360
aaggcatact acgccttcaa ggtctcgttc aacctctgca tctggggcct gtcgacattc 420
gttgttgcca agtggggcca gacctcgacc ctcgccaatg tagtttcggc tgcgcttttg 480
ggtctcttct ggcagcagtg cggatggttg gcgcacgact ttttgcatca ccaggtcttc 540
caggatcgtt tctggggcga tcttttcggt gccttcttgg gaggtgtctg ccagggtttc 600
tcatcctcct ggtggaagga caagcacaac actcaccacg ccgctcccaa cgtccacggt 660
gaggatcccg acattgacac tcaccctctg ttgacctgga gtgagcatgc tctggagatg 720
ttctcggatg tccctgacga ggagctgacc cgcatgtggt cgcgcttcat ggtcctcaac 780
cagacctggt tctacttccc cattctctcg tttgcccgtc tctcctggtg cctccagtct 840
attctctttg ttatgcctaa cggtcaggcc cacaagccct cgggtgcgcg tgtgcccatt 900
tccttggtcg agcagctgtc tctcgctatg cactggacct ggtacctcgc caccatgttc 960
ctgttcgtga aggatcccat caacatgttt gtgtactttt tggtatcgca ggctgtttgc 1020
ggcaacttgt tggcgcttgt gttctcactc aaccacaacg gtatgcctgt gatttccaag 1080
gaggaggcag tcgatatgga tttcttcacc aagcagatca tcacgggtcg tgatgtccac 1140
cctggtctgt ttgccaactg gttcacaggt ggattgaact accagattga gcatcacttg 1200
ttcccttcga tgccccgcca caacttttca aagatccagc ctgctgtcga gaccctgtgc 1260
aaaaagtaca atgtccgata ccacaccacc ggcatgattg agggaactgc agaggtcttt 1320
agccgtctga acgaggtctc cagggctgcc tccaagatgg gcaaggcaca gtaa 1374

<210> SEQ ID NO 12
<211> LENGTH: 1572
<212> TYPE: DNA
<213> ORGANISM: Mucor rouxii

<400> SEQUENCE: 12
atgcccccaa atactgcggc tgatagacta ctatcatcaa cctcaacgcg ttcatccaac 60
attgtcacag aagaaaagtt tcaagagctg atcaagcagg gagactctgt ctttatctat 120
gaacaaaaag tatatagagt caacaacttt atggccaaac atccaggcgg tgaggcagca 180
ctgagaagtg cattgggcag agatgtcacg gatgaaatcc gtaccatgca tccaccacag 240
gtatatgaaa agatgatcaa cttgtattgc attggcgact acatgccaga tgtgataagg 300
cccgcatcca tgaaacagca acacacattt acaaagccaa aggaggacaa gccagtgcta 360
acagcgacat gggaaggcgg tttcactgtg caagcatacg atgatgccat tcaagatctg 420
cataaacacc actcacacga cttgattaaa gatgcagtac ttcaaaaaga tttaaacggt 480
gatcaaatta gaaatgcata cagaaaatta gaagccgaac tatacgcgaa gggattattc 540
aaatgcaatt actggaagta cgcaagagaa ggatgtcgat acacactgct tatatttcta 600
tcgctgtggt ttacactaaa gggcaccgag acatggcact atatggcagg cgctgcgttc 660
atggctatgt tttggcatca gcttgtgttt acagcccatg atgcgggcca caatgaaatt 720
actggcaagt ctgaaatcga ccatgttatt ggtgtcatta tcgcaaactt tataggtggg 780
ctcagtttgg gctggtggaa ggataatcac aacgtgcatc atattgtgac aaatcatcca 840
gagcacgatc ccgatatcca gcatgtgcct ttcatggcca tcaccaccaa attcttcaac 900
aatatctatt ccacctacta caagcgtgtg ctgccgtttg atgctgcttc tcgcttcttt 960
gtcagacacc agcactactt gtattacctc atcctgtcct ttggtagatt caatttacat 1020

-continued

```
cgattatcat ttgcttacct tttgacttgc aagaatgtcc gtacaagaac gttggagctg   1080

gtcggtatta cctttttctt tgtttggttt ggctcgctgt tatctacttt gcctacttgg   1140

aatatccgta ttgcttatat tatggtctcg tatatgctga cattccctct tcatgtgcaa   1200

attacattgt cccatttcgg catgtcaacc gaggacagag gcccagacga accattcccc   1260

gctaaaatgt tgcgtactac aatggatgtt gattgtccag agtggcttga ctggttccac   1320

ggtggtctgc aatatcaggc agtgcatcat ttattcccta gactgcctcg tcataatttg   1380

cgtcaatgcg tacctttggt caaaaagttc tgtgatgagg tggggcttca ttattacatg   1440

tataatttct ctactggaaa cggtgtggtt ttgggcacat tgaaatctgt ggctgatcaa   1500

gttggcttta tgaatgaagt ggccaaaagt aacgccgaga tttgggctaa tgataaagaa   1560

cacgctcatt ag                                                       1572
```

```
<210> SEQ ID NO 13
<211> LENGTH: 1687
<212> TYPE: DNA
<213> ORGANISM: Borago officinalis

<400> SEQUENCE: 13

tatctgccta ccctcccaaa gagagtagtc atttttcatc aatggctgct caaatcaaga     60

aatacattac ctcagatgaa ctcaagaacc acgataaacc cggagatcta tggatctcga    120

ttcaagggaa agcctatgat gtttcggatt gggtgaaaga ccatccaggt ggcagctttc    180

ccttgaagag tcttgctggt caagaggtaa ctgatgcatt tgttgcattc catcctgcct    240

ctacatggaa gaatcttgat aagtttttca ctgggtatta tcttaaagat tactctgttt    300

ctgaggtttc taaagattat aggaagcttg tgtttgagtt ttctaaaatg ggtttgtatg    360

acaaaaaagg tcatattatg tttgcaactt tgtgctttat agcaatgctg tttgctatga    420

gtgtttatgg ggttttgttt tgtgagggtg ttttggtaca tttgttttct gggtgtttga    480

tggggtttct ttggattcag agtggttgga ttggacatga tgctgggcat tatatggtag    540

tgtctgattc aaggcttaat aagtttatgg gtatttttgc tgcaaattgt ctttcaggaa    600

taagtattgg ttggtggaaa tggaaccata atgcacatca cattgcctgt aatagccttg    660

aatatgaccc tgatttacaa tatataccat tccttgttgt gtcttccaag tttttttggtt   720

cactcacctc tcatttctat gagaaaaggt tgacttttga ctctttatca agattctttg    780

taagttatca acattggaca ttttacccta ttatgtgtgc tgctaggctc aatatgtatg    840

tacaatctct cataatgttg ttgaccaaga gaaatgtgtc ctatcgagct catgaactct    900

tgggatgcct agtgttctcg atttggtacc cgttgcttgt ttcttgtttg cctaattggg    960

gtgaaagaat tatgtttgtt attgcaagtt tgtcagtgac tggaatgcaa caagttcagt   1020

tctccttgaa ccacttctct tcaagtgttt atgttggaaa gcctaaaggg aataattggt   1080

ttgagaaaca aacggatggg acacttgaca tttcttgtcc tccttggatg gattggtttc   1140

atggtggatt gcaattccaa attgagcatc atttgtttcc caagatgcct agatgcaacc   1200

ttaggaaaat ctcgccctac gtgatcgagt tatgcaagaa acataatttg ccttacaatt   1260

atgcatcttt ctccaaggcc aatgaaatga cactcagaac attgaggaac acagcattgc   1320

aggctaggga tataaccaag ccgctcccga agaatttggt atgggaagct cttcacactc   1380

atggttaaaa ttacccttag ttcatgtaat aatttgagat tatgtatctc ctatgtttgt   1440

gtcttgtctt ggttctactt gttggagtca ttgcaacttg tcttttatgg tttattagat   1500

gtttttaat atattttaga ggttttgctt tcatctccat tattgatgaa taaggagttg    1560
```

-continued catattgtca attgttgtgc tcaatatctg atattttgga atgtactttg taccactgtg 1620
ttttcagttg aagctcatgt gtacttctat agactttgtt taaatggtta tgaaaaaaaa 1680
aaaaaaa 1687

<210> SEQ ID NO 14
<211> LENGTH: 1341
<212> TYPE: DNA
<213> ORGANISM: Anemone levellei

<400> SEQUENCE: 14
atggcagaga agagaagaag catttcttct gatgacctga ggagtcacaa caagcctgga 60
gacgtatgga tctccattca aggtaagatc tacgatgtta ccgaatgggg taaagaccat 120
cctggaggtg aaggtccttt gctaaatctg gctgggcaag atgtcacaga tgcatttgta 180
gctttccatc ctggttctgc ttggaaaaat ctcgataagt ttcatatcgg gtatttacaa 240
gattatgtag tttctgacgt gtccaaagat tatcggaaac ttgtttctga gttttcgaaa 300
gccggtctct acgagaaaaa agggcacggg cacctgattc gacttctggt catgagttta 360
gtgtttatag ctagcgtttc gggtgttgta ttatctgata aaacttctgt tcatgttggc 420
tctgctgttt tgttggctgt tatttggatg cagtttggat ttataggtca tgattcaggc 480
cattacaata tcatgactag cccggaactg aacagataca tgcagatatt ttcagtaaac 540
gtcgtttcag ggtgagcgt cggatggtgg aagcggtatc acaatgcaca tcacattgca 600
gtcaatagtc tggaatatga tccagatctt cagtatgttc ccttcttagt ggtatctacc 660
gccattttcg attcactcac atctcatttt taccgaaaga aaatgacatt tgatgctgtt 720
gcaaggtttc tagttagctt ccagcattgg actttttatc cactgatggc tattgggagg 780
gttagttttt tggcgcagtc aattggagtg ttgctatcca agaaaccgct gccggataga 840
catttggagt ggtttggttt ggtggtgttt tgggcttggt attcacttct aatttcttgc 900
ttgccgaatt ggtgggaaag agtgattttt attgcagtca actttgccgt cactggaatt 960
cagcatgttc agttctgtct aaaccattac tcagctcaaa cttacatcgg tgctccttgc 1020
gcgaatgatt ggttcgagaa gcagactaaa ggttcgatcg acatatcatg ttcgccttgg 1080
acggattggt ttcacggcgg gttacagttt cagattgagc atcatttgtt ccctagaatg 1140
cctcggtgca atttaagaaa gatttcaccc tttgtgaagg aactttgcag gaagcacaac 1200
ttggtttata ccagtgtatc attcttcgag ggcaatcgga ggactctcgc aactctgaag 1260
aatgcagctt tgaaggcgcg tgatctcacc agcccaattc cgaagaattt ggtttgggag 1320
gccgtccaca cacacggata a 1341

<210> SEQ ID NO 15
<211> LENGTH: 1332
<212> TYPE: DNA
<213> ORGANISM: Caenorhabditis elegans

<400> SEQUENCE: 15
atggtcgtcg acaagaatgc ctccgggctt cgaatgaagg tcgatggcaa atggctctac 60
cttagcgagg aattggtgaa gaaacatcca ggaggagctg ttattgaaca atatagaaat 120
tcggatgcta ctcatatttt ccacgctttc cacgaaggat cttctcaggc ttataagcaa 180
cttgaccttc tgaaaaagca cggagagcac gatgaattcc ttgagaaaca attggaaaag 240
agacttgaca aagttgatat caatgtatca gcatatgatg tcagtgttgc acaagaaaag 300

-continued

```
aaaatggttg aatcattcga aaaactacga cagaagcttc atgatgatgg attaatgaaa    360

gcaaatgaaa catatttcct gtttaaagca atttcaacac tttcaattat ggcatttgca    420

ttttatcttc agtatcttgg atggtatatt acttctgcat gtttattagc acttgcatgg    480

caacaattcg gatggttaac acatgagttc tgccatcaac agccaacaaa gaacagacct    540

ttgaatgata ctatttcttt gttctttggt aatttcttac aaggattttc aagagattgg    600

tggaaggaca agcataacac tcatcacgct gccacaaatg taattgatca tgacggtgat    660

atcgacttgg caccactttt cgcatttatt ccaggagatt tgtgcaagta taaggccagc    720

tttgaaaaag caattctcaa gattgtacca tatcaacatc tctatttcac cgcaatgctt    780

ccaatgctcc gtttctcatg gactggtcag tcagttcaat gggtattcaa agagaatcaa    840

atggagtaca aggtctatca aagaaatgca ttctgggagc aagcaacaat tgttggacat    900

tgggcttggg tattctatca attgttctta ttaccaacat ggccacttcg ggttgcttat    960

ttcattattt cacaaatggg aggaggcctt ttgattgctc acgtagtcac tttcaaccat   1020

aactctgttg ataagtatcc agccaattct cgaattttaa acaacttcgc cgctcttcaa   1080

attttgacca cacgcaacat gactccatct ccattcattg attggctttg ggtggactc   1140

aattatcaga tcgagcacca cttgttccca acaatgccac gttgcaatct gaatgcttgc   1200

atgaaatatg tgaaagaatg gtgcaaagag aataatcttc cttacctcgt cgatgactac   1260

tttgacggat atgcaatgaa tttgcaacaa ttgaaaaata tggctgagca cattcaagct   1320

aaagctgcct aa                                                        1332
```

<210> SEQ ID NO 16
<211> LENGTH: 957
<212> TYPE: DNA
<213> ORGANISM: Mortierella alpina

<400> SEQUENCE: 16

```
atggagtcga ttgcgcaatt cctgccatca aagatgccgc aagatctgtt tattgacctt     60

gctgcagcca tcggagtccg agccgcacct tatgtcgacc ctctcgaggc cgcgcttgtg    120

gcccaggccg agaagtacat tcctacgatc gtccatcaca cgcgtgggtt cctggttgcg    180

gtcgagtcac ctttggtccg tgagctgccg ttgatgaacc ccttccacgt gctgctgatc    240

gtgctcgcct acctggtcac ggtctttgtg gggatgcaga tcatgaagaa ctttgatcgg    300

ttcgaggtca agacattctc gctcttccac aacttttgtc tggtctcaat cagcgcctac    360

atgtgcggtg ggatcctgta cgaggcttac caggccaact atggactgtt tgagaacgct    420

gccgatcata ctgccaaggg ttttcctatg gccaagatga tctggctctt ctacttctcc    480

aagatcatgg agtttgtcga caccatgatc atggtcctca agaagaacaa ccgtcagatc    540

tcattcttgc acgtttacca tcacagctcc atcttcacca tctggtggtt ggtcaccttt    600

gttgcaccca acggtgaagc ctacttctct gctgcgttga actcgttcat ccatgtgatc    660

atgtacggtt actacttctt gtcggccttg ggcttcaagc aggtgtcgtt cgtcaagttc    720

tacattacgc gttcgcagat gactcagttc tgcatgatgt cgatccaatc ctcctgggat    780

atgtatgcca tgaaggtcct gggtcgcccc ggatacccat tcttcatcac cgccctgctt    840

tggttctaca tgtggaccat gctcggtctc ttctacaact tctacagaaa gaacgccaag    900

ttggccaagc aggccaaggc cgatgctgcc aaggagaagg caaggaagtt gcagtaa       957
```

<210> SEQ ID NO 17
<211> LENGTH: 1192

-continued

<212> TYPE: DNA
<213> ORGANISM: Physcomitrella patens

<400> SEQUENCE: 17

```
ctgcttcgtc tcatcttggg ggtgtgattc gggagtgggt tgagttggtg gagcgcaatg     60
gaggtcgtgg agagattcta cggtgagttg gatgggaagg tctcgcaggg cgtgaatgca    120
ttgctgggta gttttggggt ggagttgacg gatacgccca ctaccaaagg cttgcccctc    180
gttgacagtc ccacacccat cgtcctcggt gtttctgtat acttgactat tgtcattgga    240
gggcttttgt ggataaaggc cagggatctg aaaccgcgcg cctcggagcc atttttgctc    300
caagctttgg tgcttgtgca caacctgttc tgttttgcgc tcagtctgta tatgtgcgtg    360
ggcatcgctt atcaggctat tacctggcgg tactctctct ggggcaatgc atacaatcct    420
aaacataaag agatggcgat tctggtatac ttgttctaca tgtctaagta cgtggaattc    480
atggataccg ttatcatgat actgaagcgc agcaccaggc aaataagctt cctccacgtt    540
tatcatcatt cttcaatttc cctcatttgg tgggctattg ctcatcacgc tcctggcggt    600
gaagcatatt ggtctgcggc tctgaactca ggagtgcatg ttctcatgta tgcgtattac    660
ttcttggctg cctgccttcg aagtagccca aagttaaaaa ataagtacct tttttggggc    720
aggtacttga cacaattcca aatgttccag tttatgctga acttagtgca ggcttactac    780
gacatgaaaa cgaatgcgcc atatccacaa tggctgatca agattttgtt ctactacatg    840
atctcgttgc tgtttctttt cggcaatttt tacgtacaaa aatacatcaa accctctgac    900
ggaaagcaaa agggagctaa aactgagtga gctgtatcaa gccatagaaa ctctattatg    960
ttagaacctg aagttggtgc tttcttatct ccacttatct tttaagcagc atcagttttg   1020
aaatgatgtg tgggcgtggt ctgcaagtag tcatcaatat aatcggcctg agcacttcag   1080
atggattgtt agaacatgag taaaagcggt tattacggtg tttattttgt accaaatcac   1140
cgcacgggtg aattgaaata tttcagattt gatcaatttc atctgaaaaa aa           1192
```

<210> SEQ ID NO 18
<211> LENGTH: 867
<212> TYPE: DNA
<213> ORGANISM: Caenorhabditis elegans

<400> SEQUENCE: 18

```
atggctcagc atccgctcgt tcaacggctt ctcgatgtca aattcgacac gaaacgattt     60
gtggctattg ctactcatgg gccaaagaat ttccctgacg cagaaggtcg caagttcttt    120
gctgatcact ttgatgttac tattcaggct tcaatcctgt acatggtcgt tgtgttcgga    180
acaaaatggt tcatgcgtaa tcgtcaacca ttccaattga ctattccact caacatctgg    240
aatttcatcc tcgccgcatt ttccatcgca ggagctgtca aaatgacccc agagttcttt    300
ggaaccattg ccaacaaagg aattgtcgca tcctactgca aagtgtttga tttcacgaaa    360
ggagagaatg gatactgggt gtggctcttc atggcttcca aacttttcga acttgttgac    420
accatcttct tggttctccg taaacgtcca ctcatgttcc ttcactggta tcaccatatt    480
ctcaccatga tctacgcctg gtactctcat ccattgaccc caggattcaa cagatacgga    540
atttatctta actttgtcgt ccacgccttc atgtactctt actacttcct tcgctcgatg    600
aagattcgcg tgccaggatt catcgcccaa gctatcacat ctcttcaaat cgttcaattc    660
atcatctctt gcgccgttct tgctcatctt ggttatctca tgcacttcac caatgccaac    720
tgtgatttcg agccatcagt attcaagctc gcagttttca tggacacaac atacttggct    780
```

-continued

```
cttttcgtca acttcttcct ccaatcatat gttctccgcg gaggaaaaga caagtacaag    840

gcagtgccaa agaagaagaa caactaa                                        867
```

<210> SEQ ID NO 19
<211> LENGTH: 900
<212> TYPE: DNA
<213> ORGANISM: Mus musculus

<400> SEQUENCE: 19

```
atggaacatt tcgatgcgtc actcagtacc tatttcaagg ccttcctggg cccccgagat     60

acaagagtca aaggatggtt cctcctggac aattacatcc ctacgtttgt ctgttctgtt    120

atttacttac tcattgtatg gctgggacca aaatacatga agaaccggca gccgttctct    180

tgccgaggca tcctgcagtt gtataacctt ggactcaccc tgctgtctct ctacatgttc    240

tatgagttgg tgacaggtgt gtgggagggc aaatacaact ttttctgcca gggaacacgc    300

agcgcgggag aatccgatat gaagatcatc cgcgtcctct ggtggtacta cttctccaaa    360

ctcatcgaat tcatggacac ctttttcttc atccttcgca agaacaacca ccagatcacc    420

gtgctccatg tctaccacca cgctaccatg ctcaacatct ggtggtttgt gatgaactgg    480

gttccctgcg gccattcata ttttggtgcg acactcaaca gcttcatcca tgtcctcatg    540

tactcgtact atggtctgtc ctccatcccg tccatgcgtc cctacctctg gtggaaaaag    600

tacatcactc aagggcagct ggtccagttt gtgctgacaa tcatccagac gacctgcggg    660

gtcttctggc catgctcctt ccctctcggg tggctgttct tccagattgg atacatgatt    720

tccctgattg ctctcttcac aaacttctac attcagactt acaacaagaa aggggcctct    780

cggaggaaag accacctgaa gggccaccag aacgggtctg tggccgccgt caacggacac    840

accaacagct tcccttccct ggaaaacagc gtgaagccca ggaagcagcg aaaggattga    900
```

<210> SEQ ID NO 20
<211> LENGTH: 819
<212> TYPE: DNA
<213> ORGANISM: Thraustochytrium aureum

<400> SEQUENCE: 20

```
atggcaaaca gcagcgtgtg ggatgatgtg gtgggccgcg tggagaccgg cgtggaccag     60

tggatggatg gcgccaagcc gtacgcactc accgatgggc tcccgatgat ggacgtgtcc    120

accatgctgg cattcgaggt gggatacatg gccatgctgc tcttcggcat cccgatcatg    180

aagcagatgg agaagccttt tgagctcaag accatcaagc tcttgcacaa cttgtttctc    240

ttcggacttt ccttgtacat gtgcgtggag accatccgcc aggctatcct cggaggctac    300

aaagtgtttg gaaacgacat ggagaagggc aacgagtctc atgctcaggg catgtctcgc    360

atcgtgtacg tgttctacgt gtccaaggca tacgagttct tggataccgc catcatgatc    420

ctttgcaaga agttcaacca ggtttccttc ttgcatgtgt accaccatgc caccattttt    480

gccatctggt gggctatcgc caagtacgct ccaggaggtg atgcgtactt ttcagtgatc    540

ctcaactctt tcgtgcacac cgtcatgtac gcatactact tcttctcctc ccaagggttc    600

gggttcgtga agccaatcaa gccgtacatc accacccttc agatgaccca gttcatggca    660

atgcttgtgc agtccttgta cgactacctc ttcccatgcg actacccaca ggctcttgtg    720

cagctccttg gagtgtacat gatcaccttg cttgccctct tcggcaactt ttttgtgcag    780

agctatctta aaaagccaaa aaagagcaag accaactaa                           819
```

-continued

<210> SEQ ID NO 21
<211> LENGTH: 1066
<212> TYPE: DNA
<213> ORGANISM: Phytophthora infestans

<400> SEQUENCE: 21
gaattcggca cgaggttcgc acgtccatcg tctactcacc aacaagaagt catgtcgact 60
gagctactgc agagctacta cgcgtgggcc aacgccacgg aggccaagct gctggactgg 120
gtcgaccctg agggcggctg gaaggtgcat cctatggcag actacccccct agccaacttc 180 tccagcgtct acgccatctg cgtcggatac ttgctcttcg taatcttcgg cacggccctg 240
atgaaaatgg gagtccccgc catcaagacc agtccattac agtttgtgta caaccccatc 300
caagtcattg cctgctctta tatgtgcgtg gaggccgcca tccaggccta ccgcaacggc 360
tacaccgccg ccccgtgcaa cgcctttaag tccgacgacc ccgtcatggg caacgttctg 420
tacctcttct atctctccaa gatgctcgac ctgtgcgaca cagtcttcat tatcctagga 480
aagaagtgga aacagctttc catcttgcac gtgtaccacc accttaccgt gcttttcgtc 540
tactatgtga cgttccgcgc cgctcaggac ggggactcat atgctaccat cgtgctcaac 600
ggcttcgtgc acaccatcat gtacacttac tacttcgtca gcgcccacac gcgcaacatt 660
tggtggaaga agtacctcac gcgcattcag cttatccagt tcgtgaccat gaacgtgcag 720
ggctacctga cctactctcg acagtgccca ggcatgcctc ctaaggtgcc gctcatgtac 780
cttgtgtacg tgcagtcact cttctggctc ttcatgaatt tctacattcg cgcgtacgtg 840
ttcggcccca agaaaccggc cgtggaggaa tcgaagaaga agttgtaacg gcgcttgtta 900
aaaagtctaa cctcgctgta acagcttaaa acacacacac acacaacgct ttgtagagga 960
ggtaagtagt ggcaactcgt gtagaaatgc agcatgccca tcaaatacat cccgtatgat 1020
tcaaaaaaaa aaaaaaaaaa aaaaaaaaaa aaaaaaaaaa ctcgag 1066

<210> SEQ ID NO 22
<211> LENGTH: 1341
<212> TYPE: DNA
<213> ORGANISM: Mortierella alpina

<400> SEQUENCE: 22
atgggtacgg accaaggaaa aaccttcacc tgggaagcgc tggcagccca caacgccgag 60
ggcgacctac ttttggccat ccgtggcaat gtgtacgatg ttacaaagtt cttgagccgc 120
catcctggtg gaacggatac gctcctgctc ggagctggcc gagatgtcac tccggtcttt 180
gagatgtatc acgagtttgg ggctgcagat gctatcatga agaagtatta tgtcggcaca 240
ctggtctcga acgagctacc catcttcccg gagccaacgg tgttccacaa gaccatcaag 300
accagagtcg agggctactt caaggatcgg aacaaggacc ccaagaacag accggagatc 360
tggggacgat atgcccttat ctttggatcc ttgatcgcct cctactacgc gcagctcttt 420
gtaccgttcg tcgtcgagcg cacatggctc caggtggtgt ttgcaatcat tatgggattt 480
gcgtgcgcac aagtcggact caaccctctt catgatgcct ctcacttttc agtgacccat 540
aaccccactg tctggaagat tctcggagcc acgcacgact ttttcaacgg agcgtcgtat 600
cttgtgtgga tgtaccaaca tatgctcggt catcacccct ataccaacat tgctggagca 660
gatcccgatg tgtcgacctc tgagcccgat gttcgtcgta tcaagcccaa ccaaaagtgg 720
tttgttaacc acattaacca gcacatgttt gttcctttcc tgtacggact gttggcgttc 780
aaggtgcgaa ttcaggacat caacatcctg tactttgtca agaccaatga tgccatccgt 840

-continued

```
gtcaacccca tctcgacatg gcacactgtc atgttctggg gtggaaaggc cttctttgtg     900

tggtaccgct tgattgttcc cctgcagtat ctgcccctgg gcaaggtgct gctcttgttc     960

acaatcgcgg acatggtctc atcttactgg ctggcactga ccttccaggc gaaccacgtt    1020

gttgaggaag tccagtggcc gttgcctgac gagaatggaa ttatccaaaa ggactgggca    1080

gctatgcagg tcgagaccac gcaggattac gcacacgact cgcacctctg gaccagcatc    1140

acaggcagct tgaactacca ggccgttcac catctgttcc ccaacgtgtc gcagcatcat    1200

taccctgata tcctggccat catcaaggac acctgcagcg agtacaaggt gccatacctc    1260

gtcaaggata ctttttggca agcgtttgct tcccatttgg agcacttgcg tgttcttgga    1320

ctccgtccca aggaagagta g                                              1341
```

<210> SEQ ID NO 23
<211> LENGTH: 1740
<212> TYPE: DNA
<213> ORGANISM: Phytophthora megasperma

<400> SEQUENCE: 23

```
cgccaagaag gaccaacgga actccatcca tcttcttctc cagccattga cgaactagtc      60

ccgctgccat ggcccccatc gagactgtca aagacgccaa cgagggcctg caccagcgca     120

agggcgccgc tgccgcctcc aaggacacga ccaccttcac gtggcaggac gtggccaagc     180

acaacacggc caagagcgcc tgggtcacca tccgcggcgt cgtctacgac gtgaccgaat     240

gggccgaccg ccaccccgga ggccgcgagc tcgtgctgct gcactcgggc cgtgagtgca     300

cggacacgtt cgactcgtac cacccgttct ccgaccgcgc ggacaagatc ctggccaagt     360

acgccatcgg caagctcgtg ggcggctccg agttccccac gtacaagccc gacacgggct     420

tctacaagga gtgctgcgac cgcgtcaacc agtacttcaa ggacaacaag ctggacccgc     480

gcagccccta ctcgggtctg tggcgcatga tcctcgtggc catcgtcggc gctgtggcct     540

acatgggcat gaaccagctg ctgccgggca acatctacgc gcactacgcg tggggcgcgc     600

tcttcggcgt gtgccaagcg ctgccgctgc tgcacgtcat gcacgacgcg tcgcacgctg     660

ccatcaccag cagccccacg ggctggcggc tcatcggccg cctcgcgatg gactgggtgg     720

ccggcgccaa catggtctcg tggctcaacc agcacgtggt gggccaccac atctacacga     780

acgtggcagg cgcggacccg gatctgcccg tggacttcaa gagcgacgtg cgccgcatcg     840

tgtaccgcca ggtgctgctg cccatttaca agtaccagca cctgtacctg ccgccgctct     900

acggcgtgct gggcctcaag ttccgcgtgc aggacgtctt cgagacgttc gtcacgctga     960

cgaatggccc gctgcgcgtg aacccgctct cggtgggcga ctgggccgag atgatcctgt    1020

ccaaggcctt ctgggtcttc taccgcatct acctcccgct ggctgtgctc caggtggacc    1080

ccgctcgctt ctggggcgtc ttcttcctcg ccgagttctc cacgggctgg tacctggcct    1140

tcaacttcca ggtgagccac gtgtccacgg cctgcgagta cccgggcggt gacgaggaag    1200

tgacgtccat cgacgacgag tgggccatct cgcaggtcaa gtcgtcggtg gactacggcc    1260

acggctcgtt catcacgacg ttcctcacgg gcgcgctcaa ctaccaggtg acgcaccacc    1320

tcttcccggg cgtctcgcag taccattacc cggccattgc gccgctcatc ctcgacgtgt    1380

gccacaagta caaggtcaag tacaacgtgc tcccggactt cacggcggcc atggccggcc    1440

acttcgacca ccttgtcatt atgggcaaga tgggcaagcg cgtgaccatc cacatgggct    1500

aagccagcag cggtcggttg aggacaaggc cgtcttgcag ctggactgcg actgctggta    1560

agctttggct ggataacgcg ggtgagaacg gaggaagggg ctgtggtgtg aatgatctgg    1620
```

-continued

```
gagtgtgcat ttacagtagg tggcttgccg ccgacaacaa taatccatac ttttccttgc   1680

acacgccaaa aaaaaaaaaa aaaaaaaaaa aaaaaaaaaa aaaaaaaaaa aaaaaaaaaa   1740


<210> SEQ ID NO 24
<211> LENGTH: 1320
<212> TYPE: DNA
<213> ORGANISM: Thraustochytrium sp. ATCC 21685

<400> SEQUENCE: 24

atgggcaagg gcagcgaggg ccgcagcgcg gcgcgcgaga tgacggccga ggcgaacggc     60

gacaagcgga aaacgattct gatcgagggc gtcctgtacg acgcgacgaa ctttaagcac    120

ccgggcggtt cgatcatcaa cttcttgacc gagggcgagg ccggcgtgga cgcgacgcag    180

gcgtaccgcg agtttcatca gcggtccggc aaggccgaca agtacctcaa gtcgctgccg    240

aagctggatg cgtccaaggt ggagtcgcgg ttctcggcca aagagcaggc gcggcgcgac    300

gccatgacgc gcgactacgc ggcctttcgc gaggagctcg tcgccgaggg gtactttgac    360

ccgtcgatcc cgcacatgat ttaccgcgtc gtggagatcg tggcgctctt cgcgctctcg    420

ttctggctca tgtccaaggc ctcgcccacc tcgctcgtgc tgggcgtggt gatgaacggc    480

attgcgcagg gccgctgcgg ctgggtcatg cacgagatgg gccacgggtc gttcacgggc    540

gtcatctggc tcgacgaccg gatgtgcgag ttcttctacg gcgtcggctg cggcatgagc    600

gggcactact ggaagaacca gcacagcaag caccacgccg cgcccaaccg cctcgagcac    660

gatgtcgatc tcaacacgct gcccctggtc gcctttaacg agcgcgtcgt gcgcaaggtc    720

aagccgggat cgctgctggc gctctggctg cgcgtgcagg cgtacctctt tgcgcccgtc    780

tcgtgcctgc tcatcggcct tggctggacg ctctacctgc acccgcgcta catgctgcgc    840

accaagcggc acatggagtt cgtctggatc ttcgcgcgct acattggctg gttctcgctc    900

atgggcgctc tcggctactc gccgggcacc tcggtcggga tgtacctgtg ctcgttcggc    960

ctcggctgca tttacatttt cctgcagttc gccgtcagcc acacgcacct gccggtgacc   1020

aacccggagg accagctgca ctggctcgag tacgcggccg accacacggt gaacattagc   1080

accaagtcct ggctcgtcac gtggtggatg tcgaacctga actttcagat cgagcaccac   1140

ctcttcccca cggcgccgca gttccgcttc aaggaaatca gtcctcgcgt cgaggccctc   1200

ttcaagcgcc acaacctccc gtactacgac ctgccctaca cgagcgcggt ctcgaccacc   1260

tttgccaatc tttattccgt cggccactcg gtcggcgccg acaccaagaa gcaggactga   1320


<210> SEQ ID NO 25
<211> LENGTH: 1344
<212> TYPE: DNA
<213> ORGANISM: Caenorhabditis elegans

<400> SEQUENCE: 25

atggtattac gagagcaaga gcatgagcca ttcttcatta aaattgatgg aaaatggtgt     60

caaattgacg atgctgtcct gagatcacat ccaggtggta gtgcaattac tacctataaa    120

aatatggatg ccactaccgt attccacaca ttccatactg gttctaaaga agcgtatcaa    180

tggctgacag aattgaaaaa agagtgccct acacaagaac cagagatccc agatattaag    240

gatgacccaa tcaaaggaat tgatgatgtg aacatgggaa ctttcaatat ttctgagaaa    300

cgatctgccc aaataaataa aagtttcact gatctacgta tgcgagttcg tgcagaagga    360

cttatggatg gatctccttt gttctacatt agaaaaattc ttgaaacaat cttcacaatt    420
```

-continued

```
ctttttgcat tctaccttca ataccacaca tattatcttc catcagctat tctaatggga    480

gttgcgtggc aacaattggg atggttaatc catgaattcg cacatcatca gttgttcaaa    540

aacagatact acaatgattt ggccagctat ttcgttggaa actttttaca aggattctca    600

tctggtggtt ggaaagagca gcacaatgtg catcacgcag ccacaaatgt tgttggacga    660

gacggagatc ttgatttagt cccattctat gctacagtgg cagaacatct caacaattat    720

tctcaggatt catgggttat gactctattc agatggcaac atgttcattg gacattcatg    780

ttaccattcc tccgtctctc gtggcttctt cagtcaatca tttttgttag tcagatgcca    840

actcattatt atgactatta cagaaatact gcgatttatg aacaggttgg tctctctttg    900

cactgggctt ggtcattggg tcaattgtat ttcctacccg attggtcaac tagaataatg    960

ttcttccttg tttctcatct tgttggaggt ttcctgctct ctcatgtagt tactttcaat   1020

cattattcag tggagaagtt tgcattgagc tcgaacatca tgtcaaatta cgcttgtctt   1080

caaatcatga ccacaagaaa tatgagacct ggaagattca ttgactggct ttggggaggt   1140

cttaactatc agattgagca ccatcttttc ccaacgatgc cacgacacaa cttgaacact   1200

gttatgccac ttgttaagga gtttgcagca gcaaatggtt taccatacat ggtcgacgat   1260

tatttcacag gattctggct tgaaattgag caattccgaa atattgcaaa tgttgctgct   1320

aaattgacta aaaagattgc ctag                                          1344
```

<210> SEQ ID NO 26
<211> LENGTH: 1371
<212> TYPE: DNA
<213> ORGANISM: Pythium irregulare

<400> SEQUENCE: 26

```
atgaccgaga aggcgagtga cgagttcacg tggcaggagg tcgccaagca caacacggcc     60

aagagcgcgt gggtgatcat ccgcggcgag gtgtacgacg tgaccgagtg ggcggacaag    120

cacccgggcg gcagcgagct catcgtcctg cactccggtc gtgaatgcac ggacacgttc    180

tactcgtacc acccgttctc gaaccgcgcc gacaagatct tggccaagta caagatcggc    240

aagctcgtgg gcggctacga gttcccggtg ttcaagccgg actcgggctt ctacaaggaa    300

tgctcggagc gcgtggccga gtactttaag acgaacaatc tggacccaaa ggcggcgttc    360

gcgggtctct ggcgcatggt gttcgtgttc gcggtcgccg cgctcgcgta catgggcatg    420

aatgagctca tccctggaaa cgtgtacgcg cagtacgcgt ggggcgtggt gttcggtgtc    480

ttccaggcgc tgccattgct gcacgtgatg cacgactcgt cgcacgcggc atgctcgagc    540

agcccagcga tgtggcagat catcggtcgt ggtgtgatgg actggttcgc tggcgccagc    600

atggtgtcgt ggttgaacca gcacgttgtg ggccaccaca tctacacgaa cgtcgcgggc    660

gcggacccgg atctcccggt cgactttgag agcgacgtgc gccgcatcgt gcaccgccag    720

gtgctgctgc cgatctacaa gttccagcac atctacctgc caccgctcta cggcgtgctg    780

ggcctcaagt tccgcatcca ggacgtgttc gagacgttcg tgtcgctcac gaacggcccg    840

gtgcgtgtga acccgcaccc ggtgtcggac tgggtgcaaa tgatcttcgc caaggcgttc    900

tggacgttct accgcatcta catcccgttg gcgtggctca agatcacgcc gtcgacgttc    960

tggggcgtgt ttttcctcgc cgagttcacc acaggttggt acctcgcgtt caacttccag   1020

gtgagccacg tctcgaccga gtgcgagtac ccgtgcggtg atgcgccgtc ggccgaggtc   1080

ggtgacgagt gggcgatctc gcaggtcaag tcgtcggtgg actacgcgca cggctcgccg   1140

ctcgcggcgt tcctctgcgg cgcgctcaac taccaggtga cccaccactt gtacccgggc   1200
```

-continued

```
atctcacagt accactaccc tgcgatcgcg ccgatcatca tcgacgtgtg caagaagtac   1260

aacatcaagt acacggtgct gccgacgttc accgaggcgc tgctcgcgca cttcaagcac   1320

ctgaagaaca tgggcgagct cggcaagccc gtggagatcc acatgggtta a            1371
```

<210> SEQ ID NO 27
<211> LENGTH: 1652
<212> TYPE: DNA
<213> ORGANISM: Phaeodactylum tricornutum

<400> SEQUENCE: 27

```
gacccaacaa acccaacaat cccaacaatc ccatcaacag gaattgggtt tcgttgagtc     60

aataattgct agaatccaaa cagacagaca gagaccaacc gcatctatta cagaatggct    120

ccggatgcgg ataagcttcg acaacgccag acgactgcgg tagcgaagca caatgctgct    180

accatatcga cgcaggaacg cctttgcagt ctgtcttcgc tcaaaggcga agaagtctgc    240

atcgacggaa tcatctatga cctccaatca ttcgatcatc ccgggggtga aacgatcaaa    300

atgtttggtg gcaacgatgt cactgtacag tacaagatga ttcacccgta ccataccgag    360

aagcatttgg aaaagatgaa gcgtgtcggc aaggtgacgg atttcgtctg cgagtacaag    420

ttcgataccg aatttgaacg cgaaatcaaa cgagaagtct tcaagattgt gcgacgaggc    480

aaggatttcg gtactttggg atggttcttc cgtgcgtttt gctacattgc cattttcttc    540

tacctgcagt accattgggt caccacggga acctcttggc tgctggccgt ggcctacgga    600

atctcccaag cgatgattgg catgaatgtc cagcacgatg ccaaccacgg ggccacctcc    660

aagcgtccct gggtcaacga catgctaggc ctcggtgcgg attttattgg tggttccaag    720

tggctctggc aggaacaaca ctggacccac cacgcttaca ccaatcacgc cgagatggat    780

cccgatagct ttggtgccga accaatgctc ctattcaacg actatccctt ggatcatccc    840

gctcgtacct ggctacatcg ctttcaagca ttcttttaca tgcccgtctt ggctggatac    900

tggttgtccg ctgtcttcaa tccacaaatt cttgacctcc agcaacgcgg cgcactttcc    960

gtcggtatcc gtctcgacaa cgctttcatt cactcgcgac gcaagtatgc ggttttctgg   1020

cgggctgtgt acattgcggt gaacgtgatt gctccgtttt acacaaactc cggcctcgaa   1080

tggtcctggc gtgtctttgg aaacatcatg ctcatgggtg tggcggaatc gctcgcgctg   1140

gcggtcctgt tttcgttgtc gcacaatttc gaatccgcgg atcgcgatcc gaccgcccca   1200

ctgaaaaaga cgggagaacc agtcgactgg ttcaagacac aggtcgaaac ttcctgcact   1260

tacggtggat tcctttccgg ttgcttcacg ggaggtctca actttcaggt tgaacaccac   1320

ttgttcccac gcatgagcag cgcttggtat ccctacattg cccccaaggt ccgcgaaatt   1380

tgcgccaaac acggcgtcca ctacgcctac tacccgtgga tccaccaaaa ctttctctcc   1440

accgtccgct acatgcacgc ggccgggacc ggtgccaact ggcgccagat ggccagagaa   1500

aatcccttga ccggacgggc gtaaaagtac acgacacgac caaaggtggc gtatggtgat   1560

ctctagaaaa cagacatagc ctactggaaa tatcgacgtc caaacaataa ttttaaagac   1620

tatttttctg cgtaaaaaaa aaaaaaaaaa aa                                 1652
```

<210> SEQ ID NO 28
<211> LENGTH: 879
<212> TYPE: DNA
<213> ORGANISM: Mus musculus

<400> SEQUENCE: 28

-continued

```
atggagcagc tgaaggcctt tgataatgaa gtcaatgctt tcttggacaa catgtttgga      60

ccacgagatt ctcgagttcg cgggtggttc ctgctggact cttaccttcc caccttcatc     120

ctcaccatca cgtacctgct ctcgatatgg ctgggtaaca agtacatgaa gaacaggcct     180

gctctgtctc tcaggggcat cctcaccttg tataacctcg caatcacact tctttctgcg     240

tatatgctgg tggagctcat cctctccagc tgggaaggag gttacaactt gcagtgtcag     300

aatctcgaca gtgcaggaga aggtgatgtc cgggtagcca aggtcttgtg gtggtactac     360

ttctccaaac tagtggagtt cctggacacg attttctttg ttctacgaaa aaagaccaat     420

cagatcacct tccttcatgt ctatcaccac gcgtccatgt tcaacatctg gtggtgtgtt     480

ttgaactgga taccttgtgg tcaaagcttc tttggaccca ccctgaacag ctttatccac     540

attctcatgt actcctacta cggcctgtct gtgttcccgt ccatgcacaa gtacctttgg     600

tggaagaagt acctcacaca ggctcagctg gtgcagttcg tactcaccat cacgcacacg     660

ctgagtgccg tggtgaagcc ctgtggcttc ccctttggct gtctcatctt ccagtcttcc     720

tatatgatga cgctggtcat cctgttctta aacttctata ttcagacata ccggaaaaag     780

ccagtgaaga aagagctgca agagaaagaa gtgaagaatg gtttccccaa agcccactta     840

attgtggcta atggcatgac ggacaagaag gctcaataa                            879
```

<210> SEQ ID NO 29
<211> LENGTH: 900
<212> TYPE: DNA
<213> ORGANISM: Homo sapiens

<400> SEQUENCE: 29

```
atggaacatt ttgatgcatc acttagtacc tatttcaagg cattgctagg ccctcgagat      60

actagagtaa aaggatggtt tcttctggac aattatatac ccacatttat ctgctctgtc     120

atatatttac taattgtatg gctgggacca aaatacatga ggaataaaca gccattctct     180

tgccggggga ttttagtggt gtataacctt ggactcacac tgctgtctct gtatatgttc     240

tgtgagttag taacaggagt atgggaaggc aaatacaact tcttctgtca gggcacacgc     300

accgcaggag aatcagatat gaagattatc cgtgtcctct ggtggtacta cttctccaaa     360

ctcatagaat ttatggacac tttcttcttc atcctgcgca agaacaacca ccagatcacg     420

gtcctgcacg tctaccacca tgcctcgatg ctgaacatct ggtggtttgt gatgaactgg     480

gtcccctgcg gccactctta ttttggtgcc acacttaata gcttcatcca cgtcctcatg     540

tactcttact atggtttgtc gtcagtccct tccatgcgtc catacctctg gtggaagaag     600

tacatcactc aggggcagct gcttcagttt gtgctgacaa tcatccagac cagctgcggg     660

gtcatctggc cgtgcacatt ccctcttggt tggttgtatt tccagattgg atacatgatt     720

tccctgattg ctctcttcac aaacttctac attcagacct acaacaagaa aggggcctcc     780

cgaaggaaag accacctgaa ggaccaccag aatgggtcca tggctgctgt gaatggacac     840

accaacagct tttcacccct ggaaaacaat gtgaagccaa ggaagctgcg gaaggattga     900
```

<210> SEQ ID NO 30
<211> LENGTH: 1209
<212> TYPE: DNA
<213> ORGANISM: Caenorhabditis elegans

<400> SEQUENCE: 30

```
atggtcgctc attcctcaga agggttatcc gccacggctc cggtcaccgg cggagatgtt      60

ctggttgatg ctcgtgcatc tcttgaagaa aaggaggctc cacgtgatgt gaatgcaaac     120
```

-continued actaaacagg ccaccactga agagccacgc atccaattac caactgtgga tgctttccgt 180
cgtgcaattc cagcacactg tttcgaaaga gatctcgtta aatcaatcag atatttggtg 240
caagactttg cggcactcac aattctctac tttgctcttc cagcttttga gtactttgga 300
ttgtttggtt acttggtttg gaacattttt atgggagttt ttggattcgc gttgttcgtc 360
gttggacacg attgtcttca tggatcattc tctgataatc agaatctcaa tgatttcatt 420
ggacatatcg ccttctcacc actcttctct ccatacttcc catggcagaa aagtcacaag 480
cttcaccatg ctttcaccaa ccacattgac aaagatcatg gacacgtgtg gattcaggat 540
aaggattggg aagcaatgcc atcatggaaa agatggttca atccaattcc attctctgga 600
tggcttaaat ggttcccagt gtacacttta ttcggtttct gtgatggatc tcacttctgg 660
ccatactctt cactttttgt tcgtaactct gaacgtgttc aatgtgtaat ctctggaatc 720
tgttgctgtg tgtgtgcata tattgctcta acaattgctg gatcatattc caattggttc 780
tggtactatt gggttccact ttctttcttc ggattgatgc tcgtcattgt tacctatttg 840
caacatgtcg atgatgtcgc tgaggtgtac gaggctgatg aatggagctt cgtccgtgga 900
caaacccaaa ccatcgatcg ttactatgga ctcggattgg acacaacgat gcaccatatc 960
acagacggac acgttgccca tcacttcttc aacaaaatcc cacattacca tctcatcgaa 1020
gcaaccgaag gtgtcaaaaa ggtcttggag ccgttgtccg acacccaata cgggtacaaa 1080
tctcaagtga actacgattt ctttgcccgt ttcctgtggt tcaactacaa gctcgactat 1140
ctcgttcaca agaccgccgg aatcatgcaa ttccgaacaa ctctcgagga gaaggcaaag 1200
gccaagtaa 1209

<210> SEQ ID NO 31
<211> LENGTH: 1556
<212> TYPE: DNA
<213> ORGANISM: Petroselinum crispum

<400> SEQUENCE: 31
aaaacattcc tggacttcat ttttacaact ctttatagtt catactctct ttattatcct 60
cctcttcttt gttttttttg agttctgagt cacctatggc aagttgggtg atttcagaat 120
gtgggctaag gccacttcca agaatctatg ccaggcccag aagtggagct tcatgtttca 180
actccaagaa tcctgtgaag aatcttagat tcttggatga gaatgtgaag atttcaatga 240
caggctcaag gaactgggga ttgagagtga gtgtgccaat gagtgttcca agtgtaagtg 300
aagaggagga gagatttgag agtttggttg aagaagagaa tgagtttgac cctggggctg 360
caccaccttt taagttgtct gatgttagag ctgctattcc taagcattgt tgggttaagg 420
atcctgtgag atctatgagc tatgttttga gagatgtttt gattgttttt ggattggcgg 480
ttgctgcatc ttttgttaat aattgggctg tctggcctct ttattggatt gctcagggaa 540
ctatgttttg ggctcttttt gttcttggcc atgattgtgg tcatggaagc ttttcgaatg 600
atgcaaagct caatagtgtt gttggacata ttcttcactc ttcaattctt gtgccatatc 660
atggatggag aatcagccat agaactcatc atcagaacca tggacatgtt gagaatgatg 720
aatcttggca tccgttatca gagaagctat ttaacagttt ggatgattta acaaggaaat 780
ttaggttcac tttgccattc cctatgcttg cttatccttt ttatctgtgg ggtcgaagtc 840
ctgggaagaa ggggtcacat tacgatccga gcagtgattt gtttgtgcct aatgaaagaa 900
aagatgtgat cacctcgacg gtttgttgga cagcgatggc tgcactgctt gttggtttaa 960

-continued

```
actttgttat gggtcctgta aaaatgctta tgctctatgg aattccctat tggatttttg   1020
taatgtggtt ggattttgtg acatacttgc atcaccatgg tcacgatgac aaacttccat   1080
ggtaccgtgg caaggaatgg agttatctga gaggtggcct tacaacactt gatcgtgatt   1140
acggatggat caataacatc caccatgaca taggaactca tgttgtccat catttgttcc   1200
ctcagatccc acattaccac ctaatagaag ctacggaagc tgcaaagccg gtgtttggga   1260
agtactacag ggaaccaaag aagtctggac cagttccatt tcacttgttg gcaacactct   1320
ggaagagttt caagaaggat cattttgtta gtgatacagg ggatgttgtg tactaccaag   1380
cacatcctga aattgccaag acccaaaagt gaaagaaact ctgtacattt tataatataa   1440
atattgcaag cctgctatat aggctgctga ttctttaaga ccagtttttg atctttgata   1500
attgacagtt aacaatgata atacatcatt cgtaaggagt ggaaactgat aattcc       1556
```

<210> SEQ ID NO 32
<211> LENGTH: 1525
<212> TYPE: DNA
<213> ORGANISM: Arabidopsis thaliana

<400> SEQUENCE: 32

```
caagttctaa tggcgaactt ggtcttatca gaatgtggta tacgacctct ccccagaatc     60
tacacaacac ccagatccaa tttcctctcc aacaacaaca aattcagacc atcactttct    120
tcttcttctt acaaaacatc atcatctcct ctgtcttttg gtctgaattc acgagatggg    180
ttcacgagga attgggcgtt gaatgtgagc acaccattaa cgacaccaat atttgaggag    240
tctccattgg aggaagataa taaacagaga ttcgatccag gtgcgcctcc tccgttcaat    300
ttagctgata ttagagcagc tatacctaag cattgttggg ttaagaatcc atggaagtct    360
ttgagttatg tcgtcagaga cgtcgctatc gtctttgcat tggctgctgg agctgcttac    420
ctcaacaatt ggattgtttg gcctctctat tggctcgctc aaggaaccat gttttgggct    480
ctctttgttc ttggtcatga ctgtggacat ggtagtttct caaatgatcc gaagttgaac    540
agtgtggtcg gtcatcttct tcattcctca attctggtcc cataccatgg ctggagaatt    600
agtcacagaa ctcaccacca gaaccatgga catgttgaga atgacgaatc ttggcatcct    660
atgtctgaga aaatctacaa tactttggac aagccgacta gattctttag atttacactg    720
cctctcgtga tgcttgcata ccctttctac ttgtgggctc gaagtccggg gaaaaagggt    780
tctcattacc atccagacag tgacttgttc ctccctaaag agagaaagga tgtcctcact    840
tctactgctt gttggactgc aatggctgct ctgcttgttt gtctcaactt cacaatcggt    900
ccaattcaaa tgctcaaact ttatggaatt ccttactgga taaatgtaat gtggttggac    960
tttgtgactt acctgcatca ccatggtcat gaagataagc ttccttggta ccgtggcaag   1020
gagtggagtt acctgagagg aggacttaca acattggatc gtgactacgg attgatcaat   1080
aacatccatc atgatattgg aactcatgtg atacatcatc ttttcccgca gatcccacat   1140
tatcatctag tagaagcaac agaagcagct aaaccagtat tagggaagta ttacagggag   1200
cctgataagt ctggaccgtt gccattacat ttactggaaa ttctagcgaa aagtataaaa   1260
gaagatcatt acgtgagcga cgaaggagaa gttgtatact ataaagcaga tccaaatctc   1320
tatggagagg tcaaagtaag agcagattga aatgaagcag gcttgagatt gaagtttttt   1380
ctatttcaga ccagctgatt ttttgcttac tgtatcaatt tattgtgtca cccaccagag   1440
agttagtatc tctgaatacg atcgatcaga tggaaacaac aaatttgttt gcgatactga   1500
agctatatat accatacatt gcatt                                         1525
```

-continued

<210> SEQ ID NO 33
<211> LENGTH: 1336
<212> TYPE: DNA
<213> ORGANISM: Brassica napus

<400> SEQUENCE: 33
accacatttc actcagagcc cacacagttt tagagagaga gagaaacatc cctcaaagct 60
ctctctcttt ctccggcgat ggttgtcgct atggaccagc gtagcaatgc gaacggagac 120
gaaaggtttg atccgagcgc acaaccaccg ttcaagatcg gagatataag ggcggccatt 180
cctaagcatt gttgggtaaa gagtcctttg agatccatga gctatgtcgc cagagacatt 240
ttcgccgtcg tggctcttgc cgtcgccgcc gtgtattttg atagctggtt cttttggcct 300
ctttattggg ccgcccaagg aaccctgttc tgggctatct tcgtactcgg ccacgactgt 360
ggacatggga gcttctcaga cattcccctt ctgaatactg cggttggtca tattcttcat 420
tccttcattc tcgttccata ccatggttgg agaataagcc atcggacaca ccaccagaac 480
catggccatg ttgaaaacga cgagtcttgg gttccgttgc cagaaaaatt atacaagaat 540
ttgtcccaca gtacacggat gctcagatac actgtccctc tccccatgct cgcttaccct 600
ctctatctgt ggtacagaag tcctggtaaa gaagggtcac attataaccc atacagtagt 660
ttatttgccc caagcgagag aaagcttatt gcaacttcaa ctacttgctg gtcgatcatg 720
ttggccactc ttgtttatct atcattcctc gttggtccag tcacagttct aaaagtctat 780
ggtgttcctt acattatctt tgtaatgtgg ttggacgctg tcacgtactt gcatcatcat 840
ggtcacgatg ataagttgcc ttggtacaga ggcaaggaat ggagttattt acgtggagga 900
ttaacaacta ttgatagaga ttacgggatc ttcaacaaca ttcatcacga tattggaact 960
cacgtgatcc atcatctttt cccacaaatc cctcactatc acttggttga tgccacgaaa 1020
tcagctaaac atgtgttggg aagatactac agagaaccaa agacgtcagg agcaataccg 1080
atccacttgg tggaaagttt ggtggcaagt attaagaaag atcattacgt cagtgacact 1140
ggtgatattg tcttctacga gacagatcca gatctctacg tttatgcttc tgacaaatcc 1200
aaaatcaact aacctttctt cctagctcta tttaggaata aaacagtcct ttggttttta 1260
cttatttctg gttgttttta agttaaaaat gtactcgtga aacttttttt aattaaatgt 1320
atttacatta caaatc 1336

<210> SEQ ID NO 34
<211> LENGTH: 2181
<212> TYPE: DNA
<213> ORGANISM: Glycine soya

<400> SEQUENCE: 34
acaataataa atccatattt ttataattaa aagtagtaga ttacagcgat gcacttgaga 60
aacatattaa gtggactaat tctccctggt caagcaagaa aaaaaccagc tatgacccaa 120
ggtagagaga gattatacac agaatactag taattaacta agactggctc tgcaattgcc 180
aaaaactcca ttgcagtagc agccacctga gaagacacta agacctagac tagaccatac 240
atatgaagat taatacgctt acataacaac ataggacact aagaaaacac ggcttacaga 300
gaatccagct gactctataa gaggggtact tctggagatt aaaattatcc gaatcacctt 360
cccactgcgg ctgctgacgt cagcgaaagt cagaaccgaa agcggcgaag aaccttcaga 420
agaggaggaa gcacttcgac cttacaagag ttgttgtcgt tgttgttgtc gttctctggc 480

-continued

```
ggagaagcga gtttggatcg cgttttcctc ggaggcttct cggtcttccc ctgtttctgc    540

agctcagcca ggccctcgca aatggcctga agcttggcgt caacggcgga atgaagaggc    600

taatactccc cgaagtcacc accgacggag gaaccctggt gtcggaggtt ggggaagttg    660

agcctggcga agtcacctcg gagcttgtac gcggccttgt ggtacgccag agcggcttcc    720

tcggcggtgt cgaaggttcc cagccatagc ctggtccgga ttcttcggga gtctaatctc    780

agccacccac ttccccccctg agaaaagaga ggaaccacac tctctaagcc aaagcaaaag    840

cagcagcagc agcaatggtt aaagacacaa agcctttagc ctatgctgcc aataatggat    900

accaacaaaa gggttcttct tttgattttg atcctagcgc tcctccaccg tttaagattg    960

cagaaatcag agcttcaata ccaaaacatt gctgggtcaa gaatccatgg agatccctca   1020

gttatgttct cagggatgtg cttgtaattg ctgcattggt ggctgcagca attcacttcg   1080

acaactggct tctctggcta atctattgcc ccattcaagg cacaatgttc tgggctctct   1140

ttgttcttgg acatgattgt ggccatggaa gcttttcaga tagccctttg ctgaatagcc   1200

tggtgggaca catcttgcat tcctcaattc ttgtgccata ccatggatgg agaattagcc   1260

acagaactca ccatcaaaac catggacaca ttgagaagga tgagtcatgg gttccattaa   1320

cagagaagat ttacaagaat ctagacagca tgacaagact cattagattc actgtgccat   1380

ttccattgtt tgtgtatcca atttatttgt tttcaagaag ccccggaaag gaaggctctc   1440

acttcaatcc ctacagcaat ctgttcccac ccagtgagag aaaaggaata gcaatatcaa   1500

cactgtgttg ggctaccatg ttttctctgc ttatctatct ctcattcata actagtccac   1560

ttctagtgct caagctctat ggaattccat attggatatt tgttatgtgg ctggactttg   1620

tcacatactt gcatcaccat ggtcaccacc agaaactgcc ttggtaccgc ggcaaggaat   1680

ggagttattt aagaggtggc ctcaccactg tggatcgtga ctatggttgg atctataaca   1740

ttcaccatga cattggcacc catgttatcc accatctttt cccccaaatt cctcattatc   1800

acctcgttga agcgacacaa gcagcaaaac cagttcttgg agattactac cgtgagccag   1860

aaagatctgc gccattacca tttcatctaa taaagtattt aattcagagt atgagacaag   1920

accacttcgt aagtgacact ggagatgttg tttattatca gactgattct ctgctcctcc   1980

actcgcaacg agactgagtt tcaaactttt tgggttatta tttattggat tctagctact   2040

caaattactt ttttttaat gttatgtttt ttggagttta acgttttctg aacaacttgc   2100

aaattacttg catagagaga catggaatat ttatttgaaa ttagtaaggt agtaataata   2160

aattttgaat tgtcagtttc a                                              2181
```

<210> SEQ ID NO 35
<211> LENGTH: 1560
<212> TYPE: DNA
<213> ORGANISM: Thraustochytrium aureum

<400> SEQUENCE: 35

```
atgacggtcg gctacgacga ggagatcccg ttcgagcagg tccgcgcgca caacaagccg     60

gatgacgcct ggtgcgcgat ccacgggcac gtgtacgatg tgaccaagtt cgcgagcgtg    120

cacccgggcg gcgacattat cctgctggcc gcaggcaagg aggccaccgt gctgtacgag    180

acttaccatg tgcggggcgt ctcggacgcg gtgctgcgca agtaccgcat cggcaagctg    240

ccggacggcc aaggcggcgc gaacgagaag gaaaagcgga cgctctcggg cctctcgtcg    300

gcctcgtact acacgtggaa cagcgacttt tacagggtaa tgcgcgagcg cgtcgtggct    360

cggctcaagg agcgcggcaa ggcccgccgc ggaggctacg agctctggat caaggcgttc    420
```

-continued ctgctgctcg tcggcttctg gagctcgctg tactggatgt gcacgctgga cccctcgttc 480
ggggccatcc tggccgccat gtcgctgggc gtctttgccg cctttgtggg cacgtgcatc 540
cagcacgacg gcaaccacgg cgcctttgcc cagtcgcgat gggtcaacaa ggttgccggg 600
tggacgctcg acatgatcgg cgccagcggc atgacgtggg agttccagca cgtcctgggc 660
caccatccgt acacgaacct gatcgaggag gagaacggcc tgcaaaaggt gagcggcaag 720
aagatggaca ccaagctggc cgaccaggag agcgatccgg acgtcttttc cacgtacccg 780
atgatgcgcc tgcacccgtg gcaccagaag cgctggtacc accgtttcca gcacatttac 840
ggccccttca tctttggctt catgaccatc aacaaggtgg tcacgcagga cgtcggtgtg 900
gtgctccgca agcggctctt ccagattgac gccgagtgcc ggtacgcgag cccaatgtac 960
gtggcgcgtt tctggatcat gaaggcgctc acggtgctct acatggtggc cctgccgtgc 1020
tacatgcagg gcccgtggca cggcctcaag ctgttcgcga tcgcgcactt tacgtgcggc 1080
gaggtgctcg caaccatgtt cattgtgaac cacatcatcg agggcgtctc gtacgcttcc 1140
aaggacgcgg tcaagggcac gatggcgccg ccgaagacga tgcacggcgt gacgcccatg 1200
aacaacacgc gcaaggaggt ggaggcggag gcgtccaagt ctggcgccgt ggtcaagtca 1260
gtcccgctcg acgactgggc cgtcgtccag tgccagacct cggtgaactg gagcgtcggc 1320
tcgtggttct ggaatcactt ttccggcggc ctcaaccacc agattgagca ccacctgttc 1380
cccggrctca gccacgagac gtactaccac attcaggacg tctttcagtc cacctgcgcc 1440
gagtacggcg tcccgtacca gcacgagcct tcgctctgga ccgcgtactg gaagatgctc 1500
gagcacctcc gtcagctcgg caatgaggag acccacgagt cctggcagcg cgctgcctga 1560

<210> SEQ ID NO 36
<211> LENGTH: 2569
<212> TYPE: DNA
<213> ORGANISM: Euglena gracilis

<400> SEQUENCE: 36
gcggccgcta gacatgccac cagttgtggt atggttaacc gaatatgaac aaacacccga 60
ttccagtcca agattgctca ataaggaaca gggtggggga gcaacttgtg agagtttcga 120
cgccatgggt gcctacagat taagtagatc cttcttgtcc aacttgttga ccttgcgctc 180
ggcacattct gagagctggt ttcgcagccg gtagatttcg tcgttggcct gttgcaactg 240
ggtccgcagc tcggagtcgc aaagattgtt cgctgtgagg atctcagcac ggatttcttc 300
taattcagaa gccgcagcac ggagttgatt cccaagggta tcaaggcggc catatgcttg 360
ctccaataat ttctcaacac ggtcgggggt gatgctcagc ttaacagatt cttctggtgg 420
ttttggaagc tctccagcag gctccacggg gggcgcaggg ggcgcggcgg gaaccagtgg 480
aagagttggc aacgtcgaca gggggtactg tgcttgaggg ccaggaatca cggacgggac 540
ttgcggaatg taagatggac cagtaggaaa tgacggaaat gttcgagcaa atccgccaaa 600
acccgtgtac gcaggtgccg gggcgtaatt aacaatcgac agcggccgcg aattcgcggc 660
cgctcacatt ccatttatgt gtggatttgc gggtcagaga tctacccacg gcctctgact 720
gctttgcagt cgttcgtgat ggtcaatatg ttggtgctgt ttggcaattt ctatgtcaag 780
caatactccc aaaagaacgg caagccggag aacggagcca cccctgagaa cggagcgaag 840
ccgcaacctt gcgagaacgg cacggtggaa aagcgagaga atgacaccgc caacgttcgg 900
cccacccgtc cagctggacc cccgccggcc acgtactacg actccctggc agtgtcgggg 960

-continued

```
cagggcaagg agcggctgtt caccaccgat gaggtgaggc ggcacatcct ccccaccgat   1020

ggctggctga cgtgccacga aggagtctac gatgtcactg atttccttgc caagcaccct   1080

ggtggcggtg tcatcacgct gggccttgga agggactgca caatcctcat cgagtcatac   1140

caccctgctg ggcgcccgga caaggtgatg gagaagtacc gcattggtac gctgcaggac   1200

cccaagacgt tctatgcttg ggagagtcc gatttctacc ctgagttgaa gcgccgggcc   1260

cttgcaaggc tgaaggaggc tggtcaggcg cggcgcggcg gccttggggt gaaggccctc   1320

ctggtgctca ccctcttctt cgtgtcgtgg tacatgtggg tggcccacaa gtccttcctc   1380

tgggccgccg tctggggctt cgccggctcc cacgtcgggc tgagcatcca gcacgatggc   1440

aaccacggcg cgttcagccg caacacactg gtgaaccgcc tggcggggtg gggcatggac   1500

ttgatcggcg cgtcgtccac ggtgtgggag taccagcacg tcatcggcca ccaccagtac   1560

accaacctcg tgtcggacac gctattcagt ctgcctgaga acgatccgga cgtcttctcc   1620

agctacccgc tgatgcgcat gcacccggat acggcgtggc agccgcacca ccgcttccag   1680

cacctgttcg cgttcccact gttcgccctg atgacaatca gcaaggtgct gaccagcgat   1740

ttcgctgtct gcctcagcat gaagaagggg tccatcgact gctcctccag gctcgtccca   1800

ctggaggggc agctgctgtt ctggggggcc aagctggcga acttcctgtt gcagattgtg   1860

ttgccatgct acctccacgg gacagctatg ggcctggccc tcttctctgt tgctcacctt   1920

gtgtcggggg agtacctcgc gatctgcttc atcatcaacc acatcagcga gtcttgtgag   1980

tttatgaata caagctttca aaccgccgcc cggaggacag agatgcttca ggcagcacat   2040

caggcagcgg aggccaagaa ggtgaagccc accctccac cgaacgattg ggctgtgaca   2100

caggtccaat gctgcgtgaa ttggagatca ggtggcgtgt tggccaatca cctctctgga   2160

ggcttgaacc accagatcga gcatcatctg ttccccagca tctcgcatgc caactacccc   2220

accatcgccc ctgttgtgaa ggaggtgtgc gaggagtacg ggttgccgta caagaattac   2280

gtcacgttct gggatgcagt ctgtggcatg gttcagcacc tccggttgat gggtgctcca   2340

ccggtgccaa cgaacgggga caaaaagtca taagccacga catcatttgg ggctcactcc   2400

gtgcagcctt ttcttgggct gcccacgaag atgcgcgatg aggcacctgg tggttgccct   2460

ccgccggcct cggaaaacgg ttcgacgcct gctccttcag cccagagcac tccggcgaag   2520

agtgaaagag cactgacctg aattttatga tgacccattt agcggccgc              2569
```

<210> SEQ ID NO 37
<211> LENGTH: 1064
<212> TYPE: DNA
<213> ORGANISM: Isochrysis galbana

<400> SEQUENCE: 37

```
gatggccctc gcaaacgacg cgggagagcg catctgggcg gctgtgaccg acccggaaat     60

cctcattggc accttctcgt acttgctact caaaccgctg ctccgcaatt ccgggctggt    120

ggatgagaag aagggcgcat acaggacgtc catgatctgg tacaacgttc tgctggcgct    180

cttctctgcg ctgagcttct acgtgacggc gaccgccctc ggctgggact atggtacggg    240

cgcgtggctg cgcaggcaaa ccggcgacac accgcagccg ctcttccagt gcccgtcccc    300

ggtttgggac tcgaagctct tcacatggac cgccaaggca ttctattact ccaagtacgt    360

ggagtacctc gacacggcct ggctggtgct caagggcaag agggtctcct ttctccaggc    420

cttccaccac tttggcgcgc cgtgggatgt gtacctcggc attcggctgc acaacgaggg    480

cgtatggatc ttcatgtttt tcaactcgtt cattcacacc atcatgtaca cctactacgg    540
```

-continued cctcaccgcc gccgggtata agttcaaggc caagccgctc atcaccgcga tgcagatctg 600
ccagttcgtg ggcggcttcc tgttggtctg ggactacatc aacgtcccct gcttcaactc 660
ggacaaaggg aagttgttca gctgggcttt caactatgca tacgtcggct cggtcttctt 720
gctcttctgc cactttttct accaggacaa cttggcaacg aagaaatcgg ccaaggcggg 780
caagcagctc taggcctcga gccggctcgc gggttcaagg agggcgacac gggggtggga 840
cgtttgcatg gagatggatt gtggatgtcc ttacgcctta ctcatcaatg tcctcccatc 900
tctcccctct agaccttcta ctagccatct agaagggcag ctcagagacg gataccgttc 960
cccctcccct tccttttcgt ctttgctttg ccattgtttg tttgtctcta ttttttaaac 1020
tattgacgct aacgcgttac gctcgcaaaa aaaaaaaaaa aaaa 1064

<210> SEQ ID NO 38
<211> LENGTH: 1275
<212> TYPE: DNA
<213> ORGANISM: Euglena gracilis

<400> SEQUENCE: 38 atttttttc gaaatgaagt caaagcgcca agcgctatcc cccttacaat tgatggaaca 60
aacatatgat gtggtcaatt tccaccctgg tggtgcggaa attatagaga attaccaagg 120
aagggatgcc actgatgcct tcatggttat gcactttcaa gaagccttcg acaagctcaa 180
gcgcatgccc aaaatcaatc ccagttttga gttgccaccc caggctgcag tgaatgaagc 240
tcaagaggat ttccggaagc tccgagaaga gttgatcgca actggcatgt ttgatgcctc 300
ccccctctgg tactcataca aaatcagcac cacactgggc cttggagtgc tgggttattt 360
cctgatggtt cagtatcaga tgtatttcat tggggcagtg ttgcttggga tgcactatca 420
acagatgggc tggctttctc atgacatttg ccaccaccag actttcaaga accggaactg 480
gaacaacctc gtgggactgg tatttggcaa tggtctgcaa ggtttttccg tgacatgttg 540
gaaggacaga cacaatgcac atcattcggc aaccaatgtt caagggcacg accctgatat 600
tgacaacctc ccccccttag cctggtctga ggatgacgtc acacgggcgt caccgatttc 660
ccgcaagctc attcagttcc agcagtacta tttcttggtc atctgtatct tgttgcggtt 720
catttggtgt ttccagtgcg tgttgaccgt gcgcagtttg aaggacagag ataaccaatt 780
ctatcgctct cagtataaga aggaggccat tggcctcgcc ctgcactgga ccttgaaggc 840
cctgttccac ttattcttta tgcccagcat cctcacatcg ctgttggtgt ttttcgtttc 900
ggagctggtt ggcggcttcg gcattgcgat cgtggtgttc atgaaccact acccactgga 960
gaagatcggg gacccagtct gggatggcca tggattctcg gttggccaga tccatgagac 1020
catgaacatt cggcgaggga ttatcacaga ttggtttttc ggaggcttga attaccagat 1080
tgagcaccat ttgtggccga ccctccctcg ccacaacctg acagcggtta gctaccaggt 1140
ggaacagctg tgccagaagc acaacctgcc gtatcggaac ccgctgcccc atgaagggtt 1200
ggtcatcctg ctgcgctatc tggcggtgtt cgcccggatg gcggagaagc aacccgcggg 1260
gaaggctcta taagg 1275

<210> SEQ ID NO 39
<211> LENGTH: 445
<212> TYPE: PRT
<213> ORGANISM: Mortierella alpina

<400> SEQUENCE: 39

-continued

```
Met Ala Thr Pro Leu Pro Pro Ser Phe Val Val Pro Ala Thr Gln Thr
1               5                   10                  15

Glu Thr Arg Arg Asp Pro Leu Gln His Glu Glu Leu Pro Pro Leu Phe
            20                  25                  30

Pro Glu Lys Ile Thr Val Tyr Asn Ile Trp Arg Tyr Leu Asp Tyr Lys
        35                  40                  45

His Val Phe Gly Leu Gly Leu Thr Pro Leu Ile Ala Leu Tyr Gly Leu
    50                  55                  60

Leu Thr Thr Glu Ile Gln Thr Lys Thr Leu Ile Trp Ser Ile Ile Tyr
65                  70                  75                  80

Tyr Tyr Ala Thr Gly Leu Gly Ile Thr Ala Gly Tyr His Arg Leu Trp
                85                  90                  95

Ala His Arg Ala Tyr Asn Ala Gly Pro Ala Met Ser Phe Val Leu Ala
            100                 105                 110

Leu Leu Gly Ala Gly Ala Val Glu Gly Ser Ile Lys Trp Trp Ser Arg
        115                 120                 125

Gly His Arg Ala His His Arg Trp Thr Asp Thr Glu Lys Asp Pro Tyr
    130                 135                 140

Ser Ala His Arg Gly Leu Phe Phe Ser His Ile Gly Trp Met Leu Ile
145                 150                 155                 160

Lys Arg Pro Gly Trp Lys Ile Gly His Ala Asp Val Asp Asp Leu Asn
                165                 170                 175

Lys Ser Lys Leu Val Gln Trp Gln His Lys Asn Tyr Leu Pro Leu Val
            180                 185                 190

Leu Ile Met Gly Val Val Phe Pro Thr Val Val Ala Gly Leu Gly Trp
        195                 200                 205

Gly Asp Trp Arg Gly Gly Tyr Phe Phe Ala Ala Ile Leu Arg Leu Val
    210                 215                 220

Phe Val His His Ala Thr Phe Cys Val Asn Ser Leu Ala His Trp Leu
225                 230                 235                 240

Gly Asp Gly Pro Phe Asp Asp Arg His Ser Pro Arg Asp His Phe Ile
                245                 250                 255

Thr Ala Phe Val Thr Leu Gly Glu Gly Tyr His Asn Phe His His Gln
            260                 265                 270

Phe Pro Gln Asp Tyr Arg Asn Ala Ile Arg Phe Tyr Gln Tyr Asp Pro
        275                 280                 285

Thr Lys Trp Val Ile Ala Leu Cys Ala Phe Phe Gly Leu Ala Thr His
    290                 295                 300

Leu Lys Thr Phe Pro Glu Asn Glu Val Arg Lys Gly Gln Leu Gln Met
305                 310                 315                 320

Ile Glu Lys Arg Val Leu Glu Lys Lys Thr Lys Leu Gln Trp Gly Thr
                325                 330                 335

Pro Ile Ala Asp Leu Pro Ile Leu Ser Phe Glu Asp Phe Gln His Ala
            340                 345                 350

Cys Lys Asn Asp Asn Lys Lys Trp Ile Leu Leu Glu Gly Val Val Tyr
        355                 360                 365

Asp Val Ala Asp Phe Met Thr Glu His Pro Gly Gly Glu Lys Tyr Ile
    370                 375                 380

Lys Met Gly Val Gly Lys Asp Met Thr Ala Ala Phe Asn Gly Gly Met
385                 390                 395                 400

Tyr Asp His Ser Asn Ala Ala Arg Asn Leu Leu Ser Leu Met Arg Val
                405                 410                 415

Ala Val Val Glu Phe Gly Gly Glu Val Glu Ala Gln Lys Lys Asn Pro
```

-continued

```
        420                 425                 430

Ser Met Pro Ile Tyr Gly Thr Asp His Val Lys Ala Glu
        435                 440                 445


<210> SEQ ID NO 40
<211> LENGTH: 493
<212> TYPE: PRT
<213> ORGANISM: Cryptococcus curvatus

<400> SEQUENCE: 40

Met Ser Ala Ser Thr Ala Thr Ala Pro Pro Ala Thr Ala Pro Ala Val
 1               5                  10                  15

Ala Asn Pro Thr Pro Ala Ala Ala Ser Ala Ala Ala Ala Ala Pro Ala
            20                  25                  30

Ala Thr Lys Asp Lys Ala Glu Thr Ile Asp Pro Glu Ser Glu His Phe
        35                  40                  45

Val Val Ser Gln Asn Tyr Val Thr Arg Thr Val Glu Asn Met Thr Met
    50                  55                  60

Leu Pro Pro Val Thr Trp Ser Asn Leu Leu Gln Asn Ile Gln Trp Ile
65                  70                  75                  80

Ser Phe Thr Ala Leu Thr Val Pro Pro Ala Met Ala Ile Tyr Gly Leu
                85                  90                  95

Cys Thr Leu Glu Leu Gln Arg Lys Thr Val Ile Trp Ala Ile Val Tyr
            100                 105                 110

Tyr Phe Met Thr Gly Leu Gly Ile Thr Ala Gly Tyr His Arg Leu Trp
        115                 120                 125

Ala His Arg Ala Tyr Asn Ala Ser Ala Pro Leu Gln Tyr Phe Leu Ala
    130                 135                 140

Leu Cys Gly Ala Gly Ser Val Gln Gly Ser Ile Lys Trp Trp Ser Arg
145                 150                 155                 160

Gly His Arg Ala His His Arg Tyr Thr Asp Thr Lys Leu Asp Pro Tyr
                165                 170                 175

Ser Ala His Glu Gly Phe Trp Trp Ala His Val Gly Trp Met Leu Val
            180                 185                 190

Lys Pro Arg Gly Lys Ile Gly Val Ala Asp Ile Ser Asp Leu Ser Arg
        195                 200                 205

Asn Pro Val Val Lys Trp Gln His Asn Asn Tyr Val Met Leu Met Val
    210                 215                 220

Leu Met Gly Leu Val Phe Pro Thr Leu Val Ala Gly Leu Gly Trp Gly
225                 230                 235                 240

Asp Trp Lys Gly Gly Leu Leu Phe Ala Gly Ala Ala Arg Leu Val Phe
                245                 250                 255

Val His His Ser Thr Phe Cys Val Asn Ser Leu Ala His Trp Leu Gly
            260                 265                 270

Glu Thr Pro Phe Asp Asn Lys His Thr Pro Lys Asp His Phe Ile Thr
        275                 280                 285

Ala Leu Val Thr Val Gly Glu Gly Tyr His Asn Phe His His Gln Phe
    290                 295                 300

Pro Met Asp Phe Arg Asn Ala Ile Lys Trp Tyr Gln Tyr Asp Pro Thr
305                 310                 315                 320

Lys Trp Phe Ile Trp Thr Met Ser Asn Val Gly Leu Ala Ser His Leu
                325                 330                 335

Lys Lys Phe Pro Asp Asn Glu Ile Lys Lys Gly Gln Tyr Thr Met Lys
            340                 345                 350
```

-continued

```
Leu Gln Met Leu Gln Glu Gln Ser Gly Ser Ile Gln Trp Pro Lys His
        355                 360                 365

Ser Asn Asp Leu Pro Val Ile Ser Trp Glu Asp Phe Gln Ala Glu Ala
    370                 375                 380

Lys Glu Arg Ser Leu Val Ala Ile His Gly Phe Ile His Asp Cys Ser
385                 390                 395                 400

Ser Phe Leu Glu Asp His Pro Gly Gly Ile His Leu Ile Lys Lys Ala
                405                 410                 415

Ile Gly Thr Asp Ala Thr Thr Ala Phe Phe Gly Gly Val Tyr Asp His
            420                 425                 430

Ser Asn Ala Ala His Asn Leu Leu Ala Met Met Arg Val Gly Ile Leu
        435                 440                 445

Asp Gly Gly Met Glu Val Glu Ser Leu Lys Leu Glu Asn Leu Gln Arg
    450                 455                 460

Ser Met Ser Val Ser Ser Met Glu Ser Asp Ala Ala Ser Ser Ala Ser
465                 470                 475                 480

Ser Val Ser Val Ser Ser Ile Ser Pro Arg Trp Pro His
                485                 490


<210> SEQ ID NO 41
<211> LENGTH: 476
<212> TYPE: PRT
<213> ORGANISM: Histoplasma capsulatus

<400> SEQUENCE: 41

Met Ala Leu Asn Glu Ala Pro Thr Ala Ser Pro Val Ala Glu Thr Ala
 1               5                  10                  15

Ala Gly Gly Lys Asp Val Val Thr Asp Ala Ala Arg Arg Pro Asn Ser
            20                  25                  30

Glu Pro Lys Lys Val His Ile Thr Asp Thr Pro Ile Thr Leu Ala Asn
        35                  40                  45

Trp His Lys His Ile Ser Trp Leu Asn Val Thr Leu Ile Ile Ala Ile
    50                  55                  60

Pro Ile Tyr Gly Leu Val Gln Ala Tyr Trp Val Pro Leu His Leu Lys
65                  70                  75                  80

Thr Ala Leu Trp Ala Val Val Tyr Tyr Phe Met Thr Gly Leu Gly Ile
                85                  90                  95

Thr Ala Gly Tyr His Arg Leu Trp Ala His Cys Ser Tyr Ser Ala Thr
            100                 105                 110

Leu Pro Leu Lys Ile Tyr Leu Ala Ala Val Gly Gly Gly Ala Val Glu
        115                 120                 125

Gly Ser Ile Arg Trp Trp Ala Arg Gly His Arg Ala His His Arg Tyr
    130                 135                 140

Thr Asp Thr Asp Lys Asp Pro Tyr Ser Val Arg Lys Gly Leu Leu Tyr
145                 150                 155                 160

Ser His Ile Gly Trp Met Val Met Lys Gln Asn Pro Lys Arg Ile Gly
                165                 170                 175

Arg Thr Glu Ile Thr Asp Leu Asn Glu Asp Pro Val Val Val Trp Gln
            180                 185                 190

His Arg Asn Tyr Leu Lys Val Val Ile Phe Met Gly Ile Val Phe Pro
        195                 200                 205

Met Leu Val Ser Gly Leu Gly Trp Gly Asp Trp Phe Gly Gly Phe Ile
    210                 215                 220

Tyr Ala Gly Ile Leu Arg Ile Phe Phe Val Gln Gln Ala Thr Phe Cys
225                 230                 235                 240
```

-continued

```
Val Asn Ser Leu Ala His Trp Leu Gly Asp Gln Pro Phe Asp Asp Arg
                245                 250                 255

Asn Ser Pro Arg Asp His Ile Val Thr Ala Leu Val Thr Leu Gly Glu
            260                 265                 270

Gly Tyr His Asn Phe His His Glu Phe Pro Ser Asp Tyr Arg Asn Ala
        275                 280                 285

Ile Glu Trp His Gln Tyr Asp Pro Thr Lys Trp Thr Ile Trp Ile Trp
    290                 295                 300

Lys Gln Leu Gly Leu Ala Tyr Asp Leu Lys Gln Phe Arg Ala Asn Glu
305                 310                 315                 320

Ile Glu Lys Gly Arg Val Gln Gln Leu Gln Lys Lys Ile Asp Gln Arg
                325                 330                 335

Arg Ala Lys Leu Asp Trp Gly Ile Pro Leu Glu Gln Leu Pro Val Ile
            340                 345                 350

Glu Trp Asp Asp Tyr Val Asp Gln Ala Lys Asn Gly Arg Gly Leu Ile
        355                 360                 365

Ala Ile Ala Gly Val Val His Asp Val Thr Asp Phe Ile Lys Asp His
    370                 375                 380

Pro Gly Gly Lys Ala Met Ile Asn Ser Gly Ile Gly Lys Asp Ala Thr
385                 390                 395                 400

Ala Met Phe Asn Gly Gly Val Tyr Asn His Ser Asn Ala Ala His Asn
                405                 410                 415

Gln Leu Ser Thr Met Arg Val Gly Val Ile Arg Gly Gly Cys Glu Val
            420                 425                 430

Glu Ile Trp Lys Arg Ala Gln Lys Glu Asn Lys Glu Val Glu Ser Val
        435                 440                 445

Arg Asp Glu Tyr Gly Asn Arg Ile Val Arg Ala Gly Ala Gln Val Thr
    450                 455                 460

Lys Ile Pro Glu Pro Ile Thr Thr Ala Asp Ala Ala
465                 470                 475


<210> SEQ ID NO 42
<211> LENGTH: 353
<212> TYPE: PRT
<213> ORGANISM: Trichoplusia ni

<400> SEQUENCE: 42

Met Pro Pro Gln Gly Gln Thr Gly Gly Ser Trp Val Leu Tyr Glu Thr
 1               5                  10                  15

Asp Ala Val Asn Thr Asp Thr Asp Ala Pro Val Ile Val Pro Pro Ser
            20                  25                  30

Ala Glu Lys Arg Glu Trp Lys Ile Val Trp Arg Asn Val Ile Leu Met
        35                  40                  45

Gly Met Leu His Ile Gly Gly Val Tyr Gly Ala Tyr Leu Phe Leu Thr
    50                  55                  60

Lys Ala Met Trp Leu Thr Asp Leu Phe Ala Phe Phe Leu Tyr Leu Cys
65                  70                  75                  80

Ser Gly Leu Gly Ile Thr Ala Gly Ala His Arg Leu Trp Ala His Lys
                85                  90                  95

Ser Tyr Lys Ala Arg Leu Pro Leu Arg Leu Leu Leu Thr Leu Phe Asn
            100                 105                 110

Thr Leu Ala Phe Gln Asp Ala Val Ile Asp Trp Ala Arg Asp His Arg
        115                 120                 125

Met His His Lys Tyr Ser Glu Thr Asp Ala Asp Pro His Asn Ala Thr
```

-continued

```
    130                 135                 140

Arg Gly Phe Phe Phe Ser His Val Gly Trp Leu Leu Val Arg Lys His
145                 150                 155                 160

Pro Gln Ile Lys Ala Lys Gly His Thr Ile Asp Leu Ser Asp Leu Lys
                165                 170                 175

Ser Asp Pro Ile Leu Arg Phe Gln Lys Lys Tyr Tyr Leu Thr Leu Met
            180                 185                 190

Pro Leu Ile Cys Phe Ile Leu Pro Ser Tyr Ile Pro Thr Leu Trp Gly
        195                 200                 205

Glu Ser Ala Phe Asn Ala Phe Phe Val Cys Ser Ile Phe Arg Tyr Val
    210                 215                 220

Tyr Val Leu Asn Val Thr Trp Leu Val Asn Ser Ala Ala His Leu Trp
225                 230                 235                 240

Gly Ser Lys Pro Tyr Asp Lys Asn Ile Asn Pro Val Glu Thr Arg Pro
                245                 250                 255

Val Ser Leu Val Val Leu Gly Glu Gly Phe His Asn Tyr His His Thr
            260                 265                 270

Phe Pro Trp Asp Tyr Lys Thr Ala Glu Leu Gly Asp Tyr Ser Leu Asn
        275                 280                 285

Phe Thr Lys Met Phe Ile Asp Phe Met Ala Ser Ile Gly Trp Ala Tyr
    290                 295                 300

Asp Leu Lys Thr Val Ser Thr Asp Val Ile Gln Lys Arg Val Lys Arg
305                 310                 315                 320

Thr Gly Asp Gly Ser His Ala Val Trp Gly Trp Asp Asp His Glu Val
                325                 330                 335

His Gln Glu Asp Lys Lys Leu Ala Ala Ile Ile Asn Pro Glu Lys Thr
            340                 345                 350

Glu


<210> SEQ ID NO 43
<211> LENGTH: 401
<212> TYPE: PRT
<213> ORGANISM: Mortierella alpina

<400> SEQUENCE: 43

Met Ala Pro Pro Asn Thr Ile Asp Ala Gly Leu Thr Gln Arg His Ile
 1               5                  10                  15

Ser Thr Ser Ala Ala Pro Asn Ser Ala Lys Pro Thr Phe Glu Arg Asn
            20                  25                  30

Tyr Gln Leu Pro Glu Phe Thr Ile Lys Glu Ile Arg Glu Cys Ile Pro
        35                  40                  45

Ala His Cys Phe Glu Arg Ser Gly Leu Arg Gly Leu Cys His Val Ala
    50                  55                  60

Ile Asp Leu Thr Trp Ala Ser Leu Leu Phe Leu Ala Ala Thr Gln Ile
65                  70                  75                  80

Asp Lys Phe Glu Asn Pro Leu Ile Arg Tyr Leu Ala Trp Pro Val Tyr
                85                  90                  95

Trp Ile Met Gln Gly Ile Val Cys Thr Gly Ile Trp Val Leu Ala His
            100                 105                 110

Glu Cys Gly His Gln Ser Phe Ser Thr Ser Lys Thr Leu Asn Asn Thr
        115                 120                 125

Val Gly Trp Ile Leu His Ser Met Leu Leu Val Pro Tyr His Ser Trp
    130                 135                 140

Arg Ile Ser His Ser Lys His His Lys Ala Thr Gly His Met Thr Lys
```

-continued

```
145                 150                 155                 160

Asp Gln Val Phe Val Pro Lys Thr Arg Thr Gln Val Gly Leu Pro Pro
                165                 170                 175

Lys Glu Ser Ala Ala Ala Thr Val Gln Glu Glu Glu Asp Met Ser Val
            180                 185                 190

His Leu Asp Glu Glu Ala Pro Ile Val Thr Leu Phe Trp Met Val Ile
        195                 200                 205

Gln Phe Leu Phe Gly Trp Pro Ala Tyr Leu Ile Met Asn Ala Ser Gly
    210                 215                 220

Gln Asp Tyr Gly Arg Trp Thr Ser His Phe His Thr Tyr Ser Pro Ile
225                 230                 235                 240

Phe Glu Pro Arg Asn Phe Phe Asp Ile Ile Leu Ser Asp Leu Gly Val
                245                 250                 255

Leu Ala Thr Leu Gly Ala Leu Ile Tyr Ala Ser Met Gln Leu Ser Leu
            260                 265                 270

Leu Thr Val Thr Lys Tyr Tyr Ile Ile Pro Tyr Leu Phe Val Asn Phe
        275                 280                 285

Trp Leu Val Leu Ile Thr Phe Leu Gln His Thr Asp Pro Lys Leu Pro
    290                 295                 300

His Tyr Arg Glu Gly Ala Trp Asn Phe Gln Arg Gly Ala Leu Cys Thr
305                 310                 315                 320

Val Asp Arg Ser Phe Gly Lys Phe Leu Asp His Met Phe His Gly Ile
                325                 330                 335

Val His Thr His Val Ala His His Leu Phe Ser Gln Met Pro Phe Tyr
            340                 345                 350

His Ala Glu Glu Ala Thr Tyr His Leu Lys Lys Leu Leu Gly Glu Tyr
        355                 360                 365

Tyr Ile Tyr Asp Ala Ser Pro Ile Val Val Ala Val Trp Lys Ser Phe
    370                 375                 380

Arg Glu Cys Arg Phe Val Glu Asp His Gly Asp Val Val Phe Phe Lys
385                 390                 395                 400

Lys
```

<210> SEQ ID NO 44
<211> LENGTH: 396
<212> TYPE: PRT
<213> ORGANISM: Mucor rouxii

<400> SEQUENCE: 44

```
Met Ala Thr Lys Arg Asn Val Thr Ser Asn Ala Pro Ala Ala Glu Asp
 1               5                  10                  15

Ile Ser Ile Ser Asn Lys Ala Val Ile Asp Glu Ala Ile Glu Arg Asn
            20                  25                  30

Trp Glu Ile Pro Asn Phe Thr Ile Lys Glu Ile Arg Asp Ala Ile Pro
        35                  40                  45

Ala His Cys Phe Arg Arg Asp Thr Phe Arg Ser Phe Thr His Val Leu
    50                  55                  60

His Asp Ile Ile Ile Met Pro Ile Leu Ala Ile Gly Ala Ser Tyr Ile
65                  70                  75                  80

Asp Ser Ile Pro Asn Thr Tyr Ala Arg Ile Ala Leu Trp Pro Leu Tyr
                85                  90                  95

Trp Ile Ala Gln Gly Ile Val Gly Thr Gly Val Trp Val Ile Gly His
            100                 105                 110

Glu Cys Gly His Gln Ala Phe Ser Pro Ser Lys Thr Ile Asn Asn Ser
```

-continued

```
        115                 120                 125

Val Gly Tyr Val Leu His Thr Ala Leu Leu Val Pro Tyr His Ser Trp
    130                 135                 140

Arg Phe Ser His Ser Lys His His Lys Ala Thr Gly His Met Ser Lys
145                 150                 155                 160

Asp Gln Val Phe Val Pro Ser Thr Arg Lys Glu Tyr Gly Leu Pro Pro
                165                 170                 175

Arg Glu Gln Asp Pro Glu Val Asp Gly Pro His Asp Ala Leu Asp Glu
            180                 185                 190

Val Pro Leu Leu Ser Cys Ile Ala Cys Ser Phe Asn Leu Pro Leu Ala
        195                 200                 205

Gly Leu Phe Ile Ser Ser Pro Met Ser Leu Val Lys Ile Thr Pro Val
    210                 215                 220

Gly Leu Leu Ile Ser Thr Pro Ser Val Leu Ser Thr Ile Glu Asn Gln
225                 230                 235                 240

Phe Trp Asp Val Met Ser Ser Thr Ala Gly Val Leu Gly Met Ile Gly
                245                 250                 255

Phe Leu Ala Tyr Cys Gly Gln Val Leu Ala Leu Leu Leu Ser Ser Ser
            260                 265                 270

Thr Met Leu Phe Pro Tyr Leu Asn Val Asn Phe Trp Leu Val Leu Ile
        275                 280                 285

Thr Tyr Leu Gln His Thr Asp Pro Lys Leu Pro His Tyr Arg Glu Asn
    290                 295                 300

Val Trp Asn Phe Gln Arg Gly Ala Ala Leu Thr Val Asp Arg Ser Tyr
305                 310                 315                 320

Gly Phe Leu Leu Asp Tyr Phe His His His Ile Ser Asp Thr His Val
                325                 330                 335

Ala His His Phe Phe Ser Thr Met Pro His Tyr His Ala Glu Glu Ala
            340                 345                 350

Thr Val His Ile Lys Lys Ala Leu Gly Lys His Tyr His Cys Asp Asn
        355                 360                 365

Thr Pro Val Pro Ile Ala Leu Trp Lys Val Trp Lys Ser Cys Arg Phe
    370                 375                 380

Val Glu Asp Glu Gly Asp Val Val Phe Phe Lys Asn
385                 390                 395


<210> SEQ ID NO 45
<211> LENGTH: 396
<212> TYPE: PRT
<213> ORGANISM: Mucor circinelloides

<400> SEQUENCE: 45

Met Ala Thr Lys Arg Asn Val Thr Ser Asn Ala Pro Ala Ala Glu Asp
 1               5                  10                  15

Ile Ser Ile Ser Asn Lys Ala Val Ile Asp Glu Ala Ile Glu Arg Asn
            20                  25                  30

Trp Glu Ile Pro Asn Phe Thr Ile Lys Glu Ile Arg Asp Ala Ile Pro
        35                  40                  45

Ala His Cys Phe Arg Arg Asp Thr Phe Arg Ser Phe Thr His Val Leu
    50                  55                  60

His Asp Ile Ile Ile Met Ser Ile Leu Ala Ile Gly Ala Ser Tyr Ile
65                  70                  75                  80

Asp Ser Ile Pro Asn Thr Tyr Ala Arg Ile Ala Leu Trp Pro Leu Tyr
                85                  90                  95
```

-continued

```
Trp Ile Ala Gln Gly Ile Val Gly Thr Gly Val Trp Val Ile Gly His
            100                 105                 110

Glu Cys Gly His Gln Ala Phe Ser Pro Ser Lys Thr Ile Asn Asn Ser
        115                 120                 125

Val Gly Tyr Val Leu His Thr Ala Leu Leu Val Pro Tyr His Ser Trp
    130                 135                 140

Arg Phe Ser His Ser Lys His His Lys Ala Thr Gly His Met Ser Lys
145                 150                 155                 160

Asp Gln Val Phe Val Pro Ser Thr Arg Lys Glu Tyr Gly Leu Pro Pro
                165                 170                 175

Arg Glu Gln Asp Pro Glu Val Asp Gly Pro His Asp Ala Leu Asp Glu
            180                 185                 190

Ala Pro Ile Val Val Leu Tyr Arg Met Phe Leu Gln Phe Thr Phe Gly
        195                 200                 205

Trp Pro Leu Tyr Leu Phe Thr Asn Val Ser Gly Gln Asp Tyr Pro Gly
    210                 215                 220

Trp Ala Ser His Phe Asn Pro Lys Cys Ala Ile Tyr Asp Glu Asn Gln
225                 230                 235                 240

Phe Trp Asp Val Met Ser Ser Thr Ala Gly Val Leu Gly Met Ile Gly
                245                 250                 255

Phe Leu Ala Tyr Cys Gly Gln Val Phe Gly Ser Leu Ala Val Ile Lys
            260                 265                 270

Tyr Tyr Val Ile Pro Tyr Leu Asn Val Asn Phe Trp Leu Val Leu Ile
        275                 280                 285

Thr Tyr Leu Gln His Thr Asp Pro Lys Leu Pro His Tyr Arg Glu Asn
    290                 295                 300

Val Trp Asn Phe Gln Arg Gly Ala Ala Leu Thr Val Asp Arg Ser Tyr
305                 310                 315                 320

Gly Phe Leu Leu Asp Tyr Phe His His His Ile Ser Asp Thr His Val
                325                 330                 335

Ala His His Phe Phe Ser Thr Met Pro His Tyr His Ala Glu Glu Ala
            340                 345                 350

Thr Val His Ile Lys Lys Ala Leu Gly Lys His Tyr His Cys Asp Asn
        355                 360                 365

Thr Pro Val Pro Ile Ala Leu Trp Lys Val Trp Lys Ser Cys Arg Phe
    370                 375                 380

Val Glu Asp Glu Gly Asp Val Val Phe Phe Lys Asn
385                 390                 395


<210> SEQ ID NO 46
<211> LENGTH: 424
<212> TYPE: PRT
<213> ORGANISM: Aspergillus fumigatus

<400> SEQUENCE: 46

Met Ala Ser Asp Ala Glu Lys Thr Ser Ser Lys Met Ile Asp Thr Tyr
 1               5                  10                  15

Gly Asn Glu Phe Lys Ile Pro Asp Tyr Thr Ile Lys Gln Ile Arg Asp
            20                  25                  30

Ala Ile Pro Ala His Cys Tyr Gln Arg Ser Ala Ala Thr Ser Leu Tyr
        35                  40                  45

Tyr Val Phe Arg Asp Met Ala Ile Leu Ala Ser Val Phe Tyr Val Phe
    50                  55                  60

His Asn Tyr Val Thr Pro Glu Thr Val Pro Ser Met Pro Val Arg Val
65                  70                  75                  80
```

-continued

```
Val Leu Trp Thr Ile Tyr Thr Val Val Gln Gly Leu Val Gly Thr Gly
                85                  90                  95

Val Trp Val Leu Ala His Glu Cys Gly His Gln Ala Phe Ser Thr Ser
            100                 105                 110

Lys Val Leu Asn Asp Thr Val Gly Trp Ile Cys His Ser Leu Leu Leu
        115                 120                 125

Val Pro Tyr Phe Ser Trp Lys Ile Ser His Gly Lys His His Lys Ala
    130                 135                 140

Thr Gly Asn Ile Ala Arg Asp Met Val Phe Val Pro Lys Thr Arg Glu
145                 150                 155                 160

Glu Tyr Ala Thr Arg Ile Gly Arg Ala Ala His Glu Leu Ser Glu Leu
                165                 170                 175

Met Glu Glu Thr Pro Ile Leu Thr Ala Thr Asn Leu Val Leu Gln Gln
            180                 185                 190

Leu Phe Gly Trp Pro Met Tyr Leu Leu Thr Asn Val Thr Gly His Asn
        195                 200                 205

Asn His Glu Arg Gln Pro Glu Gly Arg Gly Lys Gly Lys Arg Asn Gly
    210                 215                 220

Tyr Phe Gly Gly Val Asn His Phe Asn Pro Ser Ser Pro Leu Tyr Glu
225                 230                 235                 240

Ala Lys Asp Ala Lys Leu Ile Val Leu Ser Asp Leu Gly Leu Phe Leu
                245                 250                 255

Val Gly Ser Leu Leu Tyr Tyr Ile Gly Ser Thr Tyr Gly Trp Leu Asn
            260                 265                 270

Leu Leu Val Trp Tyr Gly Ile Pro Tyr Leu Trp Val Asn His Trp Leu
        275                 280                 285

Val Ala Ile Thr Phe Leu Gln His Thr Asp Pro Thr Leu Pro His Tyr
    290                 295                 300

Gln Pro Glu Ala Trp Asp Phe Thr Arg Gly Ala Ala Ala Thr Ile Asp
305                 310                 315                 320

Arg Asp Phe Gly Phe Val Gly Arg His Ile Phe His Gly Ile Ile Glu
                325                 330                 335

Thr His Val Leu His His Tyr Val Ser Thr Ile Pro Phe Tyr His Ala
            340                 345                 350

Asp Glu Ala Ser Glu Ala Ile Gln Lys Val Met Gly Pro His Tyr Arg
        355                 360                 365

Ser Glu Ala His Thr Gly Trp Thr Gly Phe Leu Lys Ala Leu Trp Thr
    370                 375                 380

Ser Ala Arg Thr Cys Gln Trp Val Glu Pro Thr Glu Gly Ala Lys Gly
385                 390                 395                 400

Glu Ser Gln Tyr Val Leu Phe Tyr Arg Asn Ile Asn Gly Ile Gly Val
                405                 410                 415

Pro Pro Ala Lys Ile Pro Ala Lys
            420


<210> SEQ ID NO 47
<211> LENGTH: 446
<212> TYPE: PRT
<213> ORGANISM: Cryptococcus curvatus

<400> SEQUENCE: 47

Met Ser Ala Ala Thr Leu Arg Gln Arg Asn Val Asp Lys Pro Gly Ala
 1               5                  10                  15

Ala Asp Lys Ala Glu Leu Leu Arg Glu Ala Glu Asp Leu Glu Leu Thr
```

-continued

```
            20                  25                  30

Glu Gly Gln Lys Phe Val Gly Pro Asn Phe Thr Val Lys Gln Leu Leu
        35                  40                  45

Asp Ala Ile Pro Ala His Cys Tyr Lys Arg Ser Ala Phe Lys Ser Ser
    50                  55                  60

Leu Tyr Val Leu Gln Asp Phe Val Leu Leu Ala Ala Leu Val Tyr Gly
65                  70                  75                  80

Ala Tyr His Ile Asp Ser Phe Leu Ser Arg Phe Asn Leu Gly Ser Val
                85                  90                  95

Ala His Thr Ala Ala Lys Ile Gly Leu Trp Phe Thr Tyr Gln Val Leu
            100                 105                 110

Ala Gly Met Val Gly Thr Gly Ile Trp Val Ile Ala His Glu Cys Gly
        115                 120                 125

His Gln Ala Tyr Ser Glu Ser Lys Thr Ile Asn Asn Ala Val Gly Trp
    130                 135                 140

Val Leu His Ser Ile Leu Leu Val Pro Tyr His Ser Trp Arg Ile Ser
145                 150                 155                 160

His Gly Arg His His Ala Ala Thr Gly His Leu Thr Arg Asp Glu Val
                165                 170                 175

Phe Val Pro Arg Thr Arg Glu Gln Leu Gly Ile Gln Ala Pro Lys Thr
            180                 185                 190

Glu Glu Glu Lys Lys Gly Ile Asn Val Pro Ala Trp Arg Gln Ala Glu
        195                 200                 205

Leu Arg Glu Ala Leu Glu Glu Ser Pro Ile Gly Ala Leu Tyr Gly Ala
    210                 215                 220

Ile Leu His Gln Leu Phe Gly Trp Pro Met Tyr Leu Ile Arg Asn Ala
225                 230                 235                 240

Ser Gly Gln Leu Trp Tyr Pro Lys Met Thr Asn His Phe Gln Pro Ser
                245                 250                 255

Ser Ile Ile Phe Lys Pro Ser His Phe Trp Gln Ile Ile Ala Ser Asp
            260                 265                 270

Ile Gly Val Val Leu Thr Ala Ala Ala Leu Gly Val Phe Val Tyr Tyr
        275                 280                 285

Arg Gly Phe Ala Glu Met Ala Arg Ile Tyr Leu Ile Pro Tyr Leu Trp
    290                 295                 300

Val Asn His Trp Leu Val Phe Ile Thr Phe Leu Gln His Thr Asp Pro
305                 310                 315                 320

Val Leu Pro His Tyr Ser Glu Lys Thr Trp Thr Phe Ala Arg Gly Ala
                325                 330                 335

Leu Ala Thr Ile Asp Arg Asn Cys Leu Gly Pro Val Gly Pro Tyr Leu
            340                 345                 350

Phe His Gly Ile Thr Glu Thr His Val Ala His His Thr Ser Ser Arg
        355                 360                 365

Ile Pro His Tyr Asn Ala Trp Glu Ala Thr Glu Ala Leu Lys Lys Phe
    370                 375                 380

Leu Gly Pro His Tyr His Tyr Asn Pro Glu Asn Met Phe Val Ser Phe
385                 390                 395                 400

Trp Lys Ala His Arg Tyr Cys Lys Phe Ile Glu Ala Gly Glu Asp Val
                405                 410                 415

Ala Phe Tyr Arg Asn Ala Ala Gly Val Ala Gln Lys Val Gly Ile Ile
            420                 425                 430

Glu Glu Asn Gly Ala Val Ser Asp Ser Gly Val Glu His Lys
        435                 440                 445
```

-continued

<210> SEQ ID NO 48
<211> LENGTH: 376
<212> TYPE: PRT
<213> ORGANISM: Caenorhabditis elegans

<400> SEQUENCE: 48

Met Thr Ile Ala Thr Lys Val Asn Thr Asn Lys Lys Asp Leu Asp Thr
1               5                   10                  15

Ile Lys Val Pro Glu Leu Pro Ser Val Ala Ala Val Lys Ala Ala Ile
            20                  25                  30

Pro Glu His Cys Phe Val Lys Asp Pro Leu Thr Ser Ile Ser Tyr Leu
        35                  40                  45

Ile Lys Asp Tyr Val Leu Leu Ala Gly Leu Tyr Phe Ala Val Pro Tyr
    50                  55                  60

Ile Glu His Tyr Leu Gly Trp Ile Gly Leu Leu Gly Trp Tyr Trp Ala
65                  70                  75                  80

Met Gly Ile Val Gly Ser Ala Leu Phe Cys Val Gly His Asp Cys Gly
                85                  90                  95

His Gly Ser Phe Ser Asp Tyr Glu Trp Leu Asn Asp Leu Cys Gly His
            100                 105                 110

Leu Ala His Ala Pro Ile Leu Ala Pro Phe Trp Pro Trp Gln Lys Ser
        115                 120                 125

His Arg Gln His His Gln Tyr Thr Ser His Val Glu Lys Asp Lys Gly
    130                 135                 140

His Pro Trp Val Thr Glu Glu Asp Tyr Asn Asn Arg Thr Ala Ile Glu
145                 150                 155                 160

Lys Tyr Phe Ala Val Ile Pro Ile Ser Gly Trp Leu Arg Trp Asn Pro
                165                 170                 175

Ile Tyr Thr Ile Val Gly Leu Pro Asp Gly Ser His Phe Trp Pro Trp
            180                 185                 190

Ser Arg Leu Phe Glu Thr Thr Glu Asp Arg Val Lys Cys Ala Val Ser
        195                 200                 205

Gly Val Ala Cys Ala Ile Cys Ala Tyr Ile Ala Phe Val Leu Cys Asp
    210                 215                 220

Tyr Ser Val Tyr Thr Phe Val Lys Tyr Tyr Tyr Ile Pro Leu Leu Phe
225                 230                 235                 240

Gln Gly Leu Ile Leu Val Ile Ile Thr Tyr Leu Gln His Gln Asn Glu
                245                 250                 255

Asp Ile Glu Val Tyr Glu Ala Asp Glu Trp Gly Phe Val Arg Gly Gln
            260                 265                 270

Thr Gln Thr Ile Asp Arg His Trp Gly Phe Gly Leu Asp Asn Ile Met
        275                 280                 285

His Asn Ile Thr Asn Gly His Val Ala His His Phe Phe Phe Thr Lys
    290                 295                 300

Ile Pro His Tyr His Leu Leu Glu Ala Thr Pro Ala Ile Lys Lys Ala
305                 310                 315                 320

Leu Glu Pro Leu Lys Asp Thr Gln Tyr Gly Tyr Lys Arg Glu Val Asn
                325                 330                 335

Tyr Asn Trp Phe Phe Lys Tyr Leu His Tyr Asn Val Thr Leu Asp Tyr
            340                 345                 350

Leu Thr His Lys Ala Lys Gly Val Leu Gln Tyr Arg Ser Gly Val Glu
        355                 360                 365

Ala Ala Lys Ala Lys Lys Ala Gln 370 375

<210> SEQ ID NO 49
<211> LENGTH: 457
<212> TYPE: PRT
<213> ORGANISM: Mortierella alpina

<400> SEQUENCE: 49

Met Ala Ala Ala Pro Ser Val Arg Thr Phe Thr Arg Ala Glu Ile Leu
1 5 10 15

Asn Ala Glu Ala Leu Asn Glu Gly Lys Lys Asp Ala Glu Ala Pro Phe
20 25 30

Leu Met Ile Ile Asp Asn Lys Val Tyr Asp Val Arg Glu Phe Val Pro
35 40 45

Asp His Pro Gly Gly Ser Val Ile Leu Thr His Val Gly Lys Asp Gly
50 55 60

Thr Asp Val Phe Asp Thr Phe His Pro Glu Ala Ala Trp Glu Thr Leu
65 70 75 80

Ala Asn Phe Tyr Val Gly Asp Ile His Glu Ser Asp Arg Asp Ile Lys
85 90 95

Asn Asp Asp Phe Ala Ala Glu Val Arg Lys Leu Arg Thr Leu Phe Gln
100 105 110

Ser Leu Gly Tyr Tyr Asp Ser Ser Lys Ala Tyr Tyr Ala Phe Lys Val
115 120 125

Ser Phe Asn Leu Cys Ile Trp Gly Leu Ser Thr Phe Val Val Ala Lys
130 135 140

Trp Gly Gln Thr Ser Thr Leu Ala Asn Val Val Ser Ala Ala Leu Leu
145 150 155 160

Gly Leu Phe Trp Gln Gln Cys Gly Trp Leu Ala His Asp Phe Leu His
165 170 175

His Gln Val Phe Gln Asp Arg Phe Trp Gly Asp Leu Phe Gly Ala Phe
180 185 190

Leu Gly Gly Val Cys Gln Gly Phe Ser Ser Ser Trp Trp Lys Asp Lys
195 200 205

His Asn Thr His His Ala Ala Pro Asn Val His Gly Glu Asp Pro Asp
210 215 220

Ile Asp Thr His Pro Leu Leu Thr Trp Ser Glu His Ala Leu Glu Met
225 230 235 240

Phe Ser Asp Val Pro Asp Glu Glu Leu Thr Arg Met Trp Ser Arg Phe
245 250 255

Met Val Leu Asn Gln Thr Trp Phe Tyr Phe Pro Ile Leu Ser Phe Ala
260 265 270

Arg Leu Ser Trp Cys Leu Gln Ser Ile Leu Phe Val Met Pro Asn Gly
275 280 285

Gln Ala His Lys Pro Ser Gly Ala Arg Val Pro Ile Ser Leu Val Glu
290 295 300

Gln Leu Ser Leu Ala Met His Trp Thr Trp Tyr Leu Ala Thr Met Phe
305 310 315 320

Leu Phe Val Lys Asp Pro Ile Asn Met Phe Val Tyr Phe Leu Val Ser
325 330 335

Gln Ala Val Cys Gly Asn Leu Leu Ala Leu Val Phe Ser Leu Asn His
340 345 350

Asn Gly Met Pro Val Ile Ser Lys Glu Glu Ala Val Asp Met Asp Phe
355 360 365

-continued

```
Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Arg
        435                 440                 445

Ala Ala Ser Lys Met Gly Lys Ala Gln
    450                 455


<210> SEQ ID NO 50
<211> LENGTH: 523
<212> TYPE: PRT
<213> ORGANISM: Mucor rouxii

<400> SEQUENCE: 50

Met Pro Pro Asn Thr Ala Ala Asp Arg Leu Leu Ser Ser Thr Ser Thr
 1               5                  10                  15

Arg Ser Ser Asn Ile Val Thr Glu Glu Lys Phe Gln Glu Leu Ile Lys
            20                  25                  30

Gln Gly Asp Ser Val Phe Ile Tyr Glu Gln Lys Val Tyr Arg Val Asn
        35                  40                  45

Asn Phe Met Ala Lys His Pro Gly Gly Glu Ala Ala Leu Arg Ser Ala
    50                  55                  60

Leu Gly Arg Asp Val Thr Asp Glu Ile Arg Thr Met His Pro Pro Gln
65                  70                  75                  80

Val Tyr Glu Lys Met Ile Asn Leu Tyr Cys Ile Gly Asp Tyr Met Pro
                85                  90                  95

Asp Val Ile Arg Pro Ala Ser Met Lys Gln Gln His Thr Phe Thr Lys
            100                 105                 110

Pro Lys Glu Asp Lys Pro Val Leu Thr Ala Thr Trp Glu Gly Gly Phe
        115                 120                 125

Thr Val Gln Ala Tyr Asp Asp Ala Ile Gln Asp Leu His Lys His His
    130                 135                 140

Ser His Asp Leu Ile Lys Asp Ala Val Leu Gln Lys Asp Leu Asn Gly
145                 150                 155                 160

Asp Gln Ile Arg Asn Ala Tyr Arg Lys Leu Glu Ala Glu Leu Tyr Ala
                165                 170                 175

Lys Gly Leu Phe Lys Cys Asn Tyr Trp Lys Tyr Ala Arg Glu Gly Cys
            180                 185                 190

Arg Tyr Thr Leu Leu Ile Phe Leu Ser Leu Trp Phe Thr Leu Lys Gly
        195                 200                 205

Thr Glu Thr Trp His Tyr Met Ala Gly Ala Ala Phe Met Ala Met Phe
    210                 215                 220

Trp His Gln Leu Val Phe Thr Ala His Asp Ala Gly His Asn Glu Ile
225                 230                 235                 240

Thr Gly Lys Ser Glu Ile Asp His Val Ile Gly Val Ile Ile Ala Asn
                245                 250                 255

Phe Ile Gly Gly Leu Ser Leu Gly Trp Trp Lys Asp Asn His Asn Val
            260                 265                 270

His His Ile Val Thr Asn His Pro Glu His Asp Pro Asp Ile Gln His
        275                 280                 285
```

-continued

```
Val Pro Phe Met Ala Ile Thr Thr Lys Phe Phe Asn Asn Ile Tyr Ser
    290                 295                 300

Thr Tyr Tyr Lys Arg Val Leu Pro Phe Asp Ala Ala Ser Arg Phe Phe
305                 310                 315                 320

Val Arg His Gln His Tyr Leu Tyr Tyr Leu Ile Leu Ser Phe Gly Arg
                325                 330                 335

Phe Asn Leu His Arg Leu Ser Phe Ala Tyr Leu Leu Thr Cys Lys Asn
            340                 345                 350

Val Arg Thr Arg Thr Leu Glu Leu Val Gly Ile Thr Phe Phe Phe Val
        355                 360                 365

Trp Phe Gly Ser Leu Leu Ser Thr Leu Pro Thr Trp Asn Ile Arg Ile
    370                 375                 380

Ala Tyr Ile Met Val Ser Tyr Met Leu Thr Phe Pro Leu His Val Gln
385                 390                 395                 400

Ile Thr Leu Ser His Phe Gly Met Ser Thr Glu Asp Arg Gly Pro Asp
                405                 410                 415

Glu Pro Phe Pro Ala Lys Met Leu Arg Thr Thr Met Asp Val Asp Cys
            420                 425                 430

Pro Glu Trp Leu Asp Trp Phe His Gly Gly Leu Gln Tyr Gln Ala Val
        435                 440                 445

His His Leu Phe Pro Arg Leu Pro Arg His Asn Leu Arg Gln Cys Val
    450                 455                 460

Pro Leu Val Lys Lys Phe Cys Asp Glu Val Gly Leu His Tyr Tyr Met
465                 470                 475                 480

Tyr Asn Phe Ser Thr Gly Asn Gly Val Val Leu Gly Thr Leu Lys Ser
                485                 490                 495

Val Ala Asp Gln Val Gly Phe Met Asn Glu Val Ala Lys Ser Asn Ala
            500                 505                 510

Glu Ile Trp Ala Asn Asp Lys Glu His Ala His
        515                 520


<210> SEQ ID NO 51
<211> LENGTH: 448
<212> TYPE: PRT
<213> ORGANISM: Borago officinalis

<400> SEQUENCE: 51

Met Ala Ala Gln Ile Lys Lys Tyr Ile Thr Ser Asp Glu Leu Lys Asn
 1               5                  10                  15

His Asp Lys Pro Gly Asp Leu Trp Ile Ser Ile Gln Gly Lys Ala Tyr
            20                  25                  30

Asp Val Ser Asp Trp Val Lys Asp His Pro Gly Gly Ser Phe Pro Leu
        35                  40                  45

Lys Ser Leu Ala Gly Gln Glu Val Thr Asp Ala Phe Val Ala Phe His
    50                  55                  60

Pro Ala Ser Thr Trp Lys Asn Leu Asp Lys Phe Phe Thr Gly Tyr Tyr
65                  70                  75                  80

Leu Lys Asp Tyr Ser Val Ser Glu Val Ser Lys Asp Tyr Arg Lys Leu
                85                  90                  95

Val Phe Glu Phe Ser Lys Met Gly Leu Tyr Asp Lys Lys Gly His Ile
            100                 105                 110

Met Phe Ala Thr Leu Cys Phe Ile Ala Met Leu Phe Ala Met Ser Val
        115                 120                 125

Tyr Gly Val Leu Phe Cys Glu Gly Val Leu Val His Leu Phe Ser Gly
```

-continued

```
    130                 135                 140

Cys Leu Met Gly Phe Leu Trp Ile Gln Ser Gly Trp Ile Gly His Asp
145                 150                 155                 160

Ala Gly His Tyr Met Val Val Ser Asp Ser Arg Leu Asn Lys Phe Met
                165                 170                 175

Gly Ile Phe Ala Ala Asn Cys Leu Ser Gly Ile Ser Ile Gly Trp Trp
            180                 185                 190

Lys Trp Asn His Asn Ala His His Ile Ala Cys Asn Ser Leu Glu Tyr
        195                 200                 205

Asp Pro Asp Leu Gln Tyr Ile Pro Phe Leu Val Val Ser Ser Lys Phe
    210                 215                 220

Phe Gly Ser Leu Thr Ser His Phe Tyr Glu Lys Arg Leu Thr Phe Asp
225                 230                 235                 240

Ser Leu Ser Arg Phe Phe Val Ser Tyr Gln His Trp Thr Phe Tyr Pro
                245                 250                 255

Ile Met Cys Ala Ala Arg Leu Asn Met Tyr Val Gln Ser Leu Ile Met
            260                 265                 270

Leu Leu Thr Lys Arg Asn Val Ser Tyr Arg Ala His Glu Leu Leu Gly
        275                 280                 285

Cys Leu Val Phe Ser Ile Trp Tyr Pro Leu Leu Val Ser Cys Leu Pro
    290                 295                 300

Asn Trp Gly Glu Arg Ile Met Phe Val Ile Ala Ser Leu Ser Val Thr
305                 310                 315                 320

Gly Met Gln Gln Val Gln Phe Ser Leu Asn His Phe Ser Ser Ser Val
                325                 330                 335

Tyr Val Gly Lys Pro Lys Gly Asn Asn Trp Phe Glu Lys Gln Thr Asp
            340                 345                 350

Gly Thr Leu Asp Ile Ser Cys Pro Pro Trp Met Asp Trp Phe His Gly
        355                 360                 365

Gly Leu Gln Phe Gln Ile Glu His His Leu Phe Pro Lys Met Pro Arg
    370                 375                 380

Cys Asn Leu Arg Lys Ile Ser Pro Tyr Val Ile Glu Leu Cys Lys Lys
385                 390                 395                 400

His Asn Leu Pro Tyr Asn Tyr Ala Ser Phe Ser Lys Ala Asn Glu Met
                405                 410                 415

Thr Leu Arg Thr Leu Arg Asn Thr Ala Leu Gln Ala Arg Asp Ile Thr
            420                 425                 430

Lys Pro Leu Pro Lys Asn Leu Val Trp Glu Ala Leu His Thr His Gly
        435                 440                 445


<210> SEQ ID NO 52
<211> LENGTH: 446
<212> TYPE: PRT
<213> ORGANISM: Anemone levellei

<400> SEQUENCE: 52

Met Ala Glu Lys Arg Arg Ser Ile Ser Ser Asp Asp Leu Arg Ser His
 1               5                  10                  15

Asn Lys Pro Gly Asp Val Trp Ile Ser Ile Gln Gly Lys Ile Tyr Asp
            20                  25                  30

Val Thr Glu Trp Gly Lys Asp His Pro Gly Gly Glu Gly Pro Leu Leu
        35                  40                  45

Asn Leu Ala Gly Gln Asp Val Thr Asp Ala Phe Val Ala Phe His Pro
    50                  55                  60
```

-continued

Gly Ser Ala Trp Lys Asn Leu Asp Lys Phe His Ile Gly Tyr Leu Gln
65 70 75 80

Asp Tyr Val Val Ser Asp Val Ser Lys Asp Tyr Arg Lys Leu Val Ser
85 90 95

Glu Phe Ser Lys Ala Gly Leu Tyr Glu Lys Lys Gly His Gly His Leu
100 105 110

Ile Arg Leu Leu Val Met Ser Leu Val Phe Ile Ala Ser Val Ser Gly
115 120 125

Val Val Leu Ser Asp Lys Thr Ser Val His Val Gly Ser Ala Val Leu
130 135 140

Leu Ala Val Ile Trp Met Gln Phe Gly Phe Ile Gly His Asp Ser Gly
145 150 155 160

His Tyr Asn Ile Met Thr Ser Pro Glu Leu Asn Arg Tyr Met Gln Ile
165 170 175

Phe Ser Val Asn Val Val Ser Gly Val Ser Val Gly Trp Trp Lys Arg
180 185 190

Tyr His Asn Ala His His Ile Ala Val Asn Ser Leu Glu Tyr Asp Pro
195 200 205

Asp Leu Gln Tyr Val Pro Phe Leu Val Val Ser Thr Ala Ile Phe Asp
210 215 220

Ser Leu Thr Ser His Phe Tyr Arg Lys Lys Met Thr Phe Asp Ala Val
225 230 235 240

Ala Arg Phe Leu Val Ser Phe Gln His Trp Thr Phe Tyr Pro Leu Met
245 250 255

Ala Ile Gly Arg Val Ser Phe Leu Ala Gln Ser Ile Gly Val Leu Leu
260 265 270

Ser Lys Lys Pro Leu Pro Asp Arg His Leu Glu Trp Phe Gly Leu Val
275 280 285

Val Phe Trp Ala Trp Tyr Ser Leu Leu Ile Ser Cys Leu Pro Asn Trp
290 295 300

Trp Glu Arg Val Ile Phe Ile Ala Val Asn Phe Ala Val Thr Gly Ile
305 310 315 320

Gln His Val Gln Phe Cys Leu Asn His Tyr Ser Ala Gln Thr Tyr Ile
325 330 335

Gly Ala Pro Cys Ala Asn Asp Trp Phe Glu Lys Gln Thr Lys Gly Ser
340 345 350

Ile Asp Ile Ser Cys Ser Pro Trp Thr Asp Trp Phe His Gly Gly Leu
355 360 365

Gln Phe Gln Ile Glu His His Leu Phe Pro Arg Met Pro Arg Cys Asn
370 375 380

Leu Arg Lys Ile Ser Pro Phe Val Lys Glu Leu Cys Arg Lys His Asn
385 390 395 400

Leu Val Tyr Thr Ser Val Ser Phe Phe Glu Gly Asn Arg Arg Thr Leu
405 410 415

Ala Thr Leu Lys Asn Ala Ala Leu Lys Ala Arg Asp Leu Thr Ser Pro
420 425 430

Ile Pro Lys Asn Leu Val Trp Glu Ala Val His Thr His Gly
435 440 445

<210> SEQ ID NO 53
<211> LENGTH: 443
<212> TYPE: PRT
<213> ORGANISM: Caenorhabditis elegans

<400> SEQUENCE: 53

-continued

```
Met Val Val Asp Lys Asn Ala Ser Gly Leu Arg Met Lys Val Asp Gly
 1               5                  10                  15

Lys Trp Leu Tyr Leu Ser Glu Glu Leu Val Lys Lys His Pro Gly Gly
            20                  25                  30

Ala Val Ile Glu Gln Tyr Arg Asn Ser Asp Ala Thr His Ile Phe His
        35                  40                  45

Ala Phe His Glu Gly Ser Ser Gln Ala Tyr Lys Gln Leu Asp Leu Leu
    50                  55                  60

Lys Lys His Gly Glu His Asp Glu Phe Leu Glu Lys Gln Leu Glu Lys
65                  70                  75                  80

Arg Leu Asp Lys Val Asp Ile Asn Val Ser Ala Tyr Asp Val Ser Val
                85                  90                  95

Ala Gln Glu Lys Lys Met Val Glu Ser Phe Glu Lys Leu Arg Gln Lys
            100                 105                 110

Leu His Asp Asp Gly Leu Met Lys Ala Asn Glu Thr Tyr Phe Leu Phe
        115                 120                 125

Lys Ala Ile Ser Thr Leu Ser Ile Met Ala Phe Ala Phe Tyr Leu Gln
    130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                165                 170                 175

Lys Asn Arg Pro Leu Asn Asp Thr Ile Ser Leu Phe Phe Gly Asn Phe
            180                 185                 190

Leu Gln Gly Phe Ser Arg Asp Trp Trp Lys Asp Lys His Asn Thr His
        195                 200                 205

His Ala Ala Thr Asn Val Ile Asp His Asp Gly Asp Ile Asp Leu Ala
    210                 215                 220

Pro Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
                245                 250                 255

Thr Ala Met Leu Pro Met Leu Arg Phe Ser Trp Thr Gly Gln Ser Val
            260                 265                 270

Gln Trp Val Phe Lys Glu Asn Gln Met Glu Tyr Lys Val Tyr Gln Arg
        275                 280                 285

Asn Ala Phe Trp Glu Gln Ala Thr Ile Val Gly His Trp Ala Trp Val
    290                 295                 300

Phe Tyr Gln Leu Phe Leu Leu Pro Thr Trp Pro Leu Arg Val Ala Tyr
305                 310                 315                 320

Phe Ile Ile Ser Gln Met Gly Gly Gly Leu Leu Ile Ala His Val Val
                325                 330                 335

Thr Phe Asn His Asn Ser Val Asp Lys Tyr Pro Ala Asn Ser Arg Ile
            340                 345                 350

Leu Asn Asn Phe Ala Ala Leu Gln Ile Leu Thr Thr Arg Asn Met Thr
        355                 360                 365

Pro Ser Pro Phe Ile Asp Trp Leu Trp Gly Gly Leu Asn Tyr Gln Ile
    370                 375                 380

Glu His His Leu Phe Pro Thr Met Pro Arg Cys Asn Leu Asn Ala Cys
385                 390                 395                 400

Met Lys Tyr Val Lys Glu Trp Cys Lys Glu Asn Asn Leu Pro Tyr Leu
                405                 410                 415
```

-continued

```
Val Asp Asp Tyr Phe Asp Gly Tyr Ala Met Asn Leu Gln Gln Leu Lys
            420                 425                 430

Asn Met Ala Glu His Ile Gln Ala Lys Ala Ala
        435                 440


<210> SEQ ID NO 54
<211> LENGTH: 318
<212> TYPE: PRT
<213> ORGANISM: Mortierella alpina

<400> SEQUENCE: 54

Met Glu Ser Ile Ala Gln Phe Leu Pro Ser Lys Met Pro Gln Asp Leu
 1               5                  10                  15

Phe Ile Asp Leu Ala Ala Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Val Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95

Asn Phe Asp Arg Phe Glu Val Lys Thr Phe Ser Leu Phe His Asn Phe
            100                 105                 110

Cys Leu Val Ser Ile Ser Ala Tyr Met Cys Gly Gly Ile Leu Tyr Glu
        115                 120                 125

Ala Tyr Gln Ala Asn Tyr Gly Leu Phe Glu Asn Ala Ala Asp His Thr
    130                 135                 140

Ala Lys Gly Phe Pro Met Ala Lys Met Ile Trp Leu Phe Tyr Phe Ser
145                 150                 155                 160

Lys Ile Met Glu Phe Val Asp Thr Met Ile Met Val Leu Lys Lys Asn
                165                 170                 175

Asn Arg Gln Ile Ser Phe Leu His Val Tyr His His Ser Ser Ile Phe
            180                 185                 190

Thr Ile Trp Trp Leu Val Thr Phe Val Ala Pro Asn Gly Glu Ala Tyr
        195                 200                 205

Phe Ser Ala Ala Leu Asn Ser Phe Ile His Val Ile Met Tyr Gly Tyr
    210                 215                 220

Tyr Phe Leu Ser Ala Leu Gly Phe Lys Gln Val Ser Phe Val Lys Phe
225                 230                 235                 240

Tyr Ile Thr Arg Ser Gln Met Thr Gln Phe Cys Met Met Ser Ile Gln
                245                 250                 255

Ser Ser Trp Asp Met Tyr Ala Met Lys Val Leu Gly Arg Pro Gly Tyr
            260                 265                 270

Pro Phe Phe Ile Thr Ala Leu Leu Trp Phe Tyr Met Trp Thr Met Leu
        275                 280                 285

Gly Leu Phe Tyr Asn Phe Tyr Arg Lys Asn Ala Lys Leu Ala Lys Gln
    290                 295                 300

Ala Lys Ala Asp Ala Ala Lys Glu Lys Ala Arg Lys Leu Gln
305                 310                 315


<210> SEQ ID NO 55
<211> LENGTH: 290
<212> TYPE: PRT
<213> ORGANISM: Physcomitrella patens
```

<400> SEQUENCE: 55

```
Met Glu Val Val Glu Arg Phe Tyr Gly Glu Leu Asp Gly Lys Val Ser
 1               5                  10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290
```

<210> SEQ ID NO 56
<211> LENGTH: 288
<212> TYPE: PRT
<213> ORGANISM: Caenorhabditis elegans

<400> SEQUENCE: 56

```
Met Ala Gln His Pro Leu Val Gln Arg Leu Leu Asp Val Lys Phe Asp
 1               5                  10                  15

Thr Lys Arg Phe Val Ala Ile Ala Thr His Gly Pro Lys Asn Phe Pro
            20                  25                  30

Asp Ala Glu Gly Arg Lys Phe Phe Ala Asp His Phe Asp Val Thr Ile
        35                  40                  45

Gln Ala Ser Ile Leu Tyr Met Val Val Val Phe Gly Thr Lys Trp Phe
    50                  55                  60
```

-continued

```
Met Arg Asn Arg Gln Pro Phe Gln Leu Thr Ile Pro Leu Asn Ile Trp
65                  70                  75                  80

Asn Phe Ile Leu Ala Ala Phe Ser Ile Ala Gly Ala Val Lys Met Thr
                85                  90                  95

Pro Glu Phe Phe Gly Thr Ile Ala Asn Lys Gly Ile Val Ala Ser Tyr
            100                 105                 110

Cys Lys Val Phe Asp Phe Thr Lys Gly Glu Asn Gly Tyr Trp Val Trp
        115                 120                 125

Leu Phe Met Ala Ser Lys Leu Phe Glu Leu Val Asp Thr Ile Phe Leu
    130                 135                 140

Val Leu Arg Lys Arg Pro Leu Met Phe Leu His Trp Tyr His His Ile
145                 150                 155                 160

Leu Thr Met Ile Tyr Ala Trp Tyr Ser His Pro Leu Thr Pro Gly Phe
                165                 170                 175

Asn Arg Tyr Gly Ile Tyr Leu Asn Phe Val Val His Ala Phe Met Tyr
            180                 185                 190

Ser Tyr Tyr Phe Leu Arg Ser Met Lys Ile Arg Val Pro Gly Phe Ile
        195                 200                 205

Ala Gln Ala Ile Thr Ser Leu Gln Ile Val Gln Phe Ile Ile Ser Cys
    210                 215                 220

Ala Val Leu Ala His Leu Gly Tyr Leu Met His Phe Thr Asn Ala Asn
225                 230                 235                 240

Cys Asp Phe Glu Pro Ser Val Phe Lys Leu Ala Val Phe Met Asp Thr
                245                 250                 255

Thr Tyr Leu Ala Leu Phe Val Asn Phe Phe Leu Gln Ser Tyr Val Leu
            260                 265                 270

Arg Gly Gly Lys Asp Lys Tyr Lys Ala Val Pro Lys Lys Lys Asn Asn
        275                 280                 285


<210> SEQ ID NO 57
<211> LENGTH: 299
<212> TYPE: PRT
<213> ORGANISM: Mus musculus

<400> SEQUENCE: 57

Met Glu His Phe Asp Ala Ser Leu Ser Thr Tyr Phe Lys Ala Phe Leu
 1               5                  10                  15

Gly Pro Arg Asp Thr Arg Val Lys Gly Trp Phe Leu Leu Asp Asn Tyr
            20                  25                  30

Ile Pro Thr Phe Val Cys Ser Val Ile Tyr Leu Leu Ile Val Trp Leu
        35                  40                  45

Gly Pro Lys Tyr Met Lys Asn Arg Gln Pro Phe Ser Cys Arg Gly Ile
    50                  55                  60

Leu Gln Leu Tyr Asn Leu Gly Leu Thr Leu Leu Ser Leu Tyr Met Phe
65                  70                  75                  80

Tyr Glu Leu Val Thr Gly Val Trp Glu Gly Lys Tyr Asn Phe Phe Cys
                85                  90                  95

Gln Gly Thr Arg Ser Ala Gly Glu Ser Asp Met Lys Ile Ile Arg Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Val Leu His Val
    130                 135                 140

Tyr His His Ala Thr Met Leu Asn Ile Trp Trp Phe Val Met Asn Trp
```

-continued

```
145                 150                 155                 160

Val Pro Cys Gly His Ser Tyr Phe Gly Ala Thr Leu Asn Ser Phe Ile
                165                 170                 175

His Val Leu Met Tyr Ser Tyr Tyr Gly Leu Ser Ser Ile Pro Ser Met
            180                 185                 190

Arg Pro Tyr Leu Trp Trp Lys Lys Tyr Ile Thr Gln Gly Gln Leu Val
        195                 200                 205

Gln Phe Val Leu Thr Ile Ile Gln Thr Thr Cys Gly Val Phe Trp Pro
    210                 215                 220

Cys Ser Phe Pro Leu Gly Trp Leu Phe Phe Gln Ile Gly Tyr Met Ile
225                 230                 235                 240

Ser Leu Ile Ala Leu Phe Thr Asn Phe Tyr Ile Gln Thr Tyr Asn Lys
                245                 250                 255

Lys Gly Ala Ser Arg Arg Lys Asp His Leu Lys Gly His Gln Asn Gly
            260                 265                 270

Ser Val Ala Ala Val Asn Gly His Thr Asn Ser Phe Pro Ser Leu Glu
        275                 280                 285

Asn Ser Val Lys Pro Arg Lys Gln Arg Lys Asp
    290                 295


<210> SEQ ID NO 58
<211> LENGTH: 272
<212> TYPE: PRT
<213> ORGANISM: Thraustochytrium aureum

<400> SEQUENCE: 58

Met Ala Asn Ser Ser Val Trp Asp Asp Val Val Gly Arg Val Glu Thr
 1               5                  10                  15

Gly Val Asp Gln Trp Met Asp Gly Ala Lys Pro Tyr Ala Leu Thr Asp
            20                  25                  30

Gly Leu Pro Met Met Asp Val Ser Thr Met Leu Ala Phe Glu Val Gly
        35                  40                  45

Tyr Met Ala Met Leu Leu Phe Gly Ile Pro Ile Met Lys Gln Met Glu
    50                  55                  60

Lys Pro Phe Glu Leu Lys Thr Ile Lys Leu Leu His Asn Leu Phe Leu
65                  70                  75                  80

Phe Gly Leu Ser Leu Tyr Met Cys Val Glu Thr Ile Arg Gln Ala Ile
                85                  90                  95

Leu Gly Gly Tyr Lys Val Phe Gly Asn Asp Met Glu Lys Gly Asn Glu
            100                 105                 110

Ser His Ala Gln Gly Met Ser Arg Ile Val Tyr Val Phe Tyr Val Ser
        115                 120                 125

Lys Ala Tyr Glu Phe Leu Asp Thr Ala Ile Met Ile Leu Cys Lys Lys
    130                 135                 140

Phe Asn Gln Val Ser Phe Leu His Val Tyr His His Ala Thr Ile Phe
145                 150                 155                 160

Ala Ile Trp Trp Ala Ile Ala Lys Tyr Ala Pro Gly Gly Asp Ala Tyr
                165                 170                 175

Phe Ser Val Ile Leu Asn Ser Phe Val His Thr Val Met Tyr Ala Tyr
            180                 185                 190

Tyr Phe Phe Ser Ser Gln Gly Phe Gly Phe Val Lys Pro Ile Lys Pro
        195                 200                 205

Tyr Ile Thr Thr Leu Gln Met Thr Gln Phe Met Ala Met Leu Val Gln
    210                 215                 220
```

-continued

```
Ser Leu Tyr Asp Tyr Leu Phe Pro Cys Asp Tyr Pro Gln Ala Leu Val
225                 230                 235                 240

Gln Leu Leu Gly Val Tyr Met Ile Thr Leu Leu Ala Leu Phe Gly Asn
                245                 250                 255

Phe Phe Val Gln Ser Tyr Leu Lys Lys Pro Lys Lys Ser Lys Thr Asn
            260                 265                 270


<210> SEQ ID NO 59
<211> LENGTH: 278
<212> TYPE: PRT
<213> ORGANISM: Phytophthora infestans

<400> SEQUENCE: 59

Met Ser Thr Glu Leu Leu Gln Ser Tyr Tyr Ala Trp Ala Asn Ala Thr
 1               5                  10                  15

Glu Ala Lys Leu Leu Asp Trp Val Asp Pro Glu Gly Gly Trp Lys Val
            20                  25                  30

His Pro Met Ala Asp Tyr Pro Leu Ala Asn Phe Ser Ser Val Tyr Ala
        35                  40                  45

Ile Cys Val Gly Tyr Leu Leu Phe Val Ile Phe Gly Thr Ala Leu Met
    50                  55                  60

Lys Met Gly Val Pro Ala Ile Lys Thr Ser Pro Leu Gln Phe Val Tyr
65                  70                  75                  80

Asn Pro Ile Gln Val Ile Ala Cys Ser Tyr Met Cys Val Glu Ala Ala
                85                  90                  95

Ile Gln Ala Tyr Arg Asn Gly Tyr Thr Ala Ala Pro Cys Asn Ala Phe
            100                 105                 110

Lys Ser Asp Asp Pro Val Met Gly Asn Val Leu Tyr Leu Phe Tyr Leu
        115                 120                 125

Ser Lys Met Leu Asp Leu Cys Asp Thr Val Phe Ile Ile Leu Gly Lys
    130                 135                 140

Lys Trp Lys Gln Leu Ser Ile Leu His Val Tyr His His Leu Thr Val
145                 150                 155                 160

Leu Phe Val Tyr Tyr Val Thr Phe Arg Ala Ala Gln Asp Gly Asp Ser
                165                 170                 175

Tyr Ala Thr Ile Val Leu Asn Gly Phe Val His Thr Ile Met Tyr Thr
            180                 185                 190

Tyr Tyr Phe Val Ser Ala His Thr Arg Asn Ile Trp Trp Lys Lys Tyr
        195                 200                 205

Leu Thr Arg Ile Gln Leu Ile Gln Phe Val Thr Met Asn Val Gln Gly
    210                 215                 220

Tyr Leu Thr Tyr Ser Arg Gln Cys Pro Gly Met Pro Pro Lys Val Pro
225                 230                 235                 240

Leu Met Tyr Leu Val Tyr Val Gln Ser Leu Phe Trp Leu Phe Met Asn
                245                 250                 255

Phe Tyr Ile Arg Ala Tyr Val Phe Gly Pro Lys Lys Pro Ala Val Glu
            260                 265                 270

Glu Ser Lys Lys Lys Leu
        275


<210> SEQ ID NO 60
<211> LENGTH: 446
<212> TYPE: PRT
<213> ORGANISM: Mortierella alpina

<400> SEQUENCE: 60
```

-continued

```
Met Gly Thr Asp Gln Gly Lys Thr Phe Thr Trp Glu Ala Leu Ala Ala
 1               5                  10                  15

His Asn Ala Glu Gly Asp Leu Leu Leu Ala Ile Arg Gly Asn Val Tyr
            20                  25                  30

Asp Val Thr Lys Phe Leu Ser Arg His Pro Gly Gly Thr Asp Thr Leu
        35                  40                  45

Leu Leu Gly Ala Gly Arg Asp Val Thr Pro Val Phe Glu Met Tyr His
    50                  55                  60

Glu Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Lys Asp Arg Asn Lys
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
    210                 215                 220

Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
            260                 265                 270

Val Lys Thr Asn Asp Ala Ile Arg Val Asn Pro Ile Ser Thr Trp His
        275                 280                 285

Thr Val Met Phe Trp Gly Gly Lys Ala Phe Phe Val Trp Tyr Arg Leu
    290                 295                 300

Ile Val Pro Leu Gln Tyr Leu Pro Leu Gly Lys Val Leu Leu Leu Phe
305                 310                 315                 320

Thr Ile Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
            340                 345                 350

Gly Ile Ile Gln Lys Asp Trp Ala Ala Met Gln Val Glu Thr Thr Gln
        355                 360                 365

Asp Tyr Ala His Asp Ser His Leu Trp Thr Ser Ile Thr Gly Ser Leu
    370                 375                 380

Asn Tyr Gln Ala Val His His Leu Phe Pro Asn Val Ser Gln His His
385                 390                 395                 400

Tyr Pro Asp Ile Leu Ala Ile Ile Lys Asp Thr Cys Ser Glu Tyr Lys
                405                 410                 415

Val Pro Tyr Leu Val Lys Asp Thr Phe Trp Gln Ala Phe Ala Ser His
```

-continued

```
            420                 425                 430

Leu Glu His Leu Arg Val Leu Gly Leu Arg Pro Lys Glu Glu
        435                 440                 445


<210> SEQ ID NO 61
<211> LENGTH: 477
<212> TYPE: PRT
<213> ORGANISM: Phytophthora megasperma

<400> SEQUENCE: 61

Met Ala Pro Ile Glu Thr Val Lys Asp Ala Asn Glu Gly Leu His Gln
 1               5                  10                  15

Arg Lys Gly Ala Ala Ala Ala Ser Lys Asp Thr Thr Thr Phe Thr Trp
            20                  25                  30

Gln Asp Val Ala Lys His Asn Thr Ala Lys Ser Ala Trp Val Thr Ile
        35                  40                  45

Arg Gly Val Val Tyr Asp Val Thr Glu Trp Ala Asp Arg His Pro Gly
    50                  55                  60

Gly Arg Glu Leu Val Leu Leu His Ser Gly Arg Glu Cys Thr Asp Thr
65                  70                  75                  80

Phe Asp Ser Tyr His Pro Phe Ser Asp Arg Ala Asp Lys Ile Leu Ala
                85                  90                  95

Lys Tyr Ala Ile Gly Lys Leu Val Gly Gly Ser Glu Phe Pro Thr Tyr
            100                 105                 110

Lys Pro Asp Thr Gly Phe Tyr Lys Glu Cys Cys Asp Arg Val Asn Gln
        115                 120                 125

Tyr Phe Lys Asp Asn Lys Leu Asp Pro Arg Ser Pro Tyr Ser Gly Leu
    130                 135                 140

Trp Arg Met Ile Leu Val Ala Ile Val Gly Ala Val Ala Tyr Met Gly
145                 150                 155                 160

Met Asn Gln Leu Leu Pro Gly Asn Ile Tyr Ala His Tyr Ala Trp Gly
                165                 170                 175

Ala Leu Phe Gly Val Cys Gln Ala Leu Pro Leu Leu His Val Met His
            180                 185                 190

Asp Ala Ser His Ala Ala Ile Thr Ser Ser Pro Thr Gly Trp Arg Leu
        195                 200                 205

Ile Gly Arg Leu Ala Met Asp Trp Val Ala Gly Ala Asn Met Val Ser
    210                 215                 220

Trp Leu Asn Gln His Val Val Gly His His Ile Tyr Thr Asn Val Ala
225                 230                 235                 240

Gly Ala Asp Pro Asp Leu Pro Val Asp Phe Lys Ser Asp Val Arg Arg
                245                 250                 255

Ile Val Tyr Arg Gln Val Leu Leu Pro Ile Tyr Lys Tyr Gln His Leu
            260                 265                 270

Tyr Leu Pro Pro Leu Tyr Gly Val Leu Gly Leu Lys Phe Arg Val Gln
        275                 280                 285

Asp Val Phe Glu Thr Phe Val Thr Leu Thr Asn Gly Pro Leu Arg Val
    290                 295                 300

Asn Pro Leu Ser Val Gly Asp Trp Ala Glu Met Ile Leu Ser Lys Ala
305                 310                 315                 320

Phe Trp Val Phe Tyr Arg Ile Tyr Leu Pro Leu Ala Val Leu Gln Val
                325                 330                 335

Asp Pro Ala Arg Phe Trp Gly Val Phe Phe Leu Ala Glu Phe Ser Thr
            340                 345                 350
```

-continued

```
Gly Trp Tyr Leu Ala Phe Asn Phe Gln Val Ser His Val Ser Thr Ala
        355                 360                 365

Cys Glu Tyr Pro Gly Gly Asp Glu Glu Val Thr Ser Ile Asp Asp Glu
    370                 375                 380

Trp Ala Ile Ser Gln Val Lys Ser Ser Val Asp Tyr Gly His Gly Ser
385                 390                 395                 400

Phe Ile Thr Thr Phe Leu Thr Gly Ala Leu Asn Tyr Gln Val Thr His
                405                 410                 415

His Leu Phe Pro Gly Val Ser Gln Tyr His Tyr Pro Ala Ile Ala Pro
            420                 425                 430

Leu Ile Leu Asp Val Cys His Lys Tyr Lys Val Lys Tyr Asn Val Leu
        435                 440                 445

Pro Asp Phe Thr Ala Ala Met Ala Gly His Phe Asp His Leu Val Ile
    450                 455                 460

Met Gly Lys Met Gly Lys Arg Val Thr Ile His Met Gly
465                 470                 475


<210> SEQ ID NO 62
<211> LENGTH: 439
<212> TYPE: PRT
<213> ORGANISM: Thraustochytrium sp. ATCC 21685

<400> SEQUENCE: 62

Met Gly Lys Gly Ser Glu Gly Arg Ser Ala Ala Arg Glu Met Thr Ala
 1               5                  10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255
```

-continued

```
Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

Ala Asp His Thr Val Asn Ile Ser Thr Lys Ser Trp Leu Val Thr Trp
        355                 360                 365

Trp Met Ser Asn Leu Asn Phe Gln Ile Glu His His Leu Phe Pro Thr
    370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430

Ala Asp Thr Lys Lys Gln Asp
        435
```

<210> SEQ ID NO 63
<211> LENGTH: 447
<212> TYPE: PRT
<213> ORGANISM: Caenorhabditis elegans

<400> SEQUENCE: 63

```
Met Val Leu Arg Glu Gln Glu His Glu Pro Phe Phe Ile Lys Ile Asp
 1               5                  10                  15

Gly Lys Trp Cys Gln Ile Asp Asp Ala Val Leu Arg Ser His Pro Gly
            20                  25                  30

Gly Ser Ala Ile Thr Thr Tyr Lys Asn Met Asp Ala Thr Thr Val Phe
        35                  40                  45

His Thr Phe His Thr Gly Ser Lys Glu Ala Tyr Gln Trp Leu Thr Glu
    50                  55                  60

Leu Lys Lys Glu Cys Pro Thr Gln Glu Pro Glu Ile Pro Asp Ile Lys
65                  70                  75                  80

Asp Asp Pro Ile Lys Gly Ile Asp Asp Val Asn Met Gly Thr Phe Asn
                85                  90                  95

Ile Ser Glu Lys Arg Ser Ala Gln Ile Asn Lys Ser Phe Thr Asp Leu
            100                 105                 110

Arg Met Arg Val Arg Ala Glu Gly Leu Met Asp Gly Ser Pro Leu Phe
        115                 120                 125

Tyr Ile Arg Lys Ile Leu Glu Thr Ile Phe Thr Ile Leu Phe Ala Phe
    130                 135                 140

Tyr Leu Gln Tyr His Thr Tyr Tyr Leu Pro Ser Ala Ile Leu Met Gly
145                 150                 155                 160

Val Ala Trp Gln Gln Leu Gly Trp Leu Ile His Glu Phe Ala His His
                165                 170                 175

Gln Leu Phe Lys Asn Arg Tyr Tyr Asn Asp Leu Ala Ser Tyr Phe Val
```

-continued

```
            180                 185                 190

Gly Asn Phe Leu Gln Gly Phe Ser Ser Gly Gly Trp Lys Glu Gln His
        195                 200                 205

Asn Val His His Ala Ala Thr Asn Val Val Gly Arg Asp Gly Asp Leu
    210                 215                 220

Asp Leu Val Pro Phe Tyr Ala Thr Val Ala Glu His Leu Asn Asn Tyr
225                 230                 235                 240

Ser Gln Asp Ser Trp Val Met Thr Leu Phe Arg Trp Gln His Val His
                245                 250                 255

Trp Thr Phe Met Leu Pro Phe Leu Arg Leu Ser Trp Leu Leu Gln Ser
            260                 265                 270

Ile Ile Phe Val Ser Gln Met Pro Thr His Tyr Tyr Asp Tyr Tyr Arg
        275                 280                 285

Asn Thr Ala Ile Tyr Glu Gln Val Gly Leu Ser Leu His Trp Ala Trp
    290                 295                 300

Ser Leu Gly Gln Leu Tyr Phe Leu Pro Asp Trp Ser Thr Arg Ile Met
305                 310                 315                 320

Phe Phe Leu Val Ser His Leu Val Gly Gly Phe Leu Leu Ser His Val
                325                 330                 335

Val Thr Phe Asn His Tyr Ser Val Glu Lys Phe Ala Leu Ser Ser Asn
            340                 345                 350

Ile Met Ser Asn Tyr Ala Cys Leu Gln Ile Met Thr Thr Arg Asn Met
        355                 360                 365

Arg Pro Gly Arg Phe Ile Asp Trp Leu Trp Gly Gly Leu Asn Tyr Gln
    370                 375                 380

Ile Glu His His Leu Phe Pro Thr Met Pro Arg His Asn Leu Asn Thr
385                 390                 395                 400

Val Met Pro Leu Val Lys Glu Phe Ala Ala Ala Asn Gly Leu Pro Tyr
                405                 410                 415

Met Val Asp Asp Tyr Phe Thr Gly Phe Trp Leu Glu Ile Glu Gln Phe
            420                 425                 430

Arg Asn Ile Ala Asn Val Ala Ala Lys Leu Thr Lys Lys Ile Ala
        435                 440                 445


<210> SEQ ID NO 64
<211> LENGTH: 456
<212> TYPE: PRT
<213> ORGANISM: Pythium irregulare

<400> SEQUENCE: 64

Met Thr Glu Lys Ala Ser Asp Glu Phe Thr Trp Gln Glu Val Ala Lys
 1               5                  10                  15

His Asn Thr Ala Lys Ser Ala Trp Val Ile Ile Arg Gly Glu Val Tyr
            20                  25                  30

Asp Val Thr Glu Trp Ala Asp Lys His Pro Gly Gly Ser Glu Leu Ile
        35                  40                  45

Val Leu His Ser Gly Arg Glu Cys Thr Asp Thr Phe Tyr Ser Tyr His
    50                  55                  60

Pro Phe Ser Asn Arg Ala Asp Lys Ile Leu Ala Lys Tyr Lys Ile Gly
65                  70                  75                  80

Lys Leu Val Gly Gly Tyr Glu Phe Pro Val Phe Lys Pro Asp Ser Gly
                85                  90                  95

Phe Tyr Lys Glu Cys Ser Glu Arg Val Ala Glu Tyr Phe Lys Thr Asn
            100                 105                 110
```

-continued

```
Asn Leu Asp Pro Lys Ala Ala Phe Ala Gly Leu Trp Arg Met Val Phe
        115                 120                 125

Val Phe Ala Val Ala Ala Leu Ala Tyr Met Gly Met Asn Glu Leu Ile
    130                 135                 140

Pro Gly Asn Val Tyr Ala Gln Tyr Ala Trp Gly Val Val Phe Gly Val
145                 150                 155                 160

Phe Gln Ala Leu Pro Leu Leu His Val Met His Asp Ser Ser His Ala
                165                 170                 175

Ala Cys Ser Ser Ser Pro Ala Met Trp Gln Ile Ile Gly Arg Gly Val
            180                 185                 190

Met Asp Trp Phe Ala Gly Ala Ser Met Val Ser Trp Leu Asn Gln His
        195                 200                 205

Val Val Gly His His Ile Tyr Thr Asn Val Ala Gly Ala Asp Pro Asp
    210                 215                 220

Leu Pro Val Asp Phe Glu Ser Asp Val Arg Arg Ile Val His Arg Gln
225                 230                 235                 240

Val Leu Leu Pro Ile Tyr Lys Phe Gln His Ile Tyr Leu Pro Pro Leu
                245                 250                 255

Tyr Gly Val Leu Gly Leu Lys Phe Arg Ile Gln Asp Val Phe Glu Thr
            260                 265                 270

Phe Val Ser Leu Thr Asn Gly Pro Val Arg Val Asn Pro His Pro Val
        275                 280                 285

Ser Asp Trp Val Gln Met Ile Phe Ala Lys Ala Phe Trp Thr Phe Tyr
    290                 295                 300

Arg Ile Tyr Ile Pro Leu Ala Trp Leu Lys Ile Thr Pro Ser Thr Phe
305                 310                 315                 320

Trp Gly Val Phe Phe Leu Ala Glu Phe Thr Thr Gly Trp Tyr Leu Ala
                325                 330                 335

Phe Asn Phe Gln Val Ser His Val Ser Thr Glu Cys Glu Tyr Pro Cys
            340                 345                 350

Gly Asp Ala Pro Ser Ala Glu Val Gly Asp Glu Trp Ala Ile Ser Gln
        355                 360                 365

Val Lys Ser Ser Val Asp Tyr Ala His Gly Ser Pro Leu Ala Ala Phe
    370                 375                 380

Leu Cys Gly Ala Leu Asn Tyr Gln Val Thr His His Leu Tyr Pro Gly
385                 390                 395                 400

Ile Ser Gln Tyr His Tyr Pro Ala Ile Ala Pro Ile Ile Ile Asp Val
                405                 410                 415

Cys Lys Lys Tyr Asn Ile Lys Tyr Thr Val Leu Pro Thr Phe Thr Glu
            420                 425                 430

Ala Leu Leu Ala His Phe Lys His Leu Lys Asn Met Gly Glu Leu Gly
        435                 440                 445

Lys Pro Val Glu Ile His Met Gly
    450                 455


<210> SEQ ID NO 65
<211> LENGTH: 469
<212> TYPE: PRT
<213> ORGANISM: Phaeodactylum tricornutum

<400> SEQUENCE: 65

Met Ala Pro Asp Ala Asp Lys Leu Arg Gln Arg Gln Thr Thr Ala Val
 1               5                  10                  15

Ala Lys His Asn Ala Ala Thr Ile Ser Thr Gln Glu Arg Leu Cys Ser
            20                  25                  30
```

-continued

```
Leu Ser Ser Leu Lys Gly Glu Glu Val Cys Ile Asp Gly Ile Ile Tyr
        35                  40                  45

Asp Leu Gln Ser Phe Asp His Pro Gly Gly Glu Thr Ile Lys Met Phe
    50                  55                  60

Gly Gly Asn Asp Val Thr Val Gln Tyr Lys Met Ile His Pro Tyr His
65                  70                  75                  80

Thr Glu Lys His Leu Glu Lys Met Lys Arg Val Gly Lys Val Thr Asp
                85                  90                  95

Phe Val Cys Glu Tyr Lys Phe Asp Thr Glu Phe Glu Arg Glu Ile Lys
            100                 105                 110

Arg Glu Val Phe Lys Ile Val Arg Arg Gly Lys Asp Phe Gly Thr Leu
        115                 120                 125

Gly Trp Phe Phe Arg Ala Phe Cys Tyr Ile Ala Ile Phe Phe Tyr Leu
    130                 135                 140

Gln Tyr His Trp Val Thr Thr Gly Thr Ser Trp Leu Leu Ala Val Ala
145                 150                 155                 160

Tyr Gly Ile Ser Gln Ala Met Ile Gly Met Asn Val Gln His Asp Ala
                165                 170                 175

Asn His Gly Ala Thr Ser Lys Arg Pro Trp Val Asn Asp Met Leu Gly
            180                 185                 190

Leu Gly Ala Asp Phe Ile Gly Gly Ser Lys Trp Leu Trp Gln Glu Gln
        195                 200                 205

His Trp Thr His His Ala Tyr Thr Asn His Ala Glu Met Asp Pro Asp
    210                 215                 220

Ser Phe Gly Ala Glu Pro Met Leu Leu Phe Asn Asp Tyr Pro Leu Asp
225                 230                 235                 240

His Pro Ala Arg Thr Trp Leu His Arg Phe Gln Ala Phe Phe Tyr Met
                245                 250                 255

Pro Val Leu Ala Gly Tyr Trp Leu Ser Ala Val Phe Asn Pro Gln Ile
            260                 265                 270

Leu Asp Leu Gln Gln Arg Gly Ala Leu Ser Val Gly Ile Arg Leu Asp
        275                 280                 285

Asn Ala Phe Ile His Ser Arg Arg Lys Tyr Ala Val Phe Trp Arg Ala
    290                 295                 300

Val Tyr Ile Ala Val Asn Val Ile Ala Pro Phe Tyr Thr Asn Ser Gly
305                 310                 315                 320

Leu Glu Trp Ser Trp Arg Val Phe Gly Asn Ile Met Leu Met Gly Val
                325                 330                 335

Ala Glu Ser Leu Ala Leu Ala Val Leu Phe Ser Leu Ser His Asn Phe
            340                 345                 350

Glu Ser Ala Asp Arg Asp Pro Thr Ala Pro Leu Lys Lys Thr Gly Glu
        355                 360                 365

Pro Val Asp Trp Phe Lys Thr Gln Val Glu Thr Ser Cys Thr Tyr Gly
    370                 375                 380

Gly Phe Leu Ser Gly Cys Phe Thr Gly Gly Leu Asn Phe Gln Val Glu
385                 390                 395                 400

His His Leu Phe Pro Arg Met Ser Ser Ala Trp Tyr Pro Tyr Ile Ala
                405                 410                 415

Pro Lys Val Arg Glu Ile Cys Ala Lys His Gly Val His Tyr Ala Tyr
            420                 425                 430

Tyr Pro Trp Ile His Gln Asn Phe Leu Ser Thr Val Arg Tyr Met His
        435                 440                 445
```

-continued

```
Ala Ala Gly Thr Gly Ala Asn Trp Arg Gln Met Ala Arg Glu Asn Pro
    450                 455                 460

Leu Thr Gly Arg Ala
465


<210> SEQ ID NO 66
<211> LENGTH: 292
<212> TYPE: PRT
<213> ORGANISM: Mus musculus

<400> SEQUENCE: 66

Met Glu Gln Leu Lys Ala Phe Asp Asn Glu Val Asn Ala Phe Leu Asp
 1               5                  10                  15

Asn Met Phe Gly Pro Arg Asp Ser Arg Val Arg Gly Trp Phe Leu Leu
            20                  25                  30

Asp Ser Tyr Leu Pro Thr Phe Ile Leu Thr Ile Thr Tyr Leu Leu Ser
        35                  40                  45

Ile Trp Leu Gly Asn Lys Tyr Met Lys Asn Arg Pro Ala Leu Ser Leu
    50                  55                  60

Arg Gly Ile Leu Thr Leu Tyr Asn Leu Ala Ile Thr Leu Leu Ser Ala
65                  70                  75                  80

Tyr Met Leu Val Glu Leu Ile Leu Ser Ser Trp Glu Gly Gly Tyr Asn
                85                  90                  95

Leu Gln Cys Gln Asn Leu Asp Ser Ala Gly Glu Gly Asp Val Arg Val
            100                 105                 110

Ala Lys Val Leu Trp Trp Tyr Tyr Phe Ser Lys Leu Val Glu Phe Leu
        115                 120                 125

Asp Thr Ile Phe Phe Val Leu Arg Lys Lys Thr Asn Gln Ile Thr Phe
    130                 135                 140

Leu His Val Tyr His His Ala Ser Met Phe Asn Ile Trp Trp Cys Val
145                 150                 155                 160

Leu Asn Trp Ile Pro Cys Gly Gln Ser Phe Phe Gly Pro Thr Leu Asn
                165                 170                 175

Ser Phe Ile His Ile Leu Met Tyr Ser Tyr Tyr Gly Leu Ser Val Phe
            180                 185                 190

Pro Ser Met His Lys Tyr Leu Trp Trp Lys Lys Tyr Leu Thr Gln Ala
        195                 200                 205

Gln Leu Val Gln Phe Val Leu Thr Ile Thr His Thr Leu Ser Ala Val
    210                 215                 220

Val Lys Pro Cys Gly Phe Pro Phe Gly Cys Leu Ile Phe Gln Ser Ser
225                 230                 235                 240

Tyr Met Met Thr Leu Val Ile Leu Phe Leu Asn Phe Tyr Ile Gln Thr
                245                 250                 255

Tyr Arg Lys Lys Pro Val Lys Lys Glu Leu Gln Glu Lys Glu Val Lys
            260                 265                 270

Asn Gly Phe Pro Lys Ala His Leu Ile Val Ala Asn Gly Met Thr Asp
        275                 280                 285

Lys Lys Ala Gln
    290


<210> SEQ ID NO 67
<211> LENGTH: 299
<212> TYPE: PRT
<213> ORGANISM: Homo sapiens

<400> SEQUENCE: 67
```

-continued

```
Met Glu His Phe Asp Ala Ser Leu Ser Thr Tyr Phe Lys Ala Leu Leu
 1               5                  10                  15

Gly Pro Arg Asp Thr Arg Val Lys Gly Trp Phe Leu Leu Asp Asn Tyr
            20                  25                  30

Ile Pro Thr Phe Ile Cys Ser Val Ile Tyr Leu Leu Ile Val Trp Leu
        35                  40                  45

Gly Pro Lys Tyr Met Arg Asn Lys Gln Pro Phe Ser Cys Arg Gly Ile
    50                  55                  60

Leu Val Val Tyr Asn Leu Gly Leu Thr Leu Leu Ser Leu Tyr Met Phe
65                  70                  75                  80

Cys Glu Leu Val Thr Gly Val Trp Glu Gly Lys Tyr Asn Phe Phe Cys
                85                  90                  95

Gln Gly Thr Arg Thr Ala Gly Glu Ser Asp Met Lys Ile Ile Arg Val
            100                 105                 110

Leu Trp Trp Tyr Tyr Phe Ser Lys Leu Ile Glu Phe Met Asp Thr Phe
        115                 120                 125

Phe Phe Ile Leu Arg Lys Asn Asn His Gln Ile Thr Val Leu His Val
    130                 135                 140

Tyr His His Ala Ser Met Leu Asn Ile Trp Trp Phe Val Met Asn Trp
145                 150                 155                 160

Val Pro Cys Gly His Ser Tyr Phe Gly Ala Thr Leu Asn Ser Phe Ile
                165                 170                 175

His Val Leu Met Tyr Ser Tyr Tyr Gly Leu Ser Ser Val Pro Ser Met
            180                 185                 190

Arg Pro Tyr Leu Trp Trp Lys Lys Tyr Ile Thr Gln Gly Gln Leu Leu
        195                 200                 205

Gln Phe Val Leu Thr Ile Ile Gln Thr Ser Cys Gly Val Ile Trp Pro
    210                 215                 220

Cys Thr Phe Pro Leu Gly Trp Leu Tyr Phe Gln Ile Gly Tyr Met Ile
225                 230                 235                 240

Ser Leu Ile Ala Leu Phe Thr Asn Phe Tyr Ile Gln Thr Tyr Asn Lys
                245                 250                 255

Lys Gly Ala Ser Arg Arg Lys Asp His Leu Lys Asp His Gln Asn Gly
            260                 265                 270

Ser Met Ala Ala Val Asn Gly His Thr Asn Ser Phe Ser Pro Leu Glu
        275                 280                 285

Asn Asn Val Lys Pro Arg Lys Leu Arg Lys Asp
    290                 295


<210> SEQ ID NO 68
<211> LENGTH: 277
<212> TYPE: PRT
<213> ORGANISM: Pavlova

<400> SEQUENCE: 68

Met Met Leu Ala Ala Gly Tyr Leu Leu Val Leu Ser Ala Ala Arg Gln
 1               5                  10                  15

Ser Phe Gln Gln Asp Ile Asp Asn Pro Asn Gly Ala Tyr Ser Thr Ser
            20                  25                  30

Trp Thr Gly Leu Pro Ile Val Met Ser Val Val Tyr Leu Ser Gly Val
        35                  40                  45

Phe Gly Leu Thr Lys Tyr Phe Glu Asn Arg Lys Pro Met Thr Gly Leu
    50                  55                  60

Lys Asp Tyr Met Phe Thr Tyr Asn Leu Tyr Gln Val Ile Ile Asn Val
65                  70                  75                  80
```

-continued

```
Trp Cys Val Val Ala Phe Leu Leu Glu Val Arg Arg Ala Gly Met Ser
                85                  90                  95

Leu Ile Gly Asn Lys Val Asp Leu Gly Pro Asn Ser Phe Arg Leu Gly
            100                 105                 110

Phe Val Thr Trp Val His Tyr Asn Asn Lys Tyr Val Glu Leu Leu Asp
        115                 120                 125

Thr Leu Trp Met Val Leu Arg Lys Lys Thr Gln Gln Val Ser Phe Leu
    130                 135                 140

His Val Tyr His His Val Leu Leu Met Trp Ala Trp Phe Val Val Val
145                 150                 155                 160

Lys Leu Gly Asn Gly Gly Asp Ala Tyr Phe Gly Gly Leu Met Asn Ser
                165                 170                 175

Ile Ile His Val Met Met Tyr Ser Tyr Tyr Thr Met Ala Leu Leu Gly
            180                 185                 190

Trp Ser Cys Pro Trp Lys Arg Tyr Leu Thr Gln Ala Gln Leu Val Gln
        195                 200                 205

Phe Cys Ile Cys Leu Ala His Ser Thr Trp Ala Ala Val Thr Gly Ala
    210                 215                 220

Tyr Pro Trp Arg Ile Cys Leu Val Glu Val Trp Val Met Val Ser Met
225                 230                 235                 240

Leu Val Leu Phe Thr Arg Phe Tyr Arg Gln Ala Tyr Ala Lys Glu Ala
                245                 250                 255

Lys Ala Lys Glu Ala Lys Lys Leu Ala Gln Glu Ala Ser Gln Ala Lys
            260                 265                 270

Ala Val Lys Ala Glu
        275


<210> SEQ ID NO 69
<211> LENGTH: 402
<212> TYPE: PRT
<213> ORGANISM: Caenorhabditis elegans

<400> SEQUENCE: 69

Met Val Ala His Ser Ser Glu Gly Leu Ser Ala Thr Ala Pro Val Thr
 1               5                  10                  15

Gly Gly Asp Val Leu Val Asp Ala Arg Ala Ser Leu Glu Glu Lys Glu
            20                  25                  30

Ala Pro Arg Asp Val Asn Ala Asn Thr Lys Gln Ala Thr Thr Glu Glu
        35                  40                  45

Pro Arg Ile Gln Leu Pro Thr Val Asp Ala Phe Arg Arg Ala Ile Pro
    50                  55                  60

Ala His Cys Phe Glu Arg Asp Leu Val Lys Ser Ile Arg Tyr Leu Val
65                  70                  75                  80

Gln Asp Phe Ala Ala Leu Thr Ile Leu Tyr Phe Ala Leu Pro Ala Phe
                85                  90                  95

Glu Tyr Phe Gly Leu Phe Gly Tyr Leu Val Trp Asn Ile Phe Met Gly
            100                 105                 110

Val Phe Gly Phe Ala Leu Phe Val Val Gly His Asp Cys Leu His Gly
        115                 120                 125

Ser Phe Ser Asp Asn Gln Asn Leu Asn Asp Phe Ile Gly His Ile Ala
    130                 135                 140

Phe Ser Pro Leu Phe Ser Pro Tyr Phe Pro Trp Gln Lys Ser His Lys
145                 150                 155                 160

Leu His His Ala Phe Thr Asn His Ile Asp Lys Asp His Gly His Val
```

-continued

```
                165                 170                 175

Trp Ile Gln Asp Lys Asp Trp Glu Ala Met Pro Ser Trp Lys Arg Trp
            180                 185                 190

Phe Asn Pro Ile Pro Phe Ser Gly Trp Leu Lys Trp Phe Pro Val Tyr
        195                 200                 205

Thr Leu Phe Gly Phe Cys Asp Gly Ser His Phe Trp Pro Tyr Ser Ser
    210                 215                 220

Leu Phe Val Arg Asn Ser Glu Arg Val Gln Cys Val Ile Ser Gly Ile
225                 230                 235                 240

Cys Cys Cys Val Cys Ala Tyr Ile Ala Leu Thr Ile Ala Gly Ser Tyr
                245                 250                 255

Ser Asn Trp Phe Trp Tyr Tyr Trp Val Pro Leu Ser Phe Phe Gly Leu
            260                 265                 270

Met Leu Val Ile Val Thr Tyr Leu Gln His Val Asp Asp Val Ala Glu
        275                 280                 285

Val Tyr Glu Ala Asp Glu Trp Ser Phe Val Arg Gly Gln Thr Gln Thr
    290                 295                 300

Ile Asp Arg Tyr Tyr Gly Leu Gly Leu Asp Thr Thr Met His His Ile
305                 310                 315                 320

Thr Asp Gly His Val Ala His His Phe Phe Asn Lys Ile Pro His Tyr
                325                 330                 335

His Leu Ile Glu Ala Thr Glu Gly Val Lys Lys Val Leu Glu Pro Leu
            340                 345                 350

Ser Asp Thr Gln Tyr Gly Tyr Lys Ser Gln Val Asn Tyr Asp Phe Phe
        355                 360                 365

Ala Arg Phe Leu Trp Phe Asn Tyr Lys Leu Asp Tyr Leu Val His Lys
    370                 375                 380

Thr Ala Gly Ile Met Gln Phe Arg Thr Thr Leu Glu Glu Lys Ala Lys
385                 390                 395                 400

Ala Lys


<210> SEQ ID NO 70
<211> LENGTH: 438
<212> TYPE: PRT
<213> ORGANISM: Petroselinum crispum

<400> SEQUENCE: 70

Met Ala Ser Trp Val Ile Ser Glu Cys Gly Leu Arg Pro Leu Pro Arg
 1               5                  10                  15

Ile Tyr Ala Arg Pro Arg Ser Gly Ala Ser Cys Phe Asn Ser Lys Asn
            20                  25                  30

Pro Val Lys Asn Leu Arg Phe Leu Asp Glu Asn Val Lys Ile Ser Met
        35                  40                  45

Thr Gly Ser Arg Asn Trp Gly Leu Arg Val Ser Val Pro Met Ser Val
    50                  55                  60

Pro Ser Val Ser Glu Glu Glu Glu Arg Phe Glu Ser Leu Val Glu Glu
65                  70                  75                  80

Glu Asn Glu Phe Asp Pro Gly Ala Ala Pro Pro Phe Lys Leu Ser Asp
                85                  90                  95

Val Arg Ala Ala Ile Pro Lys His Cys Trp Val Lys Asp Pro Val Arg
            100                 105                 110

Ser Met Ser Tyr Val Leu Arg Asp Val Leu Ile Val Phe Gly Leu Ala
        115                 120                 125

Val Ala Ala Ser Phe Val Asn Asn Trp Ala Val Trp Pro Leu Tyr Trp
```

-continued

```
    130                 135                 140

Ile Ala Gln Gly Thr Met Phe Trp Ala Leu Phe Val Leu Gly His Asp
145                 150                 155                 160

Cys Gly His Gly Ser Phe Ser Asn Asp Ala Lys Leu Asn Ser Val Val
                165                 170                 175

Gly His Ile Leu His Ser Ser Ile Leu Val Pro Tyr His Gly Trp Arg
            180                 185                 190

Ile Ser His Arg Thr His His Gln Asn His Gly His Val Glu Asn Asp
        195                 200                 205

Glu Ser Trp His Pro Leu Ser Glu Lys Leu Phe Asn Ser Leu Asp Asp
    210                 215                 220

Leu Thr Arg Lys Phe Arg Phe Thr Leu Pro Phe Pro Met Leu Ala Tyr
225                 230                 235                 240

Pro Phe Tyr Leu Trp Gly Arg Ser Pro Gly Lys Lys Gly Ser His Tyr
                245                 250                 255

Asp Pro Ser Ser Asp Leu Phe Val Pro Asn Glu Arg Lys Asp Val Ile
            260                 265                 270

Thr Ser Thr Val Cys Trp Thr Ala Met Ala Ala Leu Leu Val Gly Leu
        275                 280                 285

Asn Phe Val Met Gly Pro Val Lys Met Leu Met Leu Tyr Gly Ile Pro
    290                 295                 300

Tyr Trp Ile Phe Val Met Trp Leu Asp Phe Val Thr Tyr Leu His His
305                 310                 315                 320

His Gly His Asp Asp Lys Leu Pro Trp Tyr Arg Gly Lys Glu Trp Ser
                325                 330                 335

Tyr Leu Arg Gly Gly Leu Thr Thr Leu Asp Arg Asp Tyr Gly Trp Ile
            340                 345                 350

Asn Asn Ile His His Asp Ile Gly Thr His Val Val His His Leu Phe
        355                 360                 365

Pro Gln Ile Pro His Tyr His Leu Ile Glu Ala Thr Glu Ala Ala Lys
    370                 375                 380

Pro Val Phe Gly Lys Tyr Tyr Arg Glu Pro Lys Lys Ser Gly Pro Val
385                 390                 395                 400

Pro Phe His Leu Leu Ala Thr Leu Trp Lys Ser Phe Lys Lys Asp His
                405                 410                 415

Phe Val Ser Asp Thr Gly Asp Val Val Tyr Tyr Gln Ala His Pro Glu
            420                 425                 430

Ile Ala Lys Thr Gln Lys
        435


<210> SEQ ID NO 71
<211> LENGTH: 446
<212> TYPE: PRT
<213> ORGANISM: Arabidopsis thaliana

<400> SEQUENCE: 71

Met Ala Asn Leu Val Leu Ser Glu Cys Gly Ile Arg Pro Leu Pro Arg
 1               5                  10                  15

Ile Tyr Thr Thr Pro Arg Ser Asn Phe Leu Ser Asn Asn Asn Lys Phe
            20                  25                  30

Arg Pro Ser Leu Ser Ser Ser Ser Tyr Lys Thr Ser Ser Ser Pro Leu
        35                  40                  45

Ser Phe Gly Leu Asn Ser Arg Asp Gly Phe Thr Arg Asn Trp Ala Leu
    50                  55                  60
```

-continued

```
Asn Val Ser Thr Pro Leu Thr Thr Pro Ile Phe Glu Glu Ser Pro Leu
65                  70                  75                  80

Glu Glu Asp Asn Lys Gln Arg Phe Asp Pro Gly Ala Pro Pro Pro Phe
                85                  90                  95

Asn Leu Ala Asp Ile Arg Ala Ala Ile Pro Lys His Cys Trp Val Lys
            100                 105                 110

Asn Pro Trp Lys Ser Leu Ser Tyr Val Val Arg Asp Val Ala Ile Val
        115                 120                 125

Phe Ala Leu Ala Ala Gly Ala Ala Tyr Leu Asn Asn Trp Ile Val Trp
    130                 135                 140

Pro Leu Tyr Trp Leu Ala Gln Gly Thr Met Phe Trp Ala Leu Phe Val
145                 150                 155                 160

Leu Gly His Asp Cys Gly His Gly Ser Phe Ser Asn Asp Pro Lys Leu
                165                 170                 175

Asn Ser Val Val Gly His Leu Leu His Ser Ser Ile Leu Val Pro Tyr
            180                 185                 190

His Gly Trp Arg Ile Ser His Arg Thr His His Gln Asn His Gly His
        195                 200                 205

Val Glu Asn Asp Glu Ser Trp His Pro Met Ser Glu Lys Ile Tyr Asn
    210                 215                 220

Thr Leu Asp Lys Pro Thr Arg Phe Phe Arg Phe Thr Leu Pro Leu Val
225                 230                 235                 240

Met Leu Ala Tyr Pro Phe Tyr Leu Trp Ala Arg Ser Pro Gly Lys Lys
                245                 250                 255

Gly Ser His Tyr His Pro Asp Ser Asp Leu Phe Leu Pro Lys Glu Arg
            260                 265                 270

Lys Asp Val Leu Thr Ser Thr Ala Cys Trp Thr Ala Met Ala Ala Leu
        275                 280                 285

Leu Val Cys Leu Asn Phe Thr Ile Gly Pro Ile Gln Met Leu Lys Leu
    290                 295                 300

Tyr Gly Ile Pro Tyr Trp Ile Asn Val Met Trp Leu Asp Phe Val Thr
305                 310                 315                 320

Tyr Leu His His His Gly His Glu Asp Lys Leu Pro Trp Tyr Arg Gly
                325                 330                 335

Lys Glu Trp Ser Tyr Leu Arg Gly Gly Leu Thr Thr Leu Asp Arg Asp
            340                 345                 350

Tyr Gly Leu Ile Asn Asn Ile His His Asp Ile Gly Thr His Val Ile
        355                 360                 365

His His Leu Phe Pro Gln Ile Pro His Tyr His Leu Val Glu Ala Thr
    370                 375                 380

Glu Ala Ala Lys Pro Val Leu Gly Lys Tyr Tyr Arg Glu Pro Asp Lys
385                 390                 395                 400

Ser Gly Pro Leu Pro Leu His Leu Leu Glu Ile Leu Ala Lys Ser Ile
                405                 410                 415

Lys Glu Asp His Tyr Val Ser Asp Glu Gly Glu Val Val Tyr Tyr Lys
            420                 425                 430

Ala Asp Pro Asn Leu Tyr Gly Glu Val Lys Val Arg Ala Asp
        435                 440                 445
```

<210> SEQ ID NO 72
<211> LENGTH: 377
<212> TYPE: PRT
<213> ORGANISM: Brassica napus

<400> SEQUENCE: 72

-continued

```
Met Val Val Ala Met Asp Gln Arg Ser Asn Ala Asn Gly Asp Glu Arg
 1               5                  10                  15

Phe Asp Pro Ser Ala Gln Pro Pro Phe Lys Ile Gly Asp Ile Arg Ala
            20                  25                  30

Ala Ile Pro Lys His Cys Trp Val Lys Ser Pro Leu Arg Ser Met Ser
        35                  40                  45

Tyr Val Ala Arg Asp Ile Phe Ala Val Val Ala Leu Ala Val Ala Ala
    50                  55                  60

Val Tyr Phe Asp Ser Trp Phe Phe Trp Pro Leu Tyr Trp Ala Ala Gln
65                  70                  75                  80

Gly Thr Leu Phe Trp Ala Ile Phe Val Leu Gly His Asp Cys Gly His
                85                  90                  95

Gly Ser Phe Ser Asp Ile Pro Leu Leu Asn Thr Ala Val Gly His Ile
            100                 105                 110

Leu His Ser Phe Ile Leu Val Pro Tyr His Gly Trp Arg Ile Ser His
        115                 120                 125

Arg Thr His His Gln Asn His Gly His Val Glu Asn Asp Glu Ser Trp
    130                 135                 140

Val Pro Leu Pro Glu Lys Leu Tyr Lys Asn Leu Ser His Ser Thr Arg
145                 150                 155                 160

Met Leu Arg Tyr Thr Val Pro Leu Pro Met Leu Ala Tyr Pro Leu Tyr
                165                 170                 175

Leu Trp Tyr Arg Ser Pro Gly Lys Glu Gly Ser His Tyr Asn Pro Tyr
            180                 185                 190

Ser Ser Leu Phe Ala Pro Ser Glu Arg Lys Leu Ile Ala Thr Ser Thr
        195                 200                 205

Thr Cys Trp Ser Ile Met Leu Ala Thr Leu Val Tyr Leu Ser Phe Leu
    210                 215                 220

Val Gly Pro Val Thr Val Leu Lys Val Tyr Gly Val Pro Tyr Ile Ile
225                 230                 235                 240

Phe Val Met Trp Leu Asp Ala Val Thr Tyr Leu His His His Gly His
                245                 250                 255

Asp Asp Lys Leu Pro Trp Tyr Arg Gly Lys Glu Trp Ser Tyr Leu Arg
            260                 265                 270

Gly Gly Leu Thr Thr Ile Asp Arg Asp Tyr Gly Ile Phe Asn Asn Ile
        275                 280                 285

His His Asp Ile Gly Thr His Val Ile His His Leu Phe Pro Gln Ile
    290                 295                 300

Pro His Tyr His Leu Val Asp Ala Thr Lys Ser Ala Lys His Val Leu
305                 310                 315                 320

Gly Arg Tyr Tyr Arg Glu Pro Lys Thr Ser Gly Ala Ile Pro Ile His
                325                 330                 335

Leu Val Glu Ser Leu Val Ala Ser Ile Lys Lys Asp His Tyr Val Ser
            340                 345                 350

Asp Thr Gly Asp Ile Val Phe Tyr Glu Thr Asp Pro Asp Leu Tyr Val
        355                 360                 365

Tyr Ala Ser Asp Lys Ser Lys Ile Asn
    370                 375
```

<210> SEQ ID NO 73
<211> LENGTH: 380
<212> TYPE: PRT
<213> ORGANISM: Glycine soya -continued

<400> SEQUENCE: 73

```
Met Val Lys Asp Thr Lys Pro Leu Ala Tyr Ala Ala Asn Asn Gly Tyr
 1               5                  10                  15

Gln Gln Lys Gly Ser Ser Phe Asp Phe Asp Pro Ser Ala Pro Pro Pro
            20                  25                  30

Phe Lys Ile Ala Glu Ile Arg Ala Ser Ile Pro Lys His Cys Trp Val
        35                  40                  45

Lys Asn Pro Trp Arg Ser Leu Ser Tyr Val Leu Arg Asp Val Leu Val
    50                  55                  60

Ile Ala Ala Leu Val Ala Ala Ala Ile His Phe Asp Asn Trp Leu Leu
65                  70                  75                  80

Trp Leu Ile Tyr Cys Pro Ile Gln Gly Thr Met Phe Trp Ala Leu Phe
                85                  90                  95

Val Leu Gly His Asp Cys Gly His Gly Ser Phe Ser Asp Ser Pro Leu
            100                 105                 110

Leu Asn Ser Leu Val Gly His Ile Leu His Ser Ser Ile Leu Val Pro
        115                 120                 125

Tyr His Gly Trp Arg Ile Ser His Arg Thr His His Gln Asn His Gly
    130                 135                 140

His Ile Glu Lys Asp Glu Ser Trp Val Pro Leu Thr Glu Lys Ile Tyr
145                 150                 155                 160

Lys Asn Leu Asp Ser Met Thr Arg Leu Ile Arg Phe Thr Val Pro Phe
                165                 170                 175

Pro Leu Phe Val Tyr Pro Ile Tyr Leu Phe Ser Arg Ser Pro Gly Lys
            180                 185                 190

Glu Gly Ser His Phe Asn Pro Tyr Ser Asn Leu Phe Pro Pro Ser Glu
        195                 200                 205

Arg Lys Gly Ile Ala Ile Ser Thr Leu Cys Trp Ala Thr Met Phe Ser
    210                 215                 220

Leu Leu Ile Tyr Leu Ser Phe Ile Thr Ser Pro Leu Leu Val Leu Lys
225                 230                 235                 240

Leu Tyr Gly Ile Pro Tyr Trp Ile Phe Val Met Trp Leu Asp Phe Val
                245                 250                 255

Thr Tyr Leu His His His Gly His His Gln Lys Leu Pro Trp Tyr Arg
            260                 265                 270

Gly Lys Glu Trp Ser Tyr Leu Arg Gly Gly Leu Thr Thr Val Asp Arg
        275                 280                 285

Asp Tyr Gly Trp Ile Tyr Asn Ile His His Asp Ile Gly Thr His Val
    290                 295                 300

Ile His His Leu Phe Pro Gln Ile Pro His Tyr His Leu Val Glu Ala
305                 310                 315                 320

Thr Gln Ala Ala Lys Pro Val Leu Gly Asp Tyr Tyr Arg Glu Pro Glu
                325                 330                 335

Arg Ser Ala Pro Leu Pro Phe His Leu Ile Lys Tyr Leu Ile Gln Ser
            340                 345                 350

Met Arg Gln Asp His Phe Val Ser Asp Thr Gly Asp Val Val Tyr Tyr
        355                 360                 365

Gln Thr Asp Ser Leu Leu Leu His Ser Gln Arg Asp
    370                 375                 380
```

<210> SEQ ID NO 74
<211> LENGTH: 519
<212> TYPE: PRT
<213> ORGANISM: Thraustochytrium aureum -continued

<400> SEQUENCE: 74

```
Met Thr Val Gly Tyr Asp Glu Glu Ile Pro Phe Glu Gln Val Arg Ala
 1               5                  10                  15

His Asn Lys Pro Asp Asp Ala Trp Cys Ala Ile His Gly His Val Tyr
            20                  25                  30

Asp Val Thr Lys Phe Ala Ser Val His Pro Gly Gly Asp Ile Ile Leu
        35                  40                  45

Leu Ala Ala Gly Lys Glu Ala Thr Val Leu Tyr Glu Thr Tyr His Val
    50                  55                  60

Arg Gly Val Ser Asp Ala Val Leu Arg Lys Tyr Arg Ile Gly Lys Leu
65                  70                  75                  80

Pro Asp Gly Gln Gly Gly Ala Asn Glu Lys Glu Lys Arg Thr Leu Ser
                85                  90                  95

Gly Leu Ser Ser Ala Ser Tyr Tyr Thr Trp Asn Ser Asp Phe Tyr Arg
            100                 105                 110

Val Met Arg Glu Arg Val Val Ala Arg Leu Lys Glu Arg Gly Lys Ala
        115                 120                 125

Arg Arg Gly Gly Tyr Glu Leu Trp Ile Lys Ala Phe Leu Leu Leu Val
    130                 135                 140

Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
            180                 185                 190

Arg Trp Val Asn Lys Val Ala Gly Trp Thr Leu Asp Met Ile Gly Ala
        195                 200                 205

Ser Gly Met Thr Trp Glu Phe Gln His Val Leu Gly His His Pro Tyr
    210                 215                 220

Thr Asn Leu Ile Glu Glu Glu Asn Gly Leu Gln Lys Val Ser Gly Lys
225                 230                 235                 240

Lys Met Asp Thr Lys Leu Ala Asp Gln Glu Ser Asp Pro Asp Val Phe
                245                 250                 255

Ser Thr Tyr Pro Met Met Arg Leu His Pro Trp His Gln Lys Arg Trp
            260                 265                 270

Tyr His Arg Phe Gln His Ile Tyr Gly Pro Phe Ile Phe Gly Phe Met
        275                 280                 285

Thr Ile Asn Lys Val Val Thr Gln Asp Val Gly Val Val Leu Arg Lys
    290                 295                 300

Arg Leu Phe Gln Ile Asp Ala Glu Cys Arg Tyr Ala Ser Pro Met Tyr
305                 310                 315                 320

Val Ala Arg Phe Trp Ile Met Lys Ala Leu Thr Val Leu Tyr Met Val
                325                 330                 335

Ala Leu Pro Cys Tyr Met Gln Gly Pro Trp His Gly Leu Lys Leu Phe
            340                 345                 350

Ala Ile Ala His Phe Thr Cys Gly Glu Val Leu Ala Thr Met Phe Ile
        355                 360                 365

Val Asn His Ile Ile Glu Gly Val Ser Tyr Ala Ser Lys Asp Ala Val
    370                 375                 380

Lys Gly Thr Met Ala Pro Pro Lys Thr Met His Gly Val Thr Pro Met
385                 390                 395                 400

Asn Asn Thr Arg Lys Glu Val Glu Ala Glu Ala Ser Lys Ser Gly Ala
```

-continued

```
                405                 410                 415

Val Val Lys Ser Val Pro Leu Asp Asp Trp Ala Val Val Gln Cys Gln
            420                 425                 430

Thr Ser Val Asn Trp Ser Val Gly Ser Trp Phe Trp Asn His Phe Ser
        435                 440                 445

Gly Gly Leu Asn His Gln Ile Glu His His Leu Phe Pro Gly Leu Ser
    450                 455                 460

His Glu Thr Tyr Tyr His Ile Gln Asp Val Phe Gln Ser Thr Cys Ala
465                 470                 475                 480

Glu Tyr Gly Val Pro Tyr Gln His Glu Pro Ser Leu Trp Thr Ala Tyr
                485                 490                 495

Trp Lys Met Leu Glu His Leu Arg Gln Leu Gly Asn Glu Glu Thr His
            500                 505                 510

Glu Ser Trp Gln Arg Ala Ala
        515


<210> SEQ ID NO 75
<211> LENGTH: 541
<212> TYPE: PRT
<213> ORGANISM: Euglena gracilis

<400> SEQUENCE: 75

Met Leu Val Leu Phe Gly Asn Phe Tyr Val Lys Gln Tyr Ser Gln Lys
 1               5                  10                  15

Asn Gly Lys Pro Glu Asn Gly Ala Thr Pro Glu Asn Gly Ala Lys Pro
            20                  25                  30

Gln Pro Cys Glu Asn Gly Thr Val Glu Lys Arg Glu Asn Asp Thr Ala
        35                  40                  45

Asn Val Arg Pro Thr Arg Pro Ala Gly Pro Pro Pro Ala Thr Tyr Tyr
    50                  55                  60

Asp Ser Leu Ala Val Ser Gly Gln Gly Lys Glu Arg Leu Phe Thr Thr
65                  70                  75                  80

Asp Glu Val Arg Arg His Ile Leu Pro Thr Asp Gly Trp Leu Thr Cys
                85                  90                  95

His Glu Gly Val Tyr Asp Val Thr Asp Phe Leu Ala Lys His Pro Gly
            100                 105                 110

Gly Gly Val Ile Thr Leu Gly Leu Gly Arg Asp Cys Thr Ile Leu Ile
        115                 120                 125

Glu Ser Tyr His Pro Ala Gly Arg Pro Asp Lys Val Met Glu Lys Tyr
    130                 135                 140

Arg Ile Gly Thr Leu Gln Asp Pro Lys Thr Phe Tyr Ala Trp Gly Glu
145                 150                 155                 160

Ser Asp Phe Tyr Pro Glu Leu Lys Arg Arg Ala Leu Ala Arg Leu Lys
                165                 170                 175

Glu Ala Gly Gln Ala Arg Arg Gly Gly Leu Gly Val Lys Ala Leu Leu
            180                 185                 190

Val Leu Thr Leu Phe Phe Val Ser Trp Tyr Met Trp Val Ala His Lys
        195                 200                 205

Ser Phe Leu Trp Ala Ala Val Trp Gly Phe Ala Gly Ser His Val Gly
    210                 215                 220

Leu Ser Ile Gln His Asp Gly Asn His Gly Ala Phe Ser Arg Asn Thr
225                 230                 235                 240

Leu Val Asn Arg Leu Ala Gly Trp Gly Met Asp Leu Ile Gly Ala Ser
                245                 250                 255
```

-continued

```
Ser Thr Val Trp Glu Tyr Gln His Val Ile Gly His His Gln Tyr Thr
            260                 265                 270

Asn Leu Val Ser Asp Thr Leu Phe Ser Leu Pro Glu Asn Asp Pro Asp
        275                 280                 285

Val Phe Ser Ser Tyr Pro Leu Met Arg Met His Pro Asp Thr Ala Trp
    290                 295                 300

Gln Pro His His Arg Phe Gln His Leu Phe Ala Phe Pro Leu Phe Ala
305                 310                 315                 320

Leu Met Thr Ile Ser Lys Val Leu Thr Ser Asp Phe Ala Val Cys Leu
                325                 330                 335

Ser Met Lys Lys Gly Ser Ile Asp Cys Ser Ser Arg Leu Val Pro Leu
            340                 345                 350

Glu Gly Gln Leu Leu Phe Trp Gly Ala Lys Leu Ala Asn Phe Leu Leu
        355                 360                 365

Gln Ile Val Leu Pro Cys Tyr Leu His Gly Thr Ala Met Gly Leu Ala
    370                 375                 380

Leu Phe Ser Val Ala His Leu Val Ser Gly Glu Tyr Leu Ala Ile Cys
385                 390                 395                 400

Phe Ile Ile Asn His Ile Ser Glu Ser Cys Glu Phe Met Asn Thr Ser
                405                 410                 415

Phe Gln Thr Ala Ala Arg Arg Thr Glu Met Leu Gln Ala Ala His Gln
            420                 425                 430

Ala Ala Glu Ala Lys Lys Val Lys Pro Thr Pro Pro Pro Asn Asp Trp
        435                 440                 445

Ala Val Thr Gln Val Gln Cys Cys Val Asn Trp Arg Ser Gly Gly Val
    450                 455                 460

Leu Ala Asn His Leu Ser Gly Gly Leu Asn His Gln Ile Glu His His
465                 470                 475                 480

Leu Phe Pro Ser Ile Ser His Ala Asn Tyr Pro Thr Ile Ala Pro Val
                485                 490                 495

Val Lys Glu Val Cys Glu Glu Tyr Gly Leu Pro Tyr Lys Asn Tyr Val
            500                 505                 510

Thr Phe Trp Asp Ala Val Cys Gly Met Val Gln His Leu Arg Leu Met
        515                 520                 525

Gly Ala Pro Pro Val Pro Thr Asn Gly Asp Lys Lys Ser
    530                 535                 540


<210> SEQ ID NO 76
<211> LENGTH: 433
<212> TYPE: PRT
<213> ORGANISM: Isochrysis galbana

<400> SEQUENCE: 76

Met Cys Asn Ala Ala Gln Val Glu Thr Gln Ala Leu Arg Ala Lys Glu
 1               5                  10                  15

Ala Ala Lys Pro Thr Trp Thr Lys Ile His Gly Arg Thr Val Asp Val
            20                  25                  30

Glu Thr Phe Arg His Pro Gly Gly Asn Ile Leu Asp Leu Phe Leu Gly
        35                  40                  45

Met Asp Ala Thr Thr Ala Phe Glu Thr Phe His Gly His His Lys Gly
    50                  55                  60

Ala Trp Lys Met Leu Lys Thr Leu Pro Glu Lys Glu Val Ala Ala Ala
65                  70                  75                  80

Asp Ile Pro Ala Gln Lys Glu Glu His Val Ala Glu Met Thr Arg Leu
                85                  90                  95
```

-continued

Met Ala Ser Trp Arg Glu Arg Gly Leu Phe Lys Pro Arg Pro Val Ala
100 105 110

Ser Ser Ile Tyr Gly Leu Cys Val Ile Phe Ala Ile Ala Ala Ser Val
115 120 125

Ala Cys Ala Pro Tyr Ala Pro Val Leu Ala Gly Ile Ala Val Gly Thr
130 135 140

Cys Trp Ala Gln Cys Gly Phe Leu Gln His Met Gly Gly His Arg Glu
145 150 155 160

Trp Gly Arg Thr Trp Ser Phe Ala Phe Gln His Leu Phe Glu Gly Leu
165 170 175

Leu Lys Gly Gly Ser Ala Ser Trp Trp Arg Asn Arg His Asn Lys His
180 185 190

His Ala Lys Thr Asn Val Leu Gly Glu Asp Gly Asp Leu Arg Thr Thr
195 200 205

Pro Phe Phe Ala Trp Asp Pro Thr Leu Ala Lys Lys Val Pro Asp Trp
210 215 220

Ser Leu Arg Thr Gln Ala Phe Thr Phe Leu Pro Ala Leu Gly Ala Tyr
225 230 235 240

Val Phe Val Phe Ala Phe Thr Val Arg Lys Tyr Ser Val Val Lys Arg
245 250 255

Leu Trp His Glu Val Ala Leu Met Val Ala His Tyr Ala Leu Phe Ser
260 265 270

Trp Ala Leu Ser Ala Ala Gly Ala Ser Leu Ser Ser Gly Leu Thr Phe
275 280 285

Tyr Cys Thr Gly Tyr Ala Trp Gln Gly Ile Tyr Leu Gly Phe Phe Phe
290 295 300

Gly Leu Ser His Phe Ala Val Glu Arg Val Pro Ser Thr Ala Thr Trp
305 310 315 320

Leu Glu Ser Thr Met Met Gly Thr Val Asp Trp Gly Gly Ser Ser Ala
325 330 335

Phe Cys Gly Tyr Leu Ser Gly Phe Leu Asn Ile Gln Ile Glu His His
340 345 350

Met Ala Pro Gln Met Pro Met Glu Asn Leu Arg Gln Ile Arg Ala Asp
355 360 365

Cys Lys Ala Ala Ala His Lys Phe Gly Leu Pro Tyr Arg Glu Leu Thr
370 375 380

Phe Val Ala Ala Thr Lys Leu Met Met Ser Gly Leu Tyr Arg Thr Gly
385 390 395 400

Lys Asp Glu Leu Lys Leu Arg Ala Asp Arg Arg Lys Phe Thr Arg Ala
405 410 415

Gln Ala Tyr Met Gly Ala Ala Ser Ala Leu Val Asp Thr Leu Lys Ala
420 425 430

Asp

<210> SEQ ID NO 77
<211> LENGTH: 509
<212> TYPE: PRT
<213> ORGANISM: Schizochytrium aggregatum

<400> SEQUENCE: 77

Met Thr Val Gly Gly Asp Glu Val Tyr Ser Met Ala Gln Val Arg Asp
1 5 10 15

His Asn Thr Pro Asp Asp Ala Trp Cys Ala Ile His Gly Glu Val Tyr
20 25 30

-continued

Glu Leu Thr Lys Phe Ala Arg Thr His Pro Gly Gly Asp Ile Ile Leu
        35                  40                  45

Leu Ala Ala Gly Lys Glu Ala Thr Ile Leu Phe Glu Thr Tyr His Val
    50                  55                  60

Arg Pro Ile Ser Asp Ala Val Leu Arg Lys Tyr Arg Ile Gly Lys Leu
65                  70                  75                  80

Ala Ala Ala Gly Lys Asp Glu Pro Ala Asn Asp Ser Thr Tyr Tyr Ser
                85                  90                  95

Trp Asp Ser Asp Phe Tyr Lys Val Leu Arg Gln Arg Val Val Ala Arg
            100                 105                 110

Leu Glu Glu Arg Lys Ile Ala Arg Arg Gly Gly Pro Glu Ile Trp Ile
        115                 120                 125

Lys Ala Ala Ile Leu Val Ser Gly Phe Trp Ser Met Leu Tyr Leu Met
    130                 135                 140

Cys Thr Leu Asp Pro Asn Arg Gly Ala Ile Leu Ala Ala Ile Ala Leu
145                 150                 155                 160

Gly Ile Val Ala Ala Phe Val Gly Thr Cys Ile Gln His Asp Gly Asn
                165                 170                 175

His Gly Ala Phe Ala Phe Ser Pro Phe Met Asn Lys Leu Ser Gly Trp
            180                 185                 190

Thr Leu Asp Met Ile Gly Ala Ser Ala Met Thr Trp Glu Met Gln His
        195                 200                 205

Val Leu Gly His His Pro Tyr Thr Asn Leu Ile Glu Met Glu Asn Gly
    210                 215                 220

Thr Gln Lys Val Thr His Ala Asp Val Asp Pro Lys Lys Ala Asp Gln
225                 230                 235                 240

Glu Ser Asp Pro Asp Val Phe Ser Thr Tyr Pro Met Leu Arg Leu His
                245                 250                 255

Pro Trp His Arg Lys Arg Phe Tyr His Arg Phe Gln His Leu Tyr Ala
            260                 265                 270

Pro Leu Leu Phe Gly Phe Met Thr Ile Asn Lys Val Ile Thr Gln Asp
        275                 280                 285

Val Gly Val Val Leu Ser Lys Arg Leu Phe Gln Ile Asp Ala Asn Cys
    290                 295                 300

Arg Tyr Ala Ser Lys Ser Tyr Val Ala Arg Phe Trp Ile Met Lys Leu
305                 310                 315                 320

Leu Thr Val Leu Tyr Met Val Ala Leu Pro Val Tyr Thr Gln Gly Leu
                325                 330                 335

Val Asp Gly Leu Lys Leu Phe Phe Ile Ala His Phe Ser Cys Gly Glu
            340                 345                 350

Leu Leu Ala Thr Met Phe Ile Val Asn His Ile Ile Glu Gly Val Ser
        355                 360                 365

Tyr Ala Ser Lys Asp Ser Val Lys Gly Thr Met Ala Pro Pro Arg Thr
    370                 375                 380

Val His Gly Val Thr Pro Met His Asp Thr Arg Asp Ala Leu Gly Lys
385                 390                 395                 400

Glu Lys Ala Ala Thr Lys His Val Pro Leu Asn Asp Trp Ala Ala Val
                405                 410                 415

Gln Cys Gln Thr Ser Val Asn Trp Ser Ile Gly Ser Trp Phe Trp Asn
            420                 425                 430

His Phe Ser Gly Gly Leu Asn His Gln Ile Glu His His Leu Phe Pro
        435                 440                 445

-continued

Gly Leu Thr His Thr Thr Tyr Val Tyr Ile Gln Asp Val Val Gln Ala
    450                 455                 460

Thr Cys Ala Glu Tyr Gly Val Pro Tyr Gln Ser Glu Gln Ser Leu Phe
465                 470                 475                 480

Ser Ala Tyr Phe Lys Met Leu Ser His Leu Arg Ala Leu Gly Asn Glu
                485                 490                 495

Pro Met Pro Ser Trp Glu Lys Asp His Pro Lys Ser Lys
            500                 505

<210> SEQ ID NO 78
<211> LENGTH: 263
<212> TYPE: PRT
<213> ORGANISM: Isochrysis galbana

<400> SEQUENCE: 78

Met Ala Leu Ala Asn Asp Ala Gly Glu Arg Ile Trp Ala Ala Val Thr
 1               5                  10                  15

Asp Pro Glu Ile Leu Ile Gly Thr Phe Ser Tyr Leu Leu Leu Lys Pro
            20                  25                  30

Leu Leu Arg Asn Ser Gly Leu Val Asp Glu Lys Lys Gly Ala Tyr Arg
        35                  40                  45

Thr Ser Met Ile Trp Tyr Asn Val Leu Leu Ala Leu Phe Ser Ala Leu
    50                  55                  60

Ser Phe Tyr Val Thr Ala Thr Ala Leu Gly Trp Asp Tyr Gly Thr Gly
65                  70                  75                  80

Ala Trp Leu Arg Arg Gln Thr Gly Asp Thr Pro Gln Pro Leu Phe Gln
                85                  90                  95

Cys Pro Ser Pro Val Trp Asp Ser Lys Leu Phe Thr Trp Thr Ala Lys
            100                 105                 110

Ala Phe Tyr Tyr Ser Lys Tyr Val Glu Tyr Leu Asp Thr Ala Trp Leu
        115                 120                 125

Val Leu Lys Gly Lys Arg Val Ser Phe Leu Gln Ala Phe His His Phe
    130                 135                 140

Gly Ala Pro Trp Asp Val Tyr Leu Gly Ile Arg Leu His Asn Glu Gly
145                 150                 155                 160

Val Trp Ile Phe Met Phe Phe Asn Ser Phe Ile His Thr Ile Met Tyr
                165                 170                 175

Thr Tyr Tyr Gly Leu Thr Ala Ala Gly Tyr Lys Phe Lys Ala Lys Pro
            180                 185                 190

Leu Ile Thr Ala Met Gln Ile Cys Gln Phe Val Gly Gly Phe Leu Leu
        195                 200                 205

Val Trp Asp Tyr Ile Asn Val Pro Cys Phe Asn Ser Asp Lys Gly Lys
    210                 215                 220

Leu Phe Ser Trp Ala Phe Asn Tyr Ala Tyr Val Gly Ser Val Phe Leu
225                 230                 235                 240

Leu Phe Cys His Phe Phe Tyr Gln Asp Asn Leu Ala Thr Lys Lys Ser
                245                 250                 255

Ala Lys Ala Gly Lys Gln Leu
            260

<210> SEQ ID NO 79
<211> LENGTH: 419
<212> TYPE: PRT
<213> ORGANISM: Euglena gracilis

<400> SEQUENCE: 79

-continued

```
Met Lys Ser Lys Arg Gln Ala Leu Ser Pro Leu Gln Leu Met Glu Gln
 1               5                  10                  15

Thr Tyr Asp Val Val Asn Phe His Pro Gly Gly Ala Glu Ile Ile Glu
            20                  25                  30

Asn Tyr Gln Gly Arg Asp Ala Thr Asp Ala Phe Met Val Met His Phe
        35                  40                  45

Gln Glu Ala Phe Asp Lys Leu Lys Arg Met Pro Lys Ile Asn Pro Ser
    50                  55                  60

Phe Glu Leu Pro Pro Gln Ala Ala Val Asn Glu Ala Gln Glu Asp Phe
65                  70                  75                  80

Arg Lys Leu Arg Glu Glu Leu Ile Ala Thr Gly Met Phe Asp Ala Ser
                85                  90                  95

Pro Leu Trp Tyr Ser Tyr Lys Ile Ser Thr Thr Leu Gly Leu Gly Val
            100                 105                 110

Leu Gly Tyr Phe Leu Met Val Gln Tyr Gln Met Tyr Phe Ile Gly Ala
        115                 120                 125

Val Leu Leu Gly Met His Tyr Gln Gln Met Gly Trp Leu Ser His Asp
    130                 135                 140

Ile Cys His His Gln Thr Phe Lys Asn Arg Asn Trp Asn Asn Leu Val
145                 150                 155                 160

Gly Leu Val Phe Gly Asn Gly Leu Gln Gly Phe Ser Val Thr Cys Trp
                165                 170                 175

Lys Asp Arg His Asn Ala His His Ser Ala Thr Asn Val Gln Gly His
            180                 185                 190

Asp Pro Asp Ile Asp Asn Leu Pro Pro Leu Ala Trp Ser Glu Asp Asp
        195                 200                 205

Val Thr Arg Ala Ser Pro Ile Ser Arg Lys Leu Ile Gln Phe Gln Gln
    210                 215                 220

Tyr Tyr Phe Leu Val Ile Cys Ile Leu Leu Arg Phe Ile Trp Cys Phe
225                 230                 235                 240

Gln Cys Val Leu Thr Val Arg Ser Leu Lys Asp Arg Asp Asn Gln Phe
                245                 250                 255

Tyr Arg Ser Gln Tyr Lys Lys Glu Ala Ile Gly Leu Ala Leu His Trp
            260                 265                 270

Thr Leu Lys Ala Leu Phe His Leu Phe Phe Met Pro Ser Ile Leu Thr
        275                 280                 285

Ser Leu Leu Val Phe Phe Val Ser Glu Leu Val Gly Gly Phe Gly Ile
    290                 295                 300

Ala Ile Val Val Phe Met Asn His Tyr Pro Leu Glu Lys Ile Gly Asp
305                 310                 315                 320

Pro Val Trp Asp Gly His Gly Phe Ser Val Gly Gln Ile His Glu Thr
                325                 330                 335

Met Asn Ile Arg Arg Gly Ile Ile Thr Asp Trp Phe Phe Gly Gly Leu
            340                 345                 350

Asn Tyr Gln Ile Glu His His Leu Trp Pro Thr Leu Pro Arg His Asn
        355                 360                 365

Leu Thr Ala Val Ser Tyr Gln Val Glu Gln Leu Cys Gln Lys His Asn
    370                 375                 380

Leu Pro Tyr Arg Asn Pro Leu Pro His Glu Gly Leu Val Ile Leu Leu
385                 390                 395                 400

Arg Tyr Leu Ala Val Phe Ala Arg Met Ala Glu Lys Gln Pro Ala Gly
                405                 410                 415

Lys Ala Leu
```

-continued

<210> SEQ ID NO 80
<211> LENGTH: 2025
<212> TYPE: DNA
<213> ORGANISM: Sordaria macrospora

<400> SEQUENCE: 80
atgccttccg caactagcac caacggtgcc aatggcaatg gtaatggtaa tggcgcctct 60
gccagccctg cccccggcaa cctctccgcg aacgacaaca tccgccgctt cgctgctccc 120
agcaggccgt tgagccctct ccccgcccat gctctcttca acgagaagac acgatgcttc 180
gtctacggtc tgcagccccg tgctgtccag ggcatgctcg atttcgactt catctgcaag 240
cgttccacac cctcggttgc tggcatcatc tataccttcg gtggtcagtt cgtcagcaag 300
atgtactggg gcaccagcga gaccctcctg cccgtctatc aggaggttca aaaggccatt 360
gccaagcatc ccgatgttga cgtcgttgtc aactttgcct cttcccgcag tgtctacagc 420
tccaccatgg agttgatgga gcaccctcag atcaagacca ttgctattat tgctgagggt 480
gtccctgagc gccgcgctcg cgagattgcc tacgttgcca agaagaaggg catcaccatc 540
atcggccctg ccaccgtcgg tggtatcaag cccggctgct tcaagatcgg taacactggt 600
ggtatgatgg acaacattgt tgcttccaag ctctaccgca agggctctgt cggctatgtc 660
tccaagtctg gtggcatgtc caacgagctc aacaacatta tctcccagac cacggatggt 720
gtttatgagg gtgttgccat tggtggtgac cgttaccccg gcaccacctt catcgaccat 780
ctcctgcgtt accaggccga tcctgcctgc aagatcctcg tcttgcttgg tgaagtcggt 840
ggtgttgagg agtacaaggt gatcgaggct gtcaagcagg gcatcatcac caagcccatc 900
gttgcttggg ccattggtac ttgcgccagc atgttcaaga ctgaggtcca gttcggtcac 960
gccggtgcct tcgccaactc tcagctcgag actgcggcca ccaagaacaa gagcatgcgt 1020
gaggctggtt tctatgttcc cgacactttc gaggacatgc ctgctcttct caagcaggtc 1080
tatgacaagc tcgtggctga tggcaccatt gtccccgccc ccgagcctgt tgtccccaag 1140
atccccatcg actactcttg ggctcaggag cttggcctta ttcgcaagcc tgctgccttc 1200
atttctacca tttccgatga tcgtggccag gagctcctct acgctggcat gcccatctcg 1260
gacgttttca gggaggagat tggtattggc ggtgtcatgt cccttctttg gttccgccgc 1320
cgtcttccgg attatgccgc caagttcctt gagatggttc tcatgcttac cgccgatcac 1380
ggtcccgccg tgtctggtgc catgaacacc attatcacca cccgtgctgg caaggatctc 1440
atcagctcct tggtcgctgg tctcttgacc attggctccc gtttcggtgg tgcccttgat 1500
ggtgctgctg aggagtttac caaagctttc gacaagggcc taagcccccg tgagtttgtc 1560
gacaccatgc gcaagcagaa caagctcatc cccggtatcg gtcaccgtgt caagtctcgc 1620
aacaaccccg atctccgtgt cgagcttgtt aaggagtacg tcaaggccaa gttcccctcc 1680
agcaagcttc tcgattacgc tctcgccgtc gagactgtca ccacctccaa gaaggacaac 1740
cttattctca acgtcgacgg ctgcattgct gtctgcttcg ttgatctcct aaggaactgc 1800
ggtgccttca gcactgagga ggctgaggac tacctctcca tgggtgtcct caacggtctc 1860
ttcgttcttg gtcgttccat tggtcttatt gcccattacc tcgatcagaa gagactccgc 1920
actggtctct accgtcatcc ttgggatgat atcacttacc tcctccccag cctccagcag 1980
cccggccctc cgggtactga gggtcgtgtt gaggtccaaa tttaa 2025

<210> SEQ ID NO 81

-continued

<211> LENGTH: 674
<212> TYPE: PRT
<213> ORGANISM: Sordaria macrospora

<400> SEQUENCE: 81

```
Met Pro Ser Ala Thr Ser Thr Asn Gly Ala Asn Gly Asn Gly Asn Gly
 1               5                  10                  15

Asn Gly Ala Ser Ala Ser Pro Ala Pro Gly Asn Leu Ser Ala Asn Asp
            20                  25                  30

Asn Ile Arg Arg Phe Ala Ala Pro Ser Arg Pro Leu Ser Pro Leu Pro
        35                  40                  45

Ala His Ala Leu Phe Asn Glu Lys Thr Arg Cys Phe Val Tyr Gly Leu
    50                  55                  60

Gln Pro Arg Ala Val Gln Gly Met Leu Asp Phe Asp Phe Ile Cys Lys
65                  70                  75                  80

Arg Ser Thr Pro Ser Val Ala Gly Ile Ile Tyr Thr Phe Gly Gly Gln
                85                  90                  95

Phe Val Ser Lys Met Tyr Trp Gly Thr Ser Glu Thr Leu Leu Pro Val
            100                 105                 110

Tyr Gln Glu Val Gln Lys Ala Ile Ala Lys His Pro Asp Val Asp Val
        115                 120                 125

Val Val Asn Phe Ala Ser Ser Arg Ser Val Tyr Ser Ser Thr Met Glu
    130                 135                 140

Leu Met Glu His Pro Gln Ile Lys Thr Ile Ala Ile Ile Ala Glu Gly
145                 150                 155                 160

Val Pro Glu Arg Arg Ala Arg Glu Ile Ala Tyr Val Ala Lys Lys Lys
                165                 170                 175

Gly Ile Thr Ile Ile Gly Pro Ala Thr Val Gly Gly Ile Lys Pro Gly
            180                 185                 190

Cys Phe Lys Ile Gly Asn Thr Gly Gly Met Met Asp Asn Ile Val Ala
        195                 200                 205

Ser Lys Leu Tyr Arg Lys Gly Ser Val Gly Tyr Val Ser Lys Ser Gly
    210                 215                 220

Gly Met Ser Asn Glu Leu Asn Asn Ile Ile Ser Gln Thr Thr Asp Gly
225                 230                 235                 240

Val Tyr Glu Gly Val Ala Ile Gly Gly Asp Arg Tyr Pro Gly Thr Thr
                245                 250                 255

Phe Ile Asp His Leu Leu Arg Tyr Gln Ala Asp Pro Ala Cys Lys Ile
            260                 265                 270

Leu Val Leu Leu Gly Glu Val Gly Gly Val Glu Glu Tyr Lys Val Ile
        275                 280                 285

Glu Ala Val Lys Gln Gly Ile Ile Thr Lys Pro Ile Val Ala Trp Ala
    290                 295                 300

Ile Gly Thr Cys Ala Ser Met Phe Lys Thr Glu Val Gln Phe Gly His
305                 310                 315                 320

Ala Gly Ala Phe Ala Asn Ser Gln Leu Glu Thr Ala Ala Thr Lys Asn
                325                 330                 335

Lys Ser Met Arg Glu Ala Gly Phe Tyr Val Pro Asp Thr Phe Glu Asp
            340                 345                 350

Met Pro Ala Leu Leu Lys Gln Val Tyr Asp Lys Leu Val Ala Asp Gly
        355                 360                 365

Thr Ile Val Pro Ala Pro Glu Pro Val Val Pro Lys Ile Pro Ile Asp
    370                 375                 380

Tyr Ser Trp Ala Gln Glu Leu Gly Leu Ile Arg Lys Pro Ala Ala Phe
```

-continued

```
385                 390                 395                 400

Ile Ser Thr Ile Ser Asp Asp Arg Gly Gln Glu Leu Leu Tyr Ala Gly
                405                 410                 415

Met Pro Ile Ser Asp Val Phe Arg Glu Glu Ile Gly Ile Gly Gly Val
            420                 425                 430

Met Ser Leu Leu Trp Phe Arg Arg Arg Leu Pro Asp Tyr Ala Ala Lys
        435                 440                 445

Phe Leu Glu Met Val Leu Met Leu Thr Ala Asp His Gly Pro Ala Val
    450                 455                 460

Ser Gly Ala Met Asn Thr Ile Ile Thr Thr Arg Ala Gly Lys Asp Leu
465                 470                 475                 480

Ile Ser Ser Leu Val Ala Gly Leu Leu Thr Ile Gly Ser Arg Phe Gly
                485                 490                 495

Gly Ala Leu Asp Gly Ala Ala Glu Glu Phe Thr Lys Ala Phe Asp Lys
            500                 505                 510

Gly Leu Ser Pro Arg Glu Phe Val Asp Thr Met Arg Lys Gln Asn Lys
        515                 520                 525

Leu Ile Pro Gly Ile Gly His Arg Val Lys Ser Arg Asn Asn Pro Asp
    530                 535                 540

Leu Arg Val Glu Leu Val Lys Glu Tyr Val Lys Ala Lys Phe Pro Ser
545                 550                 555                 560

Ser Lys Leu Leu Asp Tyr Ala Leu Ala Val Glu Thr Val Thr Thr Ser
                565                 570                 575

Lys Lys Asp Asn Leu Ile Leu Asn Val Asp Gly Cys Ile Ala Val Cys
            580                 585                 590

Phe Val Asp Leu Leu Arg Asn Cys Gly Ala Phe Ser Thr Glu Glu Ala
        595                 600                 605

Glu Asp Tyr Leu Ser Met Gly Val Leu Asn Gly Leu Phe Val Leu Gly
    610                 615                 620

Arg Ser Ile Gly Leu Ile Ala His Tyr Leu Asp Gln Lys Arg Leu Arg
625                 630                 635                 640

Thr Gly Leu Tyr Arg His Pro Trp Asp Asp Ile Thr Tyr Leu Leu Pro
                645                 650                 655

Ser Leu Gln Gln Pro Gly Pro Pro Gly Thr Glu Gly Arg Val Glu Val
            660                 665                 670

Gln Ile
```

<210> SEQ ID NO 82
<211> LENGTH: 1446
<212> TYPE: DNA
<213> ORGANISM: Sordaria macrospora

<400> SEQUENCE: 82

```
atgtctgcga agagcatcct cgaggccgac ggcaaggcca tcctcaacta ccaccttacc     60

cgtgcccccg tcatcaagcc cagcacgcta cccaacccga ccaagcacaa ccctcctccc    120

agacttgctt ccctccactt cgccgaggat gccgatgtga acggtgttct cagccaggct    180

gaggtcacct acccttggct cctccaggac ggcgctcgct tcgtcgccaa gcccgatcag    240

ttgatcaagc gccgtggcaa gagcggtctc cttgctctca acaagacttg gcctgaggcc    300

aaggcctgga ttgctgagcg cgccggtaag gctcagaagg tcgagcacac agagggcgtc    360

cttcgccagt tcctcgtcga gccgttcgtg ccccaccccc aggaaaccga atattatatc    420

aacggcgact ggattctctt ctaccacgag ggcggtgttg atgtcggtga cgtcgatgcg    480
```

-continued

```
aaggccgaga agatcctaat ccccgttgac ctttcacaat atccttccaa cgaggaactt    540

gcgagcacac tgctcaagca cgttcccaag ggcatccata acgtccttgt tgacttcatt    600

gcccgtctct atgccgtcta tgtggactgc cagttcacct acctcgagat caaccccttg    660

gttgtcattc ccaacgagga tgccacctct gctgaggttc acttcctcga tcttgctgct    720

aagctcgacc aaacggccga ttttgagtgc ggcaacaagt gggctattgc ccgctctccc    780

gctgccttgg gcattgttgc ccaaagctcc aacggcggtg tcaacattga tgccggcccc    840

cccattgagt tccccgctcc attcggtcgt gagctcacca aagaggaggc ctacattgct    900

gagcttgatg ccaagactgg tgcctcgctc aagcttactg tcttgaaccc caatggccgt    960

atctggactc tcgttgccgg tggcggtgcg tccgtcgtct acgccgatgc catcgcctca   1020

gctggttttg ccgatgagct tgccaactat ggcgagtact ctggtgcccc caccgagtct   1080

cagacatacc actacgcccg cactgttctc gatctcatgc tccgtgctcc tgtgtctgag   1140

cagggcaagg tcctcttcat cggtggtggt attgccaact tcaccaacgt tgctagcact   1200

ttcaagggtg tcatcaaggc ccttagggag tacggcaagg ctctcatcga gcacaacact   1260

caaatctggg tccgtcgtgc cggtcccaac taccaggagg gtctcaagaa cctcaaggct   1320

gcgacacaag agctcggtct taacgccaag atctttggcc ctgagatgca cgtcagcggt   1380

atcgtgcctc tggcgttggt ccctggcaag tgggaggaga gcggtgcggt ggagttccag   1440

gcctaa                                                               1446
```

```
<210> SEQ ID NO 83
<211> LENGTH: 481
<212> TYPE: PRT
<213> ORGANISM: Sordaria macrospora

<400> SEQUENCE: 83

Met Ser Ala Lys Ser Ile Leu Glu Ala Asp Gly Lys Ala Ile Leu Asn
 1               5                  10                  15

Tyr His Leu Thr Arg Ala Pro Val Ile Lys Pro Ser Thr Leu Pro Asn
            20                  25                  30

Pro Thr Lys His Asn Pro Pro Pro Arg Leu Ala Ser Leu His Phe Ala
        35                  40                  45

Glu Asp Ala Asp Val Asn Gly Val Leu Ser Gln Ala Glu Val Thr Tyr
    50                  55                  60

Pro Trp Leu Leu Gln Asp Gly Ala Arg Phe Val Ala Lys Pro Asp Gln
65                  70                  75                  80

Leu Ile Lys Arg Arg Gly Lys Ser Gly Leu Leu Ala Leu Asn Lys Thr
                85                  90                  95

Trp Pro Glu Ala Lys Ala Trp Ile Ala Glu Arg Ala Gly Lys Ala Gln
            100                 105                 110

Lys Val Glu His Thr Glu Gly Val Leu Arg Gln Phe Leu Val Glu Pro
        115                 120                 125

Phe Val Pro His Pro Gln Glu Thr Glu Tyr Tyr Ile Asn Gly Asp Trp
    130                 135                 140

Ile Leu Phe Tyr His Glu Gly Gly Val Asp Val Gly Asp Val Asp Ala
145                 150                 155                 160

Lys Ala Glu Lys Ile Leu Ile Pro Val Asp Leu Ser Gln Tyr Pro Ser
                165                 170                 175

Asn Glu Glu Leu Ala Ser Thr Leu Leu Lys His Val Pro Lys Gly Ile
            180                 185                 190

His Asn Val Leu Val Asp Phe Ile Ala Arg Leu Tyr Ala Val Tyr Val
```

-continued

```
        195                 200                 205

Asp Cys Gln Phe Thr Tyr Leu Glu Ile Asn Pro Leu Val Val Ile Pro
    210                 215                 220

Asn Glu Asp Ala Thr Ser Ala Glu Val His Phe Leu Asp Leu Ala Ala
225                 230                 235                 240

Lys Leu Asp Gln Thr Ala Asp Phe Glu Cys Gly Asn Lys Trp Ala Ile
                245                 250                 255

Ala Arg Ser Pro Ala Ala Leu Gly Ile Val Ala Gln Ser Ser Asn Gly
            260                 265                 270

Gly Val Asn Ile Asp Ala Gly Pro Pro Ile Glu Phe Pro Ala Pro Phe
        275                 280                 285

Gly Arg Glu Leu Thr Lys Glu Glu Ala Tyr Ile Ala Glu Leu Asp Ala
    290                 295                 300

Lys Thr Gly Ala Ser Leu Lys Leu Thr Val Leu Asn Pro Asn Gly Arg
305                 310                 315                 320

Ile Trp Thr Leu Val Ala Gly Gly Gly Ala Ser Val Val Tyr Ala Asp
                325                 330                 335

Ala Ile Ala Ser Ala Gly Phe Ala Asp Glu Leu Ala Asn Tyr Gly Glu
            340                 345                 350

Tyr Ser Gly Ala Pro Thr Glu Ser Gln Thr Tyr His Tyr Ala Arg Thr
        355                 360                 365

Val Leu Asp Leu Met Leu Arg Ala Pro Val Ser Glu Gln Gly Lys Val
    370                 375                 380

Leu Phe Ile Gly Gly Gly Ile Ala Asn Phe Thr Asn Val Ala Ser Thr
385                 390                 395                 400

Phe Lys Gly Val Ile Lys Ala Leu Arg Glu Tyr Gly Lys Ala Leu Ile
                405                 410                 415

Glu His Asn Thr Gln Ile Trp Val Arg Arg Ala Gly Pro Asn Tyr Gln
            420                 425                 430

Glu Gly Leu Lys Asn Leu Lys Ala Ala Thr Gln Glu Leu Gly Leu Asn
        435                 440                 445

Ala Lys Ile Phe Gly Pro Glu Met His Val Ser Gly Ile Val Pro Leu
    450                 455                 460

Ala Leu Val Pro Gly Lys Trp Glu Glu Ser Gly Ala Val Glu Phe Gln
465                 470                 475                 480

Ala


<210> SEQ ID NO 84
<211> LENGTH: 1560
<212> TYPE: DNA
<213> ORGANISM: Saccharomyces cerevisiae

<400> SEQUENCE: 84

atgacagttg gttacgatga ggaaattcct ttcgaacaag ttagagctca taataagcca      60

gacgatgctt ggtgtgctat ccatggtcat gtttatgatg ttacgaaatt tgcatccgtc     120

caccctggtg gagatattat attgctagct gcaggtaaag aagccaccgt attatatgaa     180

acctatcatg taagaggcgt ttcagatgcc gttttaagaa agtatcgtat cggtaaactt     240

ccagacggcc aaggtggagc aaacgagaag gaaaaaagaa cgcttagtgg attatcgtca     300

gctagctact atacttggaa ctcggacttc tatcgtgtta tgagagagag agtagttgct     360

agattgaagg agaggggtaa ggctagacga ggtggatacg aattatggat caaagctttt     420

cttttacttg ttggattctg gtcttcatta tactggatgt gtactttgga tccttccttc     480
```

-continued

```
ggtgctattt tggcagctat gtctcttgga gttttcgcag ccttcgtggg tacgtgtatt    540

caacatgatg gcaaccatgg tgcatttgct cagtccagat gggtaaacaa agtggccggt    600

tggaccttgg acatgatagg cgcatcagga atgacatggg aatttcaaca tgtattgggt    660

caccatccat acacgaattt aattgaagag gaaaatggtt tgcaaaaagt tagtggcaaa    720

aagatggata caaaattggc tgaccaggaa agtgatcctg acgtattctc tacatatccc    780

atgatgaggt tacacccttg gcatcagaag agatggtacc atagatttca gcatatatac    840

ggtccattta tatttggttt tatgacaatc aataaagtcg tgacccaaga tgtcggtgtc    900

gtgctaagaa aaaggttgtt ccaaattgat gctgagtgca ggtatgcctc cccaatgtat    960

gttgctcgat tttggattat gaaggctttg actgtactat atatggtggc cttaccatgt   1020

tacatgcagg gtccgtggca tggtttaaag ttatttgcca tagctcactt cacatgtggc   1080

gaggttttgg ctacaatgtt tatcgttaat catataattg aaggtgtatc ttatgcctcg   1140

aaagatgctg ttaagggcac tatggctcct ccaaaaacca tgcacggagt accccaatg    1200

aacaatactc gtaaagaggt cgaggcagaa gcatcaaaat ccggagccgt ggtaaagtct   1260

gtgccgctag atgactgggc tgtcgttcaa tgccaaacaa gtgtcaattg gagcgtcggt   1320

tcttggtttt ggaatcattt ttctggtggc ctgaaccacc aaattgaaca ccatctgttc   1380

cccggtctgt ctcatgaaac ttattaccat attcaagatg tctttcaatc aacttgcgca   1440

gaatacggtg tgccctatca acacgaaccg agcttatgga ctgcttactg gaaaatgtta   1500

gaacacctga ggcagctagg taatgaagaa actcacgaaa gttggcaaag agcagcataa   1560
```

<210> SEQ ID NO 85
<211> LENGTH: 792
<212> TYPE: DNA
<213> ORGANISM: Saccharomyces cerevisiae

<400> SEQUENCE: 85

```
atggccctag ctaacgacgc aggtgaacgt atttgggcag ctgttacaga cccagaaata     60

ttgatcggta cctttagtta cctgttactt aagcccttac tgagaaatag cggcttagtt    120

gacgaaaaga aaggtgccta tagaacttca atgatttggt ataatgttct acttgctctt    180

ttttccgctt taagttttta tgtgaccgca accgctttag gttgggatta tggtacaggt    240

gcctggttaa ggagacagac tggcgataca cctcaaccac tgttccaatg cccatcacct    300

gtttgggact ctaagttgtt tacgtggaca gccaaagcat tttactattc taaatatgtc    360

gagtatttgg atacagcttg gttagtatta aaaggtaaga gggtgtcatt cttgcaggct    420

tttcaccatt ttggcgctcc atgggatgtt tatttaggaa taagattgca taatgaagga    480

gtttggatct tcatgttctt taactctttt attcacacta ttatgtatac ttactatggt    540

ttgactgctg ccggatacaa attcaaggca aaaccattga tcactgcaat gcaaatatgt    600

caatttgtag gaggtttcct attggtctgg gattacatta atgtaccttg tttcaactcc    660

gataaaggta agttatttag ctgggcattt aactacgctt acgtcggctc tgtgtttttg    720

ctttttttgtc atttcttcta ccaagataat ttagctacga aaaagtcggc caaagctggt   780

aaacaactat ag                                                        792
```

<210> SEQ ID NO 86
<211> LENGTH: 1260
<212> TYPE: DNA
<213> ORGANISM: Saccharomyces cerevisiae

<400> SEQUENCE: 86
atgaaatcaa aaaggcaagc actgtcccca ctacagttaa tggagcaaac ttatgacgtt 60
gtcaattttc accctggtgg cgctgaaatc attgaaaact accagggaag agatgccact 120
gacgctttta tggtaatgca ttttcaggaa gctttcgata aattgaagcg tatgcccaaa 180
attaacccct cctttgagtt gcctccacaa gctgccgtta atgaagctca ggaagacttt 240
aggaagttga gagaggaatt gattgcaacc ggcatgttcg atgctagccc attatggtat 300
tcttataaga tttcgacaac cttgggttta ggtgttttag gttactttct tatggtccaa 360
taccaaatgt acttcatagg tgccgttttg ttaggcatgc attatcaaca gatgggatgg 420
ttgagtcacg atatatgtca tcaccaaaca ttcaagaaca ggaattggaa caatttggtt 480
ggcttggtat tcggtaacgg tttgcaaggc tttagtgtta catgctggaa agatagacat 540
aatgcccacc atagcgctac taatgttcaa ggtcatgatc cagatattga taatttgcct 600
ccattggctt ggtcagaaga tgacgtcact agagcatctc ctatctctcg taagctgata 660
caatttcagc aatattactt tctggtgatt tgtatcttgc taagatttat ctggtgtttc 720
cagtgtgtct tgaccgtgag aagtcttaaa gacagagata atcaatttta ccgttctcaa 780
tataagaaag aagccatagg tcttgcttta cactggactt taaaggctct gttccattta 840
tttttcatgc cttcgatcct tacgtcatta ctagtattct ttgtatctga actagtgggc 900
ggatttggta tcgctattgt agtgttcatg aaccactacc cactagagaa aataggagat 960
cccgtctggg atggtcatgg attttccgtt ggtcaaatac atgaaacaat gaatattaga 1020
aggggtatta taactgactg gtttttcggt ggactgaact atcaaattga acatcacctt 1080
tggcctacgc taccaagaca taaccttaca gcagtttcat atcaagtaga gcaattatgc 1140
cagaagcata atctaccata tagaaatcca ttgccacatg aaggtttagt tattttgtta 1200
agatatttgg ccgtgttcgc tagaatggca gaaaaacaac cagcaggtaa agcattatag 1260

<210> SEQ ID NO 87
<211> LENGTH: 1260
<212> TYPE: DNA
<213> ORGANISM: Saccharomyces kluyveri

<400> SEQUENCE: 87
atgtctattg aaacagtcgg atcatcgtct ggtgttgcta ttaactccaa ggcagtttcc 60
tctactgcca ccaccgttgt tcagccaaaa acagccattg ataccaatgg caacgtcttt 120
aaggttcctg actacactat taaagacatt ctttctgcta ttccaaaaga gtgttacaaa 180
agggacactt tatggtcctt acattacgtt gtcagagaca tcgctgctat tcttgttatt 240
ggctacctag gtaccaatta cattcctgtt ttattcccta atagtgcatt gttgagaggg 300
attgcctatg cgatccaatc ctacttgatc ggtctatttg ggtttggctt gtggattttg 360
gcccatgaat gtggccactc cgctttttcg gaatctaatg ctgtcaacga taccgttggc 420
tgggttttgc actcttggtg gatggttcct tactttcctt ggaagttttc gcacagcaag 480
catcataaag ctactggcca tatgaccagg gacatggttt tcattcctta caccaaggat 540
gagtttatta cgatgaagaa gaaatcaaag tttgccgaga tcacagagga ggcacccgtg 600
atgacgctat tcaatctgat tgctcagcag gttggaggtt tacaattata tttggctact 660
aatgctaccg gccagcctta tcctggagtc aaaaagttct tcaagtccca ttattggcca 720
acttctccag tgtttgacgc taaggacttt tggtggatca tcatgagtga tatcggtatc 780
gtatcaactc tgcttatcaa ttatttatgg taccgtgcct acggtgctca cgtcgttctg 840

-continued

```
attaactggt ttatcccatg gctatgggtt aaccactggt tagtttttgt cactttttttg    900

caacataccg atccaaccat gccacactac gatgccgagg aatggacttt tgccaaaggt    960

gctgctgcta ccatcgatag aaactttggc tttgttggac aacatatctt ccatgacatt   1020

atcgaaacgc atgttttaca ccattattgt agcagaattc ccttctacaa cgcacgcaaa   1080

gctacttcgg ccatcaagga ggttatgggt caacactacc gttacgaagg cgagaacatg   1140

tggaagtctc tctggaaagt tgctagatca tgtcaatatg ttgagggcga caacggtgtt   1200

agaatgttca gaaacaccaa tggcgttggc gtcaagccgg aagatggttc cagtcaatga   1260


<210> SEQ ID NO 88
<211> LENGTH: 419
<212> TYPE: PRT
<213> ORGANISM: Saccharomyces kluyveri

<400> SEQUENCE: 88

Met Ser Ile Glu Thr Val Gly Ser Ser Ser Gly Val Ala Ile Asn Ser
1               5                   10                  15

Lys Ala Val Ser Ser Thr Ala Thr Thr Val Val Gln Pro Lys Thr Ala
            20                  25                  30

Ile Asp Thr Asn Gly Asn Val Phe Lys Val Pro Asp Tyr Thr Ile Lys
        35                  40                  45

Asp Ile Leu Ser Ala Ile Pro Lys Glu Cys Tyr Lys Arg Asp Thr Leu
    50                  55                  60

Trp Ser Leu His Tyr Val Val Arg Asp Ile Ala Ala Ile Leu Val Ile
65                  70                  75                  80

Gly Tyr Leu Gly Thr Asn Tyr Ile Pro Val Leu Phe Pro Asn Ser Ala
                85                  90                  95

Leu Leu Arg Gly Ile Ala Tyr Ala Ile Gln Ser Tyr Leu Ile Gly Leu
            100                 105                 110

Phe Gly Phe Gly Leu Trp Ile Leu Ala His Glu Cys Gly His Ser Ala
        115                 120                 125

Phe Ser Glu Ser Asn Ala Val Asn Asp Thr Val Gly Trp Val Leu His
    130                 135                 140

Ser Trp Trp Met Val Pro Tyr Phe Pro Trp Lys Phe Ser His Ser Lys
145                 150                 155                 160

His His Lys Ala Thr Gly His Met Thr Arg Asp Met Val Phe Ile Pro
                165                 170                 175

Tyr Thr Lys Asp Glu Phe Ile Thr Met Lys Lys Lys Ser Lys Phe Ala
            180                 185                 190

Glu Ile Thr Glu Glu Ala Pro Val Met Thr Leu Phe Asn Leu Ile Ala
        195                 200                 205

Gln Gln Val Gly Gly Leu Gln Leu Tyr Leu Ala Thr Asn Ala Thr Gly
    210                 215                 220

Gln Pro Tyr Pro Gly Val Lys Lys Phe Phe Lys Ser His Tyr Trp Pro
225                 230                 235                 240

Thr Ser Pro Val Phe Asp Ala Lys Asp Phe Trp Trp Ile Ile Met Ser
                245                 250                 255

Asp Ile Gly Ile Val Ser Thr Leu Leu Ile Asn Tyr Leu Trp Tyr Arg
            260                 265                 270

Ala Tyr Gly Ala His Val Val Leu Ile Asn Trp Phe Ile Pro Trp Leu
        275                 280                 285

Trp Val Asn His Trp Leu Val Phe Val Thr Phe Leu Gln His Thr Asp
    290                 295                 300
```

-continued

```
Pro Thr Met Pro His Tyr Asp Ala Glu Glu Trp Thr Phe Ala Lys Gly
305                 310                 315                 320

Ala Ala Ala Thr Ile Asp Arg Asn Phe Gly Phe Val Gly Gln His Ile
                325                 330                 335

Phe His Asp Ile Ile Glu Thr His Val Leu His His Tyr Cys Ser Arg
            340                 345                 350

Ile Pro Phe Tyr Asn Ala Arg Lys Ala Thr Ser Ala Ile Lys Glu Val
        355                 360                 365

Met Gly Gln His Tyr Arg Tyr Glu Gly Glu Asn Met Trp Lys Ser Leu
    370                 375                 380

Trp Lys Val Ala Arg Ser Cys Gln Tyr Val Glu Gly Asp Asn Gly Val
385                 390                 395                 400

Arg Met Phe Arg Asn Thr Asn Gly Val Gly Val Lys Pro Glu Asp Gly
                405                 410                 415

Ser Ser Gln
```

```
<210> SEQ ID NO 89
<211> LENGTH: 1353
<212> TYPE: DNA
<213> ORGANISM: Mortierella alpina

<400> SEQUENCE: 89

atggcccccc ctcacgttgt cgacgaacaa gttcgacgca ggatcgtcgt tgaggacgag      60

atcaagtcta agaagcaatt tgagcgcaac tatgtgccca tggactttac gattaaggag     120

attcgagatg cgatccctgc ccacctcttc atccgtgata ccacaaagtc gatcctgcat     180

gtcgtcaagg atctggtcac catcgccatc gtcttttact gtgcaacctt cattgagact     240

ctgccctcgc tcgctctgcg agttcctgcc tggatcacct actggatcat ccaaggaact     300

gtcatggtcg gcccctggat cttggctcat ggtaaggaaa cgaaaaatcc catgtgtatt     360

tctgtactac agaaggcgaa gtttgtacct gaaaagatca gcgtcgtccc ttgatttaga     420

atgtaactaa ccttgcaatc gtatgaccta aattttcttg tgtcaacgac agagtgcggc     480

cacggagctt tctcggatag caagacgatc aacaccatct ttggatgggt cctccactct     540

gctcttttgg tgccctacca ggcctgggct atgtcacact ccaagcatca caagggtact     600

ggatcgatga ccaaagatgt cgttttcatc cctgccactc gttcctacaa gggcctccca     660

gcactggaga agcctgccgt cgaagaggag gtttcggagc aggaacacca ccaccacgag     720

gagtccatct ttgccgaaac tcccatctac acgctcggag cgcttttgtt cgtcttgacc     780

ttcggatggc ccttgtactt gatcgtcaac ttttcaggac acgaggcccc tcactgggtc     840

aaccatttcc agactgtcgc tcctctctat gagcctcacc agcgcaagaa catcttctac     900

tccaactgcg gcattgtcgc catgggttcg atcttgactt acctttcgat ggtcttctcg     960

cccttgactg tcttcatgta ctatggcatc ccttacctcg gagtcaacgc ctggatcgtc    1020

tgcattacct atctccagca caccgatccc aaggtgcctc acttccgtga taacgagtgg    1080

aacttccagc gcggtgctgc ctgcactatc gaccgatcct tcggtaccat cgtgaaccac    1140

ctgcaccacc acattggcga ctctcaccag tgccaccata tgttctcgca gatgcccttc    1200

tacaatgctg tggaggctac aaagtacttg aaggccaaac ttggcaagta ctacatattt    1260

gacgacacgc ccattgccaa agccctctac cgcaattgga gagagtgcaa attcgtggag    1320

gacgagggag atgtagtgtt ttacaagcat taa                                 1353

<210> SEQ ID NO 90
```

-continued

<211> LENGTH: 403
<212> TYPE: PRT
<213> ORGANISM: Mortierella alpina

<400> SEQUENCE: 90

```
Met Ala Pro Pro His Val Val Asp Glu Gln Val Arg Arg Arg Ile Val
 1               5                   10                  15

Val Glu Asp Glu Ile Lys Ser Lys Lys Gln Phe Glu Arg Asn Tyr Val
            20                  25                  30

Pro Met Asp Phe Thr Ile Lys Glu Ile Arg Asp Ala Ile Pro Ala His
        35                  40                  45

Leu Phe Ile Arg Asp Thr Thr Lys Ser Ile Leu His Val Val Lys Asp
    50                  55                  60

Leu Val Thr Ile Ala Ile Val Phe Tyr Cys Ala Thr Phe Ile Glu Thr
65                  70                  75                  80

Leu Pro Ser Leu Ala Leu Arg Val Pro Ala Trp Ile Thr Tyr Trp Ile
                85                  90                  95

Ile Gln Gly Thr Val Met Val Gly Pro Trp Ile Leu Ala His Glu Cys
            100                 105                 110

Gly His Gly Ala Phe Ser Asp Ser Lys Thr Ile Asn Thr Ile Phe Gly
        115                 120                 125

Trp Val Leu His Ser Ala Leu Leu Val Pro Tyr Gln Ala Trp Ala Met
    130                 135                 140

Ser His Ser Lys His His Lys Gly Thr Gly Ser Met Thr Lys Asp Val
145                 150                 155                 160

Val Phe Ile Pro Ala Thr Arg Ser Tyr Lys Gly Leu Pro Ala Leu Glu
                165                 170                 175

Lys Pro Ala Val Glu Glu Glu Val Ser Glu Gln Glu His His His His
            180                 185                 190

Glu Glu Ser Ile Phe Ala Glu Thr Pro Ile Tyr Thr Leu Gly Ala Leu
        195                 200                 205

Leu Phe Val Leu Thr Phe Gly Trp Pro Leu Tyr Leu Ile Val Asn Phe
    210                 215                 220

Ser Gly His Glu Ala Pro His Trp Val Asn His Phe Gln Thr Val Ala
225                 230                 235                 240

Pro Leu Tyr Glu Pro His Gln Arg Lys Asn Ile Phe Tyr Ser Asn Cys
                245                 250                 255

Gly Ile Val Ala Met Gly Ser Ile Leu Thr Tyr Leu Ser Met Val Phe
            260                 265                 270

Ser Pro Leu Thr Val Phe Met Tyr Tyr Gly Ile Pro Tyr Leu Gly Val
        275                 280                 285

Asn Ala Trp Ile Val Cys Ile Thr Tyr Leu Gln His Thr Asp Pro Lys
    290                 295                 300

Val Pro His Phe Arg Asp Asn Glu Trp Asn Phe Gln Arg Gly Ala Ala
305                 310                 315                 320

Cys Thr Ile Asp Arg Ser Phe Gly Thr Ile Val Asn His Leu His His
                325                 330                 335

His Ile Gly Asp Ser His Gln Cys His His Met Phe Ser Gln Met Pro
            340                 345                 350

Phe Tyr Asn Ala Val Glu Ala Thr Lys Tyr Leu Lys Ala Lys Leu Gly
        355                 360                 365

Lys Tyr Tyr Ile Phe Asp Asp Thr Pro Ile Ala Lys Ala Leu Tyr Arg
    370                 375                 380

Asn Trp Arg Glu Cys Lys Phe Val Glu Asp Glu Gly Asp Val Val Phe
```

-continued 385 390 395 400

Tyr Lys His

<210> SEQ ID NO 91
<211> LENGTH: 1428
<212> TYPE: DNA
<213> ORGANISM: Streptococcus mutans

<400> SEQUENCE: 91
atgacaaaac aatataaaaa ttatgtcaat ggcgagtgga agctttcaga aaatgaaatt 60
aaaatctacg aaccggccag tggagctgaa ttgggttcag ttccagcaat gagtactgaa 120
gaagtagatt atgtttatgc ttcagccaag aaagctcaac cagcttggcg atcactttca 180
tacatagaac gtgctgccta ccttcacaag gtagcagata ttttgatgcg tgataaagaa 240
aaaataggtg ctgttctttc caaagaggtt gctaaaggtt ataaatcagc agtcagcgaa 300
gttgttcgta ctgcagaaat cattaattat gcagctgaag aaggtcttcg tatggaaggt 360
gaagtccttg aaggcggcag ttttgaagca gccagcaaga aaaaaattgc cgttgttcgt 420
cgtgaaccag taggtcttgt attagctatt tcaccattta actaccctgt taacttggca 480
ggttcgaaaa ttgcaccggc tcttattgcg ggaaatgtta ttgcttttaa accaccgacg 540
caaggatcaa tctcagggct cttacttgct gaagcatttg ctgaagctgg acttcctgca 600
ggtgtcttta ataccattac aggtcgtggt tctgaaattg gagactatat tgtagaacat 660
caagccgtta actttatcaa ttttactggt tcaacaggaa ttggggaacg tattggcaaa 720
atggctggta tgcgtccgat tatgcttgaa ctcggtggaa aagattcagc catcgttctt 780
gaagatgcag accttgaatt gactgctaaa aatattattg caggtgcttt tggttattca 840
ggtcaacgct gtacagcagt taaacgtgtt cttgtgatgg aaagtgttgc tgatgaactg 900
gtcgaaaaaa tccgtgaaaa agttcttgca ttaacaattg gtaatccaga agacgatgca 960
gatattacac cgttgattga tacaaaatca gctgattatg tagaaggtct tattaatgat 1020
gccaatgata aaggagccac tgcccttact gaaatcaaac gtgaaggtaa tcttatctgt 1080
ccaatcctct ttgataaggt aacgacagat atgcgtcttg cttgggaaga accatttggt 1140
cctgttcttc cgatcattcg tgtgacatct gtagaagaag ccattgaaat ttctaacaaa 1200
tcggaatatg gacttcaggc ttctatcttt acaaatgatt tcccacgcgc ttttggtatt 1260
gctgagcagc ttgaagttgg tacagttcat atcaataata agacacagcg cggcacggac 1320
aacttcccat tcttaggggc taaaaaatca ggtgcaggta ttcaaggggt aaaatattct 1380
attgaagcta tgacaactgt taaatccgtc gtatttgata tcaaataa 1428

<210> SEQ ID NO 92
<211> LENGTH: 475
<212> TYPE: PRT
<213> ORGANISM: Streptococcus mutans

<400> SEQUENCE: 92

Met Thr Lys Gln Tyr Lys Asn Tyr Val Asn Gly Glu Trp Lys Leu Ser
1 5 10 15

Glu Asn Glu Ile Lys Ile Tyr Glu Pro Ala Ser Gly Ala Glu Leu Gly
20 25 30

Ser Val Pro Ala Met Ser Thr Glu Glu Val Asp Tyr Val Tyr Ala Ser
35 40 45

Ala Lys Lys Ala Gln Pro Ala Trp Arg Ser Leu Ser Tyr Ile Glu Arg
50 55 60

-continued

```
Ala Ala Tyr Leu His Lys Val Ala Asp Ile Leu Met Arg Asp Lys Glu
65                  70                  75                  80

Lys Ile Gly Ala Val Leu Ser Lys Glu Val Ala Lys Gly Tyr Lys Ser
                85                  90                  95

Ala Val Ser Glu Val Val Arg Thr Ala Glu Ile Ile Asn Tyr Ala Ala
            100                 105                 110

Glu Glu Gly Leu Arg Met Glu Gly Glu Val Leu Glu Gly Gly Ser Phe
        115                 120                 125

Glu Ala Ala Ser Lys Lys Lys Ile Ala Val Val Arg Arg Glu Pro Val
    130                 135                 140

Gly Leu Val Leu Ala Ile Ser Pro Phe Asn Tyr Pro Val Asn Leu Ala
145                 150                 155                 160

Gly Ser Lys Ile Ala Pro Ala Leu Ile Ala Gly Asn Val Ile Ala Phe
                165                 170                 175

Lys Pro Pro Thr Gln Gly Ser Ile Ser Gly Leu Leu Leu Ala Glu Ala
            180                 185                 190

Phe Ala Glu Ala Gly Leu Pro Ala Gly Val Phe Asn Thr Ile Thr Gly
        195                 200                 205

Arg Gly Ser Glu Ile Gly Asp Tyr Ile Val Glu His Gln Ala Val Asn
    210                 215                 220

Phe Ile Asn Phe Thr Gly Ser Thr Gly Ile Gly Glu Arg Ile Gly Lys
225                 230                 235                 240

Met Ala Gly Met Arg Pro Ile Met Leu Glu Leu Gly Gly Lys Asp Ser
                245                 250                 255

Ala Ile Val Leu Glu Asp Ala Asp Leu Glu Leu Thr Ala Lys Asn Ile
            260                 265                 270

Ile Ala Gly Ala Phe Gly Tyr Ser Gly Gln Arg Cys Thr Ala Val Lys
        275                 280                 285

Arg Val Leu Val Met Glu Ser Val Ala Asp Glu Leu Val Glu Lys Ile
    290                 295                 300

Arg Glu Lys Val Leu Ala Leu Thr Ile Gly Asn Pro Glu Asp Asp Ala
305                 310                 315                 320

Asp Ile Thr Pro Leu Ile Asp Thr Lys Ser Ala Asp Tyr Val Glu Gly
                325                 330                 335

Leu Ile Asn Asp Ala Asn Asp Lys Gly Ala Thr Ala Leu Thr Glu Ile
            340                 345                 350

Lys Arg Glu Gly Asn Leu Ile Cys Pro Ile Leu Phe Asp Lys Val Thr
        355                 360                 365

Thr Asp Met Arg Leu Ala Trp Glu Glu Pro Phe Gly Pro Val Leu Pro
    370                 375                 380

Ile Ile Arg Val Thr Ser Val Glu Glu Ala Ile Glu Ile Ser Asn Lys
385                 390                 395                 400

Ser Glu Tyr Gly Leu Gln Ala Ser Ile Phe Thr Asn Asp Phe Pro Arg
                405                 410                 415

Ala Phe Gly Ile Ala Glu Gln Leu Glu Val Gly Thr Val His Ile Asn
            420                 425                 430

Asn Lys Thr Gln Arg Gly Thr Asp Asn Phe Pro Phe Leu Gly Ala Lys
        435                 440                 445

Lys Ser Gly Ala Gly Ile Gln Gly Val Lys Tyr Ser Ile Glu Ala Met
    450                 455                 460

Thr Thr Val Lys Ser Val Val Phe Asp Ile Lys
465                 470                 475
```

<210> SEQ ID NO 93
<211> LENGTH: 1401
<212> TYPE: DNA
<213> ORGANISM: Aspergillus parasiticus

<400> SEQUENCE: 93
atgtcttcca cagctatccc caagcgcatg gcgctgaacc gcaacccggg cacggattcc 60
tccgtcccca gcgtctcggt gtctccgttt gacagccctc gtcattctcc gtcctcgact 120
tccctttcgt cgctggcgtc cgagtccgag aacaagggca agatgttgga cacctatgga 180
aatgagttca agatcccgga ctacaccatc aagcagatcc gtgacgccat ccccgctcac 240
tgttacgagc ggaaggctct caccagcttg tactatgtgt tccgtgacat agccatgctg 300
ggatccatat tctatgtctt ccacaactat gtcacgccgg agaccgttcc ctctttcccg 360
gctcgcgttg ctttgtggtc cctttacacc gtcgtccagg gtctgatcgc tactggtgtc 420
tgggttttgg ctcacgagtg cggtcaccag gctttctccc cctccaaggt tctgaacgac 480
actgttggct ggatctgtca ctccgccctg ctggtgccgt acttctcctg gaagatctcc 540
cacggcaagc accacaaggc cactggtaac atcgcccgtg acatggtgtt cgtccccaag 600
acccgcgagg agtatgcttc ccgcatcggc aagaccattc acgacctgaa cgaattgatg 660
gaggagactc ccatcgccac cgtcaccaac ctcattctcc agcagctctt cggatggccc 720
atgtacctcc tgaccaacgt gaccggtcac aacaaccacg agcgccagcc cgagggtcgt 780
ggaaagggaa agcgcaacgg ctactttggc ggtgtcaacc acttcaaccc tagcagccct 840
ctgtacgagg ccaaggatgc taagttgatc gtcctgagtg acctgggtct cgccatcacc 900
ggatccgtcc tctattacat cggttccacc tatggctggc tcaacctcct ggtgtggtat 960
ggaattcctt acctctgggt gaaccactgg ctggttgcca tcacttacct ccagcacacc 1020
gaccccactc tccctcacta ccagcccgag gtgtggaact tcgcccgtgg agccgctgcc 1080
accattgacc gtgacttcgg ctttgttggt cgtcacatct tgcacggtat cattgagacc 1140
cacgttcttc accactacgt cagcaccatc cccttctacc acgccgacga ggccagcgag 1200
gccatccaga aggtcatggg ctcgcactac cgcacggagg cccacactgg ctggactgga 1260
ttcttcaagg ctctcttcac cagtgcccgt gtctgccact gggttgagcc gaccgagggt 1320
gccaagggcg agagcgaagg tgtgctcttc taccgtaata ccaacggcgt tggagttcct 1380
ccggccaagc tttccaaata g 1401

<210> SEQ ID NO 94
<211> LENGTH: 466
<212> TYPE: PRT
<213> ORGANISM: Aspergillus parasiticus

<400> SEQUENCE: 94

Met Ser Ser Thr Ala Ile Pro Lys Arg Met Ala Leu Asn Arg Asn Pro
1               5                   10                  15

Gly Thr Asp Ser Ser Val Pro Ser Val Ser Val Ser Pro Phe Asp Ser
            20                  25                  30

Pro Arg His Ser Pro Ser Ser Thr Ser Leu Ser Ser Leu Ala Ser Glu
        35                  40                  45

Ser Glu Asn Lys Gly Lys Met Leu Asp Thr Tyr Gly Asn Glu Phe Lys
    50                  55                  60

Ile Pro Asp Tyr Thr Ile Lys Gln Ile Arg Asp Ala Ile Pro Ala His
65                  70                  75                  80

-continued

```
Cys Tyr Glu Arg Lys Ala Leu Thr Ser Leu Tyr Tyr Val Phe Arg Asp
                85                  90                  95

Ile Ala Met Leu Gly Ser Ile Phe Tyr Val Phe His Asn Tyr Val Thr
            100                 105                 110

Pro Glu Thr Val Pro Ser Phe Pro Ala Arg Val Ala Leu Trp Ser Leu
        115                 120                 125

Tyr Thr Val Val Gln Gly Leu Ile Ala Thr Gly Val Trp Val Leu Ala
    130                 135                 140

His Glu Cys Gly His Gln Ala Phe Ser Pro Ser Lys Val Leu Asn Asp
145                 150                 155                 160

Thr Val Gly Trp Ile Cys His Ser Ala Leu Leu Val Pro Tyr Phe Ser
                165                 170                 175

Trp Lys Ile Ser His Gly Lys His His Lys Ala Thr Gly Asn Ile Ala
            180                 185                 190

Arg Asp Met Val Phe Val Pro Lys Thr Arg Glu Glu Tyr Ala Ser Arg
        195                 200                 205

Ile Gly Lys Thr Ile His Asp Leu Asn Glu Leu Met Glu Glu Thr Pro
    210                 215                 220

Ile Ala Thr Val Thr Asn Leu Ile Leu Gln Gln Leu Phe Gly Trp Pro
225                 230                 235                 240

Met Tyr Leu Leu Thr Asn Val Thr Gly His Asn Asn His Glu Arg Gln
                245                 250                 255

Pro Glu Gly Arg Gly Lys Gly Lys Arg Asn Gly Tyr Phe Gly Gly Val
            260                 265                 270

Asn His Phe Asn Pro Ser Ser Pro Leu Tyr Glu Ala Lys Asp Ala Lys
        275                 280                 285

Leu Ile Val Leu Ser Asp Leu Gly Leu Ala Ile Thr Gly Ser Val Leu
    290                 295                 300

Tyr Tyr Ile Gly Ser Thr Tyr Gly Trp Leu Asn Leu Leu Val Trp Tyr
305                 310                 315                 320

Gly Ile Pro Tyr Leu Trp Val Asn His Trp Leu Val Ala Ile Thr Tyr
                325                 330                 335

Leu Gln His Thr Asp Pro Thr Leu Pro His Tyr Gln Pro Glu Val Trp
            340                 345                 350

Asn Phe Ala Arg Gly Ala Ala Ala Thr Ile Asp Arg Asp Phe Gly Phe
        355                 360                 365

Val Gly Arg His Ile Leu His Gly Ile Ile Glu Thr His Val Leu His
    370                 375                 380

His Tyr Val Ser Thr Ile Pro Phe Tyr His Ala Asp Glu Ala Ser Glu
385                 390                 395                 400

Ala Ile Gln Lys Val Met Gly Ser His Tyr Arg Thr Glu Ala His Thr
                405                 410                 415

Gly Trp Thr Gly Phe Phe Lys Ala Leu Phe Thr Ser Ala Arg Val Cys
            420                 425                 430

His Trp Val Glu Pro Thr Glu Gly Ala Lys Gly Glu Ser Glu Gly Val
        435                 440                 445

Leu Phe Tyr Arg Asn Thr Asn Gly Val Gly Val Pro Pro Ala Lys Leu
    450                 455                 460

Ser Lys
465
```

<210> SEQ ID NO 95
<211> LENGTH: 1263
<212> TYPE: DNA

-continued

<213> ORGANISM: Pichia pastoris

<400> SEQUENCE: 95

```
atgtctgccg tcacagttac aggtaataat ggtgatgctt caagaagtaa caccaccacc     60
accacaaaac gtacaggcaa tgtttcctcc ttcagccaat ccaaaggttt gactgccata    120
gacacctggg gtaacgtctt caaagtccct gattttacaa tcaagcaaat cttggatgct    180
attccaaagc actgctatga acgcaggcta accacgtcgt tctactacgt gttcagggac    240
atattcctca ttggttgtac catgttcatg ggtcgttca ttcccatgat tgagaatgtt     300
ttccttagag gcgctgctta cgccgctttg gtttttctct tatctgttga gtacactggt    360
ttgtgggttt tggcccacga gtgcggtcat caagctttct ccgattatgg ttgggtcaac    420
gacaccgtgg gatggatttt gcattcttac ctgttagtcc catatttttc ttggaaatac    480
agtcatggta aacatcacaa ggctactggc cacttgacta gagacatggt gtttgtacct    540
gccacaaagg agaagttctt ggaaaagaga aacgccagca aacttggcga actgggagaa    600
gatgctccca ttttcacatt atatcagttg gtagcccaac aattgggagg ctggattttg    660
tatttgttca ccaacgttac tggtcaaccc taccccaaca cccctaaatg gatgcagaac    720
cactttgttc cctcatctcc aattttcgaa aaaaaggact actggtttat cattctgagt    780
gacctgggta tcttggcaca gttgatggtt ttgtatgtgt ggagacaaca aatgggaaac    840
tggaacttat ttatttactg gttcctgcct tatgttctca ccaaccattg gctggtgttc    900
atcacattcc tgcaacactc tgatccaacg atgcctcact acgaggctga acaatggacg    960
tttgccagag gagctgccgc aaccatcgac cgtgaatttg gattcattgg acctttcttc   1020
tttcacgata tcatcgaaac tcacgtcttg catcactatg tgagtagaat tcctttctac   1080
aacgcccgag aggccagtga aggtattaag aaagttatgg gggagcatta tcgctacagt   1140
ggtgaaaaca tgtgggtctc tctttggaag agtggacgtt catgtcagtt tgttgatgga   1200
gaaaacgggg tgaaaatgta ccgtaacatc aataactggg gtattggaac cggtgagaaa   1260
tag                                                                 1263
```

<210> SEQ ID NO 96
<211> LENGTH: 420
<212> TYPE: PRT
<213> ORGANISM: Pichia pastoris

<400> SEQUENCE: 96

```
Met Ser Ala Val Thr Val Thr Gly Asn Asn Gly Asp Ala Ser Arg Ser
 1               5                  10                  15

Asn Thr Thr Thr Thr Thr Lys Arg Thr Gly Asn Val Ser Ser Phe Ser
            20                  25                  30

Gln Ser Lys Gly Leu Thr Ala Ile Asp Thr Trp Gly Asn Val Phe Lys
        35                  40                  45

Val Pro Asp Phe Thr Ile Lys Gln Ile Leu Asp Ala Ile Pro Lys His
    50                  55                  60

Cys Tyr Glu Arg Arg Leu Thr Thr Ser Phe Tyr Tyr Val Phe Arg Asp
65                  70                  75                  80

Ile Phe Leu Ile Gly Cys Thr Met Phe Met Gly Ser Phe Ile Pro Met
                85                  90                  95

Ile Glu Asn Val Phe Leu Arg Gly Ala Ala Tyr Ala Ala Leu Val Phe
            100                 105                 110

Leu Leu Ser Val Glu Tyr Thr Gly Leu Trp Val Leu Ala His Glu Cys
        115                 120                 125
```

-continued

```
Gly His Gln Ala Phe Ser Asp Tyr Gly Trp Val Asn Asp Thr Val Gly
    130                 135                 140

Trp Ile Leu His Ser Tyr Leu Leu Val Pro Tyr Phe Ser Trp Lys Tyr
145                 150                 155                 160

Ser His Gly Lys His His Lys Ala Thr Gly His Leu Thr Arg Asp Met
                165                 170                 175

Val Phe Val Pro Ala Thr Lys Glu Lys Phe Leu Glu Lys Arg Asn Ala
            180                 185                 190

Ser Lys Leu Gly Glu Leu Gly Glu Asp Ala Pro Ile Phe Thr Leu Tyr
        195                 200                 205

Gln Leu Val Ala Gln Gln Leu Gly Gly Trp Ile Leu Tyr Leu Phe Thr
    210                 215                 220

Asn Val Thr Gly Gln Pro Tyr Pro Asn Thr Pro Lys Trp Met Gln Asn
225                 230                 235                 240

His Phe Val Pro Ser Ser Pro Ile Phe Glu Lys Lys Asp Tyr Trp Phe
                245                 250                 255

Ile Ile Leu Ser Asp Leu Gly Ile Leu Ala Gln Leu Met Val Leu Tyr
            260                 265                 270

Val Trp Arg Gln Gln Met Gly Asn Trp Asn Leu Phe Ile Tyr Trp Phe
        275                 280                 285

Leu Pro Tyr Val Leu Thr Asn His Trp Leu Val Phe Ile Thr Phe Leu
    290                 295                 300

Gln His Ser Asp Pro Thr Met Pro His Tyr Glu Ala Glu Gln Trp Thr
305                 310                 315                 320

Phe Ala Arg Gly Ala Ala Ala Thr Ile Asp Arg Glu Phe Gly Phe Ile
                325                 330                 335

Gly Pro Phe Phe Phe His Asp Ile Ile Glu Thr His Val Leu His His
            340                 345                 350

Tyr Val Ser Arg Ile Pro Phe Tyr Asn Ala Arg Glu Ala Ser Glu Gly
        355                 360                 365

Ile Lys Lys Val Met Gly Glu His Tyr Arg Tyr Ser Gly Glu Asn Met
    370                 375                 380

Trp Val Ser Leu Trp Lys Ser Gly Arg Ser Cys Gln Phe Val Asp Gly
385                 390                 395                 400

Glu Asn Gly Val Lys Met Tyr Arg Asn Ile Asn Asn Trp Gly Ile Gly
                405                 410                 415

Thr Gly Glu Lys
            420
```

<210> SEQ ID NO 97
<211> LENGTH: 3175
<212> TYPE: DNA
<213> ORGANISM: Marchantia polymorpha

<400> SEQUENCE: 97

```
gtggggggtg ggactggggc ccctacaaag atcttggaaa agatcttgag gcagcgagcg      60

tctcatcgat cggctgctgt cgttgcagcg ttagtatttg agcagagctc gcgcctgctc     120

ctgttctata gatccaattt cataagtcga cgagaaaggc agaaggcgag aagcggcagg     180

cagcgagcgc gagcgccaga gctcttgctc ccctcgctca tcgctcgcat tgccgcattt     240

tgtgagtgtc ggactgatca ctcagtccgt cactgcaaac gcgagcgagc gagagtgcga     300

gtgagcgagc gagcgagcga gagccgcggt gtgtctgtga gatccaatcc tttttctgct     360

ttgcgcgctg tggggcgcga tggcctcgtc caccaccacc gccgtgaagc aatcttcggg     420
```

-continued

```
tgggctgtgg tcgaaatggg gcaccggcag caacttgagc ttcgtgtcgc gcaaggagca    480
gcagcagcag cagcagcaga gctctcccga ggcgtcgact cccgcggcgc agcaggagaa    540
atccatcagt agagaatcca tccccgaggg cttcttgacc gtggaggagg tgtcgaagca    600
cgacaatccg agcgactgct ggatcgtcat caacgacaag gtgtacgacg tgagcgcatt    660
cgggaagacg catccgggcg gccctgtgat cttcacgcag gccggccgcg acgccacgga    720
ttctttcaag gttttccact ccgccaaggc gtggcagttt ctccaggacc tgtacatcgg    780
agatctgtac aatgccgagc cagtgtcgga gctggtgaag gattaccgag acctgaggac    840
ggcgttcatg cgttctcagc tattcaagag cagtaaaatg tactacgtga ccaagtgcgt    900
cacaaatttt gcaattcttg ccgccagtct cgcagtcatc gcgtggagcc agacgtatct    960
ggcggttttg tgctccagtt tcctgttggc tctcttctgg cagcaatgtg gatggttatc   1020
gcacgatttt ctccaccacc aggtgaccga gaaccgatcg ctcaacacgt acttcggcgg   1080
cctgttctgg ggtaacttcg cccagggcta cagcgtggga tggtggaaga ccaagcacaa   1140
tgtgcaccac gcggccacga acgaatgcga cgacaagtat cagcccatcg atcccgacat   1200
cgacaccgtg cccctgctcg cctggagcaa ggaaatcttg gccaccgtcg acgaccaatt   1260
cttccgatcg atcatcagcg tgcagcacct tctgttcttc ccgctcctct tcttggcaag   1320
attcagctgg ctgcattcga gttgggccca cgccagcaac ttcgagatgc ctcggtacat   1380
gagatgggcg gagaaggcct cgctcctcgg gcactacggc gcctcaatcg gcgccgcctt   1440
ctacattttg cccatccccc aggccatctg ctggctcttc ttgtcgcaac tgttttgcgg   1500
cgctctgctc agcattgtct tcgtgatcag ccacaatggc atggatgtgt acaacgaccc   1560
ccgggacttc gtgacggccc aagtcacctc gaccagaaac atcgaaggca acttcttcaa   1620
cgactggttc accggaggcc tgaacaggca gattgagcac catctgtttc cgtctcttcc   1680
gaggcacaac ctcgccaagg tcgcgccaca cgtcaaggcg ctctgcgcca agcacggttt   1740
gcattacgaa gaattgagtc tgggcacggg agtctgtcgt gtcttcaatc ggctagtaga   1800
ggtagcatac gctgcgaaag tatagatcga cgagagtttc ccaccaacac aggtgagcct   1860
cgacattctt tgtacacatt cttcatgtct tttgaatctt gcttcaccag attcggcggc   1920
cgtagatttg ggattggagg tccctgtgat taccataacc tttgctagta cggtaaataa   1980
tgagctcgag gctattttag gtcaaagatt tcaagggaca tcacgtctat tttgtactaa   2040
attaaggatt gatccctctc aaccactgcg cgagttcgtt cgattggttc agatatgccc   2100
tgttaggaaa gtggtcacat cgtgaagtct gtcgtgtgta tattcttttt ccgctggacc   2160
tctgccatcg ctcacaattc ctcctcctcg tgtaacctag taacttacgc gtcgtgctac   2220
tgtcagatgt tcttacttta tcctcctgag cggtggtcac tgaagagaaa gaactctacg   2280
tgactccgag atcagtgtgt ttcctcagag agatggaagt aaatggtggc ctttgcaatg   2340
attctgttgt gcagttagaa caagggaata gtacgagaga aggagacagc aacctggact   2400
ttttgttcct gatgttgcat actttctcga atatacgtct ccacgccttc aagtttcagc   2460
ttcaactgat tgtcttcagt aaccatcgct tgctccaact gggcgacctg cagaattgaa   2520
gatcagtttt actgagtttg taccgagagt ttcccaaatt ttgttgtagg ctgatgaccc   2580
aatcctagca tacactttag gaataagcag tctcaacata attaggtcca tcattcagca   2640
atttcgatac agcgcctggg attcgacgag tttacacgat gagtatggct tgtaactggc   2700
cttctcaagg tagccttgga tctccccggg cctcttgcca tcccattcac ccaatcgaga   2760
```

-continued

```
ttctgcagtc tccaaccttt tctggaagtt ctcaatctgt aacctctgtt gtagagatag   2820

catacgccac aagacaaggt ctttgtgaac acagtcgtct aacaaacagc aagttgtgtg   2880

gattggcatc taaataaccg cctctggtca agtaacagca ggtgttccgc agtttccagg   2940

aacatacttt gtttctgtca cagccaggcg gtgaatagta aagccaattc aacacatacg   3000

ggagaagatg ggtcgatatt tgtatttggc agggtgtcca gatttcaccc atcagtctct   3060

cacttgcttg tatgtccctg acgtgcttca aaattttgcg cggggaatca tcaatatact   3120

taccatttgt aaagtctgct tccggtgttc tgttcccact acttgaagtt tcttg        3175


<210> SEQ ID NO 98
<211> LENGTH: 481
<212> TYPE: PRT
<213> ORGANISM: Marchantia polymorpha

<400> SEQUENCE: 98

Met Ala Ser Ser Thr Thr Thr Ala Val Lys Gln Ser Ser Gly Gly Leu
1               5                   10                  15

Trp Ser Lys Trp Gly Thr Gly Ser Asn Leu Ser Phe Val Ser Arg Lys
            20                  25                  30

Glu Gln Gln Gln Gln Gln Gln Gln Ser Ser Pro Glu Ala Ser Thr Pro
        35                  40                  45

Ala Ala Gln Gln Glu Lys Ser Ile Ser Arg Glu Ser Ile Pro Glu Gly
    50                  55                  60

Phe Leu Thr Val Glu Glu Val Ser Lys His Asp Asn Pro Ser Asp Cys
65                  70                  75                  80

Trp Ile Val Ile Asn Asp Lys Val Tyr Asp Val Ser Ala Phe Gly Lys
                85                  90                  95

Thr His Pro Gly Gly Pro Val Ile Phe Thr Gln Ala Gly Arg Asp Ala
            100                 105                 110

Thr Asp Ser Phe Lys Val Phe His Ser Ala Lys Ala Trp Gln Phe Leu
        115                 120                 125

Gln Asp Leu Tyr Ile Gly Asp Leu Tyr Asn Ala Glu Pro Val Ser Glu
    130                 135                 140

Leu Val Lys Asp Tyr Arg Asp Leu Arg Thr Ala Phe Met Arg Ser Gln
145                 150                 155                 160

Leu Phe Lys Ser Ser Lys Met Tyr Tyr Val Thr Lys Cys Val Thr Asn
                165                 170                 175

Phe Ala Ile Leu Ala Ala Ser Leu Ala Val Ile Ala Trp Ser Gln Thr
            180                 185                 190

Tyr Leu Ala Val Leu Cys Ser Ser Phe Leu Leu Ala Leu Phe Trp Gln
        195                 200                 205

Gln Cys Gly Trp Leu Ser His Asp Phe Leu His His Gln Val Thr Glu
    210                 215                 220

Asn Arg Ser Leu Asn Thr Tyr Phe Gly Gly Leu Phe Trp Gly Asn Phe
225                 230                 235                 240

Ala Gln Gly Tyr Ser Val Gly Trp Trp Lys Thr Lys His Asn Val His
                245                 250                 255

His Ala Ala Thr Asn Glu Cys Asp Asp Lys Tyr Gln Pro Ile Asp Pro
            260                 265                 270

Asp Ile Asp Thr Val Pro Leu Leu Ala Trp Ser Lys Glu Ile Leu Ala
        275                 280                 285

Thr Val Asp Asp Gln Phe Phe Arg Ser Ile Ile Ser Val Gln His Leu
    290                 295                 300
```

-continued

```
Leu Phe Phe Pro Leu Leu Phe Leu Ala Arg Phe Ser Trp Leu His Ser
305                 310                 315                 320

Ser Trp Ala His Ala Ser Asn Phe Glu Met Pro Arg Tyr Met Arg Trp
                325                 330                 335

Ala Glu Lys Ala Ser Leu Leu Gly His Tyr Gly Ala Ser Ile Gly Ala
            340                 345                 350

Ala Phe Tyr Ile Leu Pro Ile Pro Gln Ala Ile Cys Trp Leu Phe Leu
        355                 360                 365

Ser Gln Leu Phe Cys Gly Ala Leu Leu Ser Ile Val Phe Val Ile Ser
    370                 375                 380

His Asn Gly Met Asp Val Tyr Asn Asp Pro Arg Asp Phe Val Thr Ala
385                 390                 395                 400

Gln Val Thr Ser Thr Arg Asn Ile Glu Gly Asn Phe Phe Asn Asp Trp
                405                 410                 415

Phe Thr Gly Gly Leu Asn Arg Gln Ile Glu His His Leu Phe Pro Ser
            420                 425                 430

Leu Pro Arg His Asn Leu Ala Lys Val Ala Pro His Val Lys Ala Leu
        435                 440                 445

Cys Ala Lys His Gly Leu His Tyr Glu Glu Leu Ser Leu Gly Thr Gly
    450                 455                 460

Val Cys Arg Val Phe Asn Arg Leu Val Glu Val Ala Tyr Ala Ala Lys
465                 470                 475                 480

Val


<210> SEQ ID NO 99
<211> LENGTH: 1335
<212> TYPE: DNA
<213> ORGANISM: Cyprinus carpio

<400> SEQUENCE: 99

atgggtggcg gaggacagca gacggaccgg atcactggga ccaacgggag gttcggcact      60

tacacctggg aggaggtgca gaaacacacc aagtttggag atcagtggat cgaggttgaa     120

aggaaggttt ataatgtgag ccagtgggtg aagagacacc ccggaggagt gaggatcctc     180

ggacactatg ctggagaaga tgccacggag gcgtttactg catttcatcc agaccttccg     240

ctggtgagaa aatacatgaa gccgctgtta atcggggagc ttgaggcgtc tgaacccagt     300

caagaccggc agaaaaatgc tgctcttgtg gaggacttcc gagcccttcg tgagcgtctg     360

gaggctgagg ggtgtttcaa aacccagccg ctgtttctca tcttacatct gagtcacatc     420

ctgctcctgg aggccatcgc tctgatgatg gtgtggtacc tgggaaccgg ctggatcaac     480

acggccatcg tcgctgtttt actggccact gcacagtcac aggctgaatg gttgcagcac     540

gacttcggtc atctgtccgt gtttaaaacc tctcgatgga atcacctggt gcacaaattt     600

gtcgtcggac acattaaggg agcgtctgcg ggtcggtgga accatcgcca cttccagcat     660

cacgctaaac cgaacgtgtt caaaaaggac ccggacgtca acatgctcaa tgcgtttgtg     720

gctggaaaag tgcagcctgt ggagtacggc gttaagaaga tcaagcattt gccttacaac     780

catcagcaca agtacttctt cttcattgga cctcctctgc tcatcccagt gtatttccag     840

ttccagatct tccacaatat gatcgcgcat ggcctttggg tggaccttgc gtggtgtata     900

agttactacg ttcgatactt cctgtgttac acgcagtact acggtgtgtt ttgggcggtg     960

attctgttta atttcgtgag gttcctgaag agtcactggt ttgtgtgggt gacccagatg    1020

agccacatcc ccatgcagat cgactatgag aagcaccagg accggctcag catgcagctg    1080
```

-continued

```
gtcgcgacct gcaacatcga gcagtcctcc ttcaacgact ggttcagcgg acacctcaac   1140

ttccagatcg agcaccacct cttccccaca atgcctcggc acaactactg gcgcgccgcc   1200

cctcacgttc gagagttatg tgccaaatac ggaatcaagt accaagagaa gaccttgcag   1260

ggggcctttg cggacgtcgt caggtctttg gagaaatccg gagaaatctg gctggatgcg   1320

tacctcaacg aataa                                                    1335


<210> SEQ ID NO 100
<211> LENGTH: 444
<212> TYPE: PRT
<213> ORGANISM: Cyprinus carpio

<400> SEQUENCE: 100

Met Gly Gly Gly Gly Gln Gln Thr Asp Arg Ile Thr Gly Thr Asn Gly
 1               5                  10                  15

Arg Phe Gly Thr Tyr Thr Trp Glu Glu Val Gln Lys His Thr Lys Phe
            20                  25                  30

Gly Asp Gln Trp Ile Glu Val Glu Arg Lys Val Tyr Asn Val Ser Gln
        35                  40                  45

Trp Val Lys Arg His Pro Gly Gly Val Arg Ile Leu Gly His Tyr Ala
    50                  55                  60

Gly Glu Asp Ala Thr Glu Ala Phe Thr Ala Phe His Pro Asp Leu Pro
65                  70                  75                  80

Leu Val Arg Lys Tyr Met Lys Pro Leu Leu Ile Gly Glu Leu Glu Ala
                85                  90                  95

Ser Glu Pro Ser Gln Asp Arg Gln Lys Asn Ala Ala Leu Val Glu Asp
            100                 105                 110

Phe Arg Ala Leu Arg Glu Arg Leu Glu Ala Glu Gly Cys Phe Lys Thr
        115                 120                 125

Gln Pro Leu Phe Leu Ile Leu His Leu Ser His Ile Leu Leu Leu Glu
    130                 135                 140

Ala Ile Ala Leu Met Met Val Trp Tyr Leu Gly Thr Gly Trp Ile Asn
145                 150                 155                 160

Thr Ala Ile Val Ala Val Leu Leu Ala Thr Ala Gln Ser Gln Ala Glu
                165                 170                 175

Trp Leu Gln His Asp Phe Gly His Leu Ser Val Phe Lys Thr Ser Arg
            180                 185                 190

Trp Asn His Leu Val His Lys Phe Val Val Gly His Ile Lys Gly Ala
        195                 200                 205

Ser Ala Gly Arg Trp Asn His Arg His Phe Gln His His Ala Lys Pro
    210                 215                 220

Asn Val Phe Lys Lys Asp Pro Asp Val Asn Met Leu Asn Ala Phe Val
225                 230                 235                 240

Ala Gly Lys Val Gln Pro Val Glu Tyr Gly Val Lys Lys Ile Lys His
                245                 250                 255

Leu Pro Tyr Asn His Gln His Lys Tyr Phe Phe Phe Ile Gly Pro Pro
            260                 265                 270

Leu Leu Ile Pro Val Tyr Phe Gln Phe Gln Ile Phe His Asn Met Ile
        275                 280                 285

Ala His Gly Leu Trp Val Asp Leu Ala Trp Cys Ile Ser Tyr Tyr Val
    290                 295                 300

Arg Tyr Phe Leu Cys Tyr Thr Gln Tyr Tyr Gly Val Phe Trp Ala Val
305                 310                 315                 320

Ile Leu Phe Asn Phe Val Arg Phe Leu Lys Ser His Trp Phe Val Trp
```

-continued

```
                325                 330                 335

Val Thr Gln Met Ser His Ile Pro Met Gln Ile Asp Tyr Glu Lys His
            340                 345                 350

Gln Asp Arg Leu Ser Met Gln Leu Val Ala Thr Cys Asn Ile Glu Gln
        355                 360                 365

Ser Ser Phe Asn Asp Trp Phe Ser Gly His Leu Asn Phe Gln Ile Glu
    370                 375                 380

His His Leu Phe Pro Thr Met Pro Arg His Asn Tyr Trp Arg Ala Ala
385                 390                 395                 400

Pro His Val Arg Glu Leu Cys Ala Lys Tyr Gly Ile Lys Tyr Gln Glu
                405                 410                 415

Lys Thr Leu Gln Gly Ala Phe Ala Asp Val Val Arg Ser Leu Glu Lys
            420                 425                 430

Ser Gly Glu Ile Trp Leu Asp Ala Tyr Leu Asn Glu
        435                 440


<210> SEQ ID NO 101
<211> LENGTH: 894
<212> TYPE: DNA
<213> ORGANISM: Salmo salar

<400> SEQUENCE: 101

atggagactt ttaattataa actaaacatg tacatagact catggatggg acccagagat      60

gagcgggtac agggatggct gcttctggac aactaccctc caacctttgc actaacagtc     120

atgtacctgc tgatcgtatg gctggggccc aagtacatga gacacagaca gccggtgtct     180

tgccggggtc tcctgttggt ctacaatctg ggcctcacga tcttgtcctt ctatatgttc     240

tatgagatgg tgtctgctgt gtggcacggg gattataact tctattgcca agacacacac     300

agtgcaggag aaaccgatac caagatcata aatgtgctgt ggtggtacta cttctccaaa     360

gctcatagag ttttatggac accttcttct tcatccctac ggaagaacaa ccatcagatc     420

acgtttctgc acatctacca ccatgctagc atgctcaaca tctggtggtt cgtcatgaac     480

tgggtgccct gtggtcactc ctactttggt gcctccctga acagcttcat ccatgtcctg     540

atgtactctt actatgggct ctctgctgtc ccggccttgc ggccctatct atggtggaag     600

aagtatacat cacacaagca cagcttgatt cagttctttt tgaccatgtc ccagacgata     660

tgtgcagtca tttggccatg tggtttcccc agagggtggc tgtatttcca gatattctat     720

gtcgtcacac ttattgccct tttctcaaac ttctacattc agacttacaa gaaacacctt     780

gtttcacaaa agaaggagtg tcatcagaat ggctctgttg cttcattgaa tggccatgtg     840

aatggggtga cacccacgga aaccattaca cacaggaaag tgaggggga ctga            894


<210> SEQ ID NO 102
<211> LENGTH: 297
<212> TYPE: PRT
<213> ORGANISM: Salmo salar

<400> SEQUENCE: 102

Met Glu Thr Phe Asn Tyr Lys Leu Asn Met Tyr Ile Asp Ser Trp Met
 1               5                  10                  15

Gly Pro Arg Asp Glu Arg Val Gln Gly Trp Leu Leu Leu Asp Asn Tyr
            20                  25                  30

Pro Pro Thr Phe Ala Leu Thr Val Met Tyr Leu Leu Ile Val Trp Leu
        35                  40                  45

Gly Pro Lys Tyr Met Arg His Arg Gln Pro Val Ser Cys Arg Gly Leu
```

-continued

```
    50                  55                  60

Leu Leu Val Tyr Asn Leu Gly Leu Thr Ile Leu Ser Phe Tyr Met Phe
65                  70                  75                  80

Tyr Glu Met Val Ser Ala Val Trp His Gly Asp Tyr Asn Phe Tyr Cys
                85                  90                  95

Gln Asp Thr His Ser Ala Gly Glu Thr Asp Thr Lys Ile Ile Asn Val
            100                 105                 110

Leu Trp Trp Tyr Tyr Phe Ser Lys Ala His Arg Val Leu Trp Thr Pro
        115                 120                 125

Ser Ser Ser Ser Leu Arg Lys Asn Asn His Gln Ile Thr Phe Leu His
    130                 135                 140

Ile Tyr His His Ala Ser Met Leu Asn Ile Trp Trp Phe Val Met Asn
145                 150                 155                 160

Trp Val Pro Cys Gly His Ser Tyr Phe Gly Ala Ser Leu Asn Ser Phe
                165                 170                 175

Ile His Val Leu Met Tyr Ser Tyr Tyr Gly Leu Ser Ala Val Pro Ala
            180                 185                 190

Leu Arg Pro Tyr Leu Trp Trp Lys Lys Tyr Thr Ser His Lys His Ser
        195                 200                 205

Leu Ile Gln Phe Phe Leu Thr Met Ser Gln Thr Ile Cys Ala Val Ile
    210                 215                 220

Trp Pro Cys Gly Phe Pro Arg Gly Trp Leu Tyr Phe Gln Ile Phe Tyr
225                 230                 235                 240

Val Val Thr Leu Ile Ala Leu Phe Ser Asn Phe Tyr Ile Gln Thr Tyr
                245                 250                 255

Lys Lys His Leu Val Ser Gln Lys Lys Glu Cys His Gln Asn Gly Ser
            260                 265                 270

Val Ala Ser Leu Asn Gly His Val Asn Gly Val Thr Pro Thr Glu Thr
        275                 280                 285

Ile Thr His Arg Lys Val Arg Gly Asp
    290                 295
```

<210> SEQ ID NO 103
<211> LENGTH: 873
<212> TYPE: DNA
<213> ORGANISM: Marchantia polymorpha

<400> SEQUENCE: 103

```
atggaggcgt acgagatggt ggatagtttt gtgtcgaaga cggttttcga aacgctgcag      60

agactgaggg gcggagtcgt gttgacggaa tctgcgatca ccaaaggttt gccatgcgtc     120

gatagcccga cgccgatcgt tcttgggttg tcgtcctact tgacattcgt gtttctcggg     180

ctcattgtca tcaagagcct ggatcttaag ccccgctcca aggagcccgc cattttgaac     240

ctgtttgtga tcttccacaa cttcgtctgc ttcgcactca gtctgtacat gtgcgtggga     300

attgtccgtc aagctatcct caacaggtac tctctgtggg gcaatgcgta caatcccaaa     360

gaagttcaaa tgggccacct gctctacatt ttctacatgt caaagtacat cgagtttatg     420

gacacggtca ttatgatttt gaagcgcaac acgcgccaga tcactgtgtt gcatgtgtac     480

caccacgcat ccatctcctt catctggtgg atcatcgcct accatgctcc tggcggtgaa     540

gcttatttct ctgccgcatt gaactccgga gtacatgtgc tcatgtacct ctactacctt     600

ttggcagcaa ctctgggaaa gaacgagaaa gctcgccgca agtacctatg gtggggaaaa     660

tacttgacac agctgcagat gttccagttt gtccttaaca tgattcaggc ttactacgat     720
```

-continued

```
attaagaaca actcgcctta cccacaattt ttgatccaga ttttgttcta ctacatgatc    780

tcgcttttag cgctatttgg aaacttttac gttcacaaat acgtatcagc gcccgcaaaa    840

cctgcgaaga tcaagagcaa aaaggcagaa taa                                  873


<210> SEQ ID NO 104
<211> LENGTH: 290
<212> TYPE: PRT
<213> ORGANISM: Marchantia polymorpha

<400> SEQUENCE: 104

Met Glu Ala Tyr Glu Met Val Asp Ser Phe Val Ser Lys Thr Val Phe
1               5                   10                  15

Glu Thr Leu Gln Arg Leu Arg Gly Gly Val Val Leu Thr Glu Ser Ala
            20                  25                  30

Ile Thr Lys Gly Leu Pro Cys Val Asp Ser Pro Thr Pro Ile Val Leu
        35                  40                  45

Gly Leu Ser Ser Tyr Leu Thr Phe Val Phe Leu Gly Leu Ile Val Ile
    50                  55                  60

Lys Ser Leu Asp Leu Lys Pro Arg Ser Lys Glu Pro Ala Ile Leu Asn
65                  70                  75                  80

Leu Phe Val Ile Phe His Asn Phe Val Cys Phe Ala Leu Ser Leu Tyr
                85                  90                  95

Met Cys Val Gly Ile Val Arg Gln Ala Ile Leu Asn Arg Tyr Ser Leu
            100                 105                 110

Trp Gly Asn Ala Tyr Asn Pro Lys Glu Val Gln Met Gly His Leu Leu
        115                 120                 125

Tyr Ile Phe Tyr Met Ser Lys Tyr Ile Glu Phe Met Asp Thr Val Ile
    130                 135                 140

Met Ile Leu Lys Arg Asn Thr Arg Gln Ile Thr Val Leu His Val Tyr
145                 150                 155                 160

His His Ala Ser Ile Ser Phe Ile Trp Trp Ile Ile Ala Tyr His Ala
                165                 170                 175

Pro Gly Gly Glu Ala Tyr Phe Ser Ala Ala Leu Asn Ser Gly Val His
            180                 185                 190

Val Leu Met Tyr Leu Tyr Tyr Leu Leu Ala Ala Thr Leu Gly Lys Asn
        195                 200                 205

Glu Lys Ala Arg Arg Lys Tyr Leu Trp Trp Gly Lys Tyr Leu Thr Gln
    210                 215                 220

Leu Gln Met Phe Gln Phe Val Leu Asn Met Ile Gln Ala Tyr Tyr Asp
225                 230                 235                 240

Ile Lys Asn Asn Ser Pro Tyr Pro Gln Phe Leu Ile Gln Ile Leu Phe
                245                 250                 255

Tyr Tyr Met Ile Ser Leu Leu Ala Leu Phe Gly Asn Phe Tyr Val His
            260                 265                 270

Lys Tyr Val Ser Ala Pro Ala Lys Pro Ala Lys Ile Lys Ser Lys Lys
        275                 280                 285

Ala Glu
    290


<210> SEQ ID NO 105
<211> LENGTH: 1365
<212> TYPE: DNA
<213> ORGANISM: Salmo salar

<400> SEQUENCE: 105
```

-continued atgggggggcg gaggccagca gacggagtca agcgagccgg ccaagggtga cgggcttgag 60
cccgatggag ggcaaggtgg cagtgcagtc tacacctggg aagaggtcca gaggcactcc 120
cacagaagcg accagtggtt ggtcatcgac aggaaggtct ataatattac ccagtgggca 180
aagagacacc cgggtggcat cagggtcatc agtcactttg ctggagaaga tgccacggaa 240
gcattttccg cattccatct tgatgctaat tttgtcagga agtttctgaa gccgttgctg 300
attggagagc tggcaccgac agagcccagc caggaccatg ggaaaaatgc agctctggtg 360
caggacttcc aggccttgcg tgaccatgtg gagagggagg gtctcctccg tgcccgcctc 420
ctgttcttca gcctctacct gggccacatc ctgctactag aggccctggc tttgggcctg 480
ctctgggtct gggggaccag ctggagcctc acactgctct gttccctcat gctggccacg 540
tctcaggccc aggctggctg gctgcagcat gactacggcc acctgtcagt ctgcaagaaa 600
tccagctgga accacaaact gcacaagttt gtcattggac acctaaaggg tgcctctgct 660
aactggtgga accatcgtca cttccagcac cacgctaagc ccaacgtgtt tcgtaaagat 720
cctgatatca actcactgcc tgtcttcgtc ctgggagaca cacagcctgt agagtatggt 780
ataaagaagt tgaagtacat gccctaccat caccaacacc agtacttctt cctcattgga 840
cctccactaa tcgttccagt gtttttcaac atccagatat tccggaccat gttttcacaa 900
cgggactggg tggatctggc gtggtcgatg agtttctacc ttcgcttctt ctgctgttac 960
tatcccttct ttggtttctt tggctcagta gcattgatca gcttcgtcag gtttttggaa 1020
agccactggt ttgtatgggt gacccagatg aatcaccttc ctatggagat ggatcatgag 1080
agacaccagg actggctcac catgcagttg agcgctactt gcaacattga acagtcaacc 1140
ttcaacgact ggttcagtgg acacctcaac tttcagattg aacaccatct gtttcctacc 1200
atgccccgtc ataactacca cctggtggct cctctggtgc gtactttgtg tgagaaacat 1260
ggagttccct atcaggtcaa gactttgcag aaaggcatga ctgatgttgt caggtcactg 1320
aagaagtcag gggatctgtg gctggatgca tatctccata aatga 1365

<210> SEQ ID NO 106
<211> LENGTH: 454
<212> TYPE: PRT
<213> ORGANISM: Salmo salar

<400> SEQUENCE: 106

Met Gly Gly Gly Gly Gln Gln Thr Glu Ser Ser Glu Pro Ala Lys Gly
1 5 10 15

Asp Gly Leu Glu Pro Asp Gly Gly Gln Gly Gly Ser Ala Val Tyr Thr
20 25 30

Trp Glu Glu Val Gln Arg His Ser His Arg Ser Asp Gln Trp Leu Val
35 40 45

Ile Asp Arg Lys Val Tyr Asn Ile Thr Gln Trp Ala Lys Arg His Pro
50 55 60

Gly Gly Ile Arg Val Ile Ser His Phe Ala Gly Glu Asp Ala Thr Glu
65 70 75 80

Ala Phe Ser Ala Phe His Leu Asp Ala Asn Phe Val Arg Lys Phe Leu
85 90 95

Lys Pro Leu Leu Ile Gly Glu Leu Ala Pro Thr Glu Pro Ser Gln Asp
100 105 110

His Gly Lys Asn Ala Ala Leu Val Gln Asp Phe Gln Ala Leu Arg Asp
115 120 125

His Val Glu Arg Glu Gly Leu Leu Arg Ala Arg Leu Leu Phe Phe Ser

-continued

```
    130                 135                 140

Leu Tyr Leu Gly His Ile Leu Leu Leu Glu Ala Leu Ala Leu Gly Leu
145                 150                 155                 160

Leu Trp Val Trp Gly Thr Ser Trp Ser Leu Thr Leu Leu Cys Ser Leu
                165                 170                 175

Met Leu Ala Thr Ser Gln Ala Gln Ala Gly Trp Leu Gln His Asp Tyr
            180                 185                 190

Gly His Leu Ser Val Cys Lys Lys Ser Ser Trp Asn His Lys Leu His
        195                 200                 205

Lys Phe Val Ile Gly His Leu Lys Gly Ala Ser Ala Asn Trp Trp Asn
    210                 215                 220

His Arg His Phe Gln His His Ala Lys Pro Asn Val Phe Arg Lys Asp
225                 230                 235                 240

Pro Asp Ile Asn Ser Leu Pro Val Phe Val Leu Gly Asp Thr Gln Pro
                245                 250                 255

Val Glu Tyr Gly Ile Lys Lys Leu Lys Tyr Met Pro Tyr His His Gln
            260                 265                 270

His Gln Tyr Phe Phe Leu Ile Gly Pro Pro Leu Ile Val Pro Val Phe
        275                 280                 285

Phe Asn Ile Gln Ile Phe Arg Thr Met Phe Ser Gln Arg Asp Trp Val
    290                 295                 300

Asp Leu Ala Trp Ser Met Ser Phe Tyr Leu Arg Phe Phe Cys Cys Tyr
305                 310                 315                 320

Tyr Pro Phe Phe Gly Phe Phe Gly Ser Val Ala Leu Ile Ser Phe Val
                325                 330                 335

Arg Phe Leu Glu Ser His Trp Phe Val Trp Val Thr Gln Met Asn His
            340                 345                 350

Leu Pro Met Glu Met Asp His Glu Arg His Gln Asp Trp Leu Thr Met
        355                 360                 365

Gln Leu Ser Ala Thr Cys Asn Ile Glu Gln Ser Thr Phe Asn Asp Trp
    370                 375                 380

Phe Ser Gly His Leu Asn Phe Gln Ile Glu His His Leu Phe Pro Thr
385                 390                 395                 400

Met Pro Arg His Asn Tyr His Leu Val Ala Pro Leu Val Arg Thr Leu
                405                 410                 415

Cys Glu Lys His Gly Val Pro Tyr Gln Val Lys Thr Leu Gln Lys Gly
            420                 425                 430

Met Thr Asp Val Val Arg Ser Leu Lys Lys Ser Gly Asp Leu Trp Leu
        435                 440                 445

Asp Ala Tyr Leu His Lys
    450
```

<210> SEQ ID NO 107
<211> LENGTH: 1455
<212> TYPE: DNA
<213> ORGANISM: Marchantia polymorpha

<400> SEQUENCE: 107

```
atgccgccac acgcccctga ctccacaggt cttgggcccg aagttttccg cctgcctgat      60

gacgcgatcc cggcccagga tcgcagatct acacagaaga aatactcgct ttcagacgtc     120

agcaagcaca acactccgaa tgattgctgg ctcgtaattt gggggaaggt gtacgatgtt     180

acttcgtggg ttaaggtcca tccaggtgga agtctcatct ttgtgaaggc gggacaggat     240

tcaacacaac tctttgattc ttatcacccc ctctatgtca gaaagctact tgcacagttc     300
```

-continued

```
tgcattggtg aactccaaac gagtgcggga gatgagaagt tcaagtcttc aacgttggag    360

tatgctggtg aagaacatga agtattttac cacactctca agcagcgcgt ggaaacgtac    420

ttccgcaagc agaagataaa tcctcgatac catccgcaaa tgcttgtgaa gtcagccgtg    480

atcattggaa cccttcttct ctgttactat tttggcttct tctggtctca aaatgtactc    540

ctctcgatgt ttctggcaag catcatgggg ttctgcactg cggaggtggg catgtccatc    600

atgcacgatg gtaaccacgg atcgtacaca caatctacct tgcttggtta cgtcatgggc    660

gccactcttg atctggtggg agctagcagt ttcatgtgga ggcagcagca tgtggccggg    720

caccactcgt tcaccaacat cgaccattac gatccagaca ttcgtgtgaa ggatcctgat    780

ttacgacggg ttacttctca acaaccccga agatggtttc acgagtatca gcatatctac    840

ttaggagtac tctatggcgt tcttgcctta aaaagtgtgt tgattgatga tttcagcgcc    900

ttcttcagtg gtgctatcgg cccagtaaag atagctcaaa tgacaccact cgagatgggc    960

gtcttctggg gagggaaggt tgtgtacgca ctgtacatgt ttttgctccc tatgatgtat   1020

ggtcaataca acattcttac tttcattggt ctctacattc tctcacagtt agttgcaggg   1080

tggactcttg ccctcttctt tcaagtagca cacgttgtcg acgatgcagt atttcccgtt   1140

gcggaaacag atggtggaaa agcaaagatt ccttctggtt gggcagaaat gcaggtcaga   1200

accactacca atttcagctc acgatcaatg ttctggacac atattagtgg cggtctgaac   1260

catcagatcg agcaccatct tttcccgggt gtctgtcatg ttcactaccc aagcatacag   1320

ccaatcgtga aggctacctg tgacgagttc aacgtgcctt atacttccta ccccactttc   1380

tgggcggccc ttagggcaca ttttcaacat ctgaaaaacg tcggactaca agatggacta   1440

cgactggatg gctga                                                    1455
```

<210> SEQ ID NO 108
<211> LENGTH: 484
<212> TYPE: PRT
<213> ORGANISM: Marchantia polymorpha

<400> SEQUENCE: 108

```
Met Pro Pro His Ala Pro Asp Ser Thr Gly Leu Gly Pro Glu Val Phe
1               5                   10                  15

Arg Leu Pro Asp Asp Ala Ile Pro Ala Gln Asp Arg Arg Ser Thr Gln
            20                  25                  30

Lys Lys Tyr Ser Leu Ser Asp Val Ser Lys His Asn Thr Pro Asn Asp
        35                  40                  45

Cys Trp Leu Val Ile Trp Gly Lys Val Tyr Asp Val Thr Ser Trp Val
    50                  55                  60

Lys Val His Pro Gly Gly Ser Leu Ile Phe Val Lys Ala Gly Gln Asp
65                  70                  75                  80

Ser Thr Gln Leu Phe Asp Ser Tyr His Pro Leu Tyr Val Arg Lys Leu
                85                  90                  95

Leu Ala Gln Phe Cys Ile Gly Glu Leu Gln Thr Ser Ala Gly Asp Glu
            100                 105                 110

Lys Phe Lys Ser Ser Thr Leu Glu Tyr Ala Gly Glu Glu His Glu Val
        115                 120                 125

Phe Tyr His Thr Leu Lys Gln Arg Val Glu Thr Tyr Phe Arg Lys Gln
    130                 135                 140

Lys Ile Asn Pro Arg Tyr His Pro Gln Met Leu Val Lys Ser Ala Val
145                 150                 155                 160
```

-continued

```
Ile Ile Gly Thr Leu Leu Leu Cys Tyr Tyr Phe Gly Phe Phe Trp Ser
                165                 170                 175

Gln Asn Val Leu Leu Ser Met Phe Leu Ala Ser Ile Met Gly Phe Cys
            180                 185                 190

Thr Ala Glu Val Gly Met Ser Ile Met His Asp Gly Asn His Gly Ser
        195                 200                 205

Tyr Thr Gln Ser Thr Leu Leu Gly Tyr Val Met Gly Ala Thr Leu Asp
    210                 215                 220

Leu Val Gly Ala Ser Ser Phe Met Trp Arg Gln Gln His Val Ala Gly
225                 230                 235                 240

His His Ser Phe Thr Asn Ile Asp His Tyr Asp Pro Asp Ile Arg Val
                245                 250                 255

Lys Asp Pro Asp Leu Arg Arg Val Thr Ser Gln Gln Pro Arg Arg Trp
            260                 265                 270

Phe His Glu Tyr Gln His Ile Tyr Leu Gly Val Leu Tyr Gly Val Leu
        275                 280                 285

Ala Leu Lys Ser Val Leu Ile Asp Asp Phe Ser Ala Phe Phe Ser Gly
    290                 295                 300

Ala Ile Gly Pro Val Lys Ile Ala Gln Met Thr Pro Leu Glu Met Gly
305                 310                 315                 320

Val Phe Trp Gly Gly Lys Val Val Tyr Ala Leu Tyr Met Phe Leu Leu
                325                 330                 335

Pro Met Met Tyr Gly Gln Tyr Asn Ile Leu Thr Phe Ile Gly Leu Tyr
            340                 345                 350

Ile Leu Ser Gln Leu Val Ala Gly Trp Thr Leu Ala Leu Phe Phe Gln
        355                 360                 365

Val Ala His Val Val Asp Asp Ala Val Phe Pro Val Ala Glu Thr Asp
    370                 375                 380

Gly Gly Lys Ala Lys Ile Pro Ser Gly Trp Ala Glu Met Gln Val Arg
385                 390                 395                 400

Thr Thr Thr Asn Phe Ser Ser Arg Ser Met Phe Trp Thr His Ile Ser
                405                 410                 415

Gly Gly Leu Asn His Gln Ile Glu His His Leu Phe Pro Gly Val Cys
            420                 425                 430

His Val His Tyr Pro Ser Ile Gln Pro Ile Val Lys Ala Thr Cys Asp
        435                 440                 445

Glu Phe Asn Val Pro Tyr Thr Ser Tyr Pro Thr Phe Trp Ala Ala Leu
    450                 455                 460

Arg Ala His Phe Gln His Leu Lys Asn Val Gly Leu Gln Asp Gly Leu
465                 470                 475                 480

Arg Leu Asp Gly
```

<210> SEQ ID NO 109
<211> LENGTH: 1338
<212> TYPE: DNA
<213> ORGANISM: Pavlova lutheri

<400> SEQUENCE: 109

```
atgccgcctt cggccgcgag cgagggcggc gtggcggagc tgcgcgcggc ggaggtcgcc      60

tcgtacacgc gcaaggcggt ggatgagcgc cccgacctca ccatcgtcgg cgatgccgtc     120

tacgacgcca aggccttccg tgacgagcac ccgggcggcg cccactttgt gagcctcttt     180

ggcgggcgcg acgcgaccga ggcgttcatg gagtaccacc ggcgggcgtg gcccaaggcg     240

cggatgagca agttcttcgt gggctcgctc gacgcctccg agaagccgac gcaggccgac     300
```

-continued

```
agtgcctacc tccggctgtg cgcggaggtg aacgccttgc tgccaaaggg gagcggcggc    360

tttgcgccgc cctcctattg gctcaaggcg gcggcgctgg tggtggccgc cgtgtcgatt    420

gaggggtata tgctgctgcg cggcaagacg ctcctcctct ccgtctttct cggcctcgtc    480

tttgcgtgga tcggtctcaa catccagcac gacgcgaacc acggcgcgct ctcgcgccac    540

tcggtgatca actactgcct tgggtacgcg caggactgga tcggcggcaa catggtgctc    600

tggctgcagg agcacgtggt gatgcaccac ctgcacacca acgacgtcga cgccgacccg    660

gaccagaagg cgcacggcgt gctgcggctc aagccaacgg acggctggat gccgtggcat    720

gcgctccaac agctttacat tctgcccggc gaggcgatgt acgcgtttaa gctgctcttc    780

ctcgacgcgc tcgagctgct cgcgtggcga tgggagggcg agaagatctc gcccctcgcg    840

cgcgccctgt ttgcaccagc ggtggcgtgc aagcttggct tctgggcgcg cttcgtcgcg    900

ctgccgctct ggctgcagcc gacggtgcac acggcgctgt gcatctgcgc gacggtgtgc    960

acgggctcct tctacctcgc cttcttcttc ttcatctcgc acaactttga cggcgtgggt   1020

agtgtgggcc ccaagggcag cttgccgcgc tctgcaacct tcgtgcagcg gcaggtcgag   1080

acgagttcga atgtgggcgg ctactggctt ggcgtgctca atggagggct caacttccag   1140

atcgagcacc atcttttccc gcggctgcac cattcgtact acgcgcagat tgccccagtg   1200

gtgcgcacgc acatcgagaa gctcggcttc aagtacaggc acttccccac ggtgggctcc   1260

aacttgtcgt ccatgctgca gcacatgggc aagatgggca ctcgcccagg agctgagaag   1320

ggcggcaagg ccgagtga                                                  1338
```

<210> SEQ ID NO 110
<211> LENGTH: 445
<212> TYPE: PRT
<213> ORGANISM: Pavlova lutheri

<400> SEQUENCE: 110

```
Met Pro Pro Ser Ala Ala Ser Glu Gly Gly Val Ala Glu Leu Arg Ala
 1               5                  10                  15

Ala Glu Val Ala Ser Tyr Thr Arg Lys Ala Val Asp Glu Arg Pro Asp
            20                  25                  30

Leu Thr Ile Val Gly Asp Ala Val Tyr Asp Ala Lys Ala Phe Arg Asp
        35                  40                  45

Glu His Pro Gly Gly Ala His Phe Val Ser Leu Phe Gly Gly Arg Asp
    50                  55                  60

Ala Thr Glu Ala Phe Met Glu Tyr His Arg Arg Ala Trp Pro Lys Ala
65                  70                  75                  80

Arg Met Ser Lys Phe Phe Val Gly Ser Leu Asp Ala Ser Glu Lys Pro
                85                  90                  95

Thr Gln Ala Asp Ser Ala Tyr Leu Arg Leu Cys Ala Glu Val Asn Ala
            100                 105                 110

Leu Leu Pro Lys Gly Ser Gly Gly Phe Ala Pro Pro Ser Tyr Trp Leu
        115                 120                 125

Lys Ala Ala Ala Leu Val Val Ala Ala Val Ser Ile Glu Gly Tyr Met
    130                 135                 140

Leu Leu Arg Gly Lys Thr Leu Leu Leu Ser Val Phe Leu Gly Leu Val
145                 150                 155                 160

Phe Ala Trp Ile Gly Leu Asn Ile Gln His Asp Ala Asn His Gly Ala
                165                 170                 175

Leu Ser Arg His Ser Val Ile Asn Tyr Cys Leu Gly Tyr Ala Gln Asp
```

-continued

```
            180                 185                 190

Trp Ile Gly Gly Asn Met Val Leu Trp Leu Gln Glu His Val Val Met
        195                 200                 205

His His Leu His Thr Asn Asp Val Asp Ala Asp Pro Asp Gln Lys Ala
    210                 215                 220

His Gly Val Leu Arg Leu Lys Pro Thr Asp Gly Trp Met Pro Trp His
225                 230                 235                 240

Ala Leu Gln Gln Leu Tyr Ile Leu Pro Gly Glu Ala Met Tyr Ala Phe
                245                 250                 255

Lys Leu Leu Phe Leu Asp Ala Leu Glu Leu Leu Ala Trp Arg Trp Glu
            260                 265                 270

Gly Glu Lys Ile Ser Pro Leu Ala Arg Ala Leu Phe Ala Pro Ala Val
        275                 280                 285

Ala Cys Lys Leu Gly Phe Trp Ala Arg Phe Val Ala Leu Pro Leu Trp
    290                 295                 300

Leu Gln Pro Thr Val His Thr Ala Leu Cys Ile Cys Ala Thr Val Cys
305                 310                 315                 320

Thr Gly Ser Phe Tyr Leu Ala Phe Phe Phe Phe Ile Ser His Asn Phe
                325                 330                 335

Asp Gly Val Gly Ser Val Gly Pro Lys Gly Ser Leu Pro Arg Ser Ala
            340                 345                 350

Thr Phe Val Gln Arg Gln Val Glu Thr Ser Ser Asn Val Gly Gly Tyr
        355                 360                 365

Trp Leu Gly Val Leu Asn Gly Gly Leu Asn Phe Gln Ile Glu His His
    370                 375                 380

Leu Phe Pro Arg Leu His His Ser Tyr Tyr Ala Gln Ile Ala Pro Val
385                 390                 395                 400

Val Arg Thr His Ile Glu Lys Leu Gly Phe Lys Tyr Arg His Phe Pro
                405                 410                 415

Thr Val Gly Ser Asn Leu Ser Ser Met Leu Gln His Met Gly Lys Met
            420                 425                 430

Gly Thr Arg Pro Gly Ala Glu Lys Gly Gly Lys Ala Glu
        435                 440                 445


<210> SEQ ID NO 111
<211> LENGTH: 1077
<212> TYPE: DNA
<213> ORGANISM: Saproleigna diclina

<400> SEQUENCE: 111

atgactgagg ataagacgaa ggtcgagttc ccgacgctca cggagctcaa gcactcgatc      60

ccgaacgcgt gctttgagtc gaacctcggc ctctcgctct actacacggc ccgcgcgatc     120

ttcaacgcgt cggcctcggc ggcgctgctc tacgcggcgc gctcgacgcc gttcattgcc     180

gataacgttc tgctccacgc gctcgtttgc gccacctaca tctacgtgca gggcgtcatc     240

ttctggggct tcttcacggt cggccacgac tgcggccact cggccttctc gcgctaccac     300

agcgtcaact ttatcatcgg ctgcatcatg cactctgcga ttttgacgcc gttcgagagc     360

tggcgcgtga cgcaccgcca ccaccacaag aacacgggca acattgataa ggacgagatc     420

ttttacccgc accggtcggt caaggacctc caggacgtgc gccaatgggt ctacacgctc     480

ggcggtgcgt ggtttgtcta cttgaaggtc gggtatgccc cgcgcacgat gagccacttt     540

gacccgtggg acccgctcct ccttcgccgc gcgtcggccg tcatcgtgtc gctcggcgtc     600

tgggccgcct tcttcgccgc gtacgcgtac ctcacatact cgctcggctt tgccgtcatg     660
```

-continued

```
ggcctctact actatgcgcc gctctttgtc tttgcttcgt tcctcgtcat tacgaccttc    720

ttgcaccaca acgacgaagc gacgccgtgg tacggcgact cggagtggac gtacgtcaag    780

ggcaacctct cgagcgtcga ccgctcgtac ggcgcgttcg tggacaacct gagccaccac    840

attggcacgc accaggtcca ccacttgttc ccgatcattc cgcactacaa gctcaacgaa    900

gccaccaagc actttgcggc cgcgtacccg cacctcgtgc gcaggaacga cgagcccatc    960

atcacggcct tcttcaagac cgcgcacctc tttgtcaact acggcgctgt gcccgagacg   1020

gcgcagatct tcacgctcaa agagtcggcc gcggccgcca aggccaagtc ggactaa      1077


<210> SEQ ID NO 112
<211> LENGTH: 358
<212> TYPE: PRT
<213> ORGANISM: Saproleigna diclina

<400> SEQUENCE: 112

Met Thr Glu Asp Lys Thr Lys Val Glu Phe Pro Thr Leu Thr Glu Leu
 1               5                  10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
    210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
    290                 295                 300
```

-continued

```
Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
            340                 345                 350

Ala Lys Ala Lys Ser Asp
        355
```

```
<210> SEQ ID NO 113
<211> LENGTH: 1251
<212> TYPE: DNA
<213> ORGANISM: Saccharomyces kluyveri

<400> SEQUENCE: 113

atgtctgcag ttacagtcac agggtccgac ccaaagaacc gtggttcctc ctctaatacc      60

gagcaagaag ttccaaaagt tgcaattgac accaatggta atgttttcag cgtaccagat     120

tttaccatca aggatatttt gggcgccatt ccccacgaat gttacgaaag aagactagca     180

acatcgttat actatgtttt tagagacatc ttctgcatgc taacaaccgg ttaccttaca     240

cacaaaatct tatatccatt gctgatctca tacacttcta actcaataat caagtttacc     300

ttctgggctt tgtacacata cgtccaaggt ttgtttggta ctggtatctg ggtgttggcc     360

cacgaatgtg gccatcaagc cttctcagac tatggtattg tcaacgattt tgttggctgg     420

actctacact cttacttgat ggtaccatat tttcgtgga agtattccca tggtaagcat      480

cacaaggcca ccggtcacat gactagagac atggttttg ttcctgccac aaaggaggaa      540

tttaagaaaa gcagaaactt tttcggaaat ttggcagaat actccgagga ttccccatta     600

agaactttgt acgaattgct ggtacaacaa ctaggaggtt ggattgcata tctttttgtc     660

aacgttactg gtcaaccgta tccagatgtt ccttcctgga aatggaacca cttctggcta     720

acttctccat tatttgaaca aagggatgct ttgtacattt ttttgagtga tctaggtatc     780

ttgacccaag gcattgtttt gaccttgtgg tacaagaagt ttggtggctg gtctctgttc     840

atcaattggt ttgttccata catttgggtt aaccactggt tggtttttat cactttttttg     900

caacacaccg acccaactat gccccattac aatgctgagg aatggacttt tgccaagggt     960

gctgccgcca ccattgatag aaaattcggg tttattggtc ctcacatttt ccatgacatt    1020

attgaaaccc atgtgctaca ccactactgt agcagaattc cattctataa cgctcgtcca    1080

gcaagcgagg ctattaagaa agtgatgggc aagcattata gatctagtga cgaaaacatg    1140

tggaagtcct tatggaagtc ttttagatct tgtcagtatg ttgatggaga caatggtgtt    1200

ttaatgttca gaaacatcaa caactgtggt gttggcgccg ctgagaaatg a             1251
```

```
<210> SEQ ID NO 114
<211> LENGTH: 416
<212> TYPE: PRT
<213> ORGANISM: Saccharomyces kluyveri

<400> SEQUENCE: 114

Met Ser Ala Val Thr Val Thr Gly Ser Asp Pro Lys Asn Arg Gly Ser
 1               5                  10                  15

Ser Ser Asn Thr Glu Gln Glu Val Pro Lys Val Ala Ile Asp Thr Asn
            20                  25                  30

Gly Asn Val Phe Ser Val Pro Asp Phe Thr Ile Lys Asp Ile Leu Gly
        35                  40                  45
```

-continued

```
Ala Ile Pro His Glu Cys Tyr Glu Arg Arg Leu Ala Thr Ser Leu Tyr
    50                  55                  60

Tyr Val Phe Arg Asp Ile Phe Cys Met Leu Thr Thr Gly Tyr Leu Thr
65                  70                  75                  80

His Lys Ile Leu Tyr Pro Leu Leu Ile Ser Tyr Thr Ser Asn Ser Ile
                85                  90                  95

Ile Lys Phe Thr Phe Trp Ala Leu Tyr Thr Tyr Val Gln Gly Leu Phe
            100                 105                 110

Gly Thr Gly Ile Trp Val Leu Ala His Glu Cys Gly His Gln Ala Phe
        115                 120                 125

Ser Asp Tyr Gly Ile Val Asn Asp Phe Val Gly Trp Thr Leu His Ser
    130                 135                 140

Tyr Leu Met Val Pro Tyr Phe Ser Trp Lys Tyr Ser His Gly Lys His
145                 150                 155                 160

His Lys Ala Thr Gly His Met Thr Arg Asp Met Val Phe Val Pro Ala
                165                 170                 175

Thr Lys Glu Glu Phe Lys Lys Ser Arg Asn Phe Phe Gly Asn Leu Ala
            180                 185                 190

Glu Tyr Ser Glu Asp Ser Pro Leu Arg Thr Leu Tyr Glu Leu Leu Val
        195                 200                 205

Gln Gln Leu Gly Gly Trp Ile Ala Tyr Leu Phe Val Asn Val Thr Gly
    210                 215                 220

Gln Pro Tyr Pro Asp Val Pro Ser Trp Lys Trp Asn His Phe Trp Leu
225                 230                 235                 240

Thr Ser Pro Leu Phe Glu Gln Arg Asp Ala Leu Tyr Ile Phe Leu Ser
                245                 250                 255

Asp Leu Gly Ile Leu Thr Gln Gly Ile Val Leu Thr Leu Trp Tyr Lys
            260                 265                 270

Lys Phe Gly Gly Trp Ser Leu Phe Ile Asn Trp Phe Val Pro Tyr Ile
        275                 280                 285

Trp Val Asn His Trp Leu Val Phe Ile Thr Phe Leu Gln His Thr Asp
    290                 295                 300

Pro Thr Met Pro His Tyr Asn Ala Glu Glu Trp Thr Phe Ala Lys Gly
305                 310                 315                 320

Ala Ala Ala Thr Ile Asp Arg Lys Phe Gly Phe Ile Gly Pro His Ile
                325                 330                 335

Phe His Asp Ile Ile Glu Thr His Val Leu His His Tyr Cys Ser Arg
            340                 345                 350

Ile Pro Phe Tyr Asn Ala Arg Pro Ala Ser Glu Ala Ile Lys Lys Val
        355                 360                 365

Met Gly Lys His Tyr Arg Ser Ser Asp Glu Asn Met Trp Lys Ser Leu
    370                 375                 380

Trp Lys Ser Phe Arg Ser Cys Gln Tyr Val Asp Gly Asp Asn Gly Val
385                 390                 395                 400

Leu Met Phe Arg Asn Ile Asn Asn Cys Gly Val Gly Ala Ala Glu Lys
                405                 410                 415
```

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 115
atggcaactc ctcttccccc ctcc 24

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 116
ctattcggcc ttgacgtggt cagtgc 26

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 117
aacccttttt caggatggca cc 22

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 118
aaagttgtgt ccggtaaatg cttc 24

<210> SEQ ID NO 119
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 119
ggactagtcc accatggctg ctgctcccag tgtgagg 37

<210> SEQ ID NO 120
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 120
ccatcgatgg cttactgtgc cttgcccatc ttggagg 37

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 121

-continued atggagtcga ttgcgccatt cc 22

<210> SEQ ID NO 122
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 122
ttactgcaac ttccttgcct tctcc 25

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 123
atgggtacgg accaaggaaa aacc 24

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 124
ctactcttcc ttgggacgga gtcc 24

<210> SEQ ID NO 125
<211> LENGTH: 38
<212> TYPE: DNA
<213> ORGANISM: Artificial Sequence
<220> FEATURE:
<223> OTHER INFORMATION: Description of Artificial Sequence: Synthetic
primer

<400> SEQUENCE: 125
gacctcgagt aagcttatgg cacctcccaa cactattg 38

<210> SEQ ID NO 126
<211> LENGTH: 36
<212> TYPE: DNA
<213> ORGANISM: Artificial Sequence
<220> FEATURE:
<223> OTHER INFORMATION: Description of Artificial Sequence: Synthetic
primer

<400> SEQUENCE: 126
gctagccgcg gtaccaatta cttcttgaaa aagacc 36

<210> SEQ ID NO 127
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 127

-continued gacctcgagt aagcttatgg agtcgattgc gcc 33

<210> SEQ ID NO 128
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 128
gctagccgcg gtaccaatta ctgcaacttc cttgc 35

<210> SEQ ID NO 129
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
cgcactagta tcgatatggg tacggaccaa gg 32

<210> SEQ ID NO 130
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 130
ttaattaaga gctcagatct tctactcttc cttgggacg 39

<210> SEQ ID NO 131
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
ttgttattgt aatgtgatac ctattcggcc ttgacgtgg 39

<210> SEQ ID NO 132
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
gtatcacatt acaataacaa aactgcaac 29

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 133
cttgacgttc gttcgactga tgagc 25

-continued

<210> SEQ ID NO 134
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 134 gggggaaga ggagttgcca ttttgtttgt ttatgtgtg 39

<210> SEQ ID NO 135
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 135
accagcatct attaaagtaa aataccg 27

<210> SEQ ID NO 136
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
gctgaaaaga tgatgttctg agg 23

<210> SEQ ID NO 137
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
agtacataca gggaacgtcc gcggtctgca gagaaggc 38

<210> SEQ ID NO 138
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
ggacgttccc tgtatgtact aaaaatgaaa gaagcttacc ag 42

<210> SEQ ID NO 139
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 139
gagcaatgaa cccaataacg aaatc 25

-continued

<210> SEQ ID NO 140
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 140
agacattgaa atccaaagaa gactgaagg 29

<210> SEQ ID NO 141
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 141
gaagatctcc accatggagc agctgaaggc ctttgataat g 41

<210> SEQ ID NO 142
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 142
ccttaattaa ggcttattga gccttcttgt ccgtcatgcc attagc 46

<210> SEQ ID NO 143
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 143
aaatcgataa ccgcggaggg ggatcgaaga aatgatgg 38

<210> SEQ ID NO 144
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 144
ttgggccctt tcccgggtgt atatgagata gttgattgta tgc 43

<210> SEQ ID NO 145
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 145
ttgggccctt tcccgggttt tgtttgttta tgtgtg 36

-continued

```
<210> SEQ ID NO 146
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146

aaatcgataa ccgcggatga aagaagctta ccag                                34


<210> SEQ ID NO 147
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147

tggtcttgtg gagtaagcgt ccattgtata tgagatagtt gattgtatgc               50


<210> SEQ ID NO 148
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148

ttcttgctca acttccggct tcattgtata tgagatagtt gattgtatgc               50


<210> SEQ ID NO 149
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149

atggacgctt actccacaag accattaac                                      29


<210> SEQ ID NO 150
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150

ttgatataga tcacgcaatt cttcaaagta gtc                                 33


<210> SEQ ID NO 151
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151

atgaagccgg aagttgagca agaattagc                                      29


<210> SEQ ID NO 152
```

-continued

<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 152
acttcttcaa cttgtgagca accaaaacg 29

<210> SEQ ID NO 153
<211> LENGTH: 42
<212> TYPE: DNA
<213> ORGANISM: Artificial Sequence
<220> FEATURE:
<223> OTHER INFORMATION: Description of Artificial Sequence: Synthetic
primer

<400> SEQUENCE: 153
ggacgttccc tgtatgtact agggggatcg aagaaatgat gg 42

<210> SEQ ID NO 154
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 154
ccgctgtact atgcggtctc gtcc 24

<210> SEQ ID NO 155
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 155
agtacataca gggaacgtcc gtatgccaaa aatgccaaaa tgcc 44

<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 156
caactacaag gaggagaata aagagcaagc c 31

<210> SEQ ID NO 157
<211> LENGTH: 49
<212> TYPE: DNA
<213> ORGANISM: Artificial Sequence
<220> FEATURE:
<223> OTHER INFORMATION: Description of Artificial Sequence: Synthetic
primer

<400> SEQUENCE: 157
agtacataca gggaacgtcc aacgacaaca acaacgacta caatgatgg 49

<210> SEQ ID NO 158
<211> LENGTH: 26

-continued

<212> TYPE: DNA
<213> ORGANISM: Artificial Sequence
<220> FEATURE:
<223> OTHER INFORMATION: Description of Artificial Sequence: Synthetic primer

<400> SEQUENCE: 158
ctggaattcg atgatgtagt ttctgg 26

<210> SEQ ID NO 159
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 159
ctacatcatc gaattccagc tacgtatggt catttcttct tc 42

<210> SEQ ID NO 160
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 160
tttttgatta aaattaaaaa aactttttag tttatgtatg tgttttttg 49

<210> SEQ ID NO 161
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 161
agttttttta attttaatca aaaaatgagc gaagaaagct tattcgagtc 50

<210> SEQ ID NO 162
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 162
cacctaaaga cctcatggcg ttacc 25

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 163
cggtctgcat tggatggtgg taac 24

<210> SEQ ID NO 164
<211> LENGTH: 44
<212> TYPE: DNA

-continued

<213> ORGANISM: Artificial Sequence
<220> FEATURE:
<223> OTHER INFORMATION: Description of Artificial Sequence: Synthetic
primer

<400> SEQUENCE: 164
caccatccaa tgcagaccgt tttagtttat gtatgtgttt tttg 44

<210> SEQ ID NO 165
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 165
tgttctgctc tcttcaattt tcctttc 27

<210> SEQ ID NO 166
<211> LENGTH: 43
<212> TYPE: DNA
<213> ORGANISM: Artificial Sequence
<220> FEATURE:
<223> OTHER INFORMATION: Description of Artificial Sequence: Synthetic
primer

<400> SEQUENCE: 166
ctggaattcg atgatgtagt ttctaatttt ctgcgctgtt tcg 43

<210> SEQ ID NO 167
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 167
ttagagcttc attccaacaa gtgcc 25

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 168
aattcggtaa attcaatggg tagg 24

<210> SEQ ID NO 169
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 169
ttagtacata cagggaacgt ccgtaaatat agggcttaaa atgtgtcagg 50

<210> SEQ ID NO 170
<211> LENGTH: 34
<212> TYPE: DNA
<213> ORGANISM: Artificial Sequence -continued
<220> FEATURE:
<223> OTHER INFORMATION: Description of Artificial Sequence: Synthetic
primer

<400> SEQUENCE: 170
tttgtttgtt tatgtgtgtt tattcgaaac taag 34

<210> SEQ ID NO 171
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 171
cgaataaaca cacataaaca aacaaaatgt caggaacatt caatgatata 50

<210> SEQ ID NO 172
<211> LENGTH: 35
<212> TYPE: DNA
<213> ORGANISM: Artificial Sequence
<220> FEATURE:
<223> OTHER INFORMATION: Description of Artificial Sequence: Synthetic
primer

<400> SEQUENCE: 172
gttttaaatt gacagtttta atcaaactta taggg 35

<210> SEQ ID NO 173
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 173
ttttggctgt tgttccaggt cgtagg 26

<210> SEQ ID NO 174
<211> LENGTH: 50
<212> TYPE: DNA
<213> ORGANISM: Artificial Sequence
<220> FEATURE:
<223> OTHER INFORMATION: Description of Artificial Sequence: Synthetic
primer

<400> SEQUENCE: 174
agtacataca gggaacgtcc gataaacagg aaaaaaaaaa aactttggcg 50

<210> SEQ ID NO 175
<211> LENGTH: 42
<212> TYPE: DNA
<213> ORGANISM: Artificial Sequence
<220> FEATURE:
<223> OTHER INFORMATION: Description of Artificial Sequence: Synthetic
primer

<400> SEQUENCE: 175
agttttttta attttaatca aaaaatgtct gctcccgctg cc 42

<210> SEQ ID NO 176
<211> LENGTH: 23
<212> TYPE: DNA
<213> ORGANISM: Artificial Sequence
<220> FEATURE:

-continued

<223> OTHER INFORMATION: Description of Artificial Sequence: Synthetic
primer

<400> SEQUENCE: 176 aacctttttcg taaagttcac tgg 23

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 177
aggaaaaacc catagagcac g 21

<210> SEQ ID NO 178
<211> LENGTH: 43
<212> TYPE: DNA
<213> ORGANISM: Artificial Sequence
<220> FEATURE:
<223> OTHER INFORMATION: Description of Artificial Sequence: Synthetic
primer

<400> SEQUENCE: 178
agttttttta attttaatca aaaaatgccg cgaattactc aag 43

<210> SEQ ID NO 179
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 179
gactagaagg tatgggtaga tagcc 25

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 180
ggtaaagaaa actacaaatc tggg 24

<210> SEQ ID NO 181
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 181
ctggaattcg atgatgtaga agctgccact tcttcaggg 39

<210> SEQ ID NO 182
<211> LENGTH: 24
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 182
ttgctttaaa catctgtcca agac 24

<210> SEQ ID NO 183
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 183
ctggaattcg atgatgtagc cttcacctta aacccttcc 39

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 184
tgtcttccta ttttctctga ccc 23

<210> SEQ ID NO 185
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 185
ctggaattcg atgatgtagt cgcatgcact caattgg 37

<210> SEQ ID NO 186
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 186
tgtatatgag atagttgatt gtatgc 26

<210> SEQ ID NO 187
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 187
tacaatcaac tatctcatat acaatgactt ttatgcaaca gcttcaagag 50

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 188
gaccaacatt attgaccaaa acgg 24

<210> SEQ ID NO 189
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 189
gcatacaatc aactatctca tatacaatgc ctatcaccat aaaaagcc 48

<210> SEQ ID NO 190
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 190
ggaagccgta gccaaagtaa cc 22

<210> SEQ ID NO 191
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 191
gaaaaaatca ttggatgccc 20

<210> SEQ ID NO 192
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 192
agtacataca gggaacgtcc aacgctttta ttcgtgaaat ctc 43

<210> SEQ ID NO 193
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 193
gttattgaaa gcaatgggca ac 22

<210> SEQ ID NO 194
<211> LENGTH: 47
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 194
gcatacaatc aactatctca tatacaatgc cttccgcaac tagcacc 47

<210> SEQ ID NO 195
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 195
ttgttattgt aatgtgatac ttaaatttgg acctcaacac gacc 44

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 196
ttaggcctgg aactccaccg cac 23

<210> SEQ ID NO 197
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 197
cgaataaaca cacataaaca aacaaaatgt ctgcgaagag catc 44

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 198
caacgctatc cgcttttacc agt 23

<210> SEQ ID NO 199
<211> LENGTH: 48
<212> TYPE: DNA
<213> ORGANISM: Artificial Sequence
<220> FEATURE:
<223> OTHER INFORMATION: Description of Artificial Sequence: Synthetic primer

<400> SEQUENCE: 199
gcactgacca cgtcaaggcc gaatagccgc tctaaccgaa aaggaagg 48

<210> SEQ ID NO 200
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 200
gtgcggtgga gttccaggcc taacgaattt cttatgattt atgattttta 50

<210> SEQ ID NO 201
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 201
gttaccacca tccaatgcag accgtgtata tgagatagtt gattgtatgc 50

<210> SEQ ID NO 202
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 202
aagcggccgc ttttgtttgt ttatgtgtgt ttattcg 37

<210> SEQ ID NO 203
<211> LENGTH: 50
<212> TYPE: DNA
<213> ORGANISM: Artificial Sequence
<220> FEATURE:
<223> OTHER INFORMATION: Description of Artificial Sequence: Synthetic primer

<400> SEQUENCE: 203
aaatggaaaa agggtagtga aaagtttatc attatcaata ctgccatttc 50

<210> SEQ ID NO 204
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 204
tttcactacc ctttttccat ttgccatc 28

<210> SEQ ID NO 205
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 205
ttcccgggtg tatatgagat agttgattgt atgc 34

<210> SEQ ID NO 206
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 206

-continued ctagcaattc cttaattaag gaattg 26

<210> SEQ ID NO 207
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 207
tgttctcgag aaggtgttga gcgacctcat gctatacctg agaaag 46

<210> SEQ ID NO 208
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 208
ccatcgatgg cgaatttctt atgatttatg attttta 37

<210> SEQ ID NO 209
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 209
gaagatcttc ccgctctaac cgaaaaggaa gg 32

<210> SEQ ID NO 210
<211> LENGTH: 37
<212> TYPE: DNA
<213> ORGANISM: Artificial Sequence
<220> FEATURE:
<223> OTHER INFORMATION: Description of Artificial Sequence: Synthetic primer

<400> SEQUENCE: 210
aacaccttct cgagaacact tcgagcgtcc caaaacc 37

<210> SEQ ID NO 211
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 211
ggtctcgagc caccatggtt gttgctatgg accaac 36

<210> SEQ ID NO 212
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 212
ggggtaccat taattgattt tagatttgtc agaagcgtaa 40

-continued

<210> SEQ ID NO 213
<211> LENGTH: 34
<212> TYPE: DNA
<213> ORGANISM: Artificial Sequence
<220> FEATURE:
<223> OTHER INFORMATION: Description of Artificial Sequence: Synthetic
primer

<400> SEQUENCE: 213
ggtctcgagc caccatgtct attgaaacag tcgg 34

<210> SEQ ID NO 214
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 214
ggccgcggat cattgactgg aaccatctt 29

<210> SEQ ID NO 215
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 215
atcccgggac catgacagtt ggttacgatg agg 33

<210> SEQ ID NO 216
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 216
atccgcggtt atgctgctct ttgccaactt tcg 33

<210> SEQ ID NO 217
<211> LENGTH: 44
<212> TYPE: DNA
<213> ORGANISM: Artificial Sequence
<220> FEATURE:
<223> OTHER INFORMATION: Description of Artificial Sequence: Synthetic
primer

<400> SEQUENCE: 217
actacatcat cgaattccag aacgaatcaa attaacaacc atag 44

<210> SEQ ID NO 218
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 218
tcattgactg gaaccatctt 20

-continued

<210> SEQ ID NO 219
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 219
aagatggttc cagtcaatga taaggatgac ttgttgaaat ggtaa 45

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 220
ccacaagact gtttccagag c 21

<210> SEQ ID NO 221
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 221
atggcatggc cccgaagg 18

<210> SEQ ID NO 222
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 222
ctggaattcg atgatgtagt ttgaacgaaa atgaacaaga cg 42

<210> SEQ ID NO 223
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 223
ccaccatcca atgcagaccg cggggttttt tctccttgac 40

<210> SEQ ID NO 224
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 224
gttaaggaat taattcctta acgatc 26

-continued

```
<210> SEQ ID NO 225
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225

agttttttta attttaatca aaaaatgagt gtgataggta ggttcttg              48


<210> SEQ ID NO 226
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226

ctacatcatc gaattccagc tacgtatggt catttcttct tc                    42


<210> SEQ ID NO 227
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227

agtacataca gggaacgtcc aattcaaaat atgtatctct ctc                   43
```